United States Patent
Yamamoto

(10) Patent No.: US 10,905,757 B2
(45) Date of Patent: Feb. 2, 2021

(54) CROSS-REACTIVE T CELL EPITOPES OF HIV, SIV, AND FIV FOR VACCINES IN HUMANS AND CATS

(71) Applicant: UNIVERSITY OF FLORIDA RESEARCH FOUNDATION, INC., Gainesville, FL (US)

(72) Inventor: Janet K. Yamamoto, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 225 days.

(21) Appl. No.: 15/881,148

(22) Filed: Jan. 26, 2018

(65) Prior Publication Data

US 2018/0228890 A1    Aug. 16, 2018

Related U.S. Application Data

(63) Continuation of application No. 14/617,711, filed on Feb. 9, 2015, now Pat. No. 9,913,895, which is a continuation-in-part of application No. PCT/US2013/054191, filed on Aug. 8, 2013.

(60) Provisional application No. 61/841,122, filed on Jun. 28, 2013, provisional application No. 61/684,592, filed on Aug. 17, 2012, provisional application No. 61/681,014, filed on Aug. 8, 2012.

(51) Int. Cl.

| | |
|---|---|
| *A61K 39/21* | (2006.01) |
| *A61K 39/12* | (2006.01) |
| *C07K 14/005* | (2006.01) |
| *C12N 7/00* | (2006.01) |
| *C07K 16/10* | (2006.01) |
| *A61K 45/06* | (2006.01) |
| *G01N 33/569* | (2006.01) |
| *A61K 39/00* | (2006.01) |

(52) U.S. Cl.
CPC .............. *A61K 39/21* (2013.01); *A61K 39/12* (2013.01); *A61K 45/06* (2013.01); *C07K 14/005* (2013.01); *C07K 16/1045* (2013.01); *C07K 16/1054* (2013.01); *C12N 7/00* (2013.01); *G01N 33/56983* (2013.01); *A61K 2039/552* (2013.01); *A61K 2039/57* (2013.01); *C07K 2317/31* (2013.01); *C07K 2317/33* (2013.01); *C07K 2317/34* (2013.01); *C12N 2740/15022* (2013.01); *C12N 2740/15034* (2013.01); *C12N 2740/16034* (2013.01); *C12N 2740/16222* (2013.01); *C12N 2740/16234* (2013.01); *G01N 2333/52* (2013.01); *G01N 2333/57* (2013.01)

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 5,585,089 | A | 12/1996 | Queen et al. |
| 5,622,705 | A | 4/1997 | Morrow |
| 5,693,762 | A | 12/1997 | Queen et al. |
| 5,756,666 | A | 5/1998 | Takiguchi et al. |
| 5,882,645 | A | 3/1999 | Toth et al. |
| 6,180,370 | B1 | 1/2001 | Queen et al. |
| 6,407,213 | B1 | 6/2002 | Carter et al. |
| 6,645,956 | B1 | 11/2003 | Fujishita et al. |
| 7,658,927 | B2 | 2/2010 | Yamamoto |
| 2003/0091987 | A1 | 5/2003 | Yamamoto et al. |
| 2006/0147467 | A1 | 7/2006 | Yamamoto |
| 2009/0274725 | A1 | 11/2009 | Yamamoto et al. |

FOREIGN PATENT DOCUMENTS

| | | |
|---|---|---|
| KR | 10-1069391 | 3/2010 |
| WO | WO 93/22343 | 11/1993 |
| WO | WO 2014/026033 | 2/2014 |

OTHER PUBLICATIONS

Abbott, J.R. et al. "Utilization of feline ELISPOT for mapping vaccine epitopes" *Methods Mol. Biol.*, 2012, 792:47-63.

Abbott, J.R. et al. "Evolutionarily conserved T-cell epitopes on FIV for designing an HIV/AIDS vaccine" *Vet. Immunol. Immunopathol.*, 2011 143:246-254.

Ackley, C.D. et al. "Immunologic abnormalities in pathogen-free cats experimentally infected with feline immunodeficiency virus" *J. Virol.*, 1990, 64:5652-5655.

Almeida, J.R. et al. "Superior control of HIV-1 replication by CD8+ T cells is reflected by their avidity, polyfunctionality, and clonal turnover" *The Journal of Experimental Medicine*, 2007, 204(10):2473-2485.

Balla-Jhagjhoorsingh, S.S. et al. "Conserved CTL epitopes shared between HIV-infected human long-term survivors and chimpanzees" *J. Immunol.*, 1999, 162:2308-2314.

Barouch, D.H. et al. "Mosaic HIV-1 vaccines expand the breadth and depth of cellular immune responses in rhesus monkeys" *Nat Med*, 2010, 16(3):319-323.

Belyakov, I.M. and Ahlers, J.D. "Mucosal immunity and HIV-1 infection: Applications for mucosal AIDS vaccine development" *Curr Top Microbiol Immunol*, 2012, 354:157-179.

(Continued)

*Primary Examiner* — Stacy B Chen
(74) *Attorney, Agent, or Firm* — Saliwanchik, Lloyd & Eisenschenk

(57) ABSTRACT

The subject invention concerns methods and materials for inducing an immune response in an animal or person against an immunodeficiency virus, such as HIV, SIV, or FIV. In one embodiment, a method of the invention comprises administering one or more antigens and/or immunogens to the person or animal wherein the antigen and/or immunogen comprises one or more evolutionarily conserved epitopes of immunodeficiency viruses. In one embodiment, the epitope is one that is conserved between HIV and SIV, or between HIV and FIV. In another embodiment, the epitope is one that is conserved between HIV, SIV, and FIV.

20 Claims, 53 Drawing Sheets

Specification includes a Sequence Listing.

(56) References Cited

OTHER PUBLICATIONS

Betts, M.R. et al. "Human immunodeficiency virus type 1-specific cytotoxic T lymphocyte activity is inversely correlated with HIV type 1 viral load in HIV type 1-infected long-term survivors" *AIDS Res. Hum. Retroviruses*, 1999, 15(13):1219-1228.

Betts, M.R. et al. "HIV nonprogressors preferentially maintain highly functional HIV-specific CD8+T cells" *Blood*, 2006, 107:4781-4789.

Bhasin, M. and Raghava, G.P.S. "Prediction of CTL epitopes using QM, SVM and ANN techniques" *Vaccine*, 2004, 22: 3195-3204.

Buchbinder, S. et al. "Efficacy assessment of a cell-mediated immunity HIV-1 vaccine (the Step Study): a double-blind, randomised, placebo-controlled, test-of-concept trial" *Lancet*, 2008, 372:1881-1893.

Cao, H. et al. "Cytotoxic T-lymphocyte cross-reactivity among different human immunodeficiency virus type 1 clades: Implications for vaccine development" *J Virol*, 1997, 71(11):8615-8623.

Carlson, J.M. et al. "Widespread impact of HLA restriction on immune control and escape pathways of HIV-1" *Journal of virology*, 2012, 86(9):5230-5243.

Cebere, I. et al. "Phase I clinical trial safety of DNA- and modified virus Ankara-vectored human immunodeficiency virus type 1 (HIV-1) vaccines administered alone and in a prime-boost regime to healthy HIV-1-uninfected volunteers" *Vaccine*, 2006, 24:417-425.

Coleman, J.K. et al. "HIV-1 p24 vaccine protects cats against feline immunodeficiency virus infection" *AIDS*, 2005, 19:1457-1466.

Coleman, J.K. et al. "Feline immunodeficiency virus (FIV) vaccine efficacy and FIV neutralizing antibodies" *Vaccine*, 2014, 32:746-754.

Corey, L. and McElrath, M.J. "HIV vaccines: mosaic approach to virus diversity" *Nat. Med.* 2010, 16(3):268-270.

De Groot, A.S. et al. "Identification of immunogenic HLA-B7 "Achilles' heel" epitopes within highly conserved regions of HIV" *Vaccine*, 2008, 26:3059-3071.

De Souza, M.S. et al. "The Thai phase III trial (RV144) vaccine regimen induces T cell responses that preferentially target epitopes within the V2 region of HIV-1 envelope" *J Immunol.*, 2012, 188:5166-5176.

Flynn, N.M. et al. / The rgp120 HIV Vaccine Study Group "Placebo-controlled phase 3 trial of a recombinant glycoprotein 120 vaccine to prevent HIV-1 infection" *J. Infect. Dis.*, 2005, 191:654-665.

Gartland, A.J. et al. "Analysis of HLA A*02 Association with Vaccine Efficacy in the RV144 HIV-1 Vaccine Trial" *Journal of virology*, 2014, 88(15):8242-8255.

Gonzalez-Galarza, F.F. et al. "Allele frequency net: a database and online repository for immune gene frequencies in worldwide populations" *Nucleic Acids Res.*, 2011, 39:D913-D919.

Goonetilleke, N. et al. "Induction of multifunctional human immunodeficiency virus type 1 (HIV-1)-specific T cells capable of proliferation in healthy subjects by using a prime-boost regimen of DNA- and modified vaccinia virus Ankara-vectored vaccines expressing HIV-1 Gag coupled to CD8+T-cell epitopes" *J Virol*, 2006, 80(10):4717-4728.

Gorse, G.J. et al. "Safety and immunogenicity of cytotoxic T-lymphocyte poly-epitope, DNA plasmid (EP HIV-1090) vaccine in healthy, human immunodeficiency virus type 1 (HIV-1)-uninfected adults" *Vaccine*, 2008, 26:215-223.

Goulder, P.J. and Watkins, D.I. "Impact of MHC class I diversity on immune control of immunodeficiency virus replication" *Nat. Rev. Immunol.*, 2008, 8:619-630.

Hanke, T. et al. "Clinical experience with plasmid DNA- and modified vaccinia virus Ankara-vectored human immunodeficiency virus type 1 clade A vaccine focusing on T-cell induction" *J. Gen. Virol.*, 2007, 88:1-12.

He, Y. et al. "Emerging Vaccine Informatics" *J Biomed Biotechnol*, 2010, vol. 2010, Article ID 218590, 26 pages.

Hosie, M. and Jarrett, O. "Serological responses of cats to feline immunodeficiency virus" *AIDS*, 1990, 4:215-220.

Ipp, H. and Zemlin, A. "The paradox of the immune response in HIV infection: When inflammation becomes harmful" *Clin Chim Acta*, 2013, 416:96-99.

Jaoko, W. et al. "Safety and immunogenicity of recombinant low-dosage HIV-1 A vaccine candidates vectored by plasmid pTHr DNA or modified vaccinia virus Ankara (MVA) in humans in East Africa" *Vaccine*, 2008, 26:2788-2795.

Jenner, E. "An inquiry into the causes and effects of the Variolae Vaccinae, a disease discovered in some of the western counties of England, particularly Gloucestershire, and known by the name of the cow-pox" London: Sampson Low, 1798.

Johnson, R.P. et al. "HIV-1 gag-specific cytotoxic T lymphocytes recognize multiple highly conserved epitopes. Fine specificity of the gag-specific response defined by using unstimulated peripheral blood mononuclear cells and cloned effector cells" *J Immunol*, 1991, 147(5):1512-1521.

Kakinuma, S. et al. "Nucleotide Sequence of Feline Immunodeficiency Virus: Classification of Japanese Isolates into Two Subtypes Which Are Distinct from Non-Japanese Subtypes" *J. Virol.*, 1995, 69(6):3639-3646.

Kiepiela, P. et al. "CD8+T-cell responses to different HIV proteins have discordant associations with viral load" *Nature Med*, 2007, 13(1):46-53.

Koff, W.C. "HIV vaccine development: Challenges and opportunities towards solving the HIV vaccine-neutralizing antibody problem" *Vaccine*, 2012, 30:4310-4315.

Korber, B.T. et al. "T-cell vaccine strategies for human immunodeficiency virus, the virus with a thousand faces" *J Virol*, 2009, 83(17):8300-8314.

Lane, H.C. "Pathogenesis of HIV infection: Total CD4+T-cell pool, immune activation, and inflammation" *Top HIV Med*, 2010, 18(1):2-6.

Larsen, M.V. et al. "Large-scale validation of methods for cytotoxic T-lymphocyte epitope prediction" *BMC Bioinform*, 2007, 8:424 (12 pages).

Leslie, A.J. et al. "HIV evolution: CTL escape mutation and reversion after transmission" *Nat. Med.*, 2004, 10(3):282-289.

F. et al. "Mapping HIV-1 vaccine induced T-cell responses: Bias towards less-conserved regions and potential impact on vaccine efficacy in the Step study" *PloS One*, 2011, 6(6):e20479 (9 pages).

Li, F. et al. "HIV-1 CTL-based vaccine immunogen selection: Antigen diversity and cellular response features" *Curr HIV Res*, 2007, 5(1):97-107.

Lichterfeld, M. et al. "Loss of HIV-1-specific CD8+ T cell proliferation after acute HIV-1 infection and restoration by vaccine-induced HIV-1-specific CD4+ T cells" *J. Exp. Med.*, 2004, 200(6):701-712.

Llano, A. et al. "How to optimally define optimal cytotoxic T lymphocyte epitopes in HIV infection?" in HIV Molecular Immunology, Yusim, K. et al. (eds.), Los Alamos National Laboratory, Los Alamos, NM, 2009, pp. 3-24.

Louwagie, J. et al. "Phylogenetic analysis of gag genes from 70 international HIV-1 isolates provides evidence for multiple genotypes" *AIDS*, 1993, 7:769-780.

Lundegaard, et al. "NetMHC-3.0: Accurate web accessible predictions of Human, Mouse, and Monkey MHC class I affinities for peptides of length 8-11" *Nucleic Acids Res.*, 2008, 36:W509-W512.

MacDonald, K.S. et al. "Human leucocyte antigen supertypes and immune susceptibility to HIV-1, implications for vaccine design" *Immunology Letters*, 2001, 79:151-157.

McDermott, A.B. and Koup, R.A. "CD8+ T cells in preventing HIV infection and disease" *AIDS*, 2012, 26:1281-1292.

McKinnon, L.R. et al. "HIV-specific CD8+ T-cell proliferation is prospectively associated with delayed disease progression" *Immunol. Cell Biol.*, 2012, 90:346-351.

Mothe, B. et al. "Definition of the viral targets of protective HIV-1-specific T cell responses" *J. Transl. Med.*, 2011, 9:208, 20 pages.

Mwau, M. et al. "A human immunodeficiency virus 1 (HIV-1) Clade A vaccine in clinical trials: stimulation of HIV-specific T-cell responses by DNA and recombinant modified vaccinia virus Ankara (MVA) vaccines in humans" *J Gen Virol*, 2004, 85:911-919.

(56) References Cited

OTHER PUBLICATIONS

Ogg, G.S. and McMichael, A.J. "Quantitation of HIV-1-specific cytotoxic T lymphocytes and plasma load of viral RNA" *Science*, 1998, 279.5359, pp. 2103-2106.

Olmsted, R.A. et al. "Molecular cloning of feline immunodeficiency virus" *Proc. Nat. Acad. Sci. USA*, 1989, 86:2448-2452.

Olmsted, R.A. et al. "Nucleotide sequence analysis of feline immunodeficiency virus: Genome organization and relationship to other lentivirus" *Proc. Natl. Acad. Sci. USA*, 1989, 86:8088-8092.

Pattacini, L. et al. "A novel HIV vaccine adjuvanted by IC31 induces robust and persistent humoral and cellular immunity" *PloS One*, 2012, 7(7):e42163, 11 pages.

Pedersen, N.C. et al. "Isolation of a T-lymphotropic virus from domestic cats with an immunodeficiency-like syndrome" *Science*, 1987, 235:790+.

Pitisuttithum, P. et al. "Randomized, double-blind, placebo-controlled efficacy trial of a bivalent recombinant glycoprotein 120 HIV-1 vaccine among injection drug users in Bangkok, Thailand" *J. Infect. Dis.*, 2006, 194(12):1661-1671.

Plotkin, S.A. "Correlates of vaccine-induced immunity" *Vaccines: Clin. Infect. Dis.*, 2008, 47:401-409.

Posnett, D.N. et al. "A Novel Method for Producing Anti-peptide Antibodies" *J. Biol. Chem.*, 1988, 263(4):1719-1725.

Rerks-Ngarm, S. et al. "Vaccination with ALVAC and AIDSVAX to prevent HIV-1 infection in Thailand" *N. Engl. J. Med.*, 2009, 361(23):2209-2220.

Richmond, M. et al. "Epitope mapping of HIV-specific CD8+ T cell responses by multiple immunological readouts reveals distinct specificities defined by function" *J Virol.*, 2011, 85(3):1275-1286.

Rigby, M.A. et al. "Evolution of structural proteins of feline immunodeficiency virus: molecular epidemiology and evidence of selection for change" *J. Gen. Virol.*, 1993, 74:425-436.

Roff, S.R. et al. "The Significance of Interferon-gamma in HIV-1 Pathogenesis, Therapy, and Prophylaxis" *Frontiers in Immunology*, 2014, vol. 4, Article 498, 11 pages.

Roff, S. et al. "Conserved epitopes on HIV-1, FIV and SIV p24 proteins are recognized by HIV-1 infected subjects" *Human Vaccines & Immunotherapeutics*, 2015, 11(6):1540-1556.

Rolland, M. et al. "HIV-1 Group M Conserved Elements Vaccine" *PLoS Pathog.*, 2007, 3(11):e157, pp. 1551-1555.

Rowland-Jones, S. et al. "Cytotoxic T cell responses to multiple conserved HIV epitopes in HIV-resistant prostitutes in Nairobi" *J Clin Invest*, 1998, 102(9):1758-1765.

Rowland-Jones, S. et al. "HIV-specific cytotoxic T-cells in HIV-exposed but uninfected Gambian women" *Nat. Med.*, 1995, 1(1):59-64.

Salmon-Céron, D. et al. "Immunogenicity and safety of an HIV-1 lipopeptide vaccine in healthy adults: a phase 2 placebo-controlled ANRS trial" *AIDS*, 2010, 24:2211-2223.

Sanou, M.P. et al. "HIV-1 Vaccine Trials: Evolving Concepts and Designs" *The Open AIDS Journal*, 2012, 6:274-288.

Sanou, M.P. et al. "Evolutionarily conserved epitopes on human immunodeficiency virus type 1 (HIV-1) and feline immunodeficiency virus reverse transcriptases detected by HIV-1-infected subjects" *Journal of Virology*, 2013, 87(17):10004-10015.

Santra, S. et al. "Mosaic vaccines elicit CD8$^+$T lymphocyte responses that confer enhanced immune coverage of diverse HIV strains in monkeys" *Nat Med*, 2010, 16(3):324-328.

Santra, S. et al. "Breadth of cellular and humoral immune responses elicited in rhesus monkeys by multi-valent mosaic and consensus immunogens" *Virology*, 2012, 428:121-127.

Saunders, K.O. et al. "The design and evaluation of HIV-1 vaccines" *AIDS*, 2012, 26:1293-1302.

Smith, SM. "HIV CTL escape: at what cost?" *Retrovirology*, 2004, 1:8 (5 pages).

Sodora, D.L. et al. "Identification of three feline immunodeficiency virus (FIV) env gene subtype and comparison of the FIV and human immunodeficiency virus type 1 evolutionary patterns" *J. Virol.*, 1994, 68(4):2230-2238.

Soghoian, D.Z. et al. "HIV-specific cytolytic CD4 T cell responses during acute HIV infection predict disease outcome" *Sci. Transl. Med.*, 2012, 4:123ra25, 10 pages.

Spearman, P. et al. "Safety and immunogenicity of a CTL multiepitope peptide vaccine for HIV with or without GM-CSF in a phase I trial" *Vaccine*, 2009, 27:243-249.

Spina, C.A. et al. "Preferential replication of HIV-1 in the CD45RO memory cell subset of primary CD4 lymphocytes in vitro" *The Journal of Clinical Investigation*, 1997, 99(7):1774-1785.

Stamatatos, L. "HIV vaccine design: the neutralizing antibody conundrum" *Curr. Opin. Immunol.*, 2012, 24:316-323.

Stevenson, M. et al. "HIV-1 replication is controlled at the level of T cell activation and proviral integration" *The EMBO Journal*, 1990, 9(5):1551-1560.

Stranzl, T. et al. "NetCTLpan: pan-specific MHC class I pathway epitope predictions" *Immunogenetics*, 2010, 62:357-368.

Talbott, R.L. et al. "Nucleotide sequence and genomic organization of feline immunodeficiency virus" *Proc. Natl. Acad. Sci. USA*, 1989, 86:5743-5747.

Troyer, R.M. et al. "Variable fitness impact of HIV-1 escape mutations to cytotoxic T lymphocyte (CTL) response" *PLoS Pathog.*, 2009, 5(4):e1000365, 13 pages.

Walker, B.D. et al. "HIV-1 reverse transcriptase is a target for cytotoxic T lymphocytes in infected individuals" *Science*, 1988, 240:64-66.

Walther-Jallow, L. et al. "Cross-protection against mucosal simian immunodeficiency virus (SIVsm) challenge in human immunodeficiency virus type 2-vaccinated cynomolgus monkeys" *J. Gen. Virol.*, 2001, 82:1601-1612.

Wang, Y.E. et al. "Protective HLA class I alleles that restrict acute-phase CD8$^+$T-cell responses are associated with viral escape mutations located in highly conserved regions of human immunodeficiency virus type 1" *J Virol*, 2009, 83(4):1845-1855.

Yamamoto, J.K. et al. "Human alpha- and beta-interferon but not gamma-suppress the in vitro replication of LAV, HTLV-III, and ARV-2" *Journal of Interferon Research*, 1986, 6:143-152.

Yamamoto, J. et al. "Feline immunodeficiency syndrome—A comparison between feline T-lymphotropic lentivirus and feline leukemia virus" *Leukemia*, 1988, 2(12 Supp):204S-215S.

Yamamoto, J. et al. "Pathogenesis of experimentally induced feline immunodeficiency virus infection in cats" *Amer. J. Vet. Res.*, 1988, 49(8):1246-1258.

Yamamoto, J. et al. "Development of the dual-subtype feline immunodeficiency virus vaccine" *AIDScience*, 2002, vol. 2, No. 8, 7 pages.

Yamamoto, J. et al. "Feline immunodeficiency virus pathogenesis and development of a dual-subtype feline-immunodeficiency-virus vaccine" *AIDS*, 2007, 21:547-563.

Yamamoto, J. et al. "Feline Immunodeficiency Virus Model for Designing HIV/AIDS Vaccines" *Current HIV Res.*, 2010, 8:14-25.

Yusim, K. et al. "Clustering patterns of cytotoxic T-lymphocyte epitopes in human immunodeficiency virus type 1 (HIV-1) proteins reveal imprints of immune evasion on HIV-1 global variation" *J Virol*, 2002, 76(17):8757-8768.

Zhang, X. et al. "HLA-B*44 is associated with a lower viral set point and slow CD4 decline in a cohort of Chinese homosexual men acutely infected with HIV-1" *Clinical and vaccine immunology*, 2013, 20(7):1048-1054.

Dunham, S. P. "The application of nucleic acid vaccines in veterinary medicine" *Research in Veterinary Science*, 2002, 73:9-16.

Matsuo, K. et al. "Highly conserved epitope domain in major core protein p24 is structurally similar among human, simian and feline immunodeficiency viruses" *Journal of General Virology*, 1992, 73:2445-2450.

FIG. 3A

| FIV RT POOL | FRT1 | FRT2 | FRT3 | FRT4 | FRT5 | FRT6 | FRT7 | FRT8 | FRT9 | FRT10 | FRT11 |
|---|---|---|---|---|---|---|---|---|---|---|---|
| CD4+ T Prolif | 2 (8%) | 5 (21%) | 12 (12%) | 3 (4%) | 9 (4%) | 8 (4%) | 12 (4%) | 6 (8%) | 9 (12%) | 4 (12%) | 6 (12%) |
| CD8+ T Prolif | 4 (12%) | 4 (21%) | 21 (37%) | 2 (4%) | 3 (8%) | 10 (21%) | 30 (33%) | 6 (21%) | 20 (21%) | 8 (12%) | 5 (29%) |
| PBMC IFNγ | 10 (21%) | 75 (7%) | 500 (61%) | 74 (14%) | 204 (21%) | 132 (21%) | 181 (18%) | 117 (21%) | 80 (4%) | 110 (21%) | 86 (18%) |

| HIV RT POOL | HRT1 | HRT2 | HRT3 | HRT4 | HRT5 | HRT6 | HRT7 | HRT8 | HRT9 | HRT10 | HRT11 |
|---|---|---|---|---|---|---|---|---|---|---|---|
| CD4+ T Prolif | 16 (12%) | 8 (4%) | 13 (8%) | 6 (8%) | 4 (8%) | 10 (4%) | 52 (8%) | 10 (8%) | 25 (8%) | 8 (4%) | 16 (8%) |
| CD8+ T Prolif | 9 (8%) | 8 (4%) | 5 (12%) | 4 (4%) | 4 (12%) | 3 (12%) | 9 (12%) | 15 (12%) | 7 (17%) | 3 (4%) | 20 (17%) |
| PBMC IFNγ | 264 (21%) | 108 (29%) | 135 (14%) | 148 (25%) | 184 (39%) | 412 (39%) | 322 (46%) | 127 (21%) | 236 (32%) | 195 (36%) | 880 (57%) |

FIG. 3B

| FIV RT POOL | FRT12 | FRT13 | FRT14 | FRT15 | FRT16 | FRT17 | FRT18 | FRT19 | FRT20 | FRT21 | PHA |
|---|---|---|---|---|---|---|---|---|---|---|---|
| CD4+ T Prolif | 4 (8%) | 8 (12%) | 8 (8%) | 15 (16%) | 9 (8%) | 9 (8%) | 13 (4%) | 0 (0%) | 11 (8%) | 9 (12%) | 48 (79%) |
| CD8+ T Prolif | 3 (8%) | 8 (17%) | 5 (37%) | 13 (33%) | 4 (17%) | 15 (12%) | 7 (8%) | 11 (21%) | 9 (12%) | 8 (33%) | 42 (75%) |
| PBMC IFNγ | 115 (11%) | 114 (36%) | 116 (18%) | 140 (11%) | 85 (18%) | 88 (11%) | 160 (11%) | 90 (7%) | 81 (25%) | 70 (18%) | 3968 (100%) |

| HIV RT POOL | HRT12 | HRT13 | HRT14 | HRT15 | HRT16 | HRT17 | HRT18 | HRT19 | HRT20 | HRT21 | PHA |
|---|---|---|---|---|---|---|---|---|---|---|---|
| CD4+ T Prolif | 12 (4%) | 26 (12%) | 5 (8%) | 4 (4%) | 2 (4%) | 0 (0%) | 8 (8%) | 12 (4%) | 2 (4%) | 10 (4%) | 48 (79%) |
| CD8+ T Prolif | 6 (12%) | 28 (12%) | 5 (17%) | 5 (12%) | 0 (0%) | 6 (17%) | 5 (12%) | 10 (21%) | 9 (0%) | 4 (17%) | 40 (79%) |
| PBMC IFNγ | 381 (29%) | 275 (29%) | 230 (39%) | 148 (25%) | 146 (25%) | 95 (18%) | 88 (11%) | 85 (4%) | 149 (14%) | 95 (18%) | 3968 (100%) |

| FIV p24 POOL | Fp1 | Fp2 | Fp3 | Fp4 | Fp5 | Fp6 | Fp7 | Fp8 | Fp9 | Fp10 |
|---|---|---|---|---|---|---|---|---|---|---|
| CD4+ T Prolif | 0 (0%) | 0 (0%) | 3 (4%) | 0 (0%) | 26 (4%) | 5 (4%) | 0 (0%) | 3 (4%) | 7 (4%) | 4 (8%) |
| CD8+ T Prolif | 20 (12%) | 4 (4%) | 20 (4%) | 0 (0%) | 0 (0%) | 3 (17%) | 10 (4%) | 4 (8%) | 29 (21%) | 41 (8%) |
| PBMC IFNγ | 180 (6%) | 70 (3%) | 97 (10%) | 156 (13%) | 121 (6%) | 112 (13%) | 93 (16%) | 73 (10%) | 72 (13%) | 144 (13%) |
| HIV p24 POOL | Hp1 | Hp2 | Hp3 | Hp4 | Hp5 | Hp6 | Hp7 | Hp8 | Hp9 | Hp10 |
| CD4+ T Prolif | 7 (4%) | 5 (8%) | 5 (8%) | 5 (4%) | 11 (4%) | 2 (4%) | 0 (0%) | 29 (12%) | 3 (4%) | 5 (12%) |
| CD8+ T Prolif | 20 (21%) | 6 (8%) | 0 (0%) | 0 (0%) | 19 (4%) | 2 (12%) | 5 (8%) | 3 (8%) | 22 (12%) | 6 (12%) |
| PBMC IFNγ | 262 (29%) | 213 (42%) | 534 (61%) | 212 (29%) | 252 (23%) | 526 (32%) | 721 (39%) | 512 (26%) | 272 (29%) | 215 (48%) |

FIG. 4A

| FIV p24 POOL | Fp11 | Fp12 | Fp13 | Fp14 | Fp15 | Fp16 | Fp17 | | ConA |
|---|---|---|---|---|---|---|---|---|---|
| CD4+ T Prolif | 3 (12%) | 0 (0%) | 0 (0%) | 7 (4%) | 0 (0%) | 0 (0%) | 8 (4%) | | 45 (79%) |
| CD8+ T Prolif | 4 (8%) | 3 (4%) | 0 (0%) | 23 (8%) | 53 (4%) | 0 (0%) | 0 (0%) | | 44 (79%) |
| PBMC IFNγ | 126 (16%) | 215 (6%) | 107 (16%) | 302 (26%) | 145 (10%) | 85 (3%) | 160 (10%) | | 5031 (100%) |
| HIV p24 POOL | Hp11 | Hp12 | Hp13 | Hp14 | Hp15 | Hp16 | Hp17 | Hp18 | PHA |
| CD4+ T Prolif | 0 (0%) | 4 (4%) | 0 (0%) | 0 (0%) | 0 (0%) | 5 (4%) | 48 (4%) | 0 (0%) | 45 (79%) |
| CD8+ T Prolif | 32 (12%) | 7 (17%) | 0 (0%) | 4 (4%) | 15 (12%) | 5 (12%) | 0 (0%) | 4 (4%) | 44 (79%) |
| PBMC IFNγ | 470 (39%) | 293 (39%) | 120 (10%) | 324 (39%) | 218 (32%) | 211 (19%) | 176 (26%) | 109 (16%) | 5031 (100%) |

47.7% identity and 70.8% homology

HRT3 vs. FRT3
(red line region)
69% Identity
77% Homology

HRT6 vs. FRT6
(red line section)
52% Identity
63% Homology

```
              10         20         30         40         50
HIV-1   P-ISP-IETVPVKLKPGMDGPKVKQWPLTEEKIKALVEICTEMEKEGKISKIGPENPYNT
        ::  :: ::::::::: ::::::::::::::::::::::::::::::::::::::::
FIV     AQISEKIPIVKVRMKDPTQGPQVKQWPLSNEKIEALTDIVERLELEGKVKRADPNNPWNT
              10         20         30         40         50         60

70         80         90        100        110
HIV-1   PVFAIKKKDSTKWRKLVDFRELNKRTQDFWEVQLGIPHPAGLKKKKSVTVLDVGDAYFSV
        ::::::::: ::::::::::::: :::::::::::::::::::::::::: ::::::
FIV     PVFAIKKK-SGKWRMLIDFRVLNKLTDKGAEVQLGLPHPAGLMRKQVTVLDIGDAYFTI
              70         80         90        100        110

130        140        150        160        170
HIV-1   PLDEDFRKYTAFTIPSINNETPGIRYQYNVLPQGWKGSPAIFQSSMTKILEPFRKQNPDI
        ::::::::::::::  ::  ::::::::::::::  :: ::::::::: ::::::::
FIV     PLDPDYAPYTAFTLPRKNNAGPGRRYVWCSLPQGWVLSPLIYQSTLDNILQPFIRQNPEL
             130        140        150        160        170

190        200        210        220        230
HIV-1   VIYQYMDDLYVGSDLEIGQHRTKIEELRQHLLRWGLTTPDKKHQKEPPFLWMGYELHPDK
        :::::::: :::::::: ::  ::::  :::::::::::: ::::::::::::::::
FIV     DIYQYMDDIYIGSDLNKKEHKQKVEELRKLLLWWGFETPEDKLQEEPPYKWMGYELHPLT
             190        200        210        220        230
```

FIG. 5 (continued)

```
              240        250        260        270        280        290
HIV-1    WTVQP--IVLPEKDSWTVNDIQKLVGKLNWASQIYPGIKVRQLCKLLRGTKALTEVIPLT         HRT11 vs. FRT11
         ::::     :  : ::::::  :::::::::::::::    ::  : :::: :  :           (red line section)
FIV      WSIQQKQLEIPERP---TLNELQKLVGKINWASQTIPDLSIKELTTMMRGDQRLDSIREWT       57% Identity
              240        250        260        270        280        290    87% Homology 300        310        320        330        340        350
HIV-1    EEAELELAENREILKEPVHGVYYDPSKDLIAEIQKQGQGQWTYQIYQE-PFKNLKTGKYA         HRT13 vs. FRT13
         :  ::: ::  : ::  : :::::: ::::::: ::  :  :: ::  :                   (red line section)
FIV      TEAKKEVQKAKEAIETQAQLKYYDPSRELYAKLSLVGPHQICYQVYHKNPEHVLWYGKMN         32% Identity
              300        310        320        330        340        350    72% Homology 360        370        380        390        400        410
HIV-1    RTRGAHTNDVKQLTEAVQKITTESIVIWGKTPKFKLPIQKETWETWW---TEYWQATWIPE
         :  :   ::: :::  ::  :::  : : ::  : :::: ::  :::    : :: :::
FIV      RQKKKAENTCDIALRACYKIREESIIRIGKEPIYEIPASREAWESNLIRSPYLKAP-PPE
              360        370        380        390        400        410

420        430        440
HIV-1    WEFVNTPPLVKLWYQLEKE-PIVGAETFY         (SEQ ID NO:45)
         ::  :  :::  :  :::  ::::::::
FIV      VEFIHAALNIKRALSMIQDTPILGAETWY         (SEQ ID NO:46)
              420        430        440
```

GENESTREAM network server (http://xylian.igh.cnrs.fr/bin/align-guess.cgi). Pearson, W.R., Wood, T., Zhang, Z., and Miller, W. (1997). Comparison of DNA sequences with protein sequences. Genomics 46:24-36.
Red word sequence = epitope region on both HIV-1 & FIV recognized by HIV+ subjects except for HRT3 where only FIV region rec

FIG. 6

HIV-1 and SIV RT sequences: 59.6% identity and 81.9% homology

```
                  10         20         30         40         50         60
HIV-1    PISPIETVPVKLKPGMDGPKVKQWPLTEEKIKALVEICTEMEKEGKISKIGPENPYNTPV
         :::::::: ::::::::::::::::::::::::::::::::::::::::::::::::::
SIV      PIAKVEPVKVTLKPGKVGPKLKQWPLSKEKIVALREICEKMEKDGQLEEAPPTNPYNTPT              HRT3 vs. SRT3
                  10         20         30         40         50         60             77% Identity
                                                                                         91% Homology
                  70         80         90        100        110        120
HIV-1    FAIKKKDSTKWRKLVDFRELNKRTQDFWEVQLGIPHPAGLKKKKSVTVLDVGDAYFSVPL
         ::::::::::::::::::::::::::::::::::::::::::::::::::::::::::::
SIV      FAIKKKDKNKWRMLIDFRELNRVTQDFTEVQLGIPHPAGLAKRKRITVLDIGDAYFSIPL
                  70         80         90        100        110        120
              R397,R395;  R416;   R422 (FIV NPWNTPVFAIKKK peptide)

130        140        150        160        170        180
HIV-1    DEDFRKYTAFTIPSINNETPGIRYQYNVLPQGWKGSPAIFQSSMTKILEPFRKQNPDIVI
         ::::::::::::::::::::::::::::::::::::::::::::::::::::::::::::             HRT6 vs. SRT6
SIV      DEEFRQYTAFTLPSVNNAEPGKRYIYKVLPQGWKGSPAIFQYTMRHVLEPFRKANPDVTL            71% Identity
         MamuA02           130        140        150    160 MamuA01 170    180   84% Homology 190        200        210        220        230        240
HIV-1    YQYMDDLYVGSDLEIGQHRTKIEELRQHLLRWGLTTPDKKHQKEPPFLWMGYELHPDKWT
         ::::::::::::::::::::::::::::::::::::::::::::::::::::::::::::
SIV      VQYMDDILIASDRTDLEHDRVVLQLKELLNSIGFSTPEEKFQKDPPFQWMGYELWPTKWK
                 190        200        210        220        230        240
```

FIG. 6 (continued)

```
                 250        260        270        280        290        300       HRT11 vs. SRT11
HIV-1  VQPIVLPEKDSWTVNDIQKLVGKLNWASQIYPGIKVRQLCKLLRGTKALTEVIPLTEEEAE              71% Identity
       :: :::::::::::::::::::::::::::: ::::::::::::::::::::::                    91% Homology
SIV    LQKIELPQRETWTVNDIQKLVGVLNWAAAQIYPGIKTKHLCRLIRGKMTLTEEVQWTEMAE
                 250        260    R414 270        280        290        300

310        320        330        340        350        360       HRT13 vs. SRT13
HIV-1  LELAENREIIKEPVHGVYYDPSKDLIAEIQKQGQGQWTYQIYQEPFKNLKTGKYARTRGA                36% Identity
       :  ::::::::::::::::::::::::::::::::::::::::::::::::::::::::                72% Homology
SIV    AEYEENKIILSQEQEGCYYQEGKPLEATVIKSQDNQWSYKIHQED-KILKVGKFAKIKNT
       MamuA11  310  MamuA02  320        330        340        350

370        380        390        400        410        420
HIV-1  HTNDVKQLTEAVQKITTESIVIWGKTPKFKLPIQKETWETWTEYWQATWIPEWEFVNTP
       :::::::::::::::::::::::::::::::::::::::::::::::::::::::::::
SIV    HTNGVRLLAHVIQKIGKEAIVIWGQVPKFHLPVERDVWEQWWTDYWQVTWIPEWDFISTP
         360       370   MamuA01   380         390        400        410    MamuA01

430        440
HIV-1  PLVRLWYQLEKEPIVGAETFY       (SEQ ID NO:45)
       :: :: :: ::: :::
SIV    PLVRLVFNLVKDPIEGEET-Y       (SEQ ID NO:47)
                 420        430
```

Red word sequence = epitope region on both HIV-1 & FIV recognized by HIV+ subjects
except for HRT3 where only FIV region recognized.
Blue word sequence = counterpart epitope region on SIV
Underlined HIV sequence = HRT14; Over-lined HIV sequence = HRT15
Highlights: Grey on HIV-1 sequence = HRT11 sequence = Macaque reactive site on FIV
Grey on SIV sequence = Macaque reactive site on FIV
Yellow & Magenta on SIV sequence = Macaque CD8⁺ CTL epitope with reactive Mamu allele (L

FIG. 7

FIV-Pet p24 223 aa vs.
SIV-Delta B670 p24 228 aa
scoring matrix: , gap penalties: -12/-2
29.0% identity (full sequences); Global alignment score: 337

```
              10        20        30        40        50        60
FIV  PIQTVNGVPQYVALDPKMVSIFMEKAREGLGGEEVQLWFTAFSANLTPTDMATLIMAAPG
     ::  :::  :   ::    :        :        : :: :::          :
SIV  PVQQIGGNYVHLPLSPRTLDAWVKLIEEKKFGAEVVPGFQALSEGCTPYDINQMLNCVGD
              10        20        30        40        50        60
                                                          Hp10/Fp9

70        80        90       100       110
FIV  CAADKEILDESLKQLTAEYDRTHPPDAPRP--LPYFTAAEIMGIGLTQEQQAEARF----
     : :  :     :    ::        :     :: :  :      : : :
SIV  HQAAMQIIRDIINEEAADWDLQHPQPAPQQGQLREPSGSDIAGTTSSVDEQIQWMYRQQN
              70        80        90       100       110       120

120       130       140       150       160       170
FIV  -APARMQCRAWYLEALGKLAAIKAKSPRAV-QLRQGAKEDYSSFIDRLFAQIDQEQNTAE
      : :  :   :  :  :     :: :    ::   :::    :::  ::  :
SIV  PIPVGNIYRRWI--QLGLQRCVRMYNPTNILDVKQGPKEPFQSYVDRFYKSLRAEQTDAA
             130       140       150       160       170

Hp15 vs. Fp14
                                                      45.5% Identity
                                                      63.6% Homology
             180       190       200       210       220
FIV  VKLYLKQSLSIANANADCKKAMSHLKPESTLEEKLRACQEIGSPGYKMQLL   (SEQ ID NO:48)
     ::  : :: ::::: ::::    :::  ::: ::  :: :: :: ::: :
SIV  VKNWMTQTLLIQNANPDCKLVLKGLGVNPTLEEMLTACQGVEGPGQKARL-   (SEQ ID NO:49)
             180       190       200       210       220
```

FIG. 7 (continued)

```
HIV-1 HXB2 p24                231 aa vs.
FIV-Pet p24                   223 aa
scoring matrix: , gap penalties: -12/-2
31.8% identity (full sequences);   Global alignment score: 408

10         20         30         40         50         60
HIV-1   PIVQNIQGQMVHQAISPRTLNAWVKVVEEKAFSPEVIPMFSALSEGATPQDINTMLNTVG
        ::  :::::::                  ::      :  ::   :::  ::: :
FIV     PI-QTVNGVPQYVALDPKMVSIFMEKAREGLGGEEVQLWFTAFSANLTPTDMATLIMAAP
                  10         20         30         40         50

70         80         90        100        110        120
HIV-1   GHQAAMQMLKETINEEAAEWDRVHPVHAGPIAPGQMREPRGSDIAGTTSTLQEQIGWMTN
        ::  ::::: :::                   :::                             Hp10/Fp9
FIV     GCAADKEILDESLKQLTAEYDRTHP----PDAPRPLPYFTAAEIMGIGLT-QEQ---QAE
              60         70         80         90        100        110

130        140        150        160        170
HIV-1   NPPIPVGEIYKRWIILGLNKI---VRMYSPTSILDIRQGPKEPFRDYVDRFYKTLRAEQAS
        :   ::  :::::                :  ::
FIV     ARFAPARMQCRAWYLEALGKLAAIKAKSPRAV-QLRQGAKEDYSSFIDRLFAQIDQEQNT
                 120        130        140        150        160        170

180        190        200        210        220        230
HIV-1   QEVKNWMTETLLVQNANPDCKTILKALGPAATLEEMMTACQGVGGPGHKARVL       (SEQ ID NO:50)     Hp15 vs. Fp14
        :::::                              :::::                                      36.4% Identity
FIV     AEVKLYLKQSLSIANANADCKKAMSHLKPESTLEEKLRACQEIGSPGYKMQLL       (SEQ ID NO:48)    63.6% Homology
                 180        190        200        210        220

Fp9 = FIV epitope region recognized by HIV+ subjects
Hp15/Fp14 = epitope region on both HIV-1 & FIV recognized by HIV+ subjects
Hp15 = HIV epitope region recognized by SIV+ macaques
```

FIG. 7 (continued)

HIV1-HXB2 p24  231 aa vs.
SIV-Delta B670 p24  228 aa
66.4% identity full sequences; gap penalties: -12/-2, Global alignment score: 1036

```
                      10         20         30         40         50         60
HIV-1   PIVQNIQGQMVHQAISPRTLNAWVKVVEEKAFSPEVIPMFSALSEGATPQDLNTMLNTVG
        : :::::: :::::::::::::  :::::::::::::::::::   : ::: ::::::
SIV     P-VQQIGGNYVHLPLSPRTLDAWVKLIEEKKFGAEVVPGFQALSEGCTPYDINQMLNCVG
                      10         20         30         40         50

70         80         90        100        110
HIV-1   GHQAAMQMLKETINEEAAEWDRVHPVHAGPIAPGQMREPRGSDIAGTTSTLQEQIGWM-T
        .:::::::::::::::::::::::  ::::::::: ::: :::::::::::::::: :
SIV     DHQAAMQIIRDIINEEAADWDLQHP-QPAP-QQGQLREPSGSDIAGTTSSVDEQIQWMYR
                      70         80         90        100        110

120        130        140        150        160        170
HIV-1   NNPPIPVGEIYKRWIILGLNKIVRMYSPTSILDIRQGPKEPFRDYVDRFYKTLRAEQASQ
        :::::::: :: ::::  ::: ::::::::::::: :::::::::::::::::::: ::
SIV     QQNPIPVGNIYRRWIQLGLQRCVRMYNPTNILDVKQGPKEPFQSYVDRFYKSLRAEQTDA
                     120        130        140        150        160        170

180        190        200        210        220        230
HIV-1   EVKNWMTETLLVQNANPDCKTILKALGPAATLEEMMTACQGVGGPGHKARVL    (SEQ ID NO:50)
        .::::::: :::::::::::: ::: ::    ::::::::::::::::  :
SIV     AVKNWMTQTLLIQNANPDCKLVLKGLGVNPTLEEMLTACQGVEGPGQKAR-L    (SEQ ID NO:49)
                     180        190        200        210        220
```

Hp10/Sp10

Hp15 vs. Fp14
72.7% Identity
90.9% Homology

Key for p24:
Yellow on SIV sequence = recognized macaque CD8+ CTL epitope (LANL)
Green = Counterpart HIV-1 sequence of known macaque CTL epitope
Aqua Blue = Counterpart FIV sequence of known macaque CTL epitope

FIG. 10

| HIV/RT POOL | FRT1 | FRT2 | FRT3 | FRT4 | FRT5 | FRT6 | FRT7 | FRT8 | FRT9 | FRT10 | FRT11 |
|---|---|---|---|---|---|---|---|---|---|---|---|
| CD4 T Prolif. | 2 (8%) | 5 (21%) | 12 (12%) | 3 (4%) | 9 (4%) | 8 (4%) | 12 (4%) | 6 (8%) | 9 (12%) | 4 (12%) | 6 (12%) |
| CD8 T Prolif. | 4 (12%) | 4 (21%) | 21 (37%) | 2 (4%) | 3 (8%) | 10 (21%) | 30 (33%) | 6 (21%) | 20 (21%) | 8 (12%) | 5 (29%) |
| PBMC IFNγ | 110 (21%) | 75 (7%) | 500 (61%) | 74 (14%) | 204 (21%) | 132 (21%) | 181 (18%) | 117 (21%) | 80 (4%) | 110 (21%) | 86 (18%) |

| HIV/RT POOL | HRT1 | HRT2 | HRT3 | HRT4 | HRT5 | HRT6 | HRT7 | HRT8 | HRT9 | HRT10 | HRT11 |
|---|---|---|---|---|---|---|---|---|---|---|---|
| CD4 T Prolif. | 16 (12%) | 8 (4%) | 13 (8%) | 6 (8%) | 4 (8%) | 10 (4%) | 52 (8%) | 10 (8%) | 25 (8%) | 8 (4%) | 16 (8%) |
| CD8 T Prolif. | 9 (8%) | 8 (4%) | 5 (12%) | 4 (12%) | 4 (12%) | 3 (12%) | 9 (12%) | 15 (12%) | 7 (17%) | 3 (4%) | 20 (17%) |
| PBMC IFNγ | 264 (21%) | 108 (29%) | 135 (14%) | 148 (25%) | 184 (39%) | 412 (39%) | 322 (46%) | 127 (21%) | 236 (32%) | 195 (36%) | 880 (57%) |

FIG. 11A

| HIV/RT POOL | FRT12 | FRT13 | FRT14 | FRT15 | FRT16 | FRT17 | FRT18 | FRT19 | FRT20 | FRT21 | PHA |
|---|---|---|---|---|---|---|---|---|---|---|---|
| CD4 T Prolif. | 4 (8%) | 8 (8%) | 15 (16%) | 9 (8%) | 9 (8%) | 13 (4%) | 0 (0%) | 11 (8%) | 9 (12%) | 48 (79%) |
| CD8 T Prolif. | 3 (8%) | 8 (17%) | 5 (37%) | 13 (33%) | 4 (17%) | 15 (12%) | 7 (8%) | 11 (21%) | 9 (12%) | 8 (33%) | 42 (75%) |
| PBMC IFNγ | 115 (11%) | 114 (36%) | 116 (18%) | 140 (11%) | 85 (18%) | 88 (11%) | 160 (11%) | 90 (7%) | 81 (25%) | 70 (18%) | 3968 (100%) |

| HIV/RT POOL | HRT12 | HRT13 | HRT14 | HRT15 | HRT16 | HRT17 | HRT18 | HRT19 | HRT20 | HRT21 | PHA |
|---|---|---|---|---|---|---|---|---|---|---|---|
| CD4 T Prolif. | 12 (4%) | 26 (12%) | 5 (8%) | 4 (4%) | 2 (4%) | 0 (0%) | 8 (8%) | 12 (4%) | 2 (4%) | 10 (4%) | 48 (79%) |
| CD8 T Prolif. | 6 (12%) | 28 (12%) | 5 (17%) | 5 (12%) | 0 (0%) | 6 (17%) | 5 (12%) | 10 (21%) | 9 (0%) | 4 (17%) | 40 (79%) |
| PBMC IFNγ | 381 (29%) | 275 (29%) | 230 (39%) | 149 (25%) | 146 (25%) | 95 (18%) | 88 (11%) | 85 (4%) | 149 (14%) | 95 (18%) | 3968 (100%) |

| FIV p24 POOL | Fp1 | Fp2 | Fp3 | Fp4 | Fp5 | Fp6 | Fp7 | Fp8 | Fp9 |
|---|---|---|---|---|---|---|---|---|---|
| CD4+ T Prolif. | 0 (0%) | 0 (0%) | 3 (4%) | 0 (0%) | 26 (4%) | 5 (4%) | 0 (0%) | 3 (4%) | 7 (4%) |
| CD8+ T Prolif. | 20 (12%) | 4 (4%) | 20 (4%) | 0 (0%) | 0 (0%) | 3 (17%) | 10 (4%) | 4 (8%) | 29 (21%) |
| PBMC IFNγ | 180 (6%) | 70 (3%) | 97 (10%) | 156 (13%) | 121 (6%) | 112 (13%) | 93 (16%) | 73 (10%) | 72 (13%) |

| HIV p24 POOL | Hp1 | Hp2 | Hp3 | Hp4 | Hp5 | Hp6 | Hp7 | Hp8 | Hp9 | Hp10 |
|---|---|---|---|---|---|---|---|---|---|---|
| CD4+ T Prolif. | 7 (4%) | 5 (8%) | 5 (8%) | 5 (4%) | 11 (4%) | 2 (4%) | 0 (0%) | 29 (12%) | 3 (4%) | 5 (12%) |
| CD8+ T Prolif. | 20 (21%) | 6 (8%) | 0 (0%) | 0 (0%) | 19 (4%) | 2 (12%) | 5 (8%) | 3 (8%) | 22 (12%) | 6 (12%) |
| PBMC IFNγ | 262 (29%) | 213 (42%) | 534 (61%) | 212 (29%) | 252 (23%) | 526 (32%) | 721 (39%) | 512 (26%) | 272 (29%) | 215 (48%) |

(Fp7 column for HIV row: SEQUENCE SHIFT)

FIG. 12B

| HIV p24 POOL | Fp10 | Fp11 | Fp12 | Fp13 | Fp14 | Fp15 | Fp16 | Fp17 | ConA |
|---|---|---|---|---|---|---|---|---|---|
| CD4+ T Prolif. | 4 (8%) | 3 (12%) | 0 (0%) | 0 (0%) | 7 (4%) | 0 (0%) | 0 (0%) | 8 (4%) | 45 (79%) |
| CD8+ T Prolif. | 41 (8%) | 4 (8%) | 3 (4%) | 0 (0%) | 23 (8%) | 53 (4%) | 0 (0%) | 0 (0%) | 44 (79%) |
| PBMC IFNγ | 144 (13%) | 126 (16%) | 215 (6%) | 107 (16%) | 302 (26%) | 145 (10%) | 85 (3%) | 160 (10%) | 5031 (100%) |

| HIV p24 POOL | Hp11 | Hp12 | Hp13 | Hp14 | Hp15 | Hp16 | Hp17 | Hp18 | PHA |
|---|---|---|---|---|---|---|---|---|---|
| CD4+ T Prolif. | 0 (0%) | 4 (4%) | 0 (0%) | 0 (0%) | 0 (0%) | 5 (4%) | 48 (4%) | 0 (0%) | 49 (79%) |
| CD8+ T Prolif. | 32 (12%) | 7 (17%) | 120 (10%) | 4 (4%) | 15 (12%) | 5 (12%) | 0 (0%) | 4 (4%) | 43 (83%) |
| PBMC IFNγ | 470 (39%) | 293 (39%) | 120 (10%) | 324 (39%) | 218 (32%) | 211 (19%) | 176 (26%) | 109 (16%) | 4918 (100%) |

FIG. 13A

```
HIV-1          P-ISP-IETVPVKLKPGMDGPKVKQWPLTEEKIKALVEICTEMEKEGKISKIGPENPYNT
                 10         20         30         40         50
                 :  ::    : ::  : :  :   :  ::::::::   :::::::   ::::::
FIV            AQISEKIPIVKVRMKDPTQGPQVKQWPLSNEKIEALTDIVERLELEGKVKRADPNNPWNT
                 10         20         30         40         50         60

HIV-1          PVFAIKKKDSTKWRKLIVDFRELNKRTQDFWEVQLGIPHPAGLKKKKSVTVLDVGDAYFSV
                 70         80         90        100        110
               :::::::: : :::: :: ::::: :: ::::::::::::::: ::::::::::
FIV            PVFAIKKK-SGKWRMLIDFRVLNKLTDKGAEVQLGLPHPAGLKMRKQVTVLDIGDAYFTI
                 70         80         90        100        110

HIV-1          PLDEDFRKYTAFTIPSINNETPGIRYQYNVLPQGWKGSPAIFQSSMTKILEPFRKQNPDI
                120        130        140        150        160        170
               :: :: :::::::: ::::: :: ::::: ::::  ::::::::::::
FIV            PLDPDYAPYTAFTLPRKNNAGPGRRYVWCSLPQGWVLSPLIYQSTLDNILQPFIRQNPEL
                120        130        140        150        160        170

HIV-1          VIYQYMDDLYVGSDLEIGQHRTKIEELRQHLLRWGLTTPDKKHQKEPPFLWMGYELHPDK
                180        190        200        210        220        230
                :::::::: ::::::  ::: ::::: :::: :::::::: :: :::::::::::
FIV            DIYQYMDDIYIGSDLNKKEHKQKVEELRKLLLWGFETPEDKLQEEPPYKWMGYELHPLT
                180        190        200        210        220        230
```

HRT3 vs. FRT3
(lined section)
69% Identity
77% Homology

HRT6 vs. FRT6
(lined section)
52% Identity
63% Homology

FIG. 13A
(continued)

HRT11 vs. FRT11
(lined section)
57% Identity
87% Homology

```
             240       250       260       270       280       290
HIV-1   WTVQP--IVLPEKDSWTVNDIQKLVGKLNWASQIYPGIKVRQLCKLLRGTKALTEVIPLT
        ::  :  ::    ::::  :::::::::::::::::::::::  ::  ::
FIV     WSIQQKQLEIPERP--TLNELQKLVGKLNWASQTIPDLSIKELTTMMRGDQRLDSIREWT
             240       250       260       270       280       290
```

HRT13 vs. FRT13
(lined section)
32% Identity
72% Homology

```
             300       310       320       330       340       350
HIV-1   EEAELELAENREILKEPVHGVYYDPSKDLIAEIQKQGQGQWTYQIYQE-PFKNLKTGKYA
        ::  :  :  :::: : :::: ::  ::  :  ::  : :   ::
FIV     TEAKKEVQKAKEAIETQAQLKYYDPSRELYAKLSLVGPHQICYQVYHKNPEHVLWYGKMN
             300       310       320       330       340       350

360       370       380       390       400       410
HIV-1   RTRGAHTNDVKQLTEAVQKITTESIVIWGKTPKFKLPIQKETWETWW--TEYWQATWIPE
        :     :    :  : :::  ::::  :::    :
FIV     RQKKKAENTCDIALRACYKIREESIIRIGKEPIYEIPASREAWESNLIRSPYLKAP-PPE
             360       370       380       390       400       410

420       430       440
HIV-1   WEFVNTPPLVKLWYQLEKE-PIVGAETFY       (SEQ ID NO:45)
        ::  :       :::    ::::::
FIV     VEFIHAALNIKRALSMIQDTPILGAETWY       (SEQ ID NO:46)
             420       430       440
```

FIG. 13B

```
                          10        20        30        40        50        60                HRT3 vs. SRT3
HIV-1   PISPIETVPVKLKPGMDGPKVKQWPLTEEKIKALVEICTEMEKEGKISKIGPENPYNTPV                            77% Identity
        ::  ::::::::::::::  :::::::::::  :::::  ::::::::  :  ::::::                            91% Homology
SIV     PIAKVEPVKVTLKPGKVGPKLKQWPLSKEKIVALREICEKMEKDGQLEEAPPTNPYNTPT
                          10        20        30        40        50        60

70        80        90        100       110       120
HIV-1   FAIKKKDSTKWRKLVDFRELNKRTQDFWEVQLGIPHPAGLKKKKSVTVLDVGDAYFSVPL
        :::::::::::::::::::::::::::::::::::::::::::  :::::::::::::
SIV     FAIKKKDKNKWRMLIDFRELNRVTQDFTEVQLGIPHPAGLAKRKRITVLDIGDAYFSIPL
                          70        80        90        100       110       120
                          R416     R397,R395; R416; R422 reacted to FIV NPWNTPVFAIKKK peptide 130       140       150       160       170       180            HRT6 vs. SRT6
HIV-1   DEDFRKYTAFTIPSINNETPGIRYQYNVLPQGWKGSPAIFQSSMTKILEPFRKQNPDIVI                         71% Identity
        :::::::::::::::: ::: ::  :::::::::::::::::::   ::::: :::::                          84% Homology
SIV     DEEFRQYTAFTLPSVNNAEPGKRYIYKVLPQGWKGSPAIFQYTMRHVLEPFRKANPDVTL
                R397,R425,R426
                          130       140       150       160       170       180

190       200       210       220       230       240
HIV-1   YQYMDDLYVGSDLEIGQHRTKIEELRQHLLRWGLTTPDKKHQKEPPFLWMGYELHPDKWT
        :::::::  :::  :::::  :::::::::  ::::::  :::::  :::::::: ::
SIV     VQYMDDILIASDRTDLEHDRVVLQLKELLNSIGFSTPEEKFQKDPPFQWMGYELWPTKWK
                          190       200       210       220       230       240
```

FIG. 13B
(continued)

```
                    250        260        270        280        290        300
HIV-1   VQPIVLPEKDSWTVNDIQKLVGKLNWASQIYPGIKVRQLCKLLRGTKALTEVIPLTEEAE         HRT11 vs. SRT11
        :::::::::::::::::::: :::::::::: ::::::: :::::: ::: :::  ::          71% Identity
SIV     LQKIELPQRETWTVNDIQKLVGVLNWAAQIYPGIKTKHLCRLIRGKMTLTEEVQWTEMAE         91% Homology
                    250        260        270        280        290        300
                                              R414,R425,R426

310        320        330        340        350        360
HIV-1   LELAENREILKEPVHGVYYDPSKDLIAEIQKQGQGQWTYQIYQEPFKNLKTGKYARTRGA         HRT14 vs. SRT14
        ::  ::::::: : ::  ::::  : ::: :::  ::::: :::: :  ::::: :::          47% Identity
SIV     AEYEENKIILSQEQEGCYYQEGKPLEATVIKSQDNQWSYKIHQED-KILKVGKFAKIKNT         82% Homology
                    310        320        330        340        350
                                                   R397,R426

370        380        390        400        410        420
HIV-1   HTNDVKQLTEAVQKITTESIVIWGKTPKFKLPIQKETWETWWTEYWQATWIPEWEFVNTP
        ::: :: ::  :: :: ::::::: ::::    :: :  ::  :: :::: ::::: ::
SIV     HTNGVRLLAHVIQKIGKEAIVIWGQVPKFHLPVERDVWEQWWTDYWQVTWIPEWDFISTP
                    370        380        390        400        410

430        440
HIV-1   PLVKLIWYQLEKEPIVGAETFY          (SEQ ID NO:45)
        ::: : :::::: ::: :: :
SIV     PLVRLVFNLVKDPIEGEET-Y          (SEQ ID NO:47)
                    420        430
```

FIG. 15A

HIV-1 AND FIV p24 SEQUENCES AND INDIVIDUAL PEPTIDES IN THE PEPTIDE POOLS p24 aa 1-116

FIV:
Fp1 VALDPKMVSIF
    APQYVALDPKM
    TVNGAPQYVALDPKM
P1 QTVNGAPQYAL
Fp2 KAREGLGGEEVQLNF
    IPMEKAREGLGGEEV
    PKMVSIPMEKAREGL
Fp3 LNFTAFSANLPTDM
    VQLNFTAFSANL
    GEEVQLNFTAFSANL
    GLGGEEVQLNFTAF
Fp4 PTDMATLIMAAPGCA
    NLTPTDMATLIMAA
    AFSANLPTDMATLI
Fp5 APGCAADKEILDESL
    IMAAPGCAADKEIL
    ATLIMAAPGCAADK
    AADKEILDESLKQL
Fp6 KQLTAEYDRTHP
    DESLKQLTAEYDRTH
    KEILDESLKQLTAEY
Fp7 PLPYTTAAEIMGIGL
    GPRDLPYTTAAEIM
    PDGPRPLPYTTAA
    PDGPRPLPY
Fp8 LT QEQ
    MGIGLT QEQ
    FTAAEIMGIGLT QEQ

P1-QTVNGAPQYVALDPKMVSIPMEKAREGLGGEEVQLNFTAFSANLPTDMATLIMAAPGCAADKEILDESLKQLTAEYDRTHP----PDGPRPLPYTTAAEIMGIGLT-QEQ--
  ::  ::::::::::::::  :::::::: :::: :   :: :   :  :::  :    : :::   :::    ::::::    :::::::::::::: :::

HIV-1: PIVQNLQGQMVHQAISPRTLNAWVKVVEEKAFSPEVIPMFSALSEGATPQDLNTMLNTVGGHQAAMQMLKETINEEAAEWDRLHPVHAGPIAPGQMREPRGSDIAGTTSTLQEQIG 116
Hp1 PIVQNLQGQMVHQAI       EKAFSPEVIPMFSAL     NTMLNTVGGHQAAMQ          AAEWDRLHPVHAGPI    Hp9 GSDIAGTTSTLQEQI
    NLQGQMVHQAISPRT       SPEVIPMFSALSEGA  Hp5 NTVGGHQAAMQLKE      Hp7 DRLHPVHAGPIAPGQ          AGTTSTLQEQIG
    QMVHQAISPRTLNAW       IPMFSALSEGATPQD       GHQAAMQLKETINE             PVHAGPIAPGQMREPH         STLQEQIG
    QAISPRTLNAWVKV    Hp4 SALSEGATPQDLNTM      Hp6 AMQMLKETINEAAE        Hp8 GPIAPGQMREPRGSD             EQIG
Hp2 PRTLNAWVKVVEEKA        EGATPQDLNTMLNTV          LKETINEEAAEWDRL              PGQMREPRGSDIAGT
    NAWVKVVEEKAFSPE        PQDLNTMLNTVGGHQ           INEEAAEWDRLHPVH             REPRGSDIAGTTSTL
    KVVEEKAFSPEVIPMH

```
                                                            Fp14 KIYLKQSLSTANA
QAEARFAPAR  Fp10 LEALGKLAAIKAK    Fp12 RQGAKEDYSSFIDRL            AEVKLYLKQSLSIA    Fp16 LKPESTLEEKIRA
QAEARF          RAWYLEALGKLAAIK       V QLRQGAKEDYSSFI            EQNTAEVKLYLKQSL       AMSHLKPESTLEEKL
QA              RMQCRAWYLEALGKL        PRAV QLRQGAKEDY            DQEQNTAEVKLYLK        PDCKRAMSHLKPESTL
  Fp9 FAPARMQCRAWYLEA Fp11 KAKSPRAV QLRQCAK          Fp13 PAQIDQEQNTAEVKL   Fp15 ANANPDCKRAMSHLK     Fp17 RACQEVGSPGTKM

A

FIV or HIV-1 Pool and Peptides

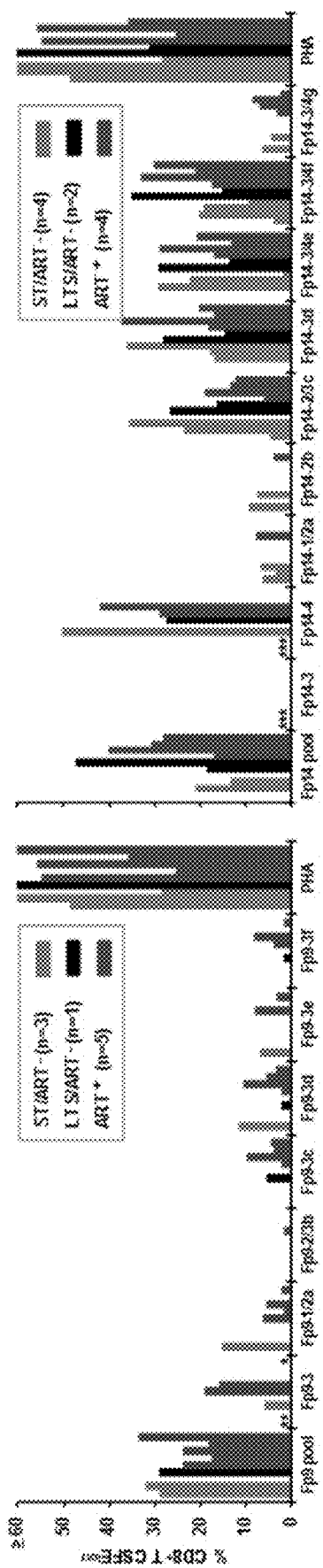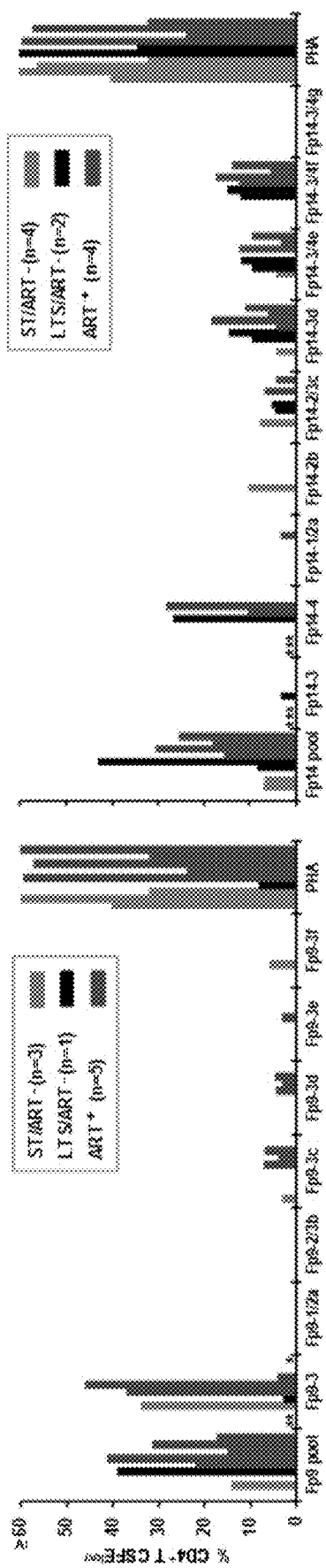
FIG. 27A  FIG. 27B  FIG. 27C  FIG. 27D

CROSS-REACTIVE T CELL EPITOPES OF HIV, SIV, AND FIV FOR VACCINES IN HUMANS AND CATS

CROSS-REFERENCE TO RELATED APPLICATIONS

The present application is a continuation of U.S. application Ser. No. 14/617,711, filed Feb. 9, 2015, which is a continuation-in-part of International Application No. PCT/US2013/054191, filed Aug. 8, 2013, which claims the benefit of U.S. Provisional Application Ser. No. 61/841,122, filed Jun. 28, 2013, U.S. Provisional Application Ser. No. 61/684,592, filed Aug. 17, 2012, and U.S. Provisional Application Ser. No. 61/681,014, filed Aug. 8, 2012, each of which is hereby incorporated by reference herein in its entirety, including any figures, tables, nucleic acid sequences, amino acid sequences, or drawings.

GOVERNMENT SUPPORT

This invention was made with government support under Grant No. R01-AI065276 and Grant No. R01-AI030904 awarded by the National Institutes of Health. The government has certain rights in the invention.

The Sequence Listing for this application is labeled 2LA0379.TXT which was created on Jan. 26, 2018 and is 159 KB. The entire contents of the sequence listing is incorporated herein by reference in its entirety.

BACKGROUND OF THE INVENTION

An effective prophylactic HIV-1 vaccine is needed to eradicate the HIV/AIDS pandemic but designing such a vaccine is a challenge. Despite many advances in vaccine technology and approaches to generate both humoral and cellular immune responses, major phase-II and -III vaccine trials against HIV/AIDS have resulted in only moderate successes. The modest achievement of the phase-III RV144 prime-boost trial in Thailand re-emphasized the importance of generating robust humoral and cellular responses against HIV. While antibody-directed approaches are being pursued by some groups, others are attempting to develop vaccines targeting cell-mediated immunity, since evidence show CTLs to be important for the control of HIV replication. Phase-I and -IIa multi-epitope vaccine trials have already been conducted with vaccine immunogens consisting of known CTL epitopes conserved across HIV subtypes, but have so far fallen short of inducing robust and consistent anti-HIV CTL responses. Thus, a need remains in the art for an effective vaccine against HIV.

Domestic cats are subject to infection by several retroviruses, including feline leukemia virus (FeLV), feline sarcoma virus (FeSV), endogenous type C oncoronavirus (RD-114), and feline syncytia-forming virus (FeSFV). Of these, FeLV is the most significant pathogen, causing diverse symptoms including lymphoreticular and myeloid neoplasms, anemias, immune-mediated disorders, and an immunodeficiency syndrome that is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (now designated as feline immunodeficiency virus, FIV) was first reported in Pedersen et al. (1987). Characteristics of FIV have been reported in Yamamoto et al. (1988a); Yamamoto et al. (1988b); and Ackley et al. (1990). Seroepidemiologic data have shown that infection by FIV is indigenous to domestic and wild felines throughout the world. A wide variety of symptoms are associated with infection by FIV, including abortion, alopecia, anemia, conjunctivitis, chronic rhinitis, enteritis, gingivitis, hematochezia, neurologic abnormalities, periodontitis, and seborrheic dermatitis. The immunologic hallmark of domestic cats infected with FIV is a chronic and progressive depletion of feline $CD4^+$ peripheral blood lymphocytes, a reduction in the CD4:CD8 cell ratio and, in some cases, an increase in CD8-bearing lymphocytes.

Cloning and sequence analysis of FIV has been reported in Olmsted et al. (1989a); Olmsted et al. (1989b); and Talbott et al. (1989). Hosie and Jarrett (1990) described the serological response of cats infected with FIV. FIV virus subtypes can be classified according to immunotype based on the level of cross-neutralizing antibodies elicited by each strain (Murphy and Kingsbury, 1990). Recently, viruses have been classified into subtypes according to genotype based on nucleotide sequence homology. Although HIV and FIV subtyping is based on genotype (Sodora et al., 1994; Rigby et al., 1993; and Louwagie et al., 1993), little is known about the correlation between the genotype and immunotype of subtypes. FIV viral isolates have been classified into five FIV subtypes: A, B, C, D, and E (Kakinuma et al., 1995; Yamamoto et al., 2007; Yamamoto et al., 2010). Infectious isolates and infectious molecular clones have been described for all FIV subtypes except for subtypes C and E (Sodora et al., 1994). Subtype C FIV has originally been identified from cellular DNA of cats from Canada (Sodora et al., 1994; Rigby et al., 1993; Kakinuma et al., 1995). Examples of FIV strains identified in the art include (subtype of the strain is shown in parenthesis) Petaluma (A), Dixon (A), UK8 (A), Dutch113 (A), Dutch19K (A), UK2 (A), SwissZ2 (A), Sendai-1 (A), USCAzepy01A (A), USCAhnky11A (A), USCAtt-10A (A), USCAlemy01 (A), USCAsam-01A (A), PPR (A), FranceWo, Netherlands, Bangston (A/B), Aomori-1 (B), Aomori-2 (B), USILbrny03B (B), TM2 (B), Sendai-2 (B), USCK1gri02B (B), Yokohama (B), USMAsboy03B (B), USTXmtex03B (B), USMCglwd03B (B), CABCpbar03C (C), CABCpbar07C (C), CABCpady02C (C), Shizuoka (D), Fukuoka (D), LP3 (E), LP20 (E), and LP24 (E).

The commercial release of an effective HIV-1 vaccine is not imminent even after completion of four major phase IIB-III vaccine trials against HIV/AIDS (Saunders et al. (2012)). Our limited understanding about the mechanisms of vaccine protection (Plotkin (2008)) and the identity of the protective viral epitopes (Mothe et al. (2011); Koff (2010)) further hampers the development of an effective vaccine. Initial studies focused on antibody-based vaccine designs with an emphasis on generating broadly virus neutralizing antibodies (bNAbs) (Stamatatos (2012)). However, two phase-III vaccine trials using envelope (Env) immunogens failed (Flynn et al. (2005); Pitisuttithum et al. (2006)). Subsequent focus was placed on the T-cell-based vaccines that generate protective cell-mediated immunity (CMI) against global HIV-1 isolates (Buchbinder et al. (2008)). The CMI responses, essential for an effective vaccine, most likely include cytotoxic T lymphocyte (CTL) activities that specifically target HIV-1 infected cells (Ogg et al. (1998); Walker et al. (1988); Belyakov et al. (2012)). Unlike NAb epitopes which reside exclusively on the Env proteins, the selection of specific vaccine epitopes for the development of T-cell-based vaccines is more difficult to achieve. A vast number of CTL-associated epitopes can be found to span the whole length of most HIV proteins (Los Alamos National Laboratory (LANL) database, hiv-web.lanl.gov/content/immunology/maps/maps.html) (Llano et al. (2009)). The goal to develop T-cell-based vaccines is challenged by the capacity of the virus to evade antiviral immunity through mutation(s) for resistance (Li et al. (2011); Leslie et al. (2004)).

A recent phase III trial consisting of priming with a gag-pr-gp41-gp120 canarypox vectored vaccine and boosting with Env gp120 induced both humoral immunity and CMI and conferred a modest overall efficacy (Rerks-Ngarm et al. (2009)). However, phase I and II vaccine trials consisting of cross-subtype conserved CTL-associated peptide epitopes have shown minimal CMI responses (Sanou et al. (2012a); Hanke et al. (2007); Salmon-Ceron et al. (2010)). Therefore, a thorough selection of potent anti-HIV T cell-associated epitopes, which are conserved among HIV-1 subtypes and do not mutate without negatively affecting viral fitness (Troyer et al. (2009); Goulder et al. (2008); Rolland et al. (2007)), would be valuable for an effective HIV-1 vaccine. One approach is to select conserved, non-mutable CTL epitopes on essential viral structural proteins or enzymes that also persist on the older subgenuses of the lentivirinae which have survived evolutionary pressure (Yamamoto et al. (2010)). Such an approach was successfully used in the development of the initial smallpox vaccines (Jenner (1798)). In line with this strategy, the recognition of conserved epitopes on other lentivirus species has been made by the PBMC from HIV-1 positive (HIV+) humans (Balla-Jhagjhoorsingh et al. (1999)), HIV-2 vaccinated and SIV-challenged non-human primates (Walther-Jallow et al. (2001)), and HIV-1 p24-vaccinated and FIV-challenged cats (Abbott et al. (2011); Coleman et al. (2005)).

The viral enzyme, reverse transcriptase (RT), is one of the most conserved viral proteins by possessing the lowest entropy value among the HIV-1 proteins from various subtypes (Yusim et al. (2002)) and contains many CTL-associated epitopes (Walker et al. (1988)). The RT proteins of HIV-1 and FIV also share the highest degree of identity in their amino acid (aa) sequences (Yamamoto et al. (2010)). The current studies were undertaken to identify the conserved CTL-associated epitopes on FIV and HIV-1 RT proteins which are recognized by the PBMC and T cells from HIV+ subjects. The major objective of such studies is to identify evolutionarily-conserved CMI epitopes that may be more resistant to mutation, and thus useful in the development of an effective, T-cell-based HIV-1 vaccine.

BRIEF SUMMARY OF THE INVENTION

The subject invention concerns methods and materials for inducing an immune response in an animal or person against an immunodeficiency virus, such as HIV, SIV, or FIV. In one embodiment, a method of the invention comprises administering one or more antigens and/or immunogens to the person or animal wherein the antigen and/or immunogen comprises one or more evolutionarily conserved epitopes of immunodeficiency viruses. In one embodiment, the epitope is one that is conserved between HIV and SIV, or between HIV and FIV. In another embodiment, the epitope is one that is conserved between HIV, SIV, and FIV. In one embodiment, the epitope is a T-cell epitope. In a specific embodiment, the T-cell epitope is a cytotoxic T lymphocyte (CTL) and T-helper (Th) epitope.

The subject invention also concerns evolutionarily conserved epitopes of immunodeficiency viruses. In one embodiment, the epitope is one that is conserved between HIV and SIV, or is one that is conserved between HIV and FIV. In another embodiment, the epitope is one that is conserved between HIV, SIV, and FIV. In one embodiment, the epitope is a T-cell epitope. In a specific embodiment, the T-cell epitope is a cytotoxic T lymphocyte (CTL) and T-helper (Th) epitope.

The subject invention also concerns antibodies that bind to HIV, SIV, and/or FIV epitopes. In one embodiment, an antibody of the invention binds specifically to an HIV protein, e.g., an FIV p24 protein. In another embodiment, an antibody of the invention binds specifically to an FIV protein, e.g., an HIV p24 protein. In a further embodiment, an antibody of the invention binds specifically to both an HIV and an FIV protein, i.e., the antibody cross-reacts with both an HIV and an FIV protein, such as a p24 protein.

BRIEF DESCRIPTION OF THE DRAWINGS

FIGS. 3A and 3B. Comparison Between FIV RT and HIV-1 RT. CD3+CD4+ and CD3+CD8+ T-cell CFSE-proliferation (n=24) and PBMC IFNγ ELISpot (n=28) responses of HIV+ subjects to overlapping FIV RT (FRT 1-21, top) and HIV-1 (HRT 1-21, bottom) peptide pools. Results are shown as a mean value of % CFSE$_{low}$, or spot forming unit (SFU) per $10^6$ PBMC with percentage of responders over total subjects tested (% Responder). Uninfected subjects (n=10) had negligible to no responses. Dark red box represents the highest response while boxes with lighter shades of red showing lesser responses with blue representing minimal to no responses. Thresholds are ≥2% for CFSE-proliferation and ≥70 SFU for ELISpot.

FIGS. 4A and 4B. Comparison Between FIV p24 and HIV-1 p24. CD3+CD4+ and CD3+CD8+ T-cell CFSE-proliferation (n=24) and PBMC IFNγ ELISpot (n=31) responses to overlapping FIV p24 (Fp 1-17, top) and HIV-1 p24 (Hp 1-18, bottom) peptide pools. Results are shown as a mean value of % CFSE$_{low}$ or spot forming unit/$10^6$ PBMC with (% Responder). Dark red box represents the highest response while lighter shades of red show lesser responses with blue representing minimal to no response.

FIG. 5. Sequence comparison between HIV-1$_{LAI}$ reverse transcriptase (RT) (441 aa) and FIV$_{FC1}$ RT (445 aa).

FIG. 6. Sequence comparison between HIV-1$_{LAI}$ RT (441 aa) and SIV$_{Mm251}$ (439 aa).

FIG. 7. Sequence comparisons between FIV-Pet p24 (223 aa) and SIV-Delta B670 p24 (228 aa), between HIV1 HXB2 p24 (231 aa) and FIV-Pet p24 (223 aa), and between HIV1-HXB2 p24 (231 aa) and SIV-Delta B670 p24 (228 aa).

FIGS. 15A and 15B. HIV-1 and FIV p24 sequences and individual peptides in the peptide pools. (SEQ ID NOs:257-262,264-319,321-335,337-370).

FIGS. 17A and 17C) and FIV RT (F1-F21; FIGS. 17B and 17D) are shown. The HIV+ subjects (panel-A insert for FIGS. 17A-17D) consisted of long-term survivors (LTS) who have had HIV infection for over 10 years without antiretroviral therapy (ART) (LTS; black bar); subjects recently diagnosed with short-term infection without ART (ST; grey bar); and subjects on ART at various duration of infection (ART+, red bar). Each bar represents a positive response by an individual with a threshold of 70 spot forming units (SFU) per $10^6$ PBMC for ELISpot or threshold of 3% CFSElow for CD3+CD8+ T-cell proliferation. Cells from each individual were stimulated with T-cell mitogen, phytohemaglutinin A (PHA), as positive control. The HIV− control subjects (n=10) had no responses (data not shown). All responses below the positive threshold are not shown to clearly distinguish those positive values close to the threshold.

The average frequencies of IFNγ and proliferation responders to HIV-1 (FIG. 17E) and FIV (FIG. 17F) RT peptide pools are derived from FIGS. 17A-17D and are shown as % responders. The solid bar for each peptide represents an average responder frequency of IFNγ responses, while the grey bar represents of the CD8+ T-cell proliferation responses.

Figure 18A:
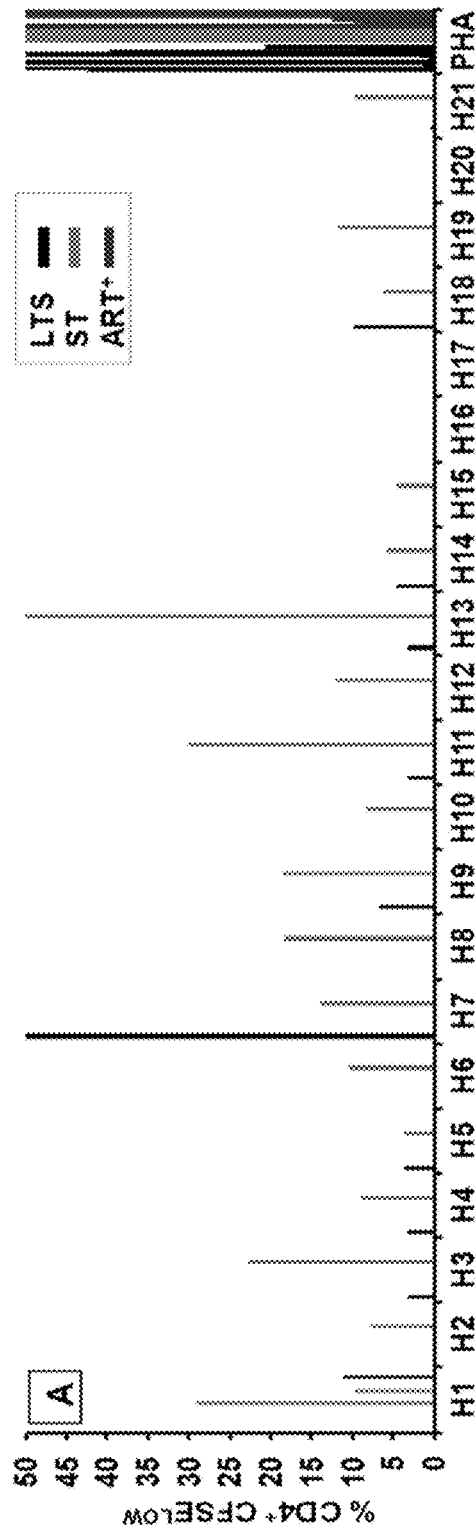
Figure 18B:
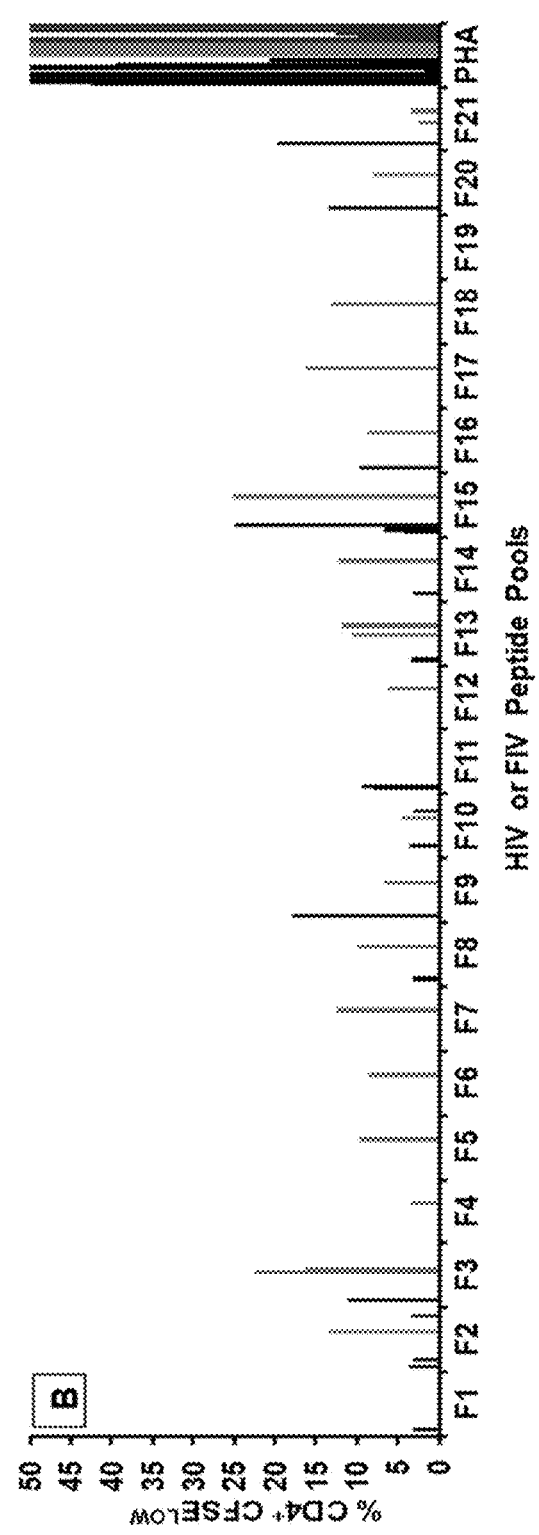

FIGS. 18A-18B. CD3+CD4+ T-cell proliferation responses to HIV and FIV RT peptide pools. The CD3+CD4+ T-cell proliferation responses to overlapping peptide pools of HIV RT (H1-H21; FIG. 18A) and FIV RT (F1-F21; FIG. 18B) are shown for HIV+ subjects (n=26; 11 LTS, 7 ST, 8 ART+). The insert in panel FIG. 18A shows the bar color codes for both panels as: LTS without ART (LTS; black bar), ST without ART (ST; grey bar), and those on ART (ART+; white bar). Each bar represents a positive response by an individual with a positive threshold of 70 SFU per $10^6$ PBMC for ELISpot or 3% $CFSE^{low}$ for CD3+CD4+ T-cell proliferation. None of the HIV− control subjects (n=10) had positive responses (data not shown). Responses below positive thresholds are not shown.

Figure 19A:
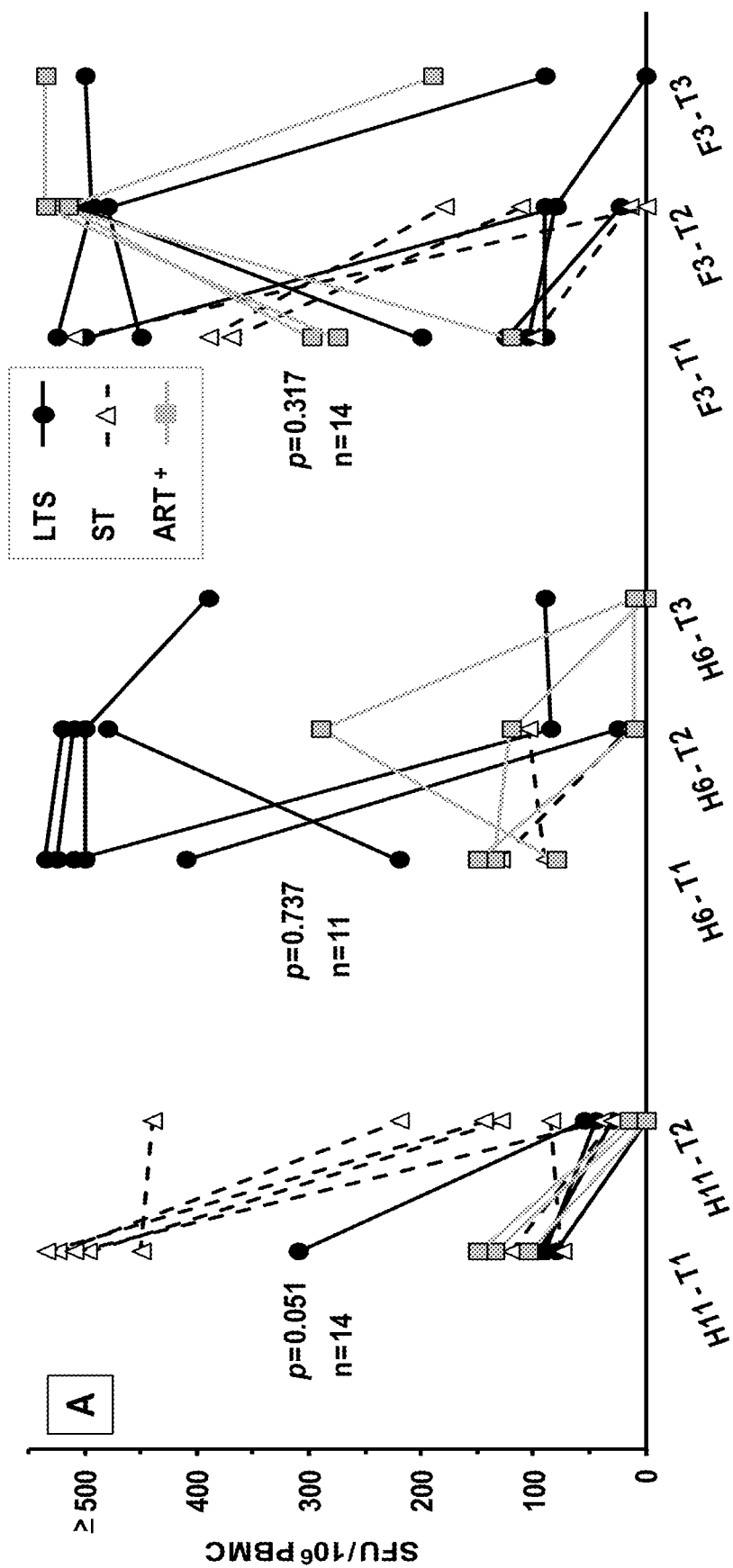
Figure 19B:
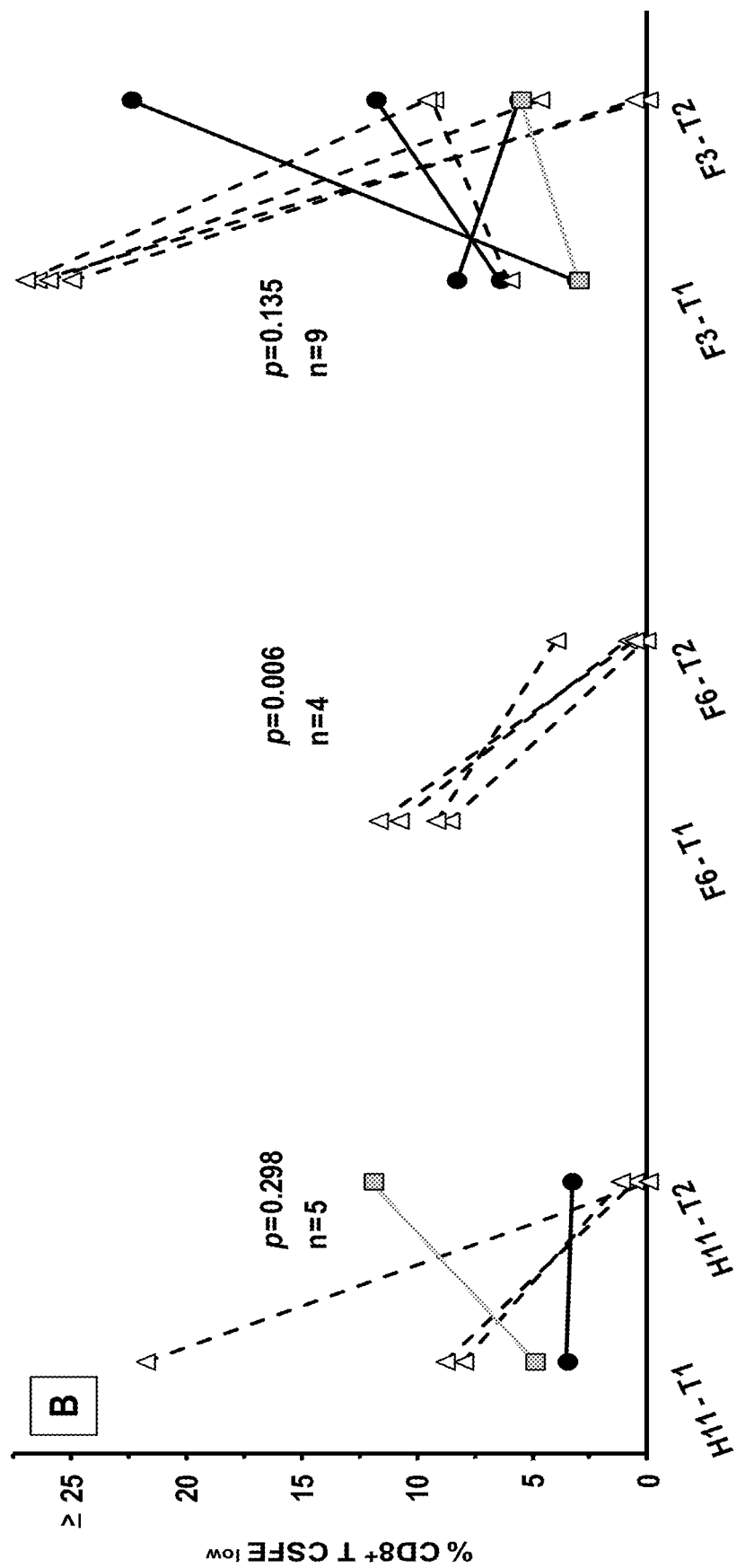

FIGS. 19A-19B. Persistence of IFNγ and CD8+ T-cell proliferation responses to selected peptide pools. The IFNγ (FIG. 19A) and CD8+ T-cell proliferation (FIG. 19B) responses of HIV+ subjects who responded first time (t1) and second time (t2, at least 1 year later) are shown for peptide-pool F3 (both analyses), H11 (both analyses), and H6 (IFNγ) or F6 (T-cell proliferation). The total number of HIV+ subjects who participated is 22 subjects (FIG. 19A: 9 LTS, 8 ST, 5 ART+) in IFNγ study and 11 subjects (FIG. 19B: 3 LTS, 6 ST, 2 ART+) in CD8+ T-cell proliferation study. However, the number of subjects with different clinical status differs among the peptide-pool groups since it is based on the number of responders to the peptide at the first time (t1). In addition, the IFNγ responses to H6 and F3 have a third time point (t3, ≥2 yr). The p-value of each peptide-pool group indicates that the results from t1 are statistically different from those from t2 when p<0.5. Only CD8+ T-cell proliferation responses to F6 at t1 are statistically different from those at t2. A statistical comparisons between t2 and t3 of H6 (n=5) and F3 (n=5) were p=0.124 and p=0.133, respectively (p-value not shown).

Figures 20A, 20B:
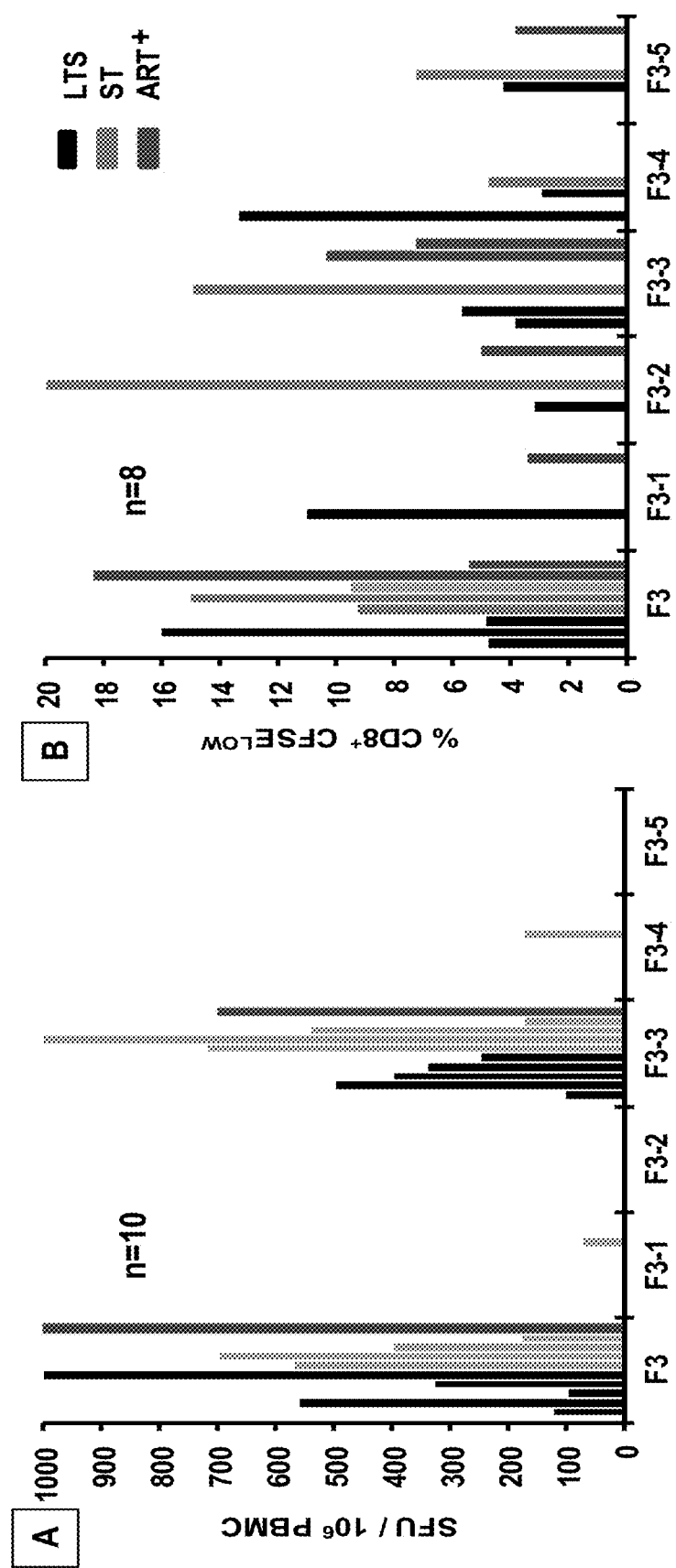

FIGS. 20A-20B. F3 peptide epitopes recognized by F3 responders. The peptide-pool F3 consists of five overlapping 13-15mer peptides spanning from amino- to carboxyl-terminal (F3-1, F3-2, F3-3, F3-4, and F3-5). IFNγ (FIG. 20A; n=10; 5 LTS, 3 ST, 2 ART+) and CD8+ T-cell proliferation (FIG. 20B; n=8; 3 LTS, 3 ST, 2 ART+) by cells from HIV-infected F3 responders to each of these peptides are shown along with responses to F3 pool. F3 responders consist of those subjects with long-term HIV-1 infection but not on ART (LTS; black bar); those with short-term infection and not on ART (ST; grey bar); and those on ART with various duration of infection (ART+; red bar). All responses below positive thresholds are not shown.

Figures 21A, 21B:
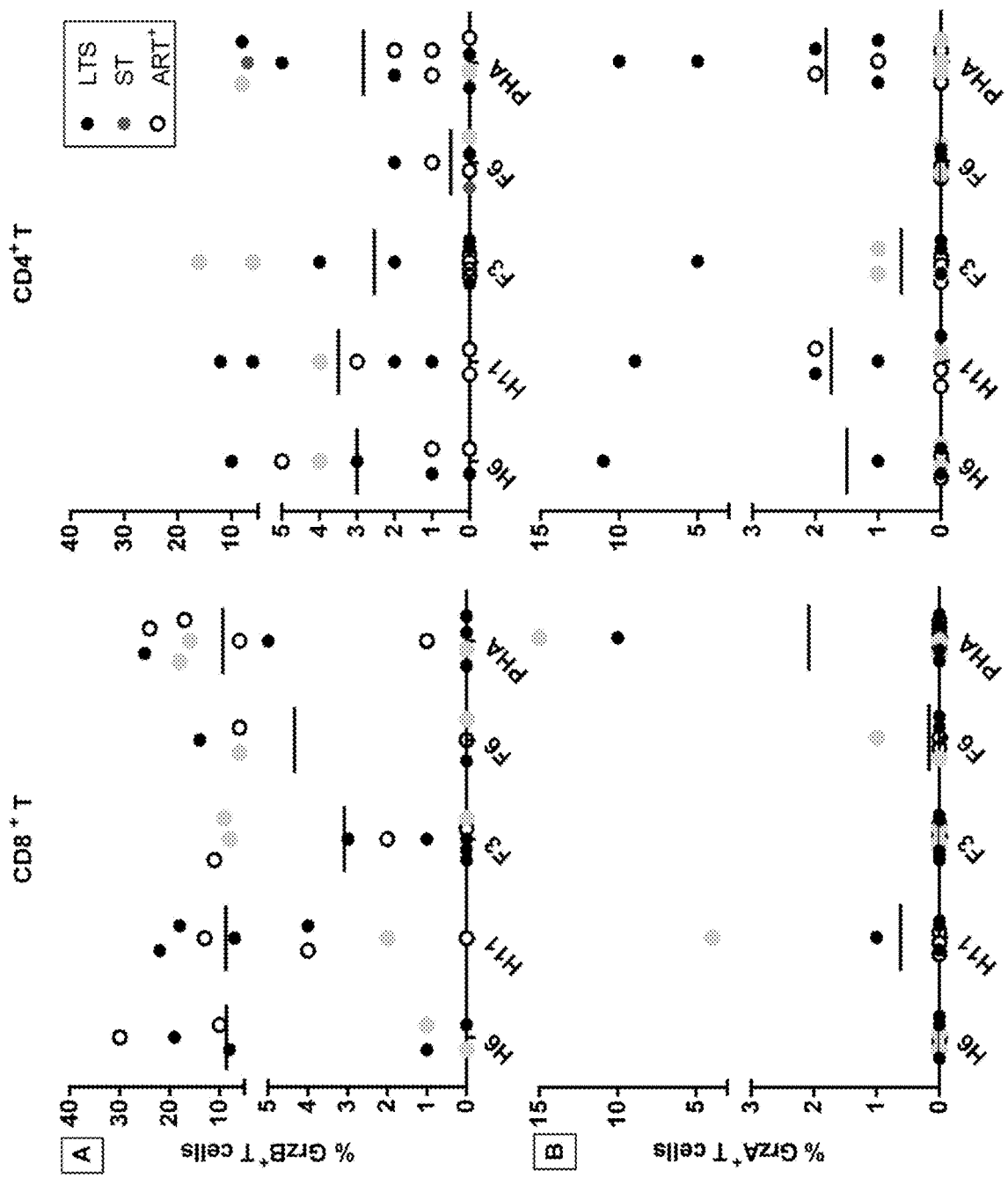
Figure 21C:
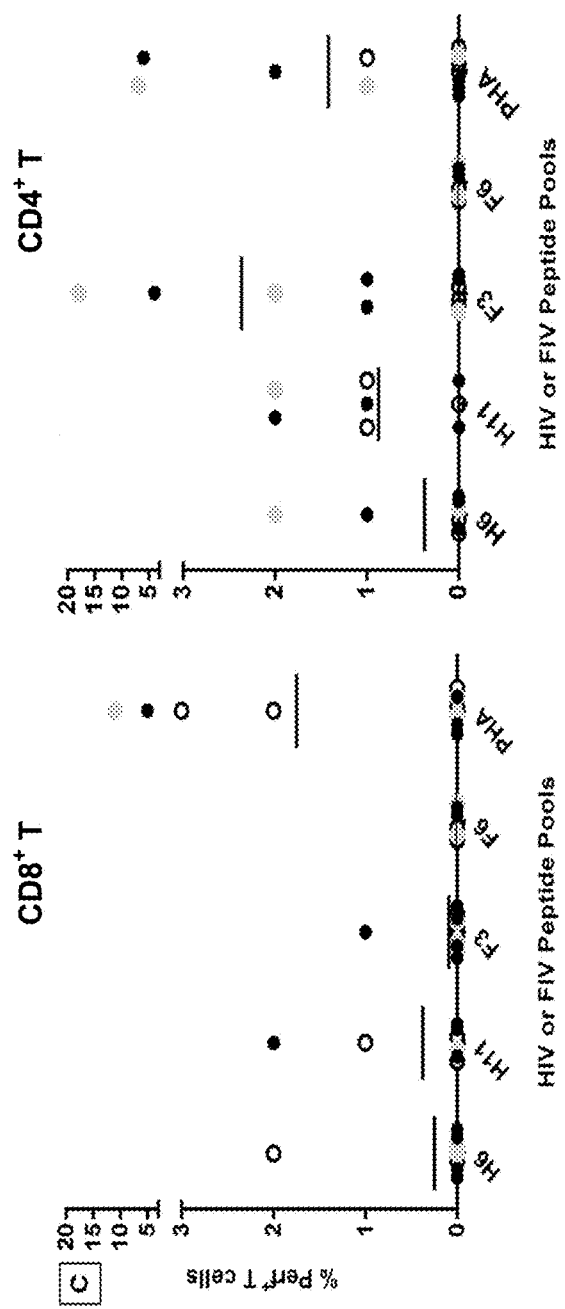
Figure 21D:
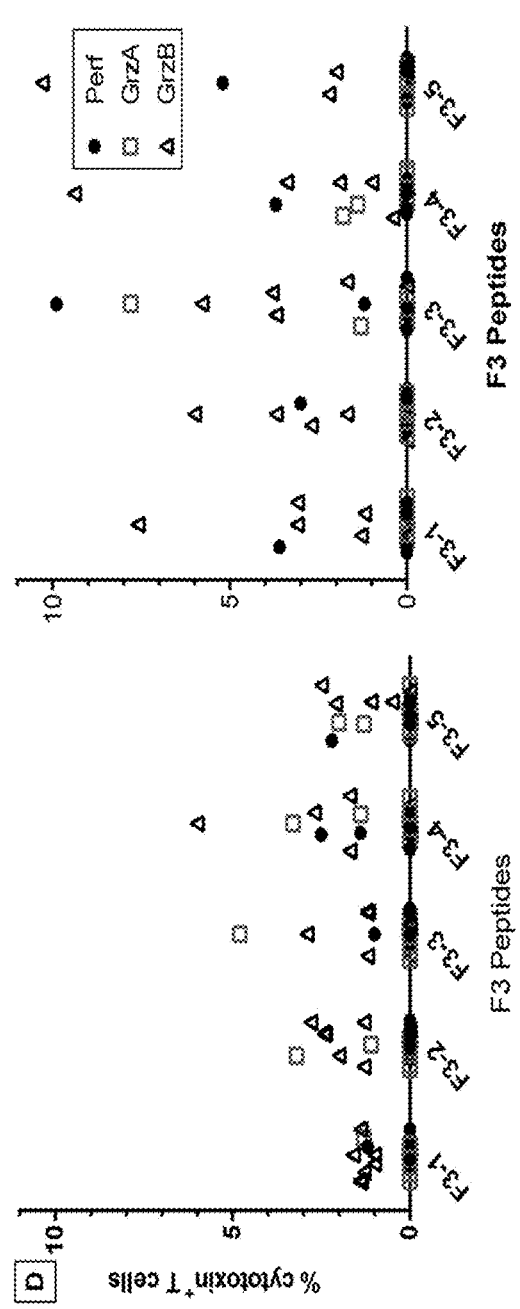

FIGS. 21A-21D. Characterization of CTL-associated epitopes on H6, H11, F3, and F6 pools. ICS analysis for perforin (Perf), granzyme A (GrzA), and granzyme B (GrzB) expression is shown for CD8+ T cells (left column) and CD4+ T cells (right column) from selected HIV+ responders of designated peptide pools (H6, n=8; H11, n=8; F3, n=11; F6, n=6; and PHA, n=12) (FIGS. 21A-21C). The HIV+ subjects (panel-A insert for FIGS. 21A-21C) consist of the following individuals: those with long-term infection without ART (LTS; black closed circle); those recently diagnosed, with short-term infection without ART (ST; grey closed circle); and those on ART with various duration of infection (ART+; open circle). The number of each clinical status group is the following for each peptide-pool group: H6 (4 LTS, 2 ST, 2 ART+), H11 (4 LTS, 1 ST, 3 ART+), F3 (5 LTS, 3 ST, 3 ART+), F6 (2 LTS, 2 ST, 2 ART+), and PHA (5 LTS, 3 ST, 4 ART+). Six F3-pool responders (5 LTS, 1 ART+) were tested for Perf (●), GrzA (□), and GrzB (△) responses to the five 13-15mer F3 peptides (FIG. 21D). Only three subjects were the same as those from above (FIGS. 21A-21C), but the blood was collected at a different timepoint.

Figure 22A:
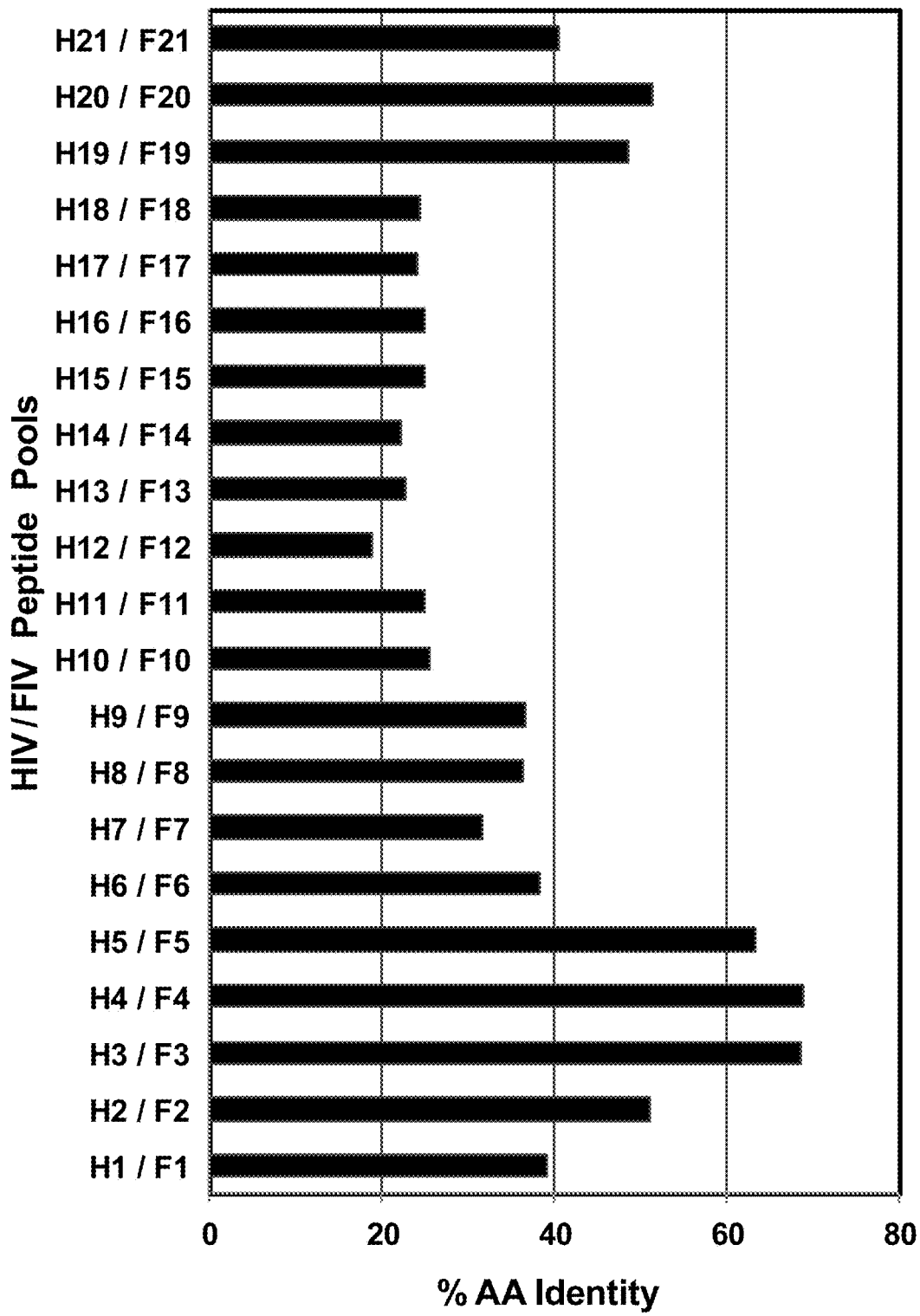
Figure 22B:
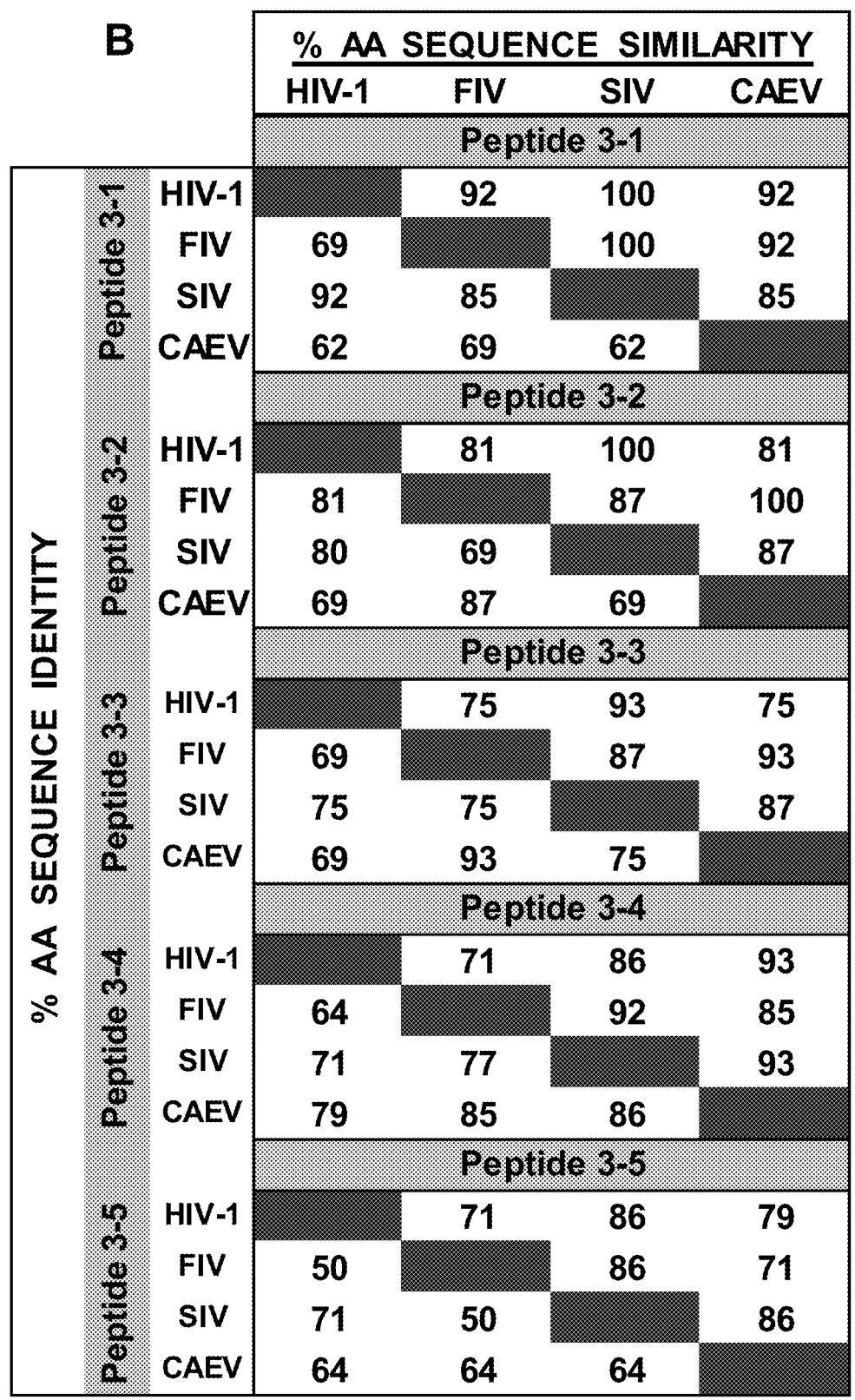

FIGS. 22A-22B. The aa sequence identity between counterpart HIV/FIV peptide pools and between various lentiviruses. The percentage of aa identity (FIG. 22A) between the sequences of each HIV (H) peptide pool and its counterpart FIV (F) peptide pool were obtained by alignment of the sequences using ebi.ac.uk/Tools/psa/emboss_needle/. Note that the highest aa identity observed is 68.7% with peptide-pools H4/F4 and the second highest is 66.7% with peptide-pools H3/F3. In FIG. 22B, the percentages shown on the right of the diagonal divider represent % aa sequence similarity and those on the left represent % aa sequence identity between the two viruses intersecting the value. The lentivirus strains compared are HIV-1HXB2 (GenBank K03455.1), FIVFC1 (DQ365597.1), SIVMm251 (AAB5-9906.1), and CAEV (AAG48629.1).

Figures 23A, 23B, 23C:
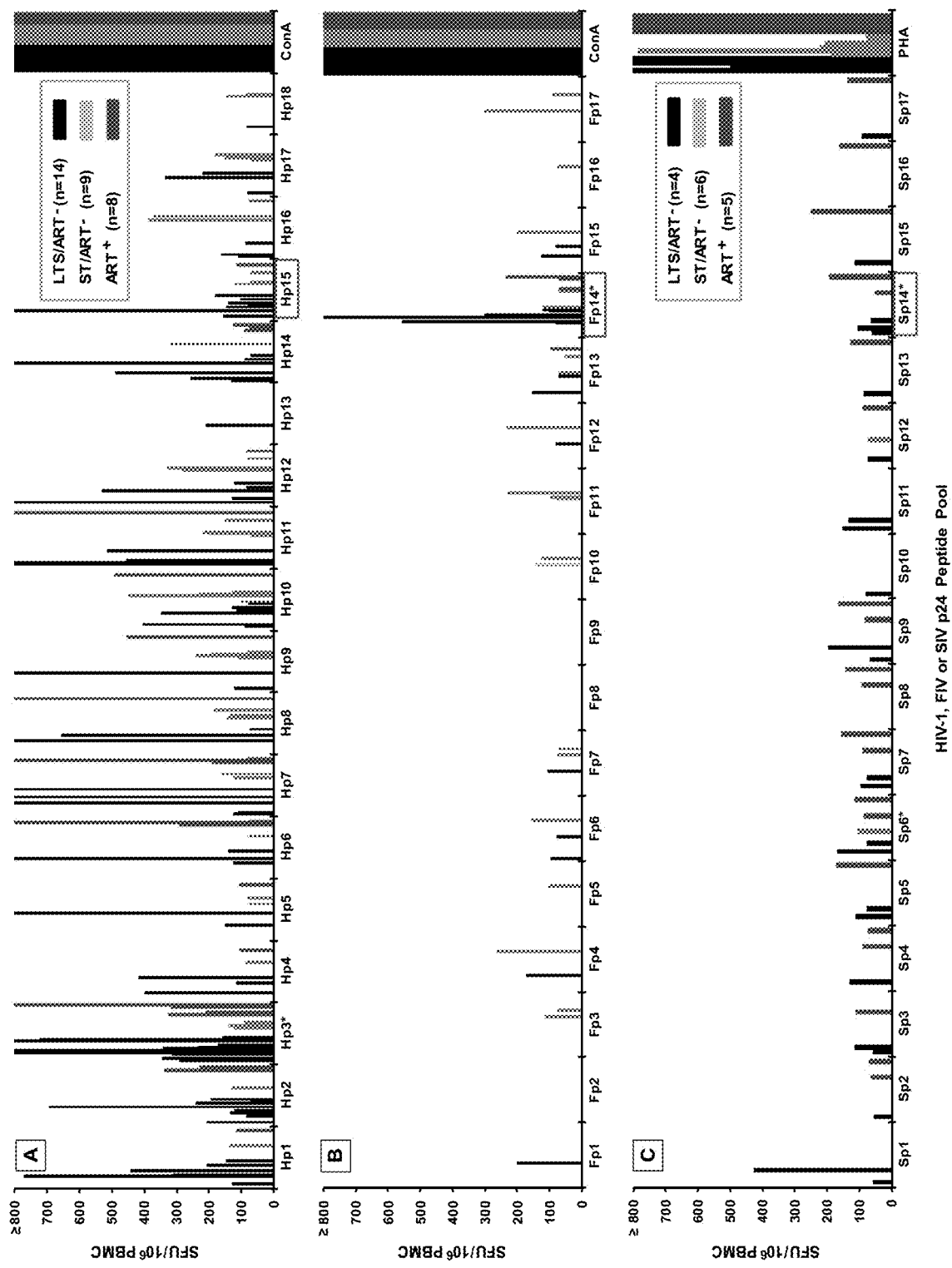

FIGS. 23A-23C. IFNγ responses to HIV, FIV and SIV p24 peptide pools. The IFNγ ELISpot responses to overlapping peptide pools of HIV p24 (Hp1-Hp18, n=31; FIG. 23A), FIV p24 (Fp1-Fp17, n=31; FIG. 23B), and SIV p24 (Sp1-Sp17, n=15; FIG. 23C) are depicted as spot forming units (SFU) per $10^6$ PBMC. The HIV$^+$ subjects (FIG. 23A insert for FIGS. 23A and 23B; FIG. 23C insert for FIG. 23C) consisted of long-term survivors (LTS) without antiretroviral therapy (ART) (LTS; black bar); recently diagnosed subjects (<1 year) with short-term infection without ART (ST; grey bar); and those receiving ART with various duration of infection (ART$^+$, red bar). Each bar represents a positive response by an individual subject with a threshold of >50 SFU per $10^6$ PBMC. Asterisk after the peptide pool(s) represent those with highest frequency of responders. The FIV p24 pool with the highest and the most frequent responses and its counterpart HIV-1 and SIV pools are highlighted in blue.

Figures 24A, 24B, 24C, 24D:
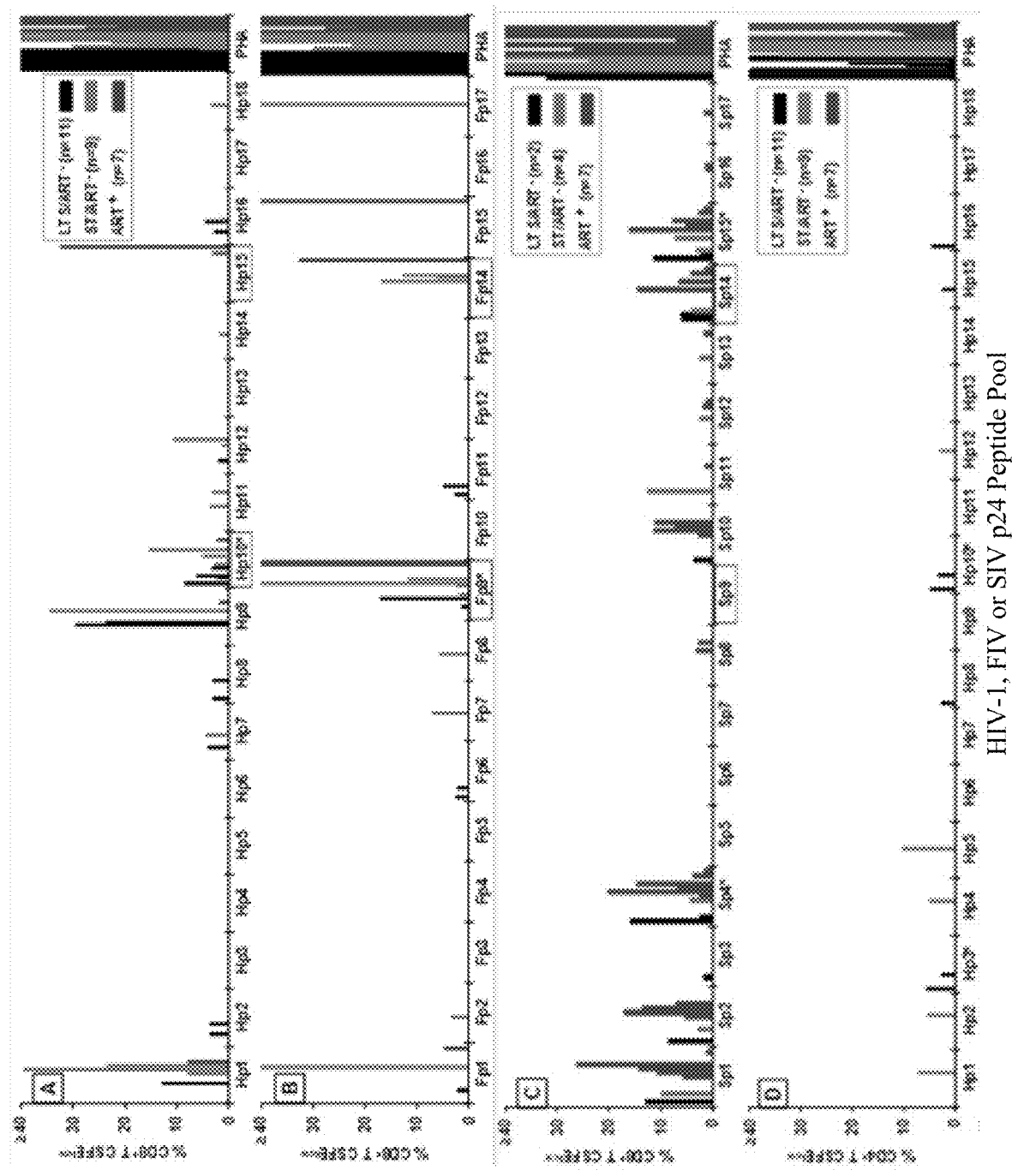

FIGS. 24A-24F. Proliferation responses to HIV, FIV and SIV p24 peptide pools. The CD3$^+$CD8$^+$ T-cell proliferation responses to overlapping peptide pools of HIV p24 (Hp1-Hp18, n=27; FIG. 24A), FIV p24 (Fp1-Fp17, n=27; FIG. 24B), and SIV p24 (Sp1-Sp17 n=13; FIG. 24C) are depicted as % CFSE$^{low}$ for CD3$^+$CD8$^+$ and CD3$^+$CD4$^+$ T-cell proliferation. The HIV$^+$ subjects (FIG. 24A insert for FIGS. 24A and 24B; FIG. 24C insert for FIG. 24C) consisted of long-term survivors (LTS) without ART (LTS; black bar); recently diagnosed subjects (<1 year) with short-term infection without ART (ST; grey bar); and those on ART with various duration of infection (ART$^+$, red bar). Each bar represents a positive response by an individual with a threshold of >1% CFSE$^{low}$ for CD3$^+$CD8$^+$ T-cell proliferation. Asterisk after the peptide pool(s) represents those with highest frequency of responders. The two FIV p24 pools with the highest and the most frequent responses and their counterpart HIV-1 and SIV pools are highlighted either in blue (Hp15/Fp14/Sp14) or red (Hp10/Fp9/Sp9).

Figures 25A, 25B:
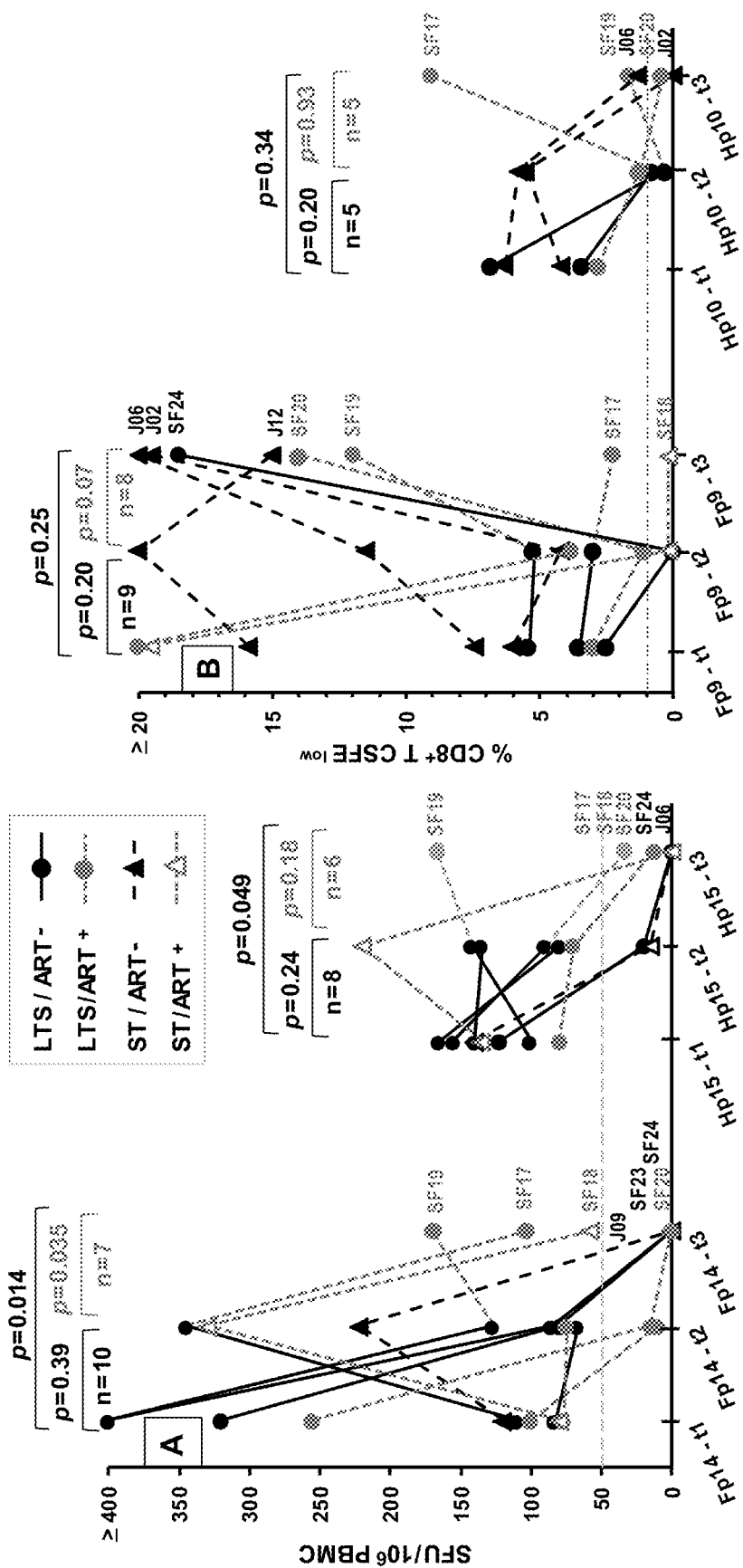

FIGS. 25A-25B. The persistence of IFNγ and T-cell proliferation responses to selected peptide pools. The IFNγ (FIG. 25A) and CD8$^+$ T cell proliferation (FIG. 25B) responses of HIV$^+$ subjects who responded at the first sample collection (t1), 2 yr later (t2), and 4 yr later (t3) are shown for peptide pool Fp14 (IFNγ), Hp15 (IFNγ), Hp10 (proliferation), and Fp9 (proliferation). The p-value indicates statistical differences between t1 and t2, t2 and t3, and t1 and t3. The threshold for IFNγ and proliferation responses are >50 SFU and >1% CFSE$^{low}$, respectively.

Figure 26A:
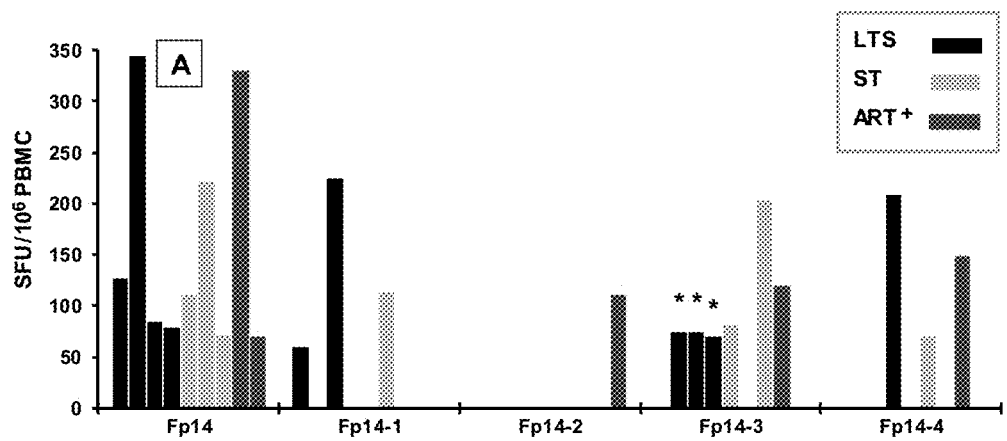
Figure 26B:
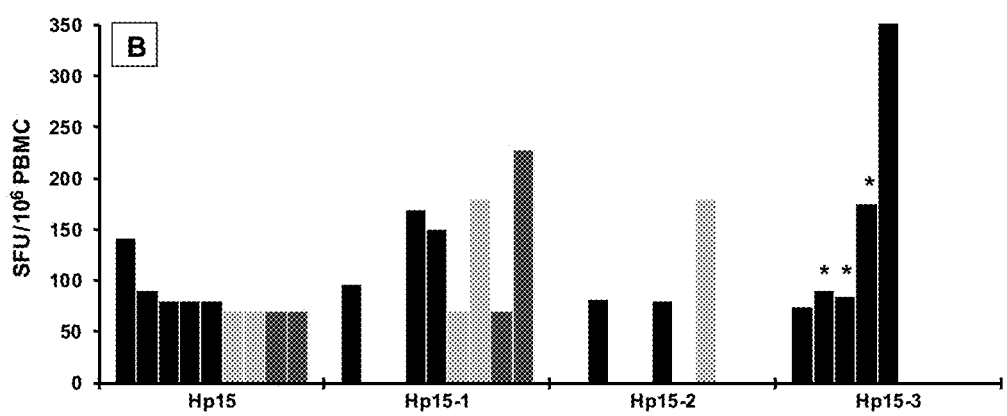
Figure 26C:
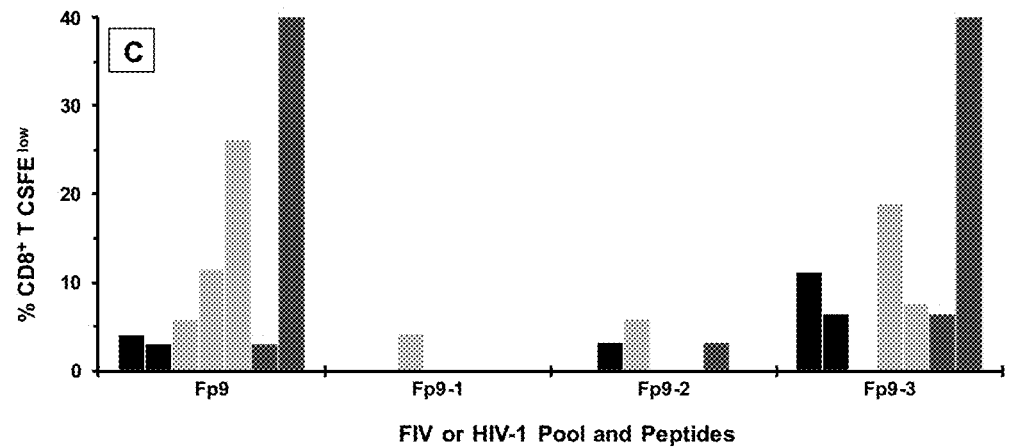

FIGS. 26A-26C. IFNγ and CD8$^+$ T-cell proliferation responses to Fp9, Fp14, and Hp15 peptide epitopes. Peptide pool Fp14 consists of four overlapping 13-15mer peptides spanning the amino- to carboxyl-terminus (Fp14-1, Fp14-2, Fp14-3, Fp14-4), while pools Hp15 (Hp15-1, Hp15-2, Hp15-3) and Fp9 (Fp9-1, Fp9-2, Fp9-3) each consist of three overlapping 13-15mer peptides. IFNγ responses to individual Fp14 peptides (FIG. 26A; n=9), Hp15 peptides (FIG. 26B; n=9) and CD8$^+$ T-cell proliferation responses to individual Fp9 peptides (FIG. 26C; n=7) are shown along with responses to their corresponding peptide pools. Only responders to pools Fp14 (FIG. 26A), Hp15 (FIG. 26B), and Fp9 (FIG. 26C) were tested. The responders consisted of long-term survivors (LTS) without ART (LTS; black bar); recently diagnosed subjects (<1 year) with short-term infection without ART (ST; grey bar); and those on ART with various duration of infection (ART$^+$, red bar). Each bar with (*) in panels A and B are from the same three LTS.

FIGS. 27A-27F. IFNγ and T-cell proliferation responses to 9-13mers of FIV peptides Fp9-3, Fp14-3, and Fp14-4. Six 9-12mer peptides for the Fp9 pool (FIGS. 27A, 27C, 27E) and seven 9-13mer peptides for the Fp14 pool (FIGS. 27B, 27D, 27F) described in Table 13 were tested for their ability to induce CD8$^+$ T-cell proliferation (FIGS. 27A and 27B), CD4$^+$ T-cell proliferation (FIGS. 27C and 27D), and IFNγ production (FIGS. 27E and 27F) and compared to results with the Fp9 and Fp14 peptide pools. 13-15mer peptides Fp9-3, Fp14-3, and Fp14-4; and mitogen (PHA) were included as controls. A total of nine HIV$^+$ responders to the Fp9 pool (FIGS. 27A, 27C, 27E) and 10 HIV$^+$ responders to the Fp14 pool (FIGS. 27B, 27D, 27F) were tested up to 4 yr after the beginning of the study. Two to four of the responders were lost to follow up. Their proliferation and IFNγ results to the 13-15mer peptides Fp9-3, Fp14-3, and Fp14-4, and are denoted with an (*) for each individual missing.

Figures 28A, 28B:
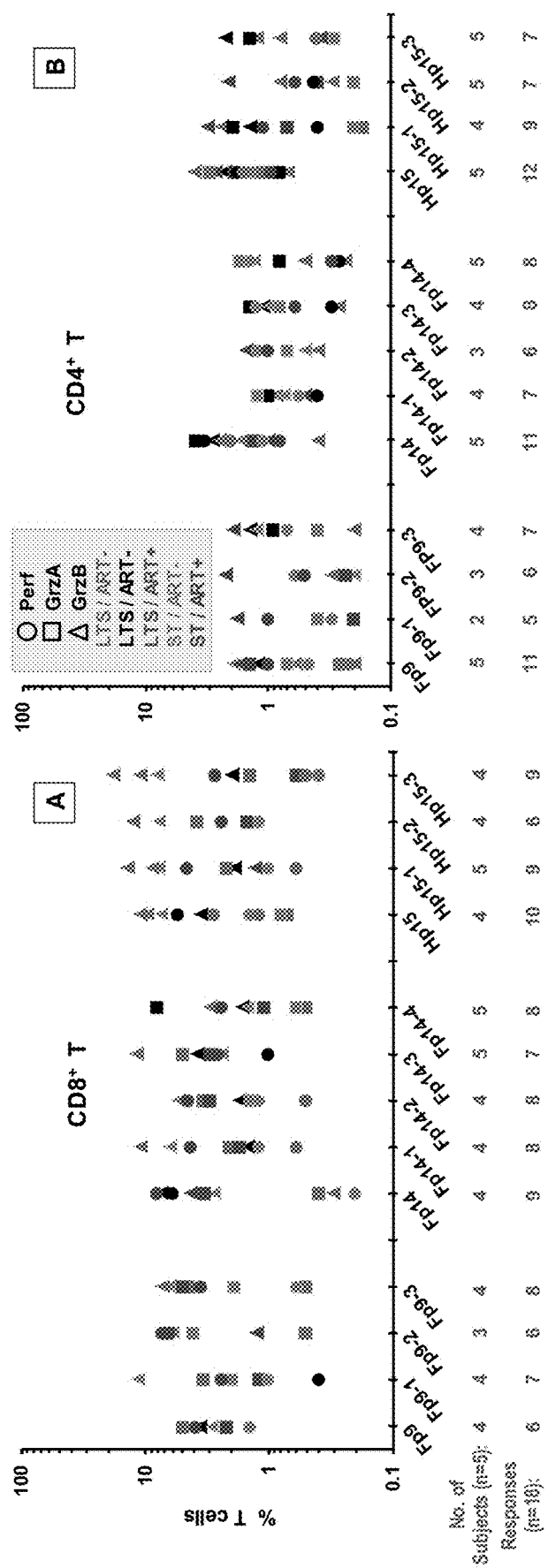
Figures 28C, 28D:
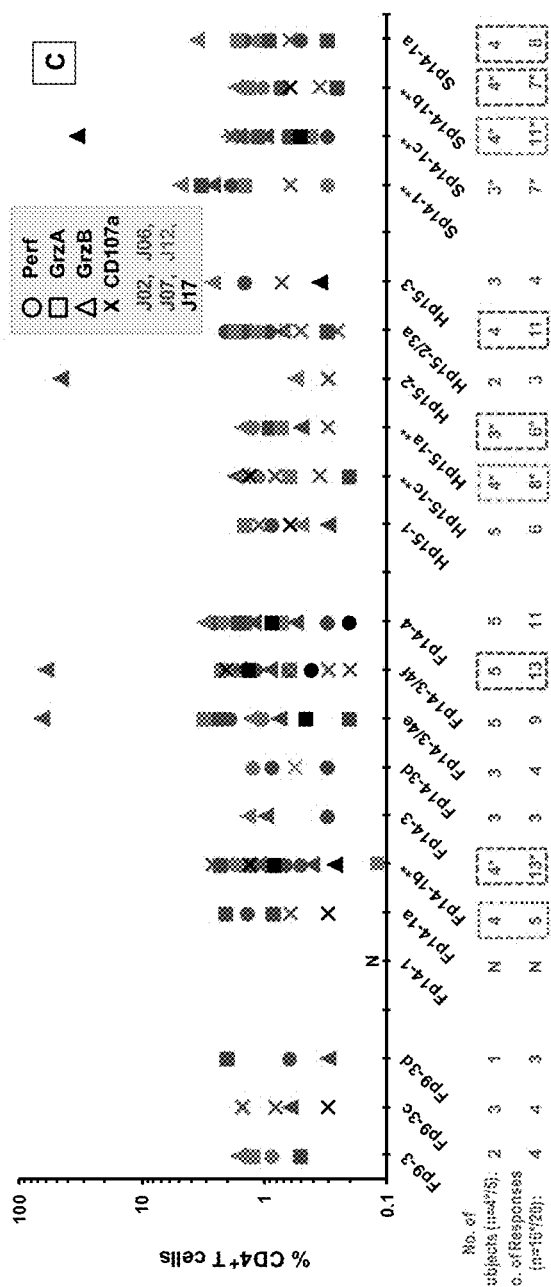

FIGS. 28A-28D. Stimulation of cytotoxins by CTL epitopes on Fp9, Fp14, and Hp15 peptide pools, and their individual peptides. The ICS analyses for perforin (Perf, ○), granzyme A (GrzA, □), and granzyme B (GrzB, Δ) are shown for CD8$^+$ T cells (FIGS. 28A, 28D) and CD4$^+$ T cells (FIGS. 28B, 28C) from five HIV$^+$ responders with or without ART. Two LTS/ART$^-$, one LTS/ART$^+$, one ST/ART$^+$, and one ST/ART$^-$ were first evaluated (FIGS. 28A, 28B). Peptides tested included Fp9, Fp14, and/or Hp15 peptide pools or large 13-15mer peptides (FIGS. 28A, 28B). Responses from five HIV$^+$ responders of short-term HIV-infected subjects not on ART (ST/ART$^-$) were tested using small 9-13mer peptides within Fp9-3, Fp14-1, Fp14-3, Fp14-4, and Sp14-1 (FIG. 28C, 28D). Note that Sp14 pool is a single 13mer peptide Sp14-1. Counterpart peptides are shown with blue-dashed box for Fp14-1a/Hp15-1c/Sp14-1c, purple-dashed box for Fp14-1b/Hp15-1a/Sp14-1b, and red-dashed box for Fp14-3/4f/Hp15-2/3a/Sp14-1a. The peptides tested with one less subject are denoted by (**), while their number of subjects and number of responses are denoted by (*). Each separate symbol color represents one subject, and each color-coded subject is shown with his/her infection status. The threshold for T cells expressing cytotoxin is set at >0.1% CD4$^+$ or CD8$^+$ T cells.

Figure 29:
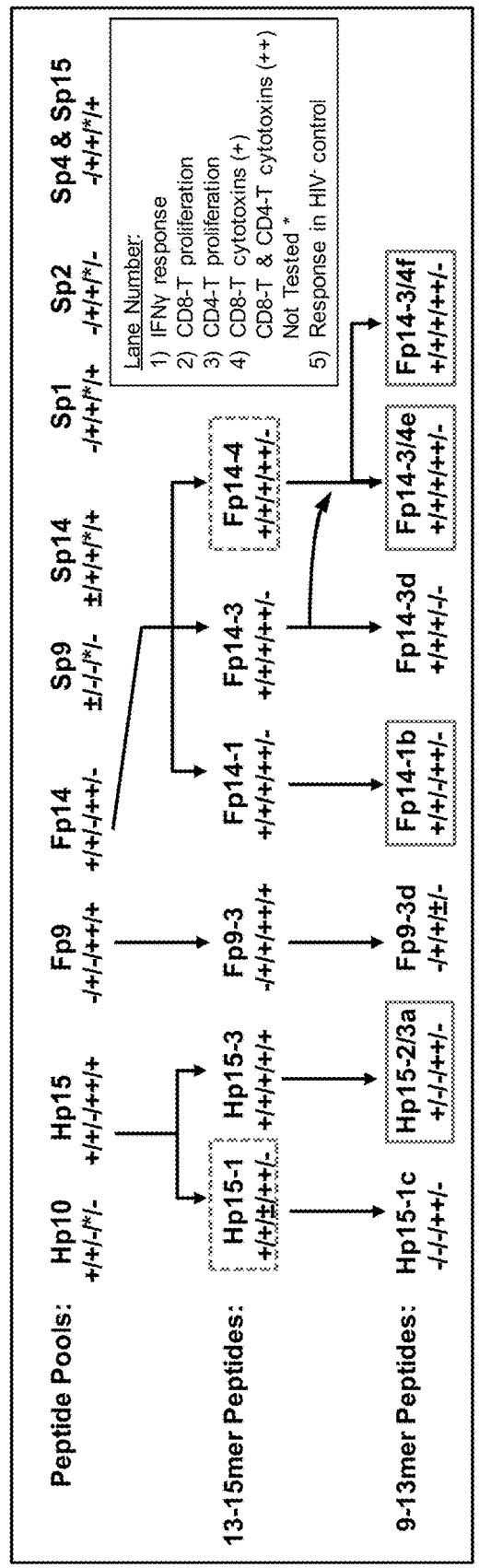
Figures 30A, 30B:
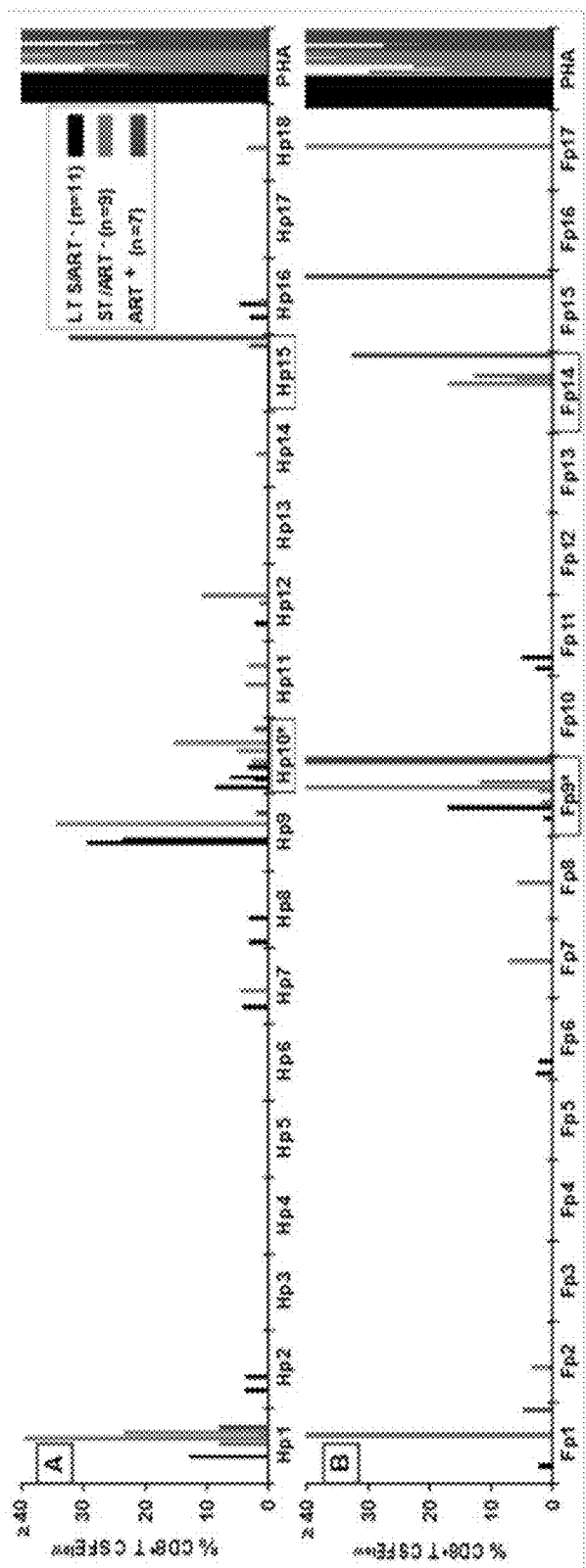
Figures 30C, 30D:
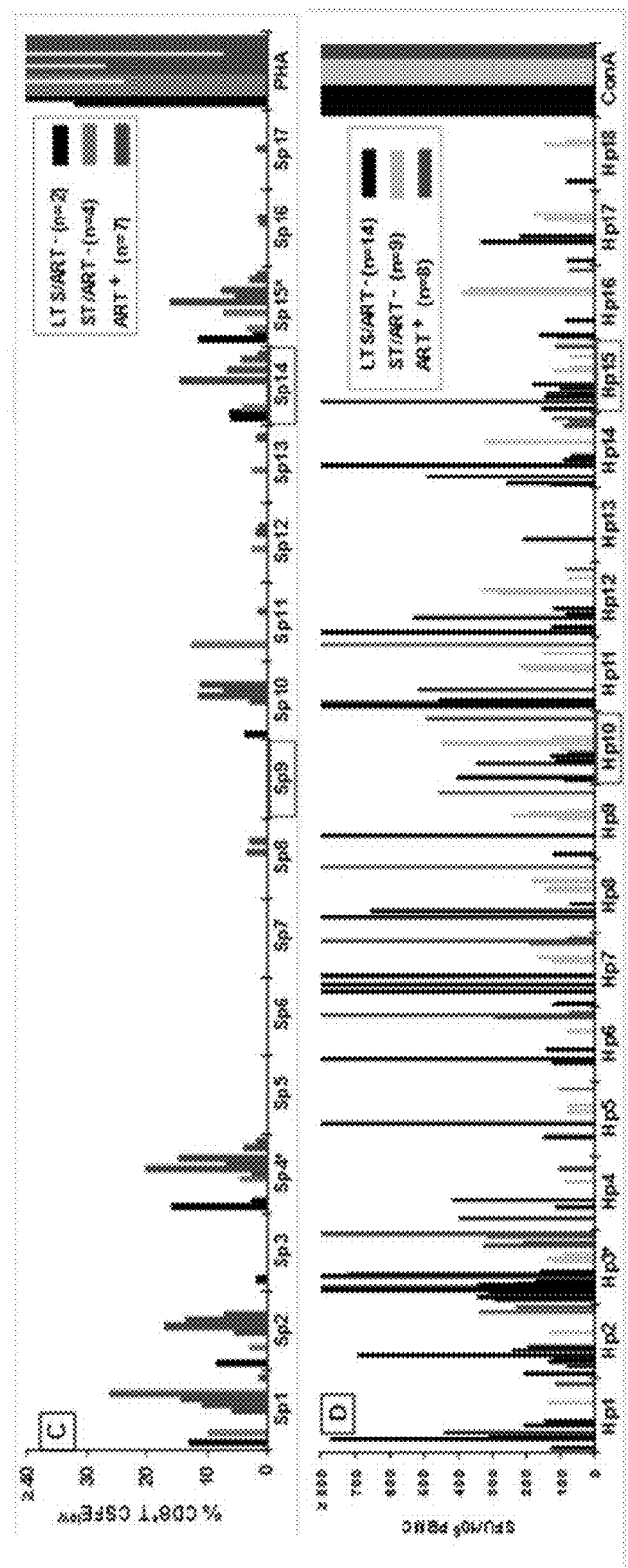
Figures 30E, 30F:
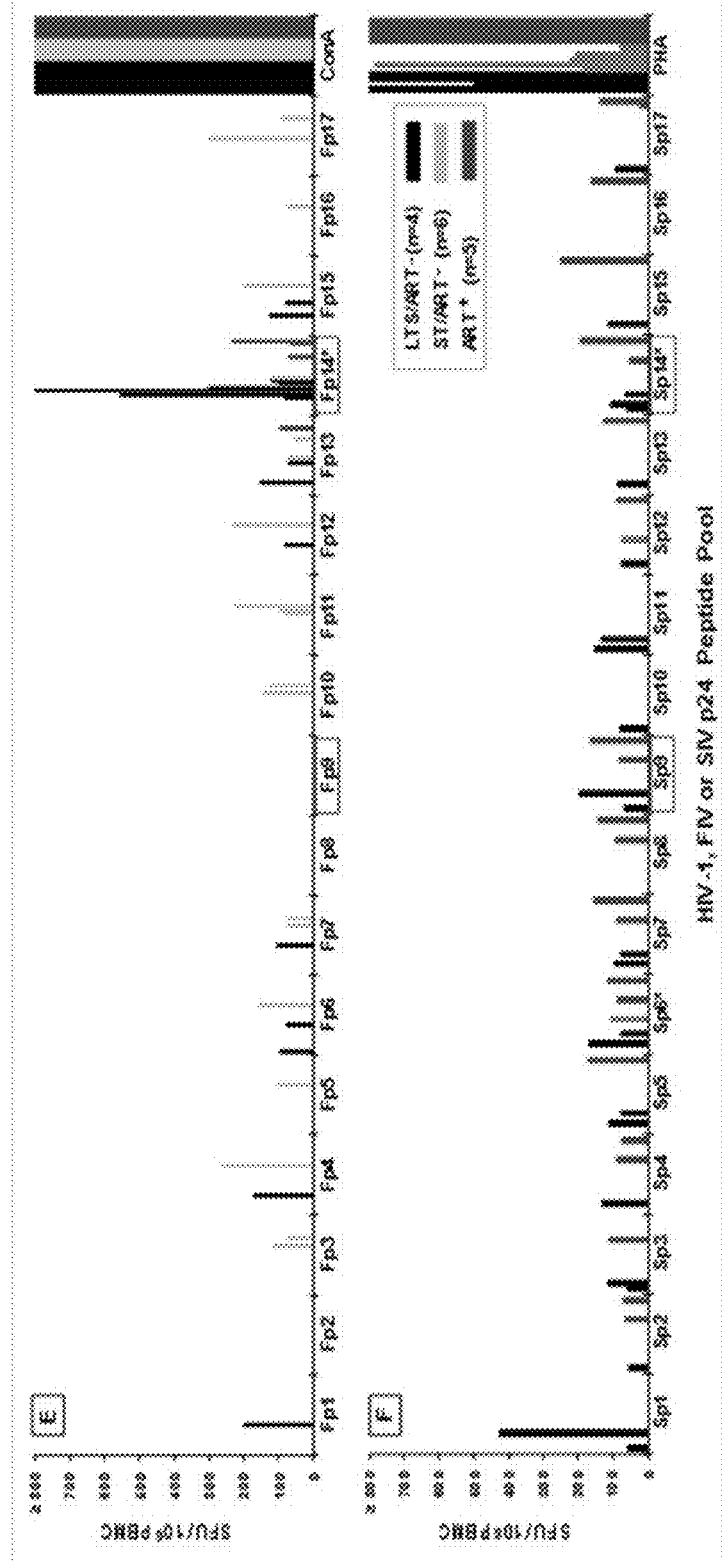

FIG. 29. Summary of functional epitope analyses. Results from three functional analyses are summarized according to frequency of HIV$^+$ (lanes 1-4) or HIV$^-$ (lane 5) responders and are shown as (+) for frequency of >25% responders, (±) for 19-25% responders, (−) for <19% responders, or as (*) for not available. Each lane, abridged in the insert, shows the ability of the peptide pool or peptide to stimulate an IFNγ response (lane 1), CD8$^+$ T-cell proliferation (lane 2), and CD4$^+$ T-cell proliferation (lane 3). Lane 4 denotes the ability to induce cytotoxin(s) in only CD8$^+$ T cells (+) or in both CD8$^+$ and CD4$^+$ T cells (++) by four or more HIV$^+$ subjects when at least nine subjects tested. In lane 5, the positive result (+) indicates substantial frequency of proliferation responses from HIV subjects and may indicate a safety concern; whereas a negative result (−) indicates no substantial HIV$^-$ response to the peptide pool or peptide. Positive response of HIV control had CD8$^+$ T-cell proliferation response in 30-42% of HIV$^-$ subjects. The large 13-15mer peptides with the best CMI responses without stimulation in HIV subjects are shown with dashed boxes, while the best small peptides are shown with solid boxes. Therefore, Hp15-1, Hp15-2/3a, Fp14-4, Fp14-1b, Fp14-3/4e, and Fp14-3/4f peptides appear to contain the best potential epitopes to target for use as HIV immunogens.

FIGS. 30A-30F. CD8$^+$ T-cell proliferation (FIGS. 30A-30C) and IFNγ (FIGS. 30D-30F) responses to HIV-1, FIV, and SIV p24 peptide pools by HIV+ subjects (Roff et al. 2015). The PBMCs were stimulated with HIV-1 (Hp1-Hp18) (FIGS. 30A, 30D) and corresponding SIV (Sp1-Sp17) (FIGS. 30C, 30F) and FIV (Fp1-Fp17) (FIGS. 30B, 30E) p24 peptide pools at 5 μg/mL peptide pool for proliferation and 6-8 μg pool/well for IFNγ. Positive control cultures were stimulated with T-cell mitogen phytohemagglutinin A (PHA) or concanavalin A (ConA) each at 5 μg/mL. The PBMCs and T cells were from long-term survivors (LTS, black bar), subjects with short-term infection without ART (ST, grey bar), and subjects on ART at various duration of infection (ART+, red bar). The results are shown after subtraction of the individual media control and responses to each peptide pool by PBMC or T cells from HIV-negative subjects. The HIV counterpart for FIV and SIV pools is offset by one additional pool starting from Fp7/Sp7 and therefore HIV counterpart for Fp9/Sp9 and Fp14/Sp14 are Hp10 and Hp1, respectively. They are shown with red and blue boxes for Hp10/Fp9/Sp9 and Hp15/Fp14/Sp14, respectively.

Figures 31A, 31B:
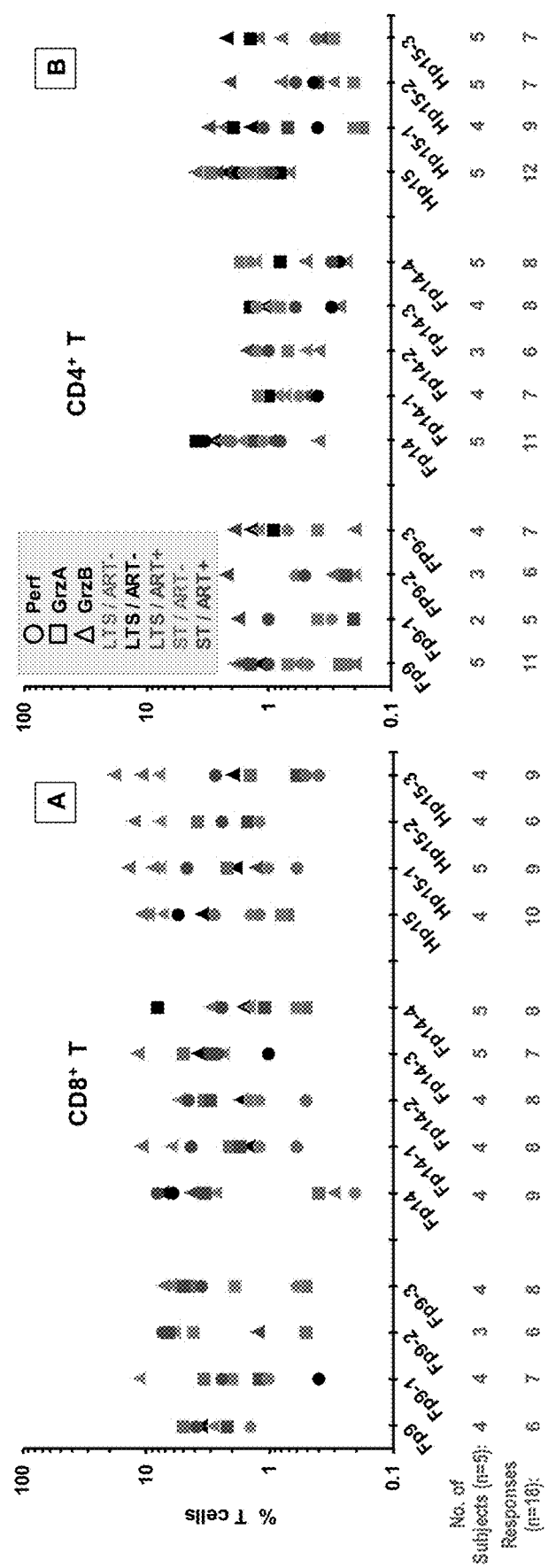

FIGS. 31A and 31B. Stimulation of cytotoxins by CTL epitopes on Fp9, Fp14, and Hp15 peptide pools, and their individual peptides by HIV+ subjects. The intracellular cytotoxin staining (ICS) analyses for perforin (Perf, ○), granzyme A (GrzA, □), and granzyme B (GrzB, Δ) are shown for CD8+ T cells (FIG. 31A) and CD4+ T cells (FIG. 31B) from five HIV+ responders with or without ART. Two LTS/ART−, one LTS/ART+, one ST/ART+, and one ST/ART− were first evaluated (FIGS. 31A, 31B). Peptides tested included Fp9, Fp14, and/or Hp15 peptide pools or large 13-15mer peptides (FIGS. 31A, 31B). Each separate symbol color represents one subject, and each color-coded subject is shown with his/her infection status. The threshold for T cells expressing cytotoxin is set at >0.1% CD4+ or CD8+ T cells. Additional five ST/ART− subjects are shown in FIG. 6 of reference (Roff et al. 2015).

Figures 32A, 32B:
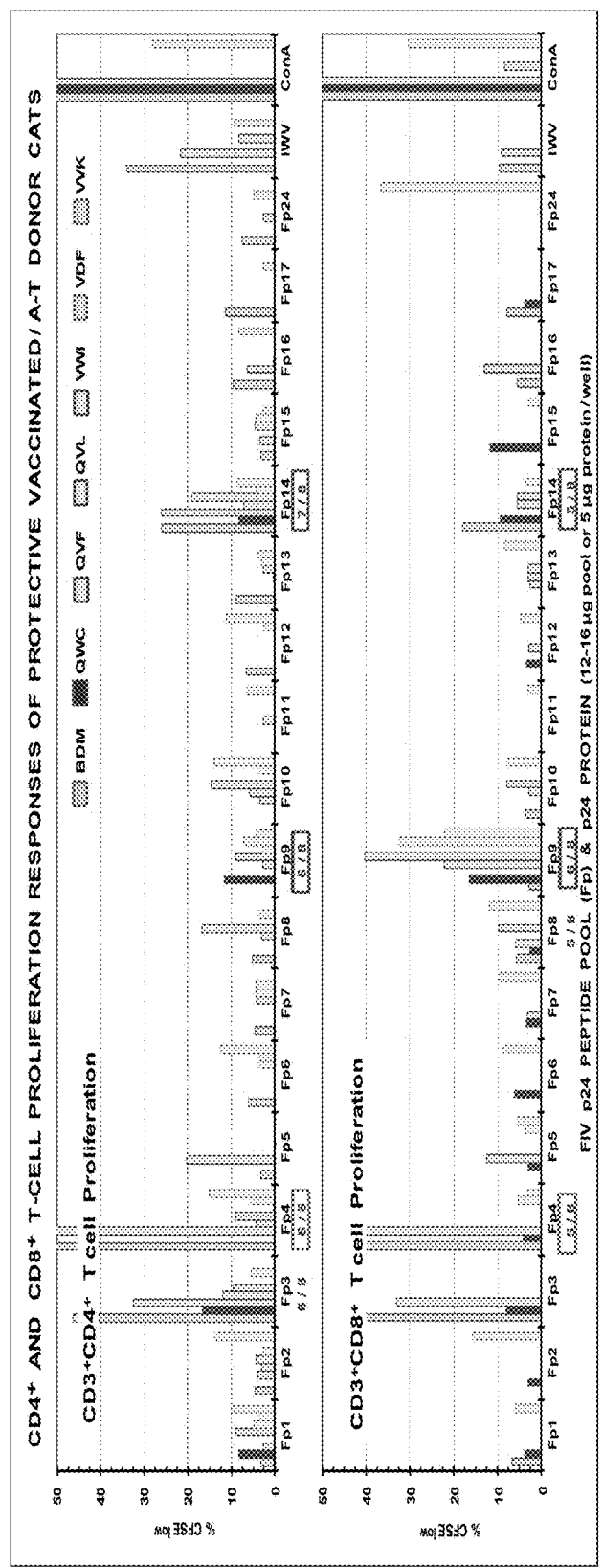

FIGS. 32A and 32B. T-cell proliferation responses to FIV p24 peptide pools by vaccinated cats. CD8+CD4+ (FIG. 32A) and CD3+CD8+ (FIG. 32B) T-cell proliferation responses are shown for prototype FIV-vaccinated cats. The FIV vaccinated cats were semi-inbred cats with blue, dark red, and pink/green bars from different MHC-lineage colonies. The semi-inbred cats with light pink and green bars are from the same MEW lineage. Pools Fp9 and Fp14 are recognized by both HIV+ subjects and vaccinated cats (i.e., evolutionarily conserved [EC] epitopes) but pools Fp3 and Fp4 are not recognized by HIV+ subjects (i.e., non-EC epitopes). The IFNγ responses of these cats were either low or below the cut-off threshold of 50 SFU/1×10⁶ PBMC. The peptides that stimulated the most proliferation responses: non-EC peptide Fp4-3 in pool Fp4 and EC peptide Fp14-1 in pool Fp14 were used in in vivo study below (FIG. 34).

Figure 33A:
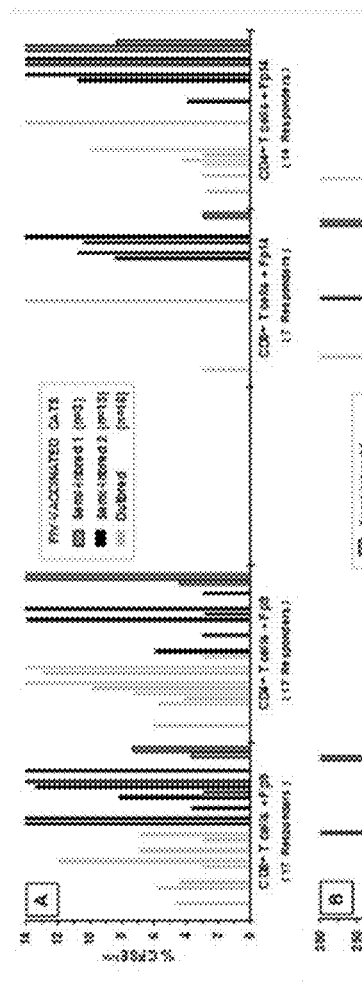
Figure 33B:
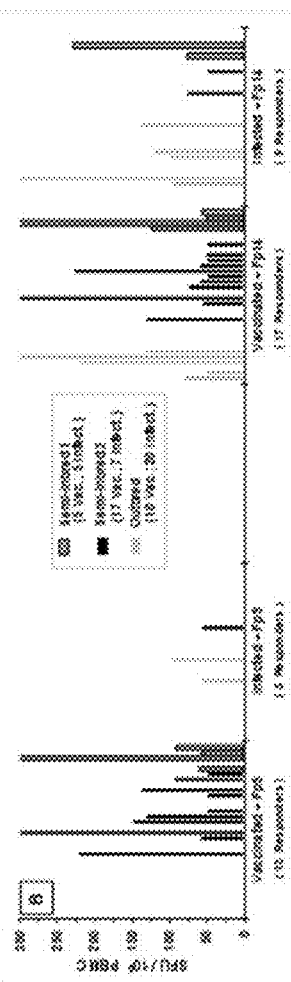
Figure 33C:
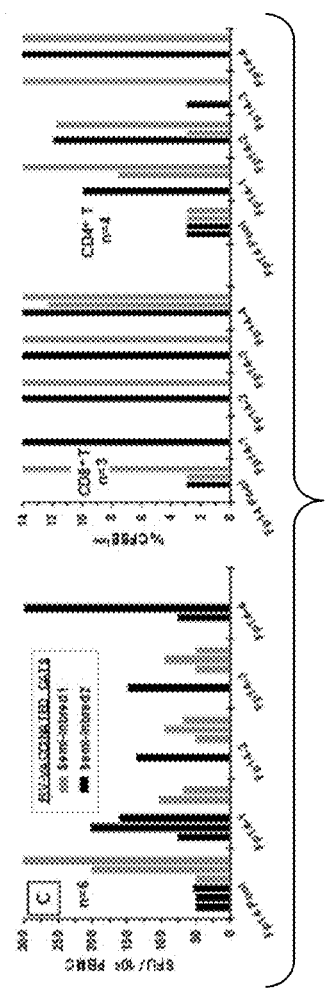

FIGS. 33A-33C. IFNγ and T-cell proliferation responses to Fp9 and Fp14 by the FIV-vaccinated cats and FIV-infected cats. The T cells or PBMC from 32 FIV-vaccinated cats were stimulated with either Fp9 or Fp14 and evaluated for proliferation (FIG. 33A) or IFNγ (FIG. 33B) responses. In addition, the PBMC from 32 FIV-infected cats at 22-52 weeks of infection and 20 HIV-1 p24-immunized cats were tested for IFNγ responses to the same peptide pools (FIG. 33B). Three types of laboratory cats were used in these studies: semi-inbred line 1 (Semi-Inbred 1), semi-inbred line 2 (Semi-Inbred 2), and outbred cats (Outbred) from laboratory cat vendors. Semi-inbred cats have been inbred for 3-5 generations with defined feline leukocyte antigen (FLA) alleles and are divided into two FLA haplotype lines. FIV vaccine consisted of prototype dual-subtype FIV vaccine (Coleman et al. 2014). The insert in each panel defines the numbers of each type of cats as well as vaccination (Vac.) or infection (Infect.) status. The number of cat responders used varies between the analyses performed for the individual Fp14 peptides (FIG. 33C, left for IFNγ and right for proliferation).

Figure 34:
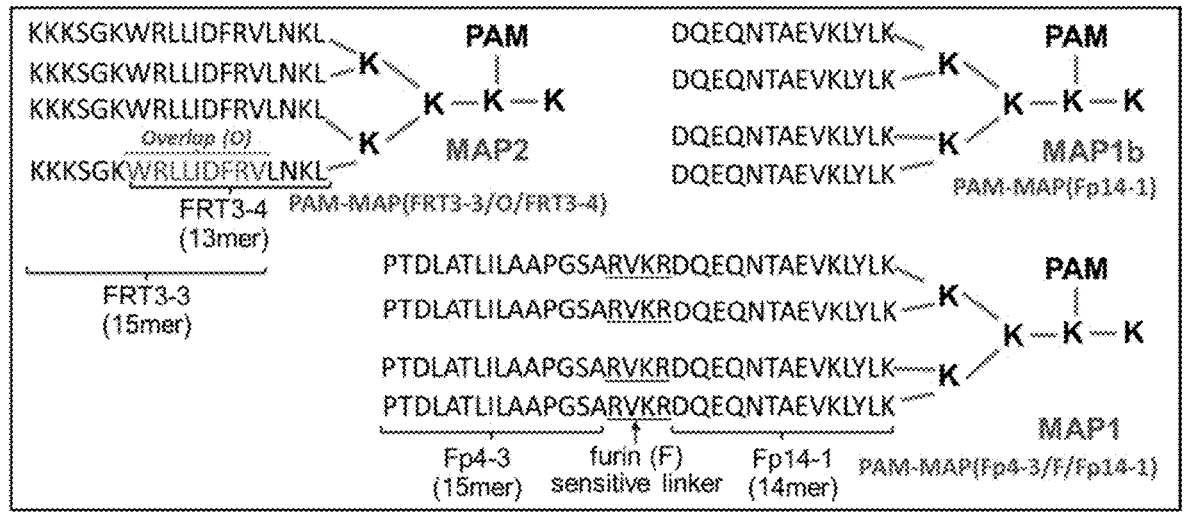

FIG. 34. 3 MAPs with 1-2 FIV peptides for Table 17. (KKKSGKWRLLIDFRVLNKL (SEQ ID NO:491); DQEQNTAEVKLYLK (SEQ ID NO:301); PTDLATLILAAP-GSARVKRDQEQNTAEVKLYLK (SEQ ID NO:493)). These peptides stimulate IL-2 and IFNγ responses in T cells from FIV-vaccinated cats. Two different formulations of lipophylic (palmitate C16, PAM) MAP were mixed in FD-1 adjuvant and immunized in prototype vaccine-primed SPF cats. Furin-sensitive sequence (RVKR) (SEQ ID NO:494) was used to link the two peptides (Nakayama 1997; Kotterman and Schaffer 2014). After entering the cell, the peptide chains can enter the endoplasmic reticulum and trans-Golgi network, where the furin processes the furin sensitive sequence into two peptides. Subsequently, these peptides bind to MEW. The peptide-MHC complexes are then transported to the cell surface where they interact with T cells.

Figure 35:
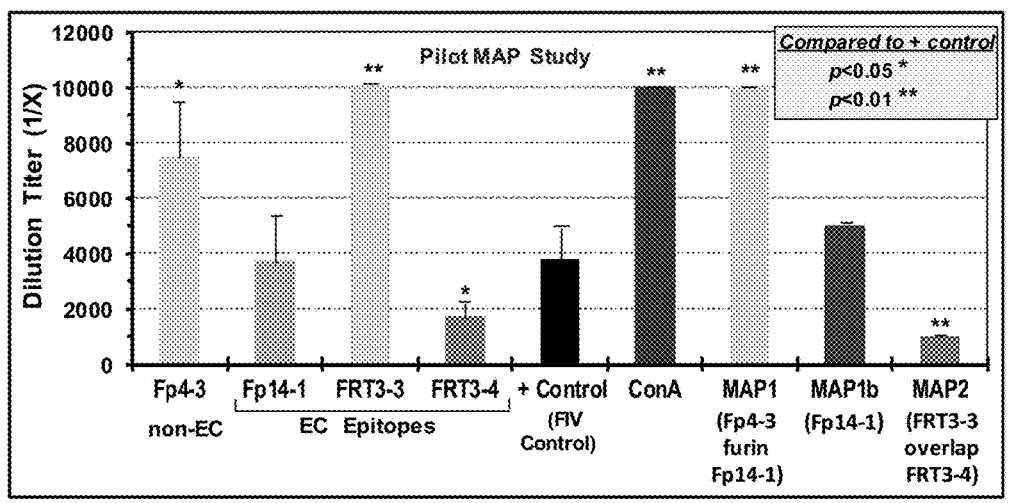

FIG. 35. FIV-enhancing versus inhibitory epitopes on peptides and MAPs used in pilot MAP Study. Statistically significant enhancement (Fp4-3, FRT3-3, MAP1) and inhibition (FRT3-4, MAP2) of in vitro FIV infection in the PBMC from naïve cats are shown. Virus+control, FIV-enhancing mitogen (ConA) control, and uninfected cell control had an average RT titer (cpm/mL) of 26,518 (1:500 dilution), 54,634 (1:10000) and 2612 (1:500), respectively. Abbreviation: MAP1 plus MAP2 mix (MAP1+2).

Figures 36A, 36B:
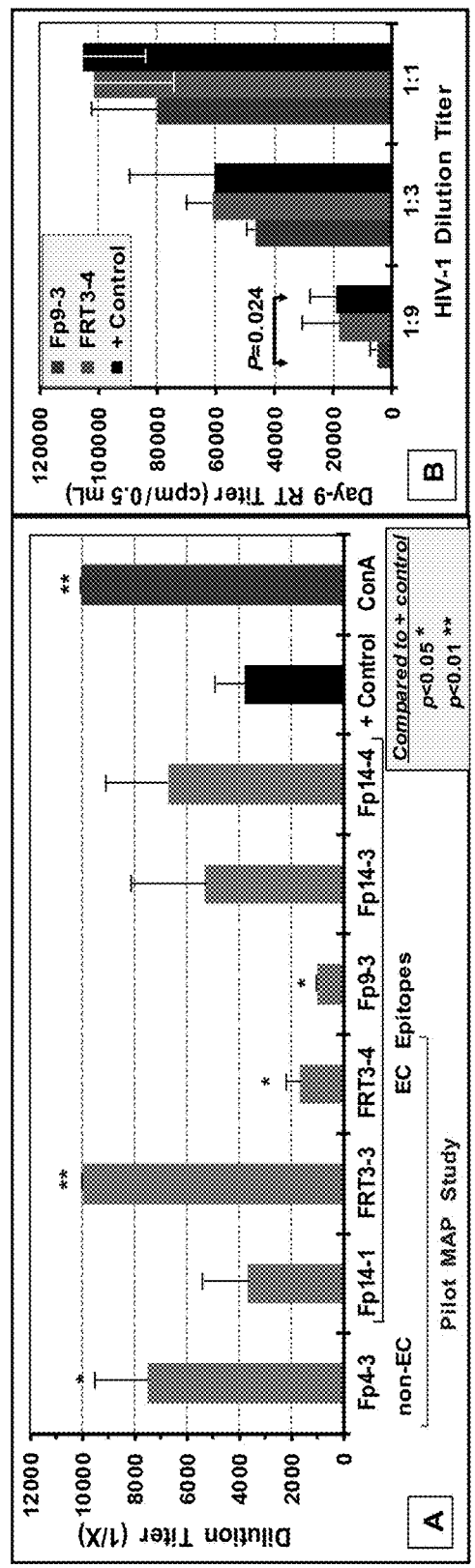

FIG. 36A and 36B. FIV/HIV-1 enhancing versus inhibitory epitopes. Statistically significant enhancement (Fp4-3 & FRT3-3) and inhibition (Fp9-3 & FRT3-4) of FIV infection of naïve cat PBMC were observed (FIG. 36A). Virus positive (+) control, enhancement-positive mitogen (concanavalin A, ConA) control, and uninfected cell control had an average RT titer of 26,518 cpm/mL (1:500 dilution), 54,634 cpm/mL (10,000 dilution), and 2612 cpm/mL (1:500 dilution), respectively (85,000 cpm/mL stock). Four epitope peptides were tested in an in vivo efficacy study with prototype vaccine prime and MAP boosts against pathogenic FIV challenge (see MAP section). Notably, inhibition of HIV-1 infection of normal human PBMC was observed with peptide Fp9-3 (lowest dose, p=0.024) but not with peptide FRT3-4 (FIG. 36B) (92,000 cpm/mL stock).

BRIEF DESCRIPTION OF THE SEQUENCES

SEQ ID NOs:1-40 are epitopes contemplated within the scope of the invention.

SEQ ID NOs:41 and 42 are chimeric polynucleotides of the present invention.

SEQ ID NOs:43 and 44 are chimeric polypeptides encoded by a chimeric polynucleotide of the invention.

SEQ ID NOs:45-450 are epitopes contemplated within the scope of the invention.

SEQ ID NOs: 451-591 are epitopes contemplated within the scope of the invention.

DETAILED DESCRIPTION OF THE INVENTION

The subject invention concerns methods and materials for providing an immune response in an animal or person against an immunodeficiency virus, such as HIV, SIV, or FIV. In one embodiment, a method of the invention comprises administering one or more antigens and/or immunogens to the person or animal wherein the antigen or immunogen comprises one or more epitopes evolutionarily conserved between different immunodeficiency viruses. In one embodiment, the epitope is one that is conserved between HIV and SIV, or between HIV and FIV. In another embodiment, the epitope is conserved between FIV and SIV. In another embodiment, the epitope is one that is conserved between HIV, SIV, and FIV. In one embodiment, where a human is administered the antigen and/or immunogen, the antigen or immunogen is from an FIV or HIV, and the epitope is evolutionarily conserved between HIV and FIV. In one embodiment, where the animal is a feline animal, the antigen and/or immunogen is from an HIV or FIV, and the epitope is evolutionarily conserved between HIV and FIV. In one embodiment of a method of the present invention, the epitope is a T-cell epitope. In a specific embodiment, the epitope induces one or more T cell responses, such as release of cytotoxins (e.g., perforin, granzymes, and/or granulysin) and/or cytokines (IFNγ, TNF-α, IL-2, IL-4, IL-5, IL-9, IL-10, IL-13, etc.). In a specific embodiment, the T-cell epitope is a cytotoxic T lymphocyte (CTL), polyfunctional T cell epitope, and/or T-helper (Th) epitope. Antigens and immunogens of the invention can be peptides and/or proteins that comprise one or more evolutionarily conserved epitopes of the invention.

Examples of epitopes contemplated within the scope of the invention include peptides or proteins comprising the amino acid sequence shown in any of SEQ ID NOs:1-40 or in any of SEQ ID NOs:45-591, independently or any possible combination thereof, or in any of the examples, figures or tables of the subject application, or an immunogenic fragment or variant of the amino acid sequence. In a specific embodiment, a peptide or protein of the invention comprises the amino acid sequence shown in any of SEQ ID NOs:10, 21, 22, 23, 61, 62, 63, 64, 65, 163, 164, 165, 166, 167, 176, 177, 178, 179, 214, 215, 216, 217, 218, 288, 301, 303, 304, 359, 361, 431, 432, 438, 442, 443, 453, 459, 460, 466, 479, 488, 492, and/or 493. In one embodiment, a plurality of peptides and/or proteins comprising an epitope of the invention are administered to the person or animal. For example, in one embodiment, two or more peptides or proteins comprising the amino acid sequence of any of SEQ ID NOs:10, 21, 22, 23, 61, 62, 63, 64, 65, 163, 164, 165, 166, 167, 176, 177, 178, 179, 214, 215, 216, 217, 218, 288, 301, 303, 304, 359, 361, 431, 432, 438, 442, 443, 453, 459, 460, 466, 479, 488, 492, and/or 493 are administered. For example, a first peptide comprising SEQ ID NO:61 and a second peptide comprising SEQ ID NO:63 can be administered. In another embodiment, a peptide or protein comprising two or more epitopes of the present invention is administered to the person or animal. In one embodiment, the peptide or protein can comprise two or more epitopes by linking two or more peptide sequences of the invention together, or by having a polynucleotide encode two or more peptide sequences together in a single protein, and expressing the polynucleotide to produce the protein. In one embodiment, a peptide or protein comprising two or more amino acid sequences shown in any of SEQ ID NOs:10, 21, 22, 23, 61, 62, 63, 64, 65, 163, 164, 165, 166, 167, 176, 177, 178, 179, 214, 215, 216, 217, 218, 288, 301, 303, 304, 359, 361, 431, 432, 438, 442, 443, 453, 459, 460, 466, 479, 488, 492, and/or 493 is administered to the person or animal. In a specific embodiment, a peptide or protein comprising the amino acid sequence of SEQ ID NO:63 and/or SEQ ID NO:64 is administered to the person or animal. In yet another embodiment, a peptide or protein utilized in the present invention comprises an amino acid sequence shown in any of SEQ ID NO:10, SEQ ID NO: 21, SEQ ID NO:22, or SEQ ID NO:23. In a further embodiment, a peptide or protein utilized in the present invention comprises an amino acid sequence shown in any of SEQ ID NOs:176, 177, 178, 179, 214, 215, 216, 217, or 218. In yet a further embodiment, a peptide or protein utilized in the present invention comprises an amino acid sequence shown in any of SEQ ID NO:288, SEQ ID NO:301, SEQ ID NO:303, SEQ ID NO:304, SEQ ID NO:359, SEQ ID NO:361, SEQ ID NO:453, SEQ ID NO:459, SEQ ID NO:460, SEQ ID NO:466, SEQ ID NO:479, SEQ ID NO:488, 492, and/or 493.

In one embodiment, the immune response induced by a method of the present invention is a T cell response, such as a CTL-associated immune response and/or a T helper cell response. In a specific embodiment, the immune response induced by a method of the present invention comprises CD4+ and/or CD8+ T cell responses, and/or gamma interferon (IFNγ) production. In one embodiment, cytotoxins (such as perforin, granzyme A, granzyme B, etc.) and/or cytokines (IFNγ, IL-4, IL-5, IL-9, IL-10, IL-13, etc.) are produced. In one embodiment, the immune response is a protective immune response that provides protection to the person or animal from infection by an immunodeficiency virus. In a specific embodiment, the immune response provides the person or animal with protection from infection by HIV or FIV. In one embodiment, the person or animal receiving the antigen or immunogen is already infected with an immunodeficiency virus. In another embodiment, the person or animal is not infected with an immunodeficiency virus prior to administration of the antigen or immunogen.

The subject invention also concerns evolutionarily conserved epitopes of immunodeficiency viruses. In one embodiment, the epitope is one that is conserved between HIV and SIV, or between HIV and FIV. In another embodiment, the epitope is one that is conserved between HIV, SIV, and FIV. In one embodiment, the epitope is a T-cell epitope. In a specific embodiment, the T-cell epitope is a cytotoxic T lymphocyte (CTL) epitope, polyfunctional T cell (CD3+CD4+ and CD3+CD8+ T cells that express multiple cytokines, cytotoxins, chemokines, and functional activities such as proliferation) epitope, and/or T-helper (Th) epitope. In one embodiment, the epitopes are from a viral integrase protein. In another embodiment, the epitopes are from a viral reverse transcriptase (RT) protein. In a further embodiment, the epitopes are from a viral core or capsid (p24) protein. Antigens and immunogens of the invention can be peptides and/or proteins that comprise one or more evolutionarily conserved epitopes of the invention. Examples of epitopes contemplated within the scope of the invention include peptides or proteins comprising the amino acid sequence shown in SEQ ID NOs:1-40 or in any of SEQ ID NOs:45-591, independently or any possible combination thereof, or in any of the examples, figures or tables of the subject application, or an immunogenic fragment or variant of the amino acid sequence. In a specific embodiment, an epitope of the invention comprises a peptide or protein comprising the amino acid sequence shown in any of SEQ ID NOs:10, 21, 22, 23, 61, 62, 63, 64, 65, 163, 164, 165, 166, 167, 176, 177, 178, 179, 214, 215, 216, 217, 218, 288, 301, 303, 304, 359, 361, 431, 432, 438, 442, 443, 453, 459, 460, 466, 479, 488, 492, and/or 493. In another embodiment, an epitope of the invention comprises a peptide or protein comprising two or more amino acid sequences of any of SEQ ID NOs:10, 21, 22, 23, 61, 62, 63, 64, 65, 163, 164, 165, 166, 167, 176, 177, 178, 179, 214, 215, 216, 217, 218, 288, 301, 303, 304, 359, 361, 431, 432, 438, 442, 443, 453, 459, 460, 466, 479, 488, 492, and/or 493. In a specific embodiment, an epitope of the invention comprises a peptide or protein comprising the amino acid sequence of SEQ ID NO:63 and/or SEQ ID NO:64. In yet another embodiment, an epitope of the invention comprises a peptide or protein comprising an amino acid sequence shown in any of SEQ ID NO:10, SEQ ID NO: 21, SEQ ID NO:22, or SEQ ID NO:23. In a further embodiment, an epitope of the invention comprises a peptide or protein comprising an amino acid sequence shown in any of SEQ ID NOs:176, 177, 178, 179, 214, 215, 216, 217, or 218. In yet a further embodiment, an epitope of the invention comprises a peptide or protein comprising an amino acid sequence shown in any of SEQ ID NO:288, SEQ ID NO:301, SEQ ID NO:303, SEQ ID NO:304, SEQ ID NO:359, SEQ ID NO:361, SEQ ID NO:453, SEQ ID NO:459, SEQ ID NO:460, SEQ ID NO:466, SEQ ID NO:479, SEQ ID NO:488, SEQ ID NO:492, and/or SEQ ID NO:493. The subject invention also concerns polynucleotides encoding the amino acid sequence of epitopes of the invention.

The subject invention also concerns vaccines comprising one or more antigens and/or immunogens that comprise or encode evolutionarily conserved epitopes of the present invention. The vaccine or immunogenic compositions of the subject invention also encompass recombinant viral vector-based or polynucleotide constructs that may comprise a nucleic acid encoding a peptide or protein comprising an evolutionarily conserved epitope of the present invention or encoding a chimeric polypeptide of the present invention. Examples of epitopes contemplated within the scope of the invention include peptides or proteins comprising the amino acid sequence shown in SEQ ID NOs:1-40 or in any of SEQ ID NOs:45-591, independently or any possible combination thereof, or in any of the examples, figures or tables of the subject application, or an immunogenic fragment or variant of the amino acid sequence. In a specific embodiment, a peptide or protein of the invention comprises the amino acid sequence shown in any of SEQ ID NOs:10, 21, 22, 23, 61, 62, 63, 64, 65, 163, 164, 165, 166, 167, 176, 177, 178, 179, 214, 215, 216, 217, 218, 288, 301, 303, 304, 359, 361, 431, 432, 438, 442, 443, 453, 459, 460, 466, 479, 488, 492, and/or 493. In another embodiment, a peptide or protein of the invention can comprise two or more amino acid sequences of any of SEQ ID NOs:10, 21, 22, 23, 61, 62, 63, 64, 65, 163, 164, 165, 166, 167, 176, 177, 178, 179, 214, 215, 216, 217, 218, 288, 301, 303, 304, 359, 361, 431, 432, 438, 442, 443, 453, 459, 460, 466, 479, 488, 492, and/or 493. In a specific embodiment, a peptide or protein comprises the amino acid sequence of SEQ ID NO:63 and/or SEQ ID NO:64. In yet another embodiment, a peptide or protein of the present invention comprises an amino acid sequence shown in any of SEQ ID NO:10, SEQ ID NO: 21, SEQ ID NO:22, or SEQ ID NO:23. In a further embodiment, a peptide or protein of the present invention comprises an amino acid sequence shown in any of SEQ ID NOs:176, 177, 178, 179, 214, 215, 216, 217, or 218. In yet a further embodiment, a peptide or protein utilized in the present invention comprises an amino acid sequence shown in any of SEQ ID NO:288, SEQ ID NO:301, SEQ ID NO:303, SEQ ID NO:304, SEQ ID NO:359, SEQ ID NO:361, SEQ ID NO:453, SEQ ID NO:459, SEQ ID NO:460, SEQ ID NO:466, SEQ ID NO:479, SEQ ID NO:488 SEQ ID NO:492, and/or SEQ ID NO:493. In an exemplified embodiment, a chimera polynucleotide comprises the sequence shown in SEQ ID NO:41 or SEQ ID NO:42. In a further exemplified embodiment, a chimera polypeptide comprises the sequence shown in SEQ ID NO:43 or SEQ ID NO:44. Any suitable viral vector that can be used to prepare a recombinant vector/virus construct is contemplated for use with the subject invention. For example, viral vectors derived from adenovirus, avipox, herpesvirus, vaccinia, canarypox, entomopox, swinepox, West Nile virus and others known in the art can be used with the compositions and methods of the present invention. Recombinant polynucleotide vectors that encode and express components can be constructed using standard genetic engineering techniques known in the art. In addition, the various vaccine compositions described herein can be used separately and in combination with each other. For example, primary immunizations of an animal may use recombinant vector-based constructs, having single or multiple strain components, followed by secondary boosts with vaccine compositions comprising inactivated virus or inactivated virus-infected cell lines. Other immunization protocols with the vaccine compositions of the invention are apparent to persons skilled in the art and are contemplated within the scope of the present invention.

The subject invention also concerns compositions comprising epitopes and/or chimeric polypeptides of the invention, or polynucleotides encoding them. In one embodiment, a composition of the invention comprises a pharmaceutically or biologically acceptable carrier, diluent, and/or adjuvant.

The subject invention also concerns antibodies, or an antigen binding fragment thereof, that bind to HIV, SIV, and/or FIV epitopes. In one embodiment, an antibody of the invention is a monoclonal antibody. In one embodiment, an antibody of the invention binds specifically to an HIV protein, e.g., an HIV p24 protein. In a specific embodiment, an antibody of the invention is the monoclonal antibody designated as HL2309 (produced by clone 2B3-1F6) or HL2310 (produced by clone 2B3-2A4). In another embodiment, an antibody of the invention binds specifically to an FIV protein, e.g., an FIV p24 protein. In a specific embodiment, an antibody of the invention is the monoclonal antibody designated as HL2350 (produced by clone 8B2-1E1) or HL2351 (produced by clone 8B2-2A1). In a further embodiment, an antibody of the invention binds specifically to both an HIV and an FIV protein, i.e., the antibody cross-reacts with an epitope that is present on both an HIV and an FIV protein, such as a p24 protein. The subject invention also concerns the epitopes recognized by an antibody of the invention. Table 1 shows monoclonal antibodies of the present invention and their reactivity with HIV p24 and FIV p24.

TABLE 1

| Monoclonal ID | clone number | antigen | isotype/light chain | cross-reactivity** |
|---|---|---|---|---|
| HL 2309 | 2B3-1F6 | HIV-1 UCD-1 p24 | IgG1/kappa | NO*** |
| HL 2310 | 2B3-2A4 | HIV-1 UCD-1 p24 | IgG1/kappa | NO*** |
| HL 2311 | 2B4-1B6 | HIV-1 UCD-1 p24 | IgG1/kappa | NO*** |
| HL 2312 | 2B4-1E8 | HIV-1 UCD-1 p24 | IgG1/kappa | NO*** |
| HL 2335 | 4C3 | HIV-1 UCD-1 p24 | IgG2b/kappa | NO*** |
| HL 2336 | 5G2 | HIV-1 UCD-1 p24 | IgM/kappa | YES |
| HL 2322 | 9D6 | FIV Petaluma p24 | IgG1/kappa | YES |
| HL 2323 | 7A3 | FIV Petaluma p24 | IgG1/kappa | NO*** |
| HL 2324 | 2G12 | FIV Petaluma p24 | IgG1/kappa | YES |
| HL 2348 | 9A12-2A3 | FIV Petaluma p24 | IgG1/kappa | YES |
| HL 2349 | 9A12-2C2 | FIV Petaluma p24 | IgG1/kappa | YES |
| HL 2350 | 8B2-1E1 | FIV Petaluma p24 | IgG1/kappa | NO*** |
| HL 2351 | 8B2-2A1 | FIV Petaluma p24 | IgG1/kappa | NO*** |

*All mouse monoclonal antibodies (MAbs) to HIV-1 p24 are positive by ELISA and Westernblot to HIV-1 p24. Similarly, all MAbs to FIV p24 are positive by ELISA and WB to FIV p24.
**Cross-reactivity denotes reactivity of anti-HIV-1 p24 MAbs to FIV p24 and vice versa.
***These MAbs differentiate between HIV-p24 and FIV p24 when used in right combinations.

The subject invention also concerns expression constructs comprising one or more polynucleotides of the invention. Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMPS promoter, TRP-1 promoter, murine mammary tumor virus long terminal repeat promoter, STAT promoter, or an immunoglobulin promoter can be used in the expression construct.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the immunogens of the invention. Chemical enhancers are cis-acting elements that increase gene transcription and can also be included in the expression construct. Chemical enhancer elements are known in the art, and include, but are not limited to, the cytomegalovirus (CMV) early promoter enhancer element and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, vectors, and expression constructs of the invention can be introduced in vivo via lipofection (DNA transfection via liposomes prepared from synthetic cationic lipids) (Feigner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced as naked DNA using methods known in the art, such as transfection, microinjection, electroporation, calcium phosphate precipitation, and by biolistic methods.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the exemplified sequences. The polynucleotide includes both the sense and antisense strands as either individual strands or in the duplex.

The methods of the present invention contemplate a primary immunization with an antigen, immunogen, peptide, polypeptide, polynucleotide, and/or composition of the invention. Subsequent or secondary immunizations are also contemplated within the scope of the subject methods. The antigen, immunogen, peptide, polypeptide, polynucleotide, and/or composition used for secondary immunizations can be the same as or vary from that used for primary immunization. For example, primary immunizations of an animal may use recombinant vector-based HIV, FIV, or SIV constructs, having single or multiple strain components, followed by secondary boosts with compositions comprising HIV-, FIV-, or SIV-infected cell lines, or HIV, FIV, or SIV polypeptides, or cell free HIV or SIV virus, also having single or multiple strain components. Primary immunizations can also use an HIV, FIV, and/or SIV DNA vaccine. In one embodiment, a recombinant vector construct is used for the primary immunization, whereas a protein, or protein plus recombinant vector construct, subunit vaccine composition is used for secondary boosts. Other immunization protocols with the vaccine compositions of the invention are apparent to persons skilled in the art and are contemplated within the scope of the present invention.

The antibodies can be polyclonal or monoclonal in form. The antibodies can be derived from any animal capable of producing antibodies to the epitopes, and include, for example, human, ape, monkey, mouse, rat, goat, sheep, pig, cow, and feline animals. Also contemplated within the scope of the invention are non-human antibodies that have been "humanized" using standard procedures known in the art, such as those described in U.S. Pat. Nos. 5,530,101; 5,585,089; 5,693,762; 6,180,370; and 6,407,213.

An antibody that is contemplated for use in the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and F(ab')$_2$ fragments.

Antibody fragments can retain an ability to selectively bind with the antigen or analyte are contemplated within the scope of the invention and include:

(1) Fab is the fragment of an antibody that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. For a review of sFv fragments, see Pluckthun in The Pharmacology of Monoclonal Antibodies, vol. 113, Rosenburg and Moore eds. Springer-Verlag, N.Y., pp. 269 315 (1994).

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies to be used in the subject invention can be genus or species specific to a target cell. Antibodies of the invention can be prepared using standard techniques known in the art. Antibodies useful in the invention can be polyclonal or monoclonal antibodies. Monoclonal antibodies can be prepared using standard methods known in the art (Kohler et al., 1975).

The subject invention also concerns hybridomas that produce monoclonal antibodies of the present invention.

Peptide and/or polypeptide antigens and immunogens of the present invention can also be provided in the form of a multiple antigenic peptide (MAP) construct, with or without lypophylic attachment to each peptide string. The preparation of MAP constructs has been described in Tam (1988) and Kowalczyk et al. (2010). MAP constructs utilize a core matrix of lysine residues onto which multiple copies of an immunogen are synthesized (Posnett et al., 1988). In one embodiment, MAP constructs of the invention can comprise one or more fatty acids attached to the core matrix. The fatty acid can comprise from about 4 to about 48 or more carbon atoms, and can be saturated and/or unsaturated. In a specific embodiment, the fatty acid is palmitic acid (hexadecanoic acid). Multiple MAP constructs, each containing the same or different immunogens, can be prepared and administered in a vaccine composition in accordance with methods of the present invention. In one embodiment, the same or different peptides are linked end to end. The same or different peptides can be linked directly to each other (i.e., without a linker sequence) or they can be linked via a linker moiety such as a short amino acid sequence (e.g., a furin-sensitive linker), examples of which include, but are not limited to, peptides comprising SEQ ID NO:494. In one embodiment, a MAP construct is provided with and/or administered with one or more adjuvants. In one embodiment, a MAP of the invention comprises one or more peptides that comprise the amino acid sequences of one or more of SEQ ID NOs:1-40 or 45-591.

Natural, recombinant or synthetic polypeptides of immunodeficiency viral proteins, and peptide fragments thereof, can also be used as vaccine compositions according to the subject methods. Procedures for preparing FIV, SIV, and HIV polypeptides are well known in the art. For example, FIV, SIV, and HIV polypeptides can be synthesized using solid-phase synthesis methods (Merrifield, 1963). FIV, SIV, and HIV polypeptides can also be produced using recombinant DNA techniques wherein a polynucleotide molecule encoding an FIV, SIV, or HIV protein or peptide is expressed in a host cell, such as bacteria, yeast, or mammalian cell lines, and the expressed protein purified using standard techniques of the art.

According to the methods of the subject invention, the antigenic and immunogenic compositions described herein can be administered to susceptible hosts in an effective amount and manner to induce an immune response and/or protective immunity against subsequent challenge or infection of the host by FIV, SIV, or HIV. The immunogens are typically administered parenterally, by injection, for example, either subcutaneously, intradermally, intraperitoneally, or intramuscularly, or by oral or nasal administration, or any combination of such routes of administration. Usually, the immunogens are administered to a host animal at least two times, with an interval of one or more weeks between each administration. However, other regimens for the initial and booster administrations of the immunogens are contemplated, and may depend on the judgment of the practitioner and the particular host animal being treated.

Antigens and immunogens that can be used in accordance with the present invention can be provided with a pharmaceutically-acceptable carrier or diluent. Compounds and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin, Easton Pa., Mack Publishing Company, $19^{th}$ ed., 1995, describes formulations which can be used in connection with the subject invention. In general, the compositions of the subject invention will be formulated such that an effective amount of an antigen or immunogen is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptidomimetics include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of an immunogen of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the antigen, antigens, immunogen or immunogens based on the weight of the total composition including carrier or diluent.

The immunogenic compositions of the subject invention can be prepared by procedures well known in the art. For example, the antigens or immunogens are typically prepared as injectables, e.g., liquid solutions or suspensions. The antigens or immunogens are administered in a manner that is compatible with dosage formulation, and in such amount as will be therapeutically effective and immunogenic in the recipient. The optimal dosages and administration patterns for a particular antigen or immunogen formulation can be readily determined by a person skilled in the art.

Virus and cells in an antigenic or immunogenic formulation may be inactivated or attenuated using methods known in the art. The amount of cell-free whole or partial virus in a vaccine dose will usually be in the range from about 0.1 mg to about 5 mg, and more usually being from about 0.2 mg to about 2 mg. The dosage for formulations comprising virus-infected cell lines will usually contain from about $10^6$ to about $10^8$ cells per dose, and more usually from about $5\times10^6$ to about $7.5\times10^7$ cells per dose. The amount of protein or peptide immunogen in a dose for a feline animal can vary from about 0.1 µg to 10000 µg, or about 1 µg to 5000 µg, or about 10 µg to 1000 µg, or about 25 µg to 750 µg, or about 50 µg to 500 or 100 µg to 250 depending upon the size, age, etc., of the animal receiving the dose.

In one embodiment, an antigen or immunogen of the invention is provided with one or more adjuvants that increase the person or animal's immune response against the antigen or immunogen. Antigens and immunogens of the invention can be provided with and/or administered with any suitable adjuvant or adjuvants known in the art. In one embodiment, the adjuvant is one that helps induce a strong cellular immune response. Adjuvants that can be used in the antigen and immunogen formulations of the invention include threonyl muramyl dipeptide (MDP) (Byars et al., 1987), Ribi adjuvant system components (Corixa Corp., Seattle, Wash.) including the cell wall skeleton (CWS) component, Freund's complete, and Freund's incomplete adjuvants, bacterial lipopolysaccharide (LPS), such as from *E. coli*, or a combination thereof. A variety of other adjuvants suitable for use with the methods and vaccines of the subject invention, such as alum, aluminum hydroxide, and saponin are well known in the art and are contemplated for use with the subject invention. Cytokines (γ-IFN, GM-CSF, CSF, etc.) and lymphokines and interleukins (IL-1, IL-2, IL-3, IL-4, IL-5, IL-6, IL-7, IL-8. IL-9, IL-10, IL-11, IL-12, IL-13, IL-14, IL-15, IL-16, IL-17, IL-18, IL-19, IL-20, IL-21, and IL-22) have also been used as adjuvants and/or supplements to vaccine compositions and are contemplated within the scope of the present invention. One or more different cytokines and lymphokines can be included in a composition comprising an antigen or immunogen of the invention. In one embodiment, an antigen or immunogen of the invention is administered to an animal in combination with the lymphokine interleukin-12 (IL-12) in combination with another adjuvant. Also specifically contemplated within the scope of the invention is the use of the lymphokine interleukin-18 (IL-18) as part of an adjuvant composition. In one embodiment, an adjuvant composition used with the subject invention comprises a combination of IL-12 and IL-15, or IL-15 and IL-18, or IL-12 and IL-18, or IL-12, IL-15, and IL-18. The cytokine selected is of a species that has biological activity in the animal receiving the antigen or immunogen. For example, if the animal is a cat, then the cytokine can be a human cytokine or a feline cytokine, e.g., feline IL-12, feline IL-15, feline IL-18, etc.

Abbreviations of FIV strains used herein are shown below:

| Strain (subtype) | Abbreviation | Strain (subtype) | Abbreviation |
| --- | --- | --- | --- |
| Petaluma (A) | $FIV_{Pet}$ | PPR (A) | $FIV_{PPR}$ |
| Dixon (A) | $FIV_{Dix}$ | FranceWo | $FIV_{Fra}$ |
| UK8 (A) | $FIV_{UK8}$ | Netherlands | $FIV_{Net}$ |
| Bangston (B) | $FIV_{Bang}$ | USILbrny03B (B) | $FIV_{USI03}$ |
| Aomori-1 (B) | $FIV_{Aom1}$ | TM2 (B) | $FIV_{TM2}$ |
| Aomori-2 (B) | $FIV_{Aom2}$ | USCKlgri02B (B) | $FIV_{USC02}$ |
| FC1 (B) | $FIV_{FC1}$ | Yokohama (B) | $FIV_{Yok}$ |
| Shizuoka (D) | $FIV_{Shi}$ | USMAsboy03B (B) | $FIV_{USMA03}$ |
| Dutch113 (A) | $FIV_{Dut113}$ | USTXmtex03B (B) | $FIV_{UST03}$ |
| Dutch19K (A) | $FIV_{Dut19}$ | USMCglwd03B (B) | $FIV_{USMC03}$ |
| UK2 (A) | $FIV_{UK2}$ | CABCpbar03C (C) | $FIV_{CAB03}$ |

| Strain (subtype) | Abbreviation | Strain (subtype) | Abbreviation |
|---|---|---|---|
| SwissZ2 (A) | $FIV_{SwiZ2}$ | CABCpbar07C (C) | $FIV_{CAB07}$ |
| Sendai-1 (A) | $FIV_{Sen1}$ | CABCpady02C (C) | $FIV_{CAB02}$ |
| Sendai-2 (B) | $FIV_{Sen2}$ | Fukuoka (D) | $FIV_{Fuku}$ |
| USCAzepy01A (A) | FIV | | |
| USCAhnky11A (A) | $FIV_{USC11}$ | | |
| USCAtt-10A (A) | $FIV_{USC10}$ | | |
| USCAlemy01 (A) | FIV | | |
| USCAsam-01A (A) | FIV | | |

Antigens and immunogens of the invention are typically administered parenterally, by injection, for example, either subcutaneously, intradermally, intraperitoneally, or intramuscularly. Other suitable modes of administration include oral or nasal administration. Usually, the antigens and immunogens are administered to a human or animal at least two times, with an interval of one or more weeks between each administration. However, other regimens for the initial and booster administrations of the antigens and immunogens are contemplated, and may depend on the judgment of the practitioner and the patient being treated.

Antigenic and immunogenic compositions of the subject invention can be prepared by procedures well known in the art. For example, the antigens and immunogens are typically prepared as injectables, e.g., liquid solutions or suspensions. The antigens and immunogens are administered in a manner that is compatible with dosage formulation, and in such amount as will be therapeutically effective and immunogenic in the recipient. The optimal dosages and administration patterns for a particular antigen and immunogen formulation can be readily determined by a person skilled in the art.

Antigens and immunogens that can be used in accordance with the present invention can be provided with a pharmaceutically-acceptable carrier or diluent. In one embodiment, an antigen or immunogen of the invention is provided with one or more adjuvants that increase the human or animal's immune response against the antigen or immunogen. Antigens and immunogens of the invention can be provided with and/or administered with any suitable adjuvant or adjuvants known in the art.

The antigenic or immunogenic peptides contemplated in the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 15 or more amino acids added to, or 1 to 10 amino acids removed from, either or both ends of the disclosed peptides using standard techniques known in the art. Any added amino acids can be different or the same as the corresponding amino acids of the full-length protein from which the peptide is derived. The skilled artisan, having the benefit of the teachings disclosed in the subject application, could easily determine whether a longer or shorter peptide retained the immunogenic activity of the specific peptides exemplified herein.

Substitution of amino acids other than those specifically exemplified or naturally present in a peptide of the invention are also contemplated within the scope of the present invention. For example, non-natural amino acids can be substituted for the amino acids of a peptide, so long as the peptide having the substituted amino acids retains substantially the same immunogenic activity as the peptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a peptide of the present invention having an amino acid of one class is replaced with another amino acid of the same class fall within the scope of the subject invention so long as the peptide having the substitution still retains substantially the same immunogenic activity as the peptide that does not have the substitution. Table 2 below provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Polynucleotides encoding a specifically exemplified peptide or chimeric polypeptide of the invention, or a shorter or longer peptide or chimeric polypeptide, or a peptide having one or more amino acid substitutions in the sequence are contemplated within the scope of the present invention. The subject invention also concerns variants of the polynucleotides of the present invention that encode a peptide of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a peptide or a chimeric polypeptide of the present invention can be generated as described herein and tested for the presence of immunogenic activity using standard techniques known in the art.

Polynucleotides, peptides, and chimeric polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and)(BLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and)(BLAST) can be used. See Worldwide Website: ncbi.nlm.nih.gov.

Factors affecting the preferred dosage regimen may include, for example, the age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art using conventional means. It should further be noted that live attenuated viruses are generally self-propagating; thus, the specific amount of such a virus administered is not necessarily critical.

It is contemplated that the vaccine may be administered to the patient a single time; or, alternatively, two or more times over days, weeks, months, or years. In some embodiments, the vaccine is administered at least two times. In some such embodiments, for example, the vaccine is administered twice, with the second dose (e.g., the booster) being administered at least about 2 weeks after the first. In some embodiments, the vaccine is administered twice, with the second dose being administered no greater than 8 weeks after the first. In some embodiments, the second dose is administered at from about 2 weeks to about 4 years after the first dose, from about 2 to about 8 weeks after the first dose, or from about 3 to about 4 weeks after the first dose. In some embodiments, the second dose is administered about 4 weeks after the first dose. In the above embodiments, the first and subsequent dosages may vary, such as, for example, in amount and/or form. Often, however, the dosages are the same as to amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount.

In some embodiments, the vaccine is administered before the recipient is infected with virus. In such embodiments, the vaccine may, for example, be administered to prevent, reduce the risk of, or delay the onset of one or more (typically two or more) clinical symptoms.

In some embodiments, the vaccine is administered after the recipient is infected with influenza. In such embodiments, the vaccine may, for example, ameliorate, suppress, or eradicate the virus or one or more (typically two or more) clinical symptoms.

It is contemplated that the vaccine may be administered via the feline patient's drinking water and/or food. It is further contemplated that the vaccine may be administered in the form of a treat or toy.

"Parenteral administration" includes subcutaneous injections, submucosal injections, intravenous injections, intramuscular injections, intrasternal injections, transcutaneous injections, and infusion. Injectable preparations (e.g., sterile injectable aqueous or oleaginous suspensions) can be formulated according to the known art using suitable excipients, such as vehicles, solvents, dispersing, wetting agents, emulsifying agents, and/or suspending agents. These typically include, for example, water, saline, dextrose, glycerol, ethanol, corn oil, cottonseed oil, peanut oil, sesame oil, benzyl alcohol, benzyl alcohol, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), propylene glycol, and/or polyethylene glycols. Excipients also may include small amounts of other auxiliary substances, such as pH buffering agents.

The vaccine may include one or more excipients that enhance a patient's immune response (which may include an antibody response, cellular response, or both), thereby increasing the effectiveness of the vaccine. Use of such excipients (or "adjuvants") may be particularly beneficial when using an inactivated vaccine. The adjuvant(s) may be a substance that has a direct (e.g., cytokine or Bacillé Calmette-Guerin ("BCG")) or indirect effect (liposomes) on cells of the patient's immune system. Examples of often suitable adjuvants include oils (e.g., mineral oils), metallic salts (e.g., aluminum hydroxide or aluminum phosphate), bacterial components (e.g., bacterial liposaccharides, Freund's adjuvants, and/or MDP), plant components (e.g., Quil A), and/or one or more substances that have a carrier effect (e.g., bentonite, latex particles, liposomes, and/or Quil A, ISCOM). It should be recognized that this invention encompasses both vaccines that comprise an adjuvant(s), as well as vaccines that do not comprise any adjuvant.

It is contemplated that the vaccine may be freeze-dried (or otherwise reduced in liquid volume) for storage, and then reconstituted in a liquid before or at the time of administration. Such reconstitution may be achieved using, for example, vaccine-grade water.

The present invention further comprises kits that are suitable for use in performing the methods described above. The kit comprises a dosage form comprising a vaccine described above. The kit also comprises at least one additional component, and, typically, instructions for using the vaccine with the additional component(s). The additional component(s) may, for example, be one or more additional ingredients (such as, for example, one or more of the excipients discussed above, food, and/or a treat) that can be mixed with the vaccine before or during administration. The additional component(s) may alternatively (or additionally) comprise one or more apparatuses for administering the vaccine to the patient. Such an apparatus may be, for example, a syringe, inhaler, nebulizer, pipette, forceps, or any medically acceptable delivery vehicle. In some embodiments, the apparatus is suitable for subcutaneous administration of the vaccine. In some embodiments, the apparatus is suitable for intranasal administration of the vaccine.

Other excipients and modes of administration known in the pharmaceutical or biologics arts also may be used.

The subject invention also concerns a method for selecting antigens and/or immunogens for use in a vaccine against an immunodeficiency virus, such as HIV or FIV, wherein the method comprises identifying evolutionarily conserved epitopes of the target protein from two or more immunodeficiency viruses, wherein one or more of the identified epitopes are selected for use as an antigen or immunogen in the vaccine. In one embodiment, one or more overlapping peptides of an FIV protein and a corresponding HIV protein, or an FIV protein and a corresponding SIV protein, or an SIV protein and a corresponding HIV protein are assayed to identify those that are capable of inducing one or more T cell responses (cell mediated immune responses). Cells are contacted with the one or more peptides for a period of time and then assays are conducted to determine if one or more T cell responses was induced. In one embodiment, a response assayed for is IFNγ production. In another embodiment, a response assayed for is induction of T cell proliferation, such as proliferation of CD4+ and/or CD8+ T cells. In another embodiment, a response assayed for is the production and/or expression of cytotoxic T cell-associated molecules (e.g., cytotoxins), such as granzyme A, granzyme B, perforin, and/or CD107a. In one embodiment, a method of the invention comprises testing one or more peptides for induction of IFNγ production by cells (e.g., peripheral blood mononuclear cells (PBMS)) using an enzyme-linked immunosorbent spot (ELISpot) assay for IFNγ. In one embodiment, a method of the invention comprises testing one or more peptides for induction of T cell proliferation using a carboxyfluorescein diacetate succinimide ester (CFSE) proliferation assay. The assays contemplated for determining the induction of a T cell response can provide quantitative and/or qualitative results. In one embodiment, the cells contacted with the one or more peptides are cells from a feline animal. In one embodiment, the feline animal is infected with FIV or has been vaccinated against FIV. In another embodiment, the feline animal has not been infected with FIV or vaccinated against FIV. In another embodiment, the cells are from a primate or a human. In one embodiment, the primate or human has not been infected with HIV. In another embodiment, the primate or human has been infected with HIV (HIV+). In one embodiment, the HIV+ subject is a long-term survivor (LTS). In another embodiment, the subject is a short-term (ST) survivor. The HIV+ subject can be one that has received antiretroviral therapy (ART) or one that has not received ART.

The subject invention also concerns chimeric polynucleotides and polypeptides that comprise sequences from more than one immunodeficiency virus. In one embodiment, a chimera of the invention comprises sequences of HIV and FIV. In a specific embodiment, a chimera of the invention is a chimeric Gag protein wherein matrix (MA) and nucleocapsid (NC) sequences are from FIV and wherein the core or capsid (CA) (p24) sequences are from an HIV. In an exemplified embodiment, a chimera polynucleotide comprises the sequence shown in SEQ ID NO:41 or SEQ ID NO:42. In a further exemplified embodiment, a chimera polypeptide comprises the sequence shown in SEQ ID NO:43 or SEQ ID NO:44. The subject invention contemplates that HIV proteins can be substituted for corresponding FIV proteins in other chimeric polynucleotides and polypeptides of the invention. For example, HIV pol sequences can be substituted into corresponding FIV pol sequences.

The subject invention also concerns methods for determining whether an animal, such as a feline animal, has been vaccinated against FIV with an FIV vaccine of the present invention, or is infected by FIV or has been infected by FIV. In one embodiment, a biological sample, such as a blood or serum sample, is obtained from a feline animal, and the sample is assayed to determine whether the animal has antibodies that bind specifically to HIV antigens. In a specific embodiment, if an animal is vaccinated with a chimeric polynucleotide or polypeptide of the present invention wherein p24 of FIV is replaced with p24 of HIV, then antibodies specific for the HIV p24 will be present in the animal and can be detected. In one embodiment, a chimera polypeptide comprises the sequence shown in SEQ ID NO:43 or SEQ ID NO:44. If an animal has been infected with FIV, then that animal will not have antibodies that bind to certain HIV p24 epitopes. If an animal has been vaccinated with a chimera polypeptide comprising an HIV protein and an FIV protein, then the animal will have antibodies that bind to HIV. Epitopes of an HIV protein that are only recognized by HIV antibodies and that are not recognized by FIV antibodies can be used in the subject invention.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Selection of HIV Immunogens and Conserved Epitopes

Careful design of vaccine immunogens for protection against a wide number of HIV variants will be required to deal with the large antigenic diversity. Conserved viral antigens, subtype-matched antigens, consensus antigens, variants of single antigens and multiple antigens have all been used alone or in combination (Li et al. (2007); Korber et al. (2009)). Table 7 shows a few examples for each of the strategies. CTL responses have been shown to preferentially target the conserved regions over the more variable ones (Cao et al. (1997)), and these responses have been associated with better HIV disease outcomes or no disease manifestation (Kiepiela et al. (2007); Rowland-Jones et al. (1998); Johnson et al. (1991)).

The most conserved regions of HIV, especially those conserved across subtypes (Korber et al. (2009)) or among lentiviruses (Yamamoto et al. (2010)), may be the best targets of the immune system for inducing vaccine protection. Some of these regions may be protective and are less likely to mutate because they hold a functional or structural importance to the virus species (possibly to the genus); a mutation would induce impairment to viral fitness (Santra et al. (2010); Barouch et al. (2010)). This possibility makes the identification of conserved epitopes an important aspect of immunogen selection in vaccine design. One means of including these conserved regions is to construct polyvalent mosaic proteins as vaccine immunogens; thus far, preclinical evaluations of the mosaic vaccine have demonstrated great potential for broad T-cell responses, across subtypes (Korber et al. (2009); Smith (2004); Wang et al. (2009)).

A method of selecting highly conserved regions is to identify those with the lowest entropy, which is the lowest variability at each aa position. Based on this concept, the most conserved HIV proteins have been shown to be (in order of lowest variability): integrase (IN), core capsid (Gag-p24), reverse transcriptase (RT), and protease (PR) (Table 3) (Yusim et al. (2002)). They were followed by Vpr, Vif, matrix (Gag-p17), Nef, Rev, and the surface envelope (SU-Env). Tat and Vpu have the highest variability (Table 3). This observation suggests that the selection of conserved vaccine epitopes should be done first from IN, Gag-p24, RT, and PR.

While Jenner may not have considered functional conservation when developing his smallpox vaccine, he can be considered to have been the first developer of a vaccine that was based on conserved features between two different viral species (Jenner (1798)). In a similar fashion, comparisons with other lentiviruses could help identify highly conserved epitopes that are required for viral function and survival. FIV is a lentivirus that is only distantly related to HIV-1, but may still be relevant to the evolutionary conserved approach of vaccine development because of the shared similarities between the HIV and FIV viruses in terms of aa sequence, structure, and pathogenesis (Yamamoto et al. (2007)). A comparison of the aa composition of proteins between HIV-1 and FIV demonstrates the following percentages of identity/homology: RT, 47/72; IN, 37/65; Gag-p24, 32/63; nucleocapsid (Gag-p7), 30/54; PR, 24/48; Gag-p17, 20/50; SU-Env, 19/43; transmembrane envelope (TM-Env) 18/42 (Yamamoto et al. (2010)) (Table 3). The three most conserved proteins are also those that have the lowest entropy calculation, as shown in Table 3 (Yusim et al. (2002)). Hence, the IN, RT, and Gag-p24 proteins appear to be excellent targets for identifying evolutionary conserved regions that may also contain conserved T-cell epitopes.

TABLE 3

HIV-1/FIV proteins.

|  | IN | Gag-p24 | RT | PR | Gag-p17 | SU-Env | Ref. |
|---|---|---|---|---|---|---|---|
| Approximate average entropy scores [a] | 0.16 | 0.18 | 0.21 | 0.23 | 0.45 | 0.6 | † |
| HIV/FIV protein % aa identity/homology [b] | 37/65 | 32/63 | 47/72 | 24/48 | 20/50 | 19/43 | ‡ |

[a] The average Shannon entropy score is the average value of variability of a given protein at each aa position, calculated by using many aligned sequences. The approximate values shown are derived from the figure of HIV-1 (group M) protein variability from Yusim et al (Yusim et al. (2002))), where the proteins are presented from lowest to highest variability. Lower scores represent lower variability and therefore higher aa conservation.
[b] The percentage of aa identity and homology between HIV and FIV proteins are shown, with the three most conserved HIV and FIV proteins bolded.
† (Yusim et al. (2002))
‡ (Yamamoto et al. (2010))

Example 2

Identification of Evolutionary Conserved HIV CTL Epitopes: Use of FIV Proteins

Immunoninformatics has become an integral part in the design of new vaccines with great promise of rapid and effective vaccine discovery (Ardito et al. (2011); Moss et al. (2011); De Groot et al. (2008)). A number of tools and databases are now available online including HLA class-I and -II binding predictions (Los Alamos National Laboratory. HIV molecular immunology database: Best-defined CTL/CD8$^+$ Epitope Summary: (www.hiv.lanl.gov/content/immunology/tables/optimal_ctl_summary.html); Yongqun et al. (2010)), and a number of tools that are useful for the prediction of CTL epitopes (Table 4). In one study performed by our group, NetCTL-1.2 was used to identify CTL epitopes on the integrase sequences of HIV, SIV and FIV (FIG. 1A). For the twelve HLA supertypes shown in FIG. 1, a large number of CTL epitopes were predicted on each integrase sequence regardless of the virus: HIV with 78 epitopes, SIV with 74 epitopes, and FIV with 85 epitopes. Some of these were conserved between HIV and SIV (34 epitopes), as well as between HIV and FIV (25 epitopes) (FIG. 1B). A smaller number (17 epitopes) was conserved among all three viruses, reducing the target epitopes to the expected most evolutionary conserved.

TABLE 4

CTL-epitope prediction tools.

| Name | Website | Developer | Ref. |
|---|---|---|---|
| CTLPred | www.imtech.res.in/raghava/ctlpred/ | India | † |
| NetCTL | www.cbs.dtu.dk/services/NetCTL/ | Denmark | ‡ |
| NetCTLpan | www.cbs.dtu.dk/services/NetCTLpan/ | Denmark | § |

† Bhasin et al. (2004)
‡ Larsen et al. (2007)
§ Stranzl et al. (2010)

Thirteen HIV CTL epitopes termed best-defined CTL epitopes have been identified empirically on HIV integrase by different laboratories and compiled on the Los Alamos National Laboratory (LANL) website (Table 5). In this regard, based on observations using SIV and FIV, an evolutionary conserved HIV CTL epitope can be defined as a CTL epitope with a direct or indirect SIV and/or FIV CTL counterpart (FIG. 2). Using the direct counterpart approach (FIG. 2, arrow a), three of these epitopes are predicted to be CTL epitopes conserved between HIV, SIV, and FIV and one was shown to be an indirect FIV counterpart (Table 6). They share the same HLA binding and CTL supertype predictions (Larsen et al. (2007); Lundegaard et al. (2008)). The evolutionary conserved (FIG. 2, arrow c). An indirect counterpart to an HIV epitope (bolded in Table 6), located upstream on FIV integrase, has higher aa identity and homology than the direct counterpart (FIG. 2, arrow b). This indirect FIV counterpart has the same binding alleles and predicted CTL supertype as the HIV epitope.

TABLE 5

Best defined CTL epitopes on HIV integrase[a].

| | Epitope | Position on HXB2 | HLA |
|---|---|---|---|
| 1 | LPPIVAKEI (SEQ ID NO: 1) | 28-36 | B42 |
| 2 | THLEGKIIL (SEQ ID NO: 2) | 66-74 | B*1510 |
| 3 | STTVKAACWW (SEQ ID NO: 3) | 123-132 | B57 |
| 4 | IQQEFGIPY (SEQ ID NO: 4) | 135-143 | B*1503 |
| 5 | VRDQAEHL (SEQ ID NO: 5) | 165-172 | Cw18 |
| 6 | KTAVQMAVF (SEQ ID NO: 6) | 173-181 | B*5701 |
| 7 | AVFIHNFKRK (SEQ ID NO: 7) | 179-188 | A*0301, A*1101 |

TABLE 5-continued

Best defined CTL epitopes on HIV integrase[a].

| | Epitope | Position on HXB2 | HLA |
|---|---|---|---|
| 8 | FKRKGGIGGY (SEQ ID NO: 8) | 185-194 | B*1503 |
| 9 | KRKGGIGGY (SEQ ID NO: 9) | 186-194 | B*2705 |
| 10 | IIATDIQTK (SEQ ID NO: 10) | 203-211 | A*1101 |
| 11 | KIQNFRVYY (SEQ ID NO: 11) | 219-227 | A*3002 |
| 12 | VPRRKAKII (SEQ ID NO: 12) | 260-268 | B42 |
| 13 | RKAKIIRDY (SEQ ID NO: 13) | 263-271 | B*1503 |

[a]Adapted from LANL (hiv.lanl.gov/content/immunology/tables/optimal_ctl_summary.html) which was last updated on 2009-08-31. The best defined CTL epitopes or "A list" represent the epitopes whose specific HLA class I allele has been demonstrated with strong certainty and are judged to be at their optimal length.

TABLE 6

HIV-1 integrase CTL epitopes and direct FIV counterparts

| Allele (super-type) | Virus | Epitopes | Iden. | Hom. | IEDB Prediction Binding (nM value) | Super-type (Total # of binding alleles) | Net CTL Super-type |
|---|---|---|---|---|---|---|---|
| B*1510 (B39) | HIV | THLEGKIIL (SEQ ID NO: 2) | | | | B*3901 (9); B*1501 (425) | B39 |
| | SIV | THLEGKIII (SEQ ID NO: 14) | 78 | 100 | | B*3901 (44) | B39 |
| | FIV | THFNGKIII (SEQ ID NO: 15) | 56 | 78 | | B*3901 (64); B*1501 (373) | B39 |
| A*0301 (A3) A*1101 (A3) | HIV | MAVFIHNFK (SEQ ID NO: 16) | | | | A*0301 (363); A*1101 (20) | A3 (5); A1 (1) |
| | SIV | MAVHCMNFK (SEQ ID NO: 17) | 67 | 67 | | A*0301 (174); A*1101 (25) | A3 (4); A1 (1) |
| | FIV | LALYCLNFK (SEQ ID NO: 18) | 44 | 78 | | A*3001 (113); A*1101 (55) | A3 (3); A1 (1) |
| B42 (B7) | HIV | VPRRKAKII (SEQ ID NO: 12) | | | | B*0702 (43); B*0801 (53) | B7 (1); B8 (1) |

TABLE 6-continued

HIV-1 integrase CTL epitopes and direct FIV counterparts

| Allele (super-type) | Virus | Epitopes | Iden. | Hom. | IEDB Prediction Binding (nM value) | Super-type (Total # of binding alleles) | Net CTL Super-type |
|---|---|---|---|---|---|---|---|
| | SIV | VPRRKAKII (SEQ ID NO: 12) | 100 | 100 | | B*0702 (43); B*0801 (53) | B7 (1); B8 (1) | B7; B8 |
| | FIV | VPRRHIRRV (SEQ ID NO: 19) | 44 | 67 | | B*0702 (20); B*0801 (124) | B7 (1); B8 (1) | B7; B8 |
| A*1101 (A3) | HIV | IIATDIQTK (SEQ ID NO: 10) | | | | A*1101 (404); A*6801 (204) | A3 (3) | A3 |
| | SIV | ILATDIQTT (SEQ ID NO: 21) | 78 | 89 | | A*0250 (10) | A2 (5) | None |
| | FIV | QESLRIQDY (SEQ ID NO: 22) | 22 | 33 | | B*4402 (88) | B44 (3) | None |
| | FIV | IVAEEIKRK[d] (SEQ ID NO: 23) | 44 | 78 | | A*1101 (338); A*6801 (206) | A3 (2) | A3 |

[a]The HIV epitope sequences are from the LANL list of the best defined CTL epitopes for HIV integrase. The SIV counterpart sequences are derived from LANL SIVmm239 and the FIV counterpart sequences are derived from GenBank (ABD16378) after aa alignment with HXB2 sequence.
[b]The identity (iden.) and homology (hom.) values were obtained using EMBOSS Stretcher - Pairwise Sequence Alignment (www.ebi.ac.uk/Tools/psa/emboss_stretcher/).
[c]MHC binding for HIV, SIV and FIV counterpart epitopes were predicted using the Immune Epitope Database (IEDB) MHC class I binding prediction tool (http://tools.immuneepitope.org/analyze/html/mhc_binding.html). The matching binding alleles are shown along with their binding affinity values (nM) which are derived from the Artificial Neural Network (ANN) analysis, where lower values represent higher binding affinity and potential for CD8+ T-cell activity. The total numbers of binding alleles with affinity below 500 nM are shown in parenthesis next to the supertypes.
[d]HIV epitope with non-matching SIV and FIV (direct counterparts) is in italics and the bolded FIV epitope is an indirect counterpart with matching alleles to the HIV epitope.

The predicted results of SIV sequences can be explained by the high aa identity between HIV and SIV as SIV is more closely related to HIV than FIV. However, despite the relatively lower aa identity between HIV and FIV, FIV counterpart epitopes still appear to be potentially effective HIV antigens (see Table 6), most likely due to the slightly higher aa homology observed between the two viruses. This finding indicates that both SIV and FIV epitopes could induce CTL responses in human PBMCs. Therefore, conserved SIV and FIV integrase peptides can be used as immunogens in vitro to compare and identify conserved immune responses generated by the PBMCs of HIV+ individuals.

TABLE 7

Phase I and IIa clinical trials of HIV CTL multi-epitope vaccine.

| Trial[a] | Site (# subjects enrolled in the study)[b] | Vaccine type (Regimen)[c] | Dose/route DNA (mg), MVA (p.f.u.)[d] | HIV Antigens (# of CTL epitopes)[e] |
|---|---|---|---|---|
| IAVI-001 | UK (18) | DNA (d: 0, 21) | 0.1 or .05 mg/i.m. | p24/p17 gene [contains TH epitopes] + 24 CTL epitopes [p24(6), pol(6), nef(8), Env (4)] |
| IAVI-002 | Kenya (18) | DNA (d: 0, 21) | 0, 0.1 or 0.5 mg/i.m. | |
| IAVI-003 | UK (8) | MVA (d: 0, 21) | $5 \times 10^7$ p.f.u./i.d. | |
| IAVI-004 | Kenya (18) | MVA (mo: 0, 1) (mo: 0) | 0 or $5 \times 10^7$ p.f.u./i.d. | |
| IAVI-011 | Switzerland/UK/SA (81) | MVA (mo: 0, 2) | 0, $5 \times 10^6$, $5 \times 10^7$ or $2.5 \times 10^8$ p.f.u./i.d., i.m. or s.c. | |
| IAVI-005 | UK (9) | p-DNA (d: 0, 21)[i] b-MVA | 0.1 or 0.5 mg/i.m. $5 \times 10^7$ p.f.u./i.d. | |
| IAVI-006 | UK (119) | p-DNA (mo: 0) b-MVA (mo: 2, 3 or 5, 6) | 0, 0.5 or 2 mg/i.m. 0 or $5 \times 10^7$ p.f.u./i.d. | |
| IAVI-008 | Kenya (10) | p-DNA (d: 0, 21) b-MVA (mo: 9, 10) | 0.5 or 1 mg/i.m. $5 \times 10^7$ p.f.u./i.d. | |
| IAVI-009 | Uganda (50) | p-DNA (mo: 0, 1 or 0) b-MVA (mo: 5, 8) | 0 or 0.5 mg 1x or 2x/i.m. 0 or $5 \times 10^7$ p.f.u./i.d. | |
| IAVI-010 | Kenya/UK (114) | p-DNA (mo: 0, 1) b-MVA (mo: 5, 8) | 0.5 mg/i.m. 0, $5 \times 10^6$, $5 \times 10^7$ or $2.5 \times 10^8$ p.f.u./i.d. | |
| IAVI-016 | UK (24) | p-DNA (mo: 0, 1) b-MVA (mo: 2 or 0, 1) | 0 or 4 mg/i.m. 0 or $2.5 \times 10^8$ p.f.u./i.d. | |
| HVTN-048 | USA, Bostwana (36) | DNA (mo: 0, 1, 3, 6) | 0.5 mg 4x/i.m. 2 mg 4x/i.m. 4 mg 4x/i.m. | 21 CTL epitopes [Gag(4), Pol(8), Vpr(1), Nef(2), Rev(1), Env(5)] + TH epitope (1 pan-DR) |
| HVTN-056 | USA (40) | MEP [peptides + adjuvant] (mo: 0, 1, 3) | 1 mg MEP + 50 µg adjuvant 3x/i.m. | 4 peptides (55 CTL epitopes): Env-TH/Gag-CTL(5) Gag-TH/GagCTL(19) Env-TH/Nef-CTL(15) Env-TH/Gag-CTL(16) |
| | USA (40) | MEP [peptides + adjuvant + GM-CSF] (mo: 0, 1, 3) | 1 mg MEP/50 µg adjuvant + 50 ug GM-CSF 3x/i.m. | |
| ANRS VAC18 | France (99) | Lipopeptides (mo: 0, 1, 3, 6) | 50 µg 4x/i.m. 150 µg 4x/i.m. 500 µg 4x/i.m. | 5 lipopeptides (77 CTL epitopes, containing 7 TH epitopes): [Gag1(9), Gag2(21), Nef1(16), Nef2(21), Pol (10)] |

| Trial[a] | HIV subtypes involved[f] | HLA supertype of CTL epitopes | Epitope selection method | (%)IFNγ[g] responders | REF[h] |
|---|---|---|---|---|---|
| IAVI-001 | A* [A, B, C, D, E, F, G, H][j] | A2, A3, A24, B7, B8, B27, B44 | Most common HIV subtype in Kenya | 78% | [129, 130] |
| IAVI-002 | | | | 15% | [131] |
| IAVI-003 | | | | 78% | [129] |
| IAVI-004 | | | | 25% | [131] |
| IAVI-011 | | | Conserved epitopes | 6% | [132] |
| IAVI-005 | | | | 89% | [129] |
| IAVI-006 | | | | 12% | [132] |
| IAVI-008 | | | | 10% | [131] |
| IAVI-009 | | | | 15% | [131] |
| IAVI-010 | | | | 3% | [132] |
| IAVI-016 | | | | 50% | [133] |
| HVTN-048 | A, B, C, D, AE, AG | A2, A3, B7 | Conserved Epitopes HLA coverage | 0% 0% 13% | [134] |
| HVTN-056 | B* | A1, A2, A3, A24, B7, B8, B27, B58, B62 | Epitope clustering on LANL | 13% 3% | [135] |

TABLE 7-continued

Phase I and IIa clinical trials of HIV CTL multi-epitope vaccine.

| ANRS VAC18 | A1, A2, A3, A24, B7, B8, B27, B58, B62 | Conserved regions | 71%[k] 60%[k] 70%[k] | [136] |

[a]All trials are phase I clinical trials except for the bolded trial numbers which are phase IIa (with subjects not at risks of HIV infection); International AIDS Vaccine Initiative (IAVI); HIV Vaccine Trials Network (HVTN); Agence National de Recherche sur le SIDA (ANRS).
[b]United Kingdom (UK); South Africa (SA); United States of America (USA).
[c]Prime (p); boost (b); day (d); month (mo); modified vaccinia Ankara (MVA); multi-epitope peptide (MEP); granulocyte macrophage colony stimulating factor (GM-CSF).
[i]Nine of the 18 volunteers from IAVI-001 who were primed with HIVA-DNA agreed to receive a boost 9-14 months later.
[d]Intramuscular immunization (i.m.); intradermal immunization (i.d.); subcutaneous immunization (s.c.).
[e]MHC class I molecules can accommodate CTL epitopes of 8 to 11 aa in length [137]. The p24/p17 represents 73% of the Gag and contains both CTL and T-helper epitopes. The pan-DR T-helper epitope is a 13-mer that binds to all common HLA-DR alleles. Each of the four peptides in the MEP vaccine is made up of both TH and CTL epitopes; T helper (TH).
[f]The HIV subtypes used in the vaccine.
*Consensus sequence.
[j]The CTL epitopes are present in 50-90% of HIV isolates from the different subtypes.
[g]Percentage of vaccinees with detected IFNγ ELISpot responses to the CTL epitopes. The responses were detected at different time points, before or after the end of the immunization schedule for the IAVI studies; after the last immunization for HVTN 064; and after the $2^{nd}$ or 3rd vaccination (single time point) for HVTN 056.
[k]Cultured ELISpot assay results.
[h]Reference (REF).

Example 3

Monoclonal Antibodies to HIV-1 and FIV Recombinant p24 Antibodies

Figure 1A:
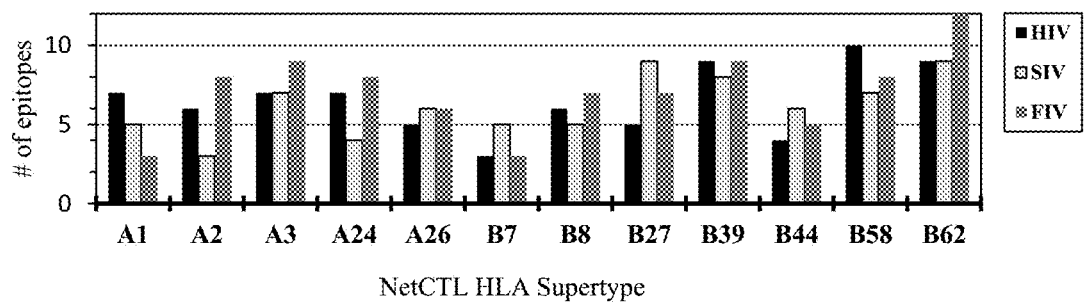
FIGS. 1A and 1B. NetCTL-1.2 prediction of HIV, SIV, and FIV CTL epitopes.NetCTL-1.2, which is based on proteosomic C-terminal cleavage, TAP transport efficiency, and epitope binding to MHC class I alleles, was used to predict CTL epitopes shown by HLA supertypes (cbs.dtu.dk/services/NetCTL/). The total number of predicted epitopes by HLA supertype (FIG. 1A): HIV (78), SIV (74), and FIV (85) were tallied after analysis of the full-length integrase sequence from each virus. The predicted CTL epitopes were compared and the conserved epitopes between the viruses were identified based on aa position and same predicted HLA supertype (FIG. 1B): HIV-SIV (34), HIV-FIV (25), and HIV-SIV-FIV (17).
Figure 1B:
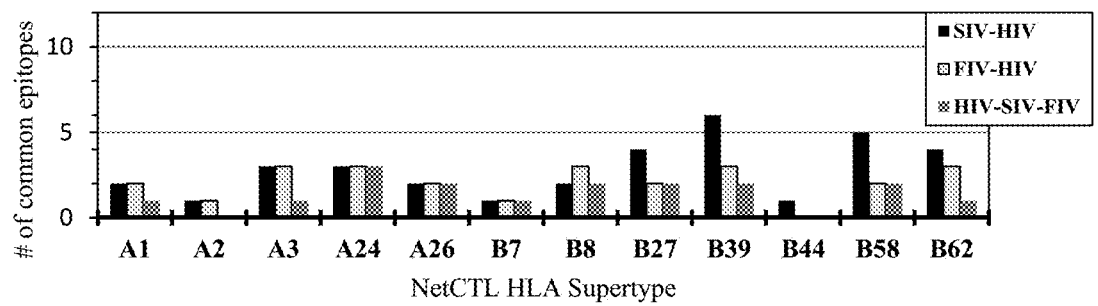
Figure 2:
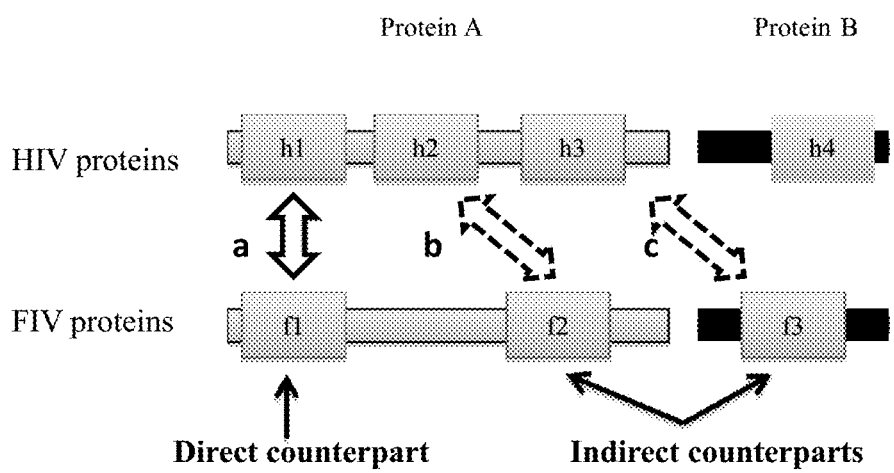
FIG. 2. Possible Location of Counterpart Epitopes. HIV proteins (A, B) aligned to FIV proteins (A, B) showing four HIV epitopes (h1, h2, h3, h4) and three FIV epitopes (f1, f2, f3) with arrows indicating the location of the direct counterpart (arrow a) and indirect counterpart epitopes (arrows b, and c).
Figure 8A:
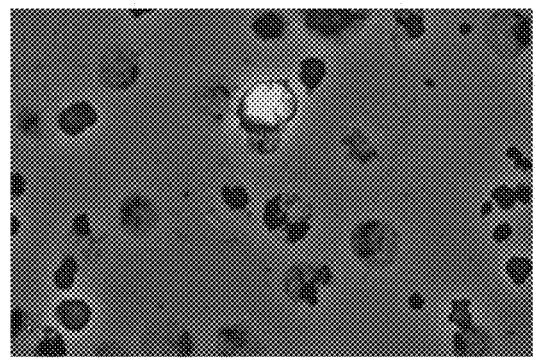
FIGS. 8A-8C. Chimera HIVp24/FIV-Shizuoka infected PBMC (batch 10) with MAb reactive to both FIV p24 and HIV-1 p24 (FIG. 8A). Chimera HIVp24/FIV-Shizuoka infected PBMC (batch 10) with MAb reactive to FIV gp95 (surface envelope) (FIG. 8B). Chimera HIVp24/FIV-Shizuoka infected PBMC (batch 10) with isotype IgG control antibody (FIG. 8C). Indirect fluorescent antibody (IFA) analysis of feline PBMC infected with chimera HIVp24/FIV-Shizuoka (subtype-D backbone) virus. Note HIV-1$_{UCD1}$ belongs to HIV-1 subtype B. The culture supernatant from chimera transinfected 293T cells was inoculated into uninfected feline PBMC culture, and then 2-3 weeks later when the used at a concentration of 15 μg/mL. Each bar represents an individual primate's response in spot forming units (SFU/$10^6$ PBMC) after subtraction of 2 times the media control; except for the black and red bars. The black bar represents the average response of the pre-infection responders (Av. n=3) and the red bar represents the average response of all 4 pre-infection samples (Av. total n=4). Since these cells were frozen for over 5 years, positive responses are values of ≥50 SFU. We believe that fresh (non-cryopreserved) cells will give higher responses to HIV p24 peptide pools (FIG. 14A: Hp1-Hp18) and HIV RT peptide pools (FIG. 14B: Hr1-Hr21). Various mitogens (Mito.) (concanavalin A, *Staphyloccocal* enterotoxin A, phytohemaglutinin A) were used since these frozen cells did not always respond to mitogen.
Figure 8B:
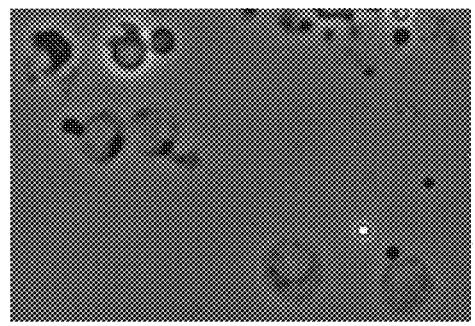
Figure 8C:
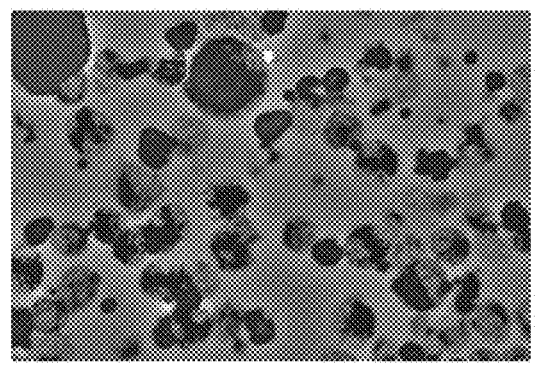
Figure 9A:
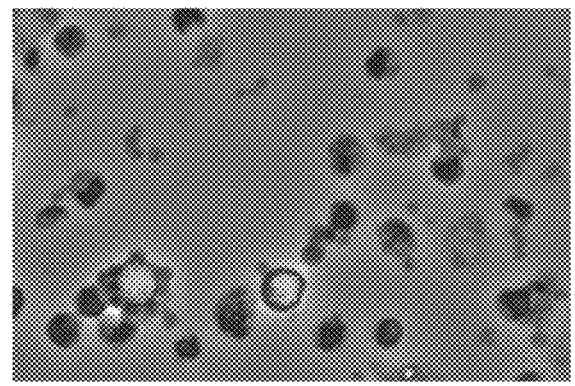
Figure 9B:
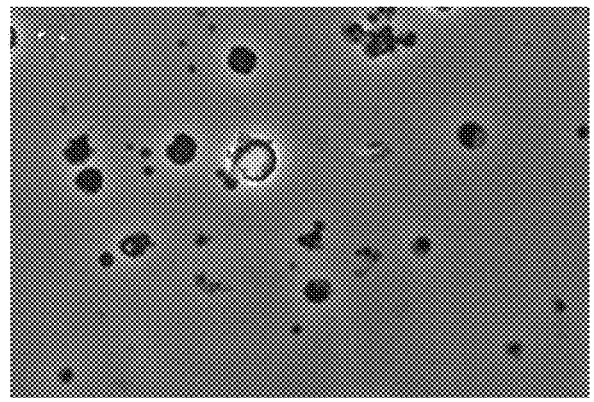
Figure 9C:
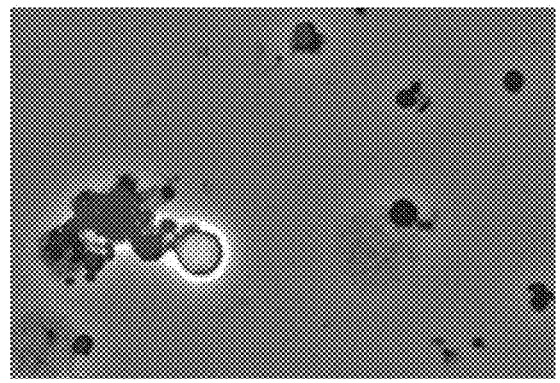
Figure 9D:
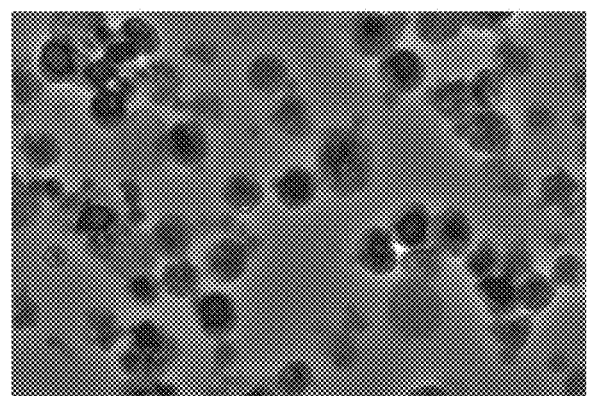

Monoclonal antibodies (MAbs) to HIV-1 p24 and FIV p24 were produced by immunizing mice with recombinant HIV-1 p24 and recombinant FIV p24, respectively (Table 8). Two of seven MAbs to HIV-1 p24 (HL2309 and HL2310) were only reactive to HIV-1 p24, while remaining five MAbs were reactive to both HIV-1 and FIV p24 proteins. Two of six MAbs to FIV p24 (HL2350 and HL2351) were only reactive to FIV p24, while remaining four MAbs were reactive to both HIV-1 and FIV p24 proteins. Based on Western blot (WB) and ELISA results (FIG. 8), the epitopes recognized by HIV-1 p24-specific MAbs HL2309 and HL2310 are specific for HIV-1 and are not likely to be specific for FIV. Hence, such HIV-1-specific epitopes can be used in Western blot or ELISA to detect HIV-1 p24 specific antibodies in chimera HIV-1 p24/FIV backbone vaccine (hereon called chimera HIV/FIV vaccine) immunized cats but such Western blot or ELISA should not react with antibodies from FIV-infected cats since HL2309 and HL2310 epitopes are specific for HIV-1 and not for FIV. Using the same concept, the epitopes recognized by FIV p24-specific MAbs HL2350 and HL2351 are specific for FIV and are not likely to be specific for HIV-1. Therefore, HL2350 and HL2351 epitopes can be used in WB or ELISA to detect antibodies from FIV-infected cats but should not react to antibodies from cats immunized with chimera HIV/FIV vaccine. HL2309, HL2310, HL2350, and HL2351 epitope peptides can be used in WB or ELISA based assays to differentiate chimera HIV/FIV vaccinated cats from FIV-infected cats.

TABLE 8

ELISA Reactivity of Monoclonal Antibodies to HIV-1$_{UCD-1}$ p24 and FIV$_{Pet}$ p24

| Monoclonal ID | clone number | Antigen | isotype/light chain | cross-reactivity** |
|---|---|---|---|---|
| HL 2309 | 2B3-1F6 | HIV-1 UCD-1 p24 | IgG1/kappa | NO |
| HL 2310 | 2B3-2A4 | HIV-1 UCD-1 p24 | IgG1/kappa | NO |
| HL 2311 | 2B4-1B6 | HIV-1 UCD-1 p24 | IgG1/kappa | NO |
| HL 2312 | 2B4-1E8 | HIV-1 UCD-1 p24 | IgG1/kappa | NO |
| HL 2335 | 4C3 | HIV-1 UCD-1 p24 | IgG2b/kappa | NO |
| HL 2336 | 5G2 | HIV-1 UCD-1 p24 | IgM/kappa | YES |
| HL 2322 | 9D6 | FIV Petaluma p24 | IgG1/kappa | YES |
| HL 2323 | 7A3 | FIV Petaluma p24 | IgG1/kappa | NO |
| HL 2324 | 2G12 | FIV Petaluma p24 | IgG1/kappa | YES |
| HL 2348 | 9A12-2A3 | FIV Petaluma p24 | IgG1/kappa | YES |
| HL 2349 | 9A12-2C2 | FIV Petaluma p24 | IgG1/kappa | YES |
| HL 2350 | 8B2-1E1 | FIV Petaluma p24 | IgG1/kappa | NO |
| HL 2351 | 8B2-2A1 | FIV Petaluma p24 | IgG1/kappa | NO |

*All mouse monoclonal antibodies (MAbs) to HIV-1 p24 are positive by ELISA and Western blot to HIV-1 p24. Similarly, all MAbs to FIV p24 are positive by ELISA and WB to FIV p24.
**Cross-reactivity denotes reactivity of anti-HIV-1 p24 MAbs to FIV p24 and vice versa.

Example 4

See FIGS. 11 and 12. To investigate evolutionarily conserved CTL epitopes using FIV peptides, the individual 11-16-mer peptides in the pools with high responses such as FRT3/HRT3, FRT11/HRT11, FP9/Hp10, and Fp14/Hp15 are being tested with PBMCs from the peptide-pool responders. IFNγ and CD3+CD8+ T-cell proliferation responses to FIV RT peptide FRT3-3 ("KKKSGKWRMLIDFRV" (SEQ ID NO:63), 15mer) are highly conserved among HIV+ subjects and no normal (HIV-negative) individuals responded. Since FRT3 induced perforin response in PBMCs from HIV+ subjects, FRT3-3 should have excellent probability in inducing CTL responses detected by perforin.

Human PBMC Assays

Stimulants:

HIV-1 p24 (Hp1-Hp18) & FIV p24 (Fp1-Fp17) peptide pools were 3-4 overlapping peptides of 11-15 aa long per pool, while HIV-1 RT (HRT1-HRT21) & FIV RT (FRT1-FRT21) peptide pools 3-5 overlapping peptides of 11-15 aa long per pool. These peptides had an overlap of 9 aa spanning the entire length of the proteins.

IFNγ-ELISpot $1.0 \times 10^5$-$2.0 \times 10^5$ PBMCs were stimulated with peptides (15 µg peptide/well) in ELISpot plates for 18 hours in AIMS V medium (at 10% normal human serum). The spots were counted with an ELISpot reader and adjusted to spot forming units (SFU) per $10^6$ cells.

Positive reactivity was defined at ≥70 SFU/$10^6$ cells after subtracting the background derived from non-specific peptide control or media control, and the average of 3 HIV-1 negative controls (<30 SFU/$10^6$ cells).

CFSE-Proliferation $2 \times 10^5$-$5 \times 10^5$ CFSE labeled PBMCs were incubated with 15-20 µg of peptides in 600 µL of RPMI media with 10% FBS for 5 days at 37° C. (5% $CO_2$). After harvesting, they were labeled with allophycocyanin (APC), APC-H7, and Pacific Blue labeled monoclonal antibodies (MAb) to human CD3, CD4, and CD8, respectively and analyzed for T-cell proliferation by flow cytometry using BD LSRII (BD Biosciences). The proliferating $CD4^+$ or $CD8^+$ T cell populations were defined from the $CD3^+$ cell population as either $CD3^+CD8^+$ or $CD3^+CD4^+$T cells (mutually exclusive) with low CFSE ($CFSE^{low}$) staining.

Intracellular Staining (ICS)

Briefly, $1 \times 10^6$ PBMCs (freshly isolated) are stimulated with 20 µg of peptides for 6 hours in a total volume of 200 µL in a 96-well plate in presence of Golgi transport inhibitor (37° C., 5% $CO_2$). The cells are processed as previously described (Horton et al. (2007)). Cells were stained with the LIVE/DEAD® fixable yellow dye (Invitrogen, Eugene, Oreg.). The monoclonal antibodies fluorochome-conjugated to human cytokines used are: APC-H7 to CD3 (clone SK7); BD Horizon V450 to CD4 (clone RPA-T4); Qdot to CD8 (clone 3B5); PE-cy7 to IFN-γ (clone 4S.B3); APC to IL-2 (clone MQ1-17H12) PerCP to perforin (clone B-D48); Alexa F1.700 to granzyme-B (clone GB11) and PE to granzyme-A (clone CB9). The flow cytometry data is collected using BD LSRII and analyzed with the FACS DIVA software.

Population of Study

HIV-1 positive adult males and females were evaluated for IFNγ ELISpot (n=28 for p24 & n=31 for RT), $CD3^+CD4^+$ T-cell CSFE-proliferation (n=24), and $CD3^+CD8^+$ T-cell CFSE-proliferation (n=24) responses to overlapping HIV-1 p24, HIV-1 RT, FIV p24, or FIV RT peptide pools. A total of 10 normal healthy (HIV-1 negative) males and females were used as uninfected control group. All patients have signed an approved IRB consent form.

Figure 14A:
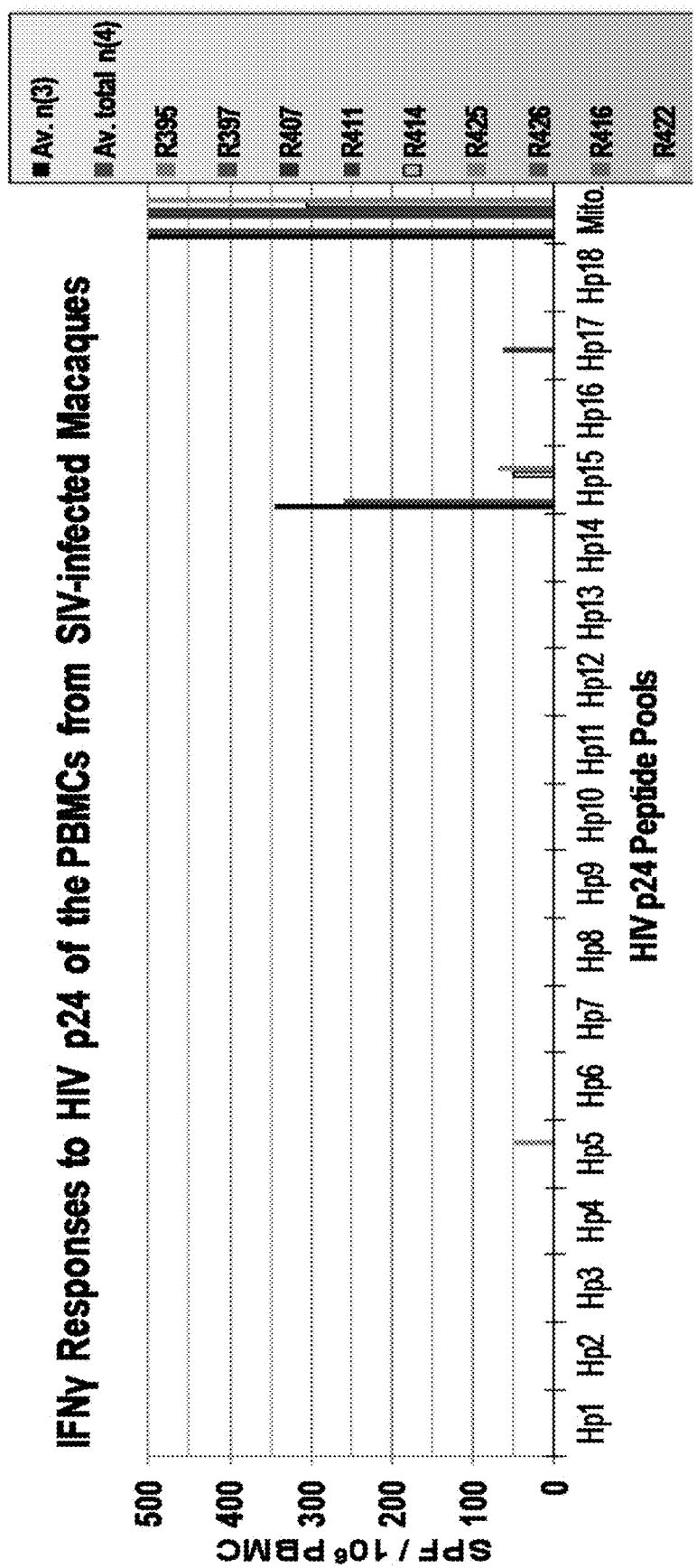
Figure 14B:
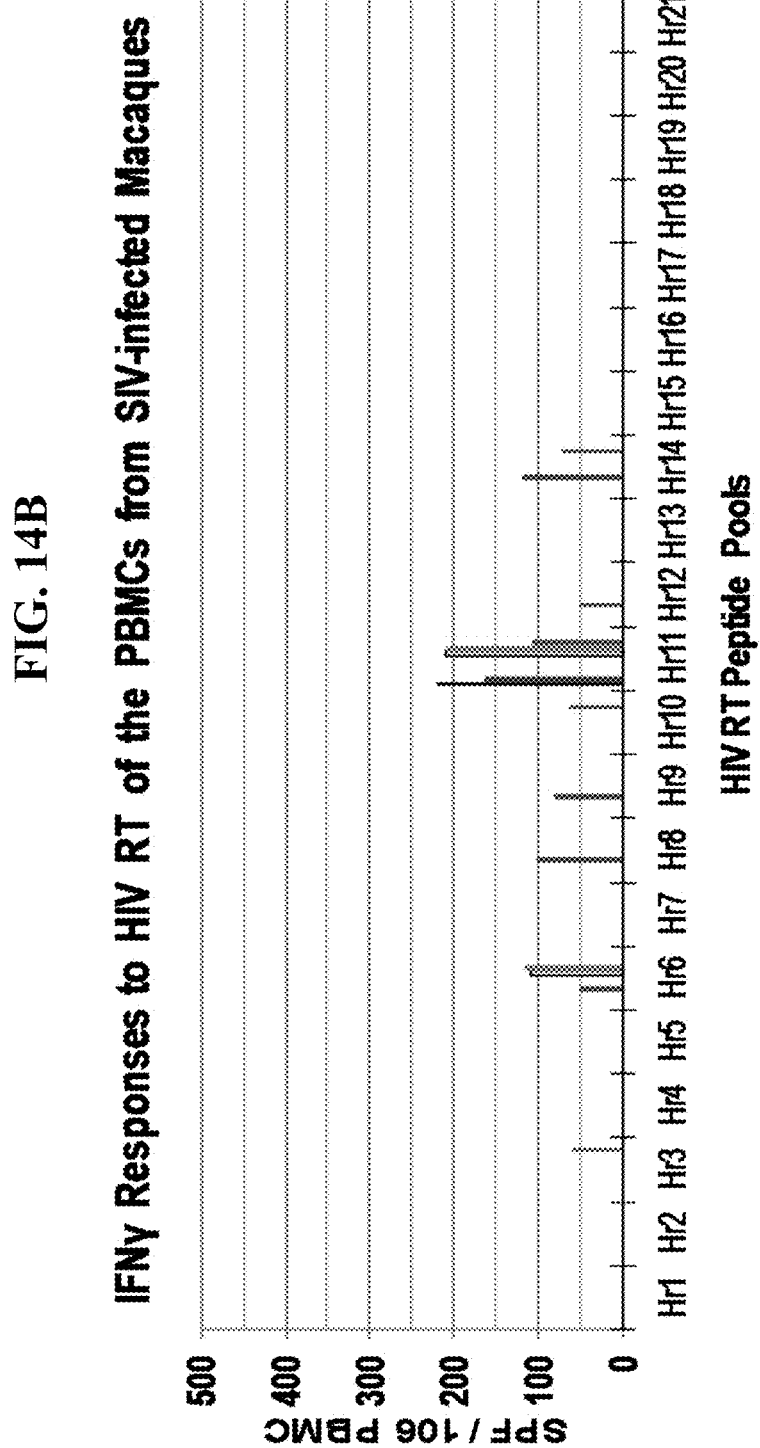
Figure 16:
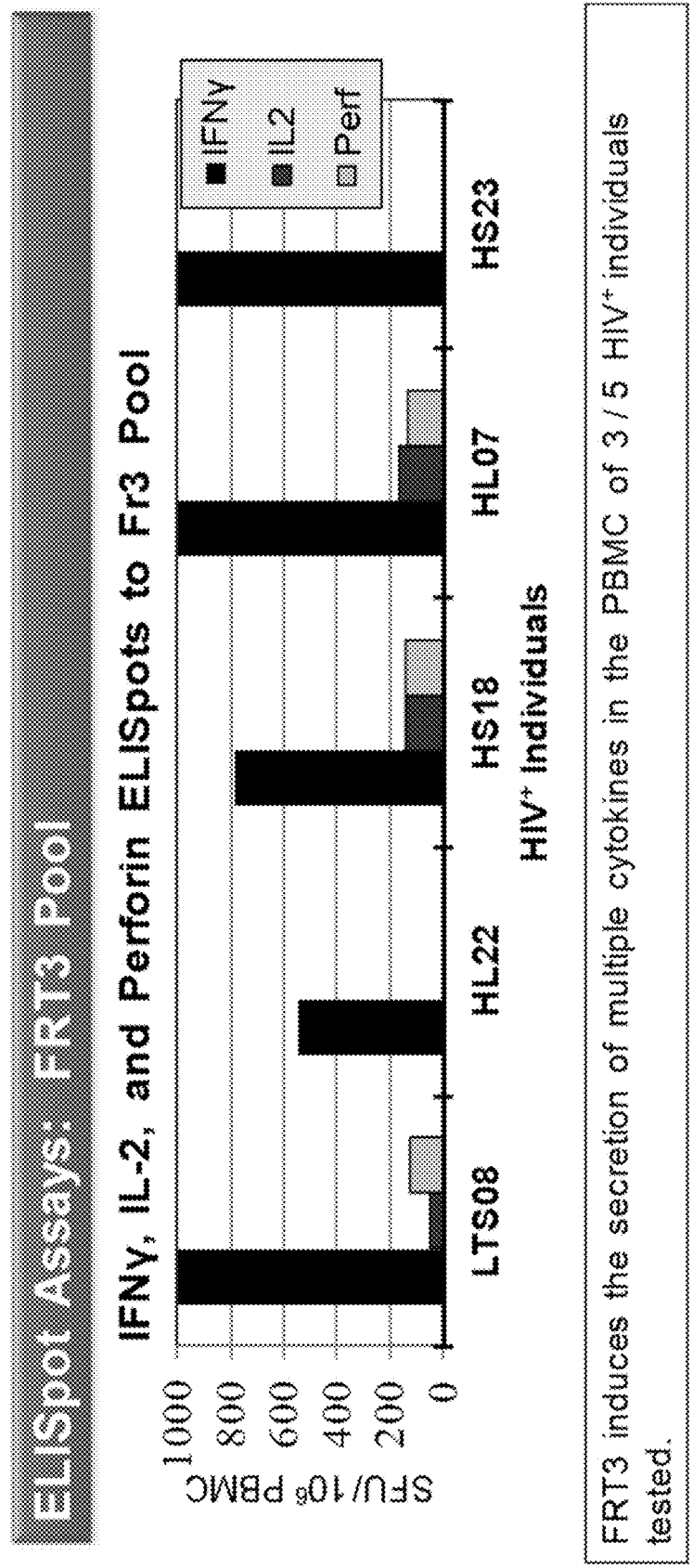
FIG. 16. FRT3 induces the secretion of multiple cytokines in the PBMC of 3/5 HIV+ individuals tested.

FIGS. 14A-14B. IFNγ ELISpot Responses to HIV RT (reverse transcriptase) and HIV p24 (core protein) of the Primate PBMCs.

Overlapping HIV-1 p24 (FIG. 14A) and RT (FIG. 14B) peptide pool analyses are shown for nine SIV-infected rhesus macaques and four pre-infection macaques. Frozen PBMC were thawed and plated at the concentration of $1.4 \times 10^5$ viable cells per mL. Peptides were used at a concentration of 15 µg/mL. Each bar represents an individual primate's response in spot forming units (SFU/$10^6$ PBMC) after subtraction of 2 times the media control; except for the black and red bars. The black bar represents the average response of the pre-infection responders (Av. n=3) and the red bar represents the average response of all 4 pre-infection samples (Av. total n=4). Since these cells were frozen for over 5 years, positive responses are values of ≥50 SFU. We believe that fresh (non-cryopreserved) cells will give higher responses to HIV p24 peptide pools (FIG. 14A: Hp1-Hp18) and HIV RT peptide pools (FIG. 14B: Hr1-Hr21). Various mitogens (Mito.) (concanavalin A, Staphyloccocal enterotoxin A, phytohemaglutinin A) were used since these frozen cells did not always respond to mitogen.

Note that only two infected macaques responded to Hp15 while three pre-infection macaques also responded. Similarly three infected macaques responded to Hr11 (i.e., HRT11) while three pre-infection macaques also responded. These results suggest that the PBMC from uninfected macaques recognize these Hp15 and Hr11. Consequently the epitopes to these peptide pools are cross-reacting with epitopes already present in the uninfected macaques. In contrast three infected macaques are responding to Hr6 and two infected macaques are responding to Hr14 (i.e., HRT14), but the uninfected macaques do not respond to these peptide epitopes, indicating that recognition of these peptide pools are due to SIV infection. The PBMCs from HIV+ subjects respond robustly to Hr6 and Hr14 but those of uninfected subjects did not. Thus, Hr6 (i.e., HRT6) and Hr14 may be conserved between HIV and SIV, and is currently being evaluated for the presence of conserved CTL epitopes.

NOTE that in the text we call individual peptides in the pool according to the order below. In the case of FRT2, individual peptide FRT2-3 is the same as Peptide 8 (VERLELEGKVKRA (SEQ ID NO:51)) or the third one listed under Pool FRT2.

FIV-FC1 RT (12-17-mer) with RNASE in bold.

```
Pool FRT1
  1)   AQISEKIPIVKVRMK         (SEQ ID NO: 52)

2)   IPIVKVRMKDPTQGPQV       (SEQ ID NO: 53)

3)   KDPTQGPQVKQWPL          (SEQ ID NO: 54)

4)   GPQVKQWPLSNEKI          (SEQ ID NO: 55)

5)   KQWPLSNEKIEAL           (SEQ ID NO: 56)

Pool FRT2
  6)   LSNEKIEALTDIVER         (SEQ ID NO: 57)

7)   EALTDIVERLELEGK         (SEQ ID NO: 58)

8)   VERLELEGKVKRA = FRT2-3  (SEQ ID NO: 51)

9)   ELEGKVKRADPNNPW         (SEQ ID NO: 59)

10)   KRADPNNPWNTPVFA         (SEQ ID NO: 60)

Pool FRT3
 11)   NPWNTPVFAIKKK           (SEQ ID NO: 61)

12)   TPVFAIKKKSGKWRM         (SEQ ID NO: 62)

13)   KKKSGKWRMLIDFRV         (SEQ ID NO: 63)

14)   WRMLIDFRVLNKL           (SEQ ID NO: 64)

15)   IDFRVLNKLTDKGA          (SEQ ID NO: 65)

Pool FRT4
 16)   LNKLTDKGAEVQLGL         (SEQ ID NO: 66)

17)   KGAEVQLGLPHPAGL         (SEQ ID NO: 67)

18)   LGLPHPAGLKMRKQV         (SEQ ID NO: 68)

19)   AGLKMRKQVTVLDI          (SEQ ID NO: 69)

Pool FRT5
 20)   RKQVTVLDIGDAYF          (SEQ ID NO: 70)

21)   VLDIGDAYFTIPL           (SEQ ID NO: 71)
```

| | | |
|---|---|---|
| 22) | GDAYFTIPLDPDYA | (SEQ ID NO: 72) |
| 23) | TIPLDPDYAPYTAF | (SEQ ID NO: 73) |

Pool FRT6
| | | |
|---|---|---|
| 24) | PDYAPYTAFTLPRK | (SEQ ID NO: 74) |
| 25) | YTAFTLPRKNNA | (SEQ ID NO: 75) |
| 26) | FTLPRKNNAGPGRRY | (SEQ ID NO: 76) |
| 27) | NNAGPGRRYVWCSL | (SEQ ID NO: 77) |

Pool FRT7
| | | |
|---|---|---|
| 28) | GRRYVWCSLPQGWVL | (SEQ ID NO: 78) |
| 29) | CSLPQGWVLSPLIY | (SEQ ID NO: 79) |
| 30) | GWVLSPLIYQSTL | (SEQ ID NO: 80) |
| 31) | SPLIYQSTLDNIL | (SEQ ID NO: 81) |

Pool FRT8
| | | |
|---|---|---|
| 32) | YQSTLDNILQPFIR | (SEQ ID NO: 82) |
| 33) | DNILQPFIRQNPEL | (SEQ ID NO: 83) |
| 34) | PFIRQNPELDIYQYM | (SEQ ID NO: 84) |
| 35) | PELDIYQYMDDIYI | (SEQ ID NO: 85) |
| 36) | YQYMDDIYIGSDLNK | (SEQ ID NO: 86) |

Pool FRT9
| | | |
|---|---|---|
| 37) | IYIGSDLNKKEHKQK | (SEQ ID NO: 87) |
| 38) | LNKKEHKQKVEELRK | (SEQ ID NO: 88) |
| 39) | KQKVEELRKLLLWW | (SEQ ID NO: 89) |
| 40) | ELRKLLLWWGFETPEDK | (SEQ ID NO: 90) |
| 41) | WGFETPEDKLQEEPPY | (SEQ ID NO: 91) |

Pool FRT10
| | | |
|---|---|---|
| 42) | DKLQEEPPYKWMGY | (SEQ ID NO: 92) |
| 43) | EPPYKWMGYELHPL | (SEQ ID NO: 93) |
| 44) | WMGYELHPLTWSI | (SEQ ID NO: 94) |
| 45) | ELHPLTWSIQQKQL | (SEQ ID NO: 95) |
| 46) | TWSIQQKQLEIPER | (SEQ ID NO: 96) |

Pool FRT11
| | | |
|---|---|---|
| 47) | IQQKQLEIPERPTL | (SEQ ID NO: 97) |
| 48) | LEIPERPTLNELQKL | (SEQ ID NO: 98) |
| 49) | PTLNELQKLVGKINW | (SEQ ID NO: 99) |
| 50) | LQKLVGKINWASQTI | (SEQ ID NO: 100) |
| 51) | KINWASQTIPDLSIK | (SEQ ID NO: 101) |

Pool FRT12
| | | |
|---|---|---|
| 52) | SQTIPDLSIKELTTM | (SEQ ID NO: 102) |
| 53) | LSIKELTTMMRGDQR | (SEQ ID NO: 103) |
| 54) | TTMMRGDQRLDSIR | (SEQ ID NO: 104) |
| 55) | GDQRLDSIREWTTEA | (SEQ ID NO: 105) |
| 56) | SIREWTTEAKKEVQK | (SEQ ID NO: 106) |

Pool FRT13
| | | |
|---|---|---|
| 57) | TEAKKEVQKAKEAI | (SEQ ID NO: 107) |
| 58) | EVQKAKEAIETQAQL | (SEQ ID NO: 108) |
| 59) | EAIETQAQLKYY | (SEQ ID NO: 109) |
| 60) | ETQAQLKYYDPSREL | (SEQ ID NO: 110) |
| 61) | KYYDPSRELYAKLSL | (SEQ ID NO: 111) |

Pool FRT14
| | | |
|---|---|---|
| 62) | RELYAKLSLVGPHQI | (SEQ ID NO: 112) |
| 63) | LSLVGPHQICYQVYH | (SEQ ID NO: 113) |
| 64) | HQICYQVYHKNPEHV | (SEQ ID NO: 114) |
| 65) | VYHKNPEHVLWYGKM | (SEQ ID NO: 115) |
| 66) | EHVLWYGKMNRQKKK | (SEQ ID NO: 116) |

Pool FRT15
| | | |
|---|---|---|
| 67) | GKMNRQKKKAENTCDI | (SEQ ID NO: 117) |
| 68) | KKAENTCDIALRACY | (SEQ ID NO: 118) |
| 69) | CDIALRACYKIR | (SEQ ID NO: 119) |
| 70) | ALRACYKIREESIIR | (SEQ ID NO: 120) |
| 71) | KIREESIIRIGKEPI | (SEQ ID NO: 121) |

Pool FRT16
| | | |
|---|---|---|
| 72) | IIRIGKEPIYEIPA | (SEQ ID NO: 122) |
| 73) | KEPIYEIPASREAW | (SEQ ID NO: 123) |
| 74) | EIPASREAWESNLIR | (SEQ ID NO: 124) |
| 75) | EAWESNLIRSPYLKA | (SEQ ID NO: 125) |
| 76) | LIRSPYLKAPPPEV | (SEQ ID NO: 126) |

PoolFRT17
| | | |
|---|---|---|
| 77) | YLKAPPPEVEFIHAA | (SEQ ID NO: 127) |
| 78) | PEVEFIHAALNIKRA | (SEQ ID NO: 128) |
| 79) | HAALNIKRALSMI | (SEQ ID NO: 129) |
| 80) | NIKRALSMIQDTPIL | (SEQ ID NO: 130) |
| 81) | SMIQDTPILGAETWY | (SEQ ID NO: 131) |
| 82) | PILGAETWYIDGGRK | (SEQ ID NO: 132) |

Pool FRT18
| | | |
|---|---|---|
| 83) | TWYIDGGRKQGKAAR | (SEQ ID NO: 133) |
| 84) | GRKQGKAARAAYW | (SEQ ID NO: 134) |
| 85) | GKAARAAYWTDTGKW | (SEQ ID NO: 135) |
| 86) | AYWIDIGKWQVMEI | (SEQ ID NO: 136) |
| 87) | TGKWQVMEIEGSNQK | (SEQ ID NO: 137) |

Pool FRT19
| | | |
|---|---|---|
| 88) | MEIEGSNQKAEVQAL | (SEQ ID NO: 138) |
| 89) | NQKAEVQALLLALQA | (SEQ ID NO: 139) |
| 90) | VQALLLALQAGPEEM | (SEQ ID NO: 140) |
| 91) | ALQAGPEEMNII | (SEQ ID NO: 141) |
| 92) | AGPEEMNIITDSQYI | (SEQ ID NO: 142) |

Pool FRT20
| | | |
|---|---|---|
| 93) | NIITDSQYILNII | (SEQ ID NO: 143) |
| 94) | DSQYILNIITQQPDL | (SEQ ID NO: 144) |
| 95) | NIITQQPDLMEGLW | (SEQ ID NO: 145) |

```
 96)  TQQPDLMEGLWQEVL       (SEQ ID NO: 146)
 97)  MEGLWQEVLEEMEKK       (SEQ ID NO: 147)
Pool FRT21
 98)  EVLEEMEKKIAIFI        (SEQ ID NO: 148)
 99)  MEKKIAIFIDWVPGH       (SEQ ID NO: 149)
100)  IFIDWVPGHKGI          (SEQ ID NO: 150)
101)  DWVPGHKGIPGNEEV       (SEQ ID NO: 151)
102)  KGIPGNEEVDKLCQTM      (SEQ ID NO: 152)
```

Subtype-B HIV-1-UCD1 RT (11-16-mer) with RNAse in bold.

```
Pool HRT1
  1)  PISPIETVPVKLK         (SEQ ID NO: 153)
  2)  IETVPVKLKPGM          (SEQ ID NO: 154)
  3)  VPVKLKPGMDGPKVK       (SEQ ID NO: 155)
  4)  PGMDGPKVKQWPL         (SEQ ID NO: 156)
  5)  GPKVKQWPLTEEKIK       (SEQ ID NO: 157)
Pool HRT2
  6)  WPLTEEKIKALIEI        (SEQ ID NO: 158)
  7)  EKIKALIEICTEMEK       (SEQ ID NO: 159)
  8)  IEICTEMEKEGKISK       (SEQ ID NO: 160)
  9)  MEKEGKISKIGPENPY      (SEQ ID NO: 161)
 10)  SKIGPENPYNTPVFA       (SEQ ID NO: 162)
Pool HRT3
 11)  NPYNTPVFAIKKK         (SEQ ID NO: 163)
 12)  TPVFAIKKKDSTKWR       (SEQ ID NO: 164)
 13)  KKKDSTKWRKLVDFR       (SEQ ID NO: 165)
 14)  KWRKLVDFRELNKR        (SEQ ID NO: 166)
 15)  VDFRELNKRTQDFW        (SEQ ID NO: 167)
Pool HRT4
 16)  LNKRTQDFWEVQLGI       (SEQ ID NO: 168)
 17)  DFWEVQLGIPHPAGL       (SEQ ID NO: 169)
 18)  LGIPHPAGLKKKKSV       (SEQ ID NO: 170)
 19)  AGLKKKKSVTVLDV        (SEQ ID NO: 171)
Pool HRT5
 20)  KKSVTVLDVGDAYF        (SEQ ID NO: 172)
 21)  VLDVGDAYFSVPLDK       (SEQ ID NO: 173)
 22)  AYFSVPLDKDFRKY        (SEQ ID NO: 174)
 23)  PLDKDFRKYTAFTI        (SEQ ID NO: 175)
Pool HRT6
 24)  FRKYTAFTIPSI          (SEQ ID NO: 176)
 25)  FTIPSTNNETPGIRY       (SEQ ID NO: 177)
 26)  NNETPGIRYQYNVL        (SEQ ID NO: 178)
 27)  GIRYQYNVLPQGWK        (SEQ ID NO: 179)
Pool HRT7
 28)  YNVLPQGWKGSPAIF       (SEQ ID NO: 180)
 29)  GWKGSPAIFQSSMTK       (SEQ ID NO: 181)
 30)  AIFQSSMTKILEPFR       (SEQ ID NO: 182)
 31)  MTKILEPFRKQNPDI       (SEQ ID NO: 183)
Pool HRT8
 32)  PFRKQNPDIVIYQYM       (SEQ ID NO: 184)
 33)  PDIVIYQYMDDLYV        (SEQ ID NO: 185)
 34)  YQYMDDLYVGSDLEI       (SEQ ID NO: 186)
 35)  LYVGSDLEIGQHRTK       (SEQ ID NO: 187)
 36)  LEIGQHRTKIEELR        (SEQ ID NO: 188)
Pool HRT9
 37)  HRTKIEELRQHLLRW       (SEQ ID NO: 189)
 38)  ELRQHLLRWGFTTPDK      (SEQ ID NO: 190)
 39)  RWGFTTPDKKHQK         (SEQ ID NO: 191)
 40)  TTPDKKHQKEPPFLW       (SEQ ID NO: 192)
 41)  HQKEPPFLWMGYELH       (SEQ ID NO: 193)
Pool HRT10
 42)  FLWMGYELHPDKWTV       (SEQ ID NO: 194)
 43)  ELHPDKWTVQPIML        (SEQ ID NO: 195)
 44)  KWTVQPIMLPEKDSW       (SEQ ID NO: 196)
 45)  IMLPEKDSWTVNDI        (SEQ ID NO: 197)
 46)  KDSWTVNDIQKLVGK       (SEQ ID NO: 198)
Pool HRT11
 47)  NDIQKLVGKLNWA         (SEQ ID NO: 199)
 48)  KLVGKLNWASQIYA        (SEQ ID NO: 200)
 49)  LNWASQIYAGIKVR        (SEQ ID NO: 201)
 50)  SQIYAGIKVRQLCKL       (SEQ ID NO: 202)
 51)  IKVRQLCKLLRGAKA       (SEQ ID NO: 203)
Pool HRT12
 52)  CKLLRGAKALTEVI        (SEQ ID NO: 204)
 53)  GAKALTEVIPLTKEA       (SEQ ID NO: 205)
 54)  EVIPLTKEAELELA        (SEQ ID NO: 206)
 55)  TKEAELELAENREIL       (SEQ ID NO: 207)
 56)  ELAENREILKEPVH        (SEQ ID NO: 208)
Pool HRT13
 57)  REILKEPVHGVYY         (SEQ ID NO: 209)
 58)  KEPVHGVYYDPSKDL       (SEQ ID NO: 210)
 59)  VYYDPSKDLIAEIQK       (SEQ ID NO: 211)
 60)  KDLIAEIQKQGQGQW       (SEQ ID NO: 212)
 61)  IQKQGQGQWTYQIY        (SEQ ID NO: 213)
Pool HRT14
 62)  GQGQWTYQIYQEPFK       (SEQ ID NO: 214)
 63)  YQIYQEPFKNLKTGK       (SEQ ID NO: 215)
 64)  PFKNLKTGKYARMR        (SEQ ID NO: 216)
```

```
                        -continued
   65)   KTGKYARMRGAH              (SEQ ID NO: 217)
   66)   KYARMRGAHTNDVK            (SEQ ID NO: 218)
Pool HRT15
   67)   RGAHTNDVKQLTEAV           (SEQ ID NO: 219)
   68)   DVKQLTEAVQKIV             (SEQ ID NO: 220)
   69)   LTEAVQKIVTESIVI           (SEQ ID NO: 221)
   70)   KIVTESIVIWGKTPK           (SEQ ID NO: 222)
   71)   IVIWGKTPKFKLPI            (SEQ ID NO: 223)
Pool HRT16
   72)   KTPKFKLPIQKETW            (SEQ ID NO: 224)
   73)   KLPIQKETWEAWW             (SEQ ID NO: 225)
   74)   IQKETWEAWWTEYW            (SEQ ID NO: 226)
   75)   WEAWWTEYWQATWI            (SEQ ID NO: 227)
   76)   TEYWQATWIPEWELV           (SEQ ID NO: 228)
Pool HRT17
   77)   TWIPEWELVNTPPLV           (SEQ ID NO: 229)
   78)   ELVNTPPLVKLWYQL           (SEQ ID NO: 230)
   79)   PLVKLWYQLEKEPI            (SEQ ID NO: 231)
   80)   WYQLEKEPIEGAETF           (SEQ ID NO: 232)
   81)   EPIEGAETFYVDGAA           (SEQ ID NO: 233)
   82)   ETFYVDGAANRETKL           (SEQ ID NO: 234)
Pool HRT18
   83)   GAANRETKLGKAGYV           (SEQ ID NO: 235)
   84)   TKLGKAGYVTNRGR            (SEQ ID NO: 236)
   85)   AGYVTNRGRQKVVPL           (SEQ ID NO: 237)
   86)   RGRQKVVPLTDA              (SEQ ID NO: 238)
   87)   RQKVVPLTDATNQK            (SEQ ID NO: 239)
Pool HRT19
   88)   PLTDATNQKTELEAI           (SEQ ID NO: 240)
   89)   NQKTELEAIHLAL             (SEQ ID NO: 241)
   90)   ELEAIHLALQDSGL            (SEQ ID NO: 242)
   91)   HLALQDSGLEVNIV            (SEQ ID NO: 243)
   92)   DSGLEVNIVTDSQYA           (SEQ ID NO: 244)
Pool HRT20
   93)   NIVTDSQYALGIIQA           (SEQ ID NO: 245)
   94)   SQYALGIIQAQPDK            (SEQ ID NO: 246)
   95)   GIIQAQPDKSESELV           (SEQ ID NO: 247)
   96)   PDKSESELVSQII             (SEQ ID NO: 248)
   97)   ESELVSQIIEQLIKK           (SEQ ID NO: 249)
Pool HRT21
   98)   SQIIEQLIKKEKVYL           (SEQ ID NO: 250)
   99)   LIKKEKVYLAWVPAH           (SEQ ID NO: 251)
  100)   VYLAWVPAHKGI              (SEQ ID NO: 252)
  101)   AWVPAHKGIGGNEQV           (SEQ ID NO: 253)

-continued
  102)   KGIGGNEQVDKLV             (SEQ ID NO: 254)
  103)   GNEQVDKLVSSGIRK           (SEQ ID NO: 255)
  104)   KLVSSGIRKVL               (SEQ ID NO: 256)
```

NOTE that in the text we call individual peptides in the pool according to the order below each pool. In the case of Fp3, individual peptide Fp3-3 is the same as Peptide 10 (VQLWFTAFSANL) (SEQ ID NO:257) or the third one listed under Pool Fp3.

FIV p24 Overlapping Peptides (subtype-A FIV-Bangston backbone with subtype-B FIV-FC1 (tubes 47-51))

```
Pool Fp1
    1)   PIQTVNGAPQYVAL            (SEQ ID NO: 258)
    2)   TVNGAPQYVALDPKM           (SEQ ID NO: 259)
    3)   APQYVALDPKMVSIF           (SEQ ID NO: 260)
    4)   VALDPKMVSIFMEKA           (SEQ ID NO: 261)
Pool Fp2
    5)   PKMVSIFMEKAREGL           (SEQ ID NO: 262)
    6)   SIFMEKAREGLGGEEV          (SEQ ID NO: 263)
    7)   KAREGLGGEEVQLWF           (SEQ ID NO: 265)
Pool Fp3
    8)   GLGGEEVQLWFTAF            (SEQ ID NO: 266)
    9)   GEEVQLWFTAFSANL           (SEQ ID NO: 267)
   10)   VQLWFTAFSANL  = Fp3-3     (SEQ ID NO: 257)
   11)   LWFTAFSANLTPTDM           (SEQ ID NO: 268)
Pool Fp4
   12)   AFSANLTPTDMATLI           (SEQ ID NO: 269)
   13)   NLTPTDMATLIMAA            (SEQ ID NO: 270)
   14)   PTDMATLIMAAPGCA           (SEQ ID NO: 271)
Pool Fp5
   15)   ATLIMAAPGCAADK            (SEQ ID NO: 272)
   16)   IMAAPGCAADKEIL            (SEQ ID NO: 273)
   17)   APGCAADKEILDESL           (SEQ ID NO: 274)
Pool Fp6
   18)   AADKEILDESLKQL            (SEQ ID NO: 275)
   19)   KEILDESLKQLTAEY           (SEQ ID NO: 276)
   20)   DESLKQLTAEYDRTH           (SEQ ID NO: 277)
   21)   KQLTAEYDRTHPPDGPR         (SEQ ID NO: 278)
Pool Fp7
   22)   YDRTHPPDGPRPLPY           (SEQ ID NO: 279)
   23)   HPPDGPRPLPYFTAA           (SEQ ID NO: 280)
   24)   GPRPLPYFTAAEIM            (SEQ ID NO: 281)
   25)   PLPYFTAAEIMGIGL           (SEQ ID NO: 282)
Pool Fp8
   26)   FTAAEIMGIGLTQEQQA         (SEQ ID NO: 283)
   27)   MGIGLTQEQQAEARF           (SEQ ID NO: 284)
   28)   LTQEQQAEARFAPAR           (SEQ ID NO: 285)
```

Pool Fp9
29) EQQAEARFAPARM (SEQ ID NO: 286)

30) AEARFAPARMQCRAW (SEQ ID NO: 287)

31) FAPARMQCRAWYLEA (SEQ ID NO: 288)

Pool Fp10
32) RMQCRAWYLEALGKL (SEQ ID NO: 289)

33) RAWYLEALGKLAAIK (SEQ ID NO: 290)

34) LEALGKLAAIKAK (SEQ ID NO: 291)

Pool Fp11
35) ALGKLAAIKAKSPRA (SEQ ID NO: 292)

36) LAAIKAKSPRAVQLR (SEQ ID NO: 293)

37) KAKSPRAVQLRQGAK (SEQ ID NO: 294)

Pool Fp12
38) PRAVQLRQGAKEDY (SEQ ID NO: 295)

39) VQLRQGAKEDYSSFI (SEQ ID NO: 296)

40) RQGAKEDYSSFIDRL (SEQ ID NO: 297)

Pool Fp13
41) KEDYSSFIDRLFAQI (SEQ ID NO: 298)

42) DRLFAQIDQEQNTA (SEQ ID NO: 299)

43) FAQIDQEQNTAEVKL (SEQ ID NO: 300)

Pool Fp14
44) DQEQNTAEVKLYLK (SEQ ID NO: 301)

45) EQNTAEVKLYLKQSL (SEQ ID NO: 302)

46) AEVKLYLKQSLSIA (SEQ ID NO: 303)

47) KLYLKQSLSIANA (SEQ ID NO: 304)

Pool Fp15
48) YLKQSLSIANANPDCK (SEQ ID NO: 305)

49) LSIANANPDCKRAM (SEQ ID NO: 306)

50) ANANPDCKRAMSHLK (SEQ ID NO: 307)

Pool Fp16
51) PDCKRAMSHLKPESTL (SEQ ID NO: 308)

52) AMSHLKPESTLEEKL (SEQ ID NO: 309)

53) LKPESTLEEKLRA (SEQ ID NO: 310)

Pool Fp17
54) PESTLEEKLRACQEV (SEQ ID NO: 311)

55) LEEKLRACQEVGSPGY (SEQ ID NO: 312)

56) RACQEVGSPGYKMQLL (SEQ ID NO: 313)

Consensus Subtype-B HIV-1 p24 Overlapping Peptides

Pool Hp1
1) PIVQNLQGQMVHQAI (SEQ ID NO: 314)

2) NLQGQMVHQAISPRT (SEQ ID NO: 315)

3) QMVHQAISPRTLNAW (SEQ ID NO: 316)

4) QAISPRTLNAWVKVV (SEQ ID NO: 317)

Pool Hp2
5) PRTLNAWVKVVEEKA (SEQ ID NO: 318)

6) NAWVKVVEEKAFSPE (SEQ ID NO: 319)

7) KVVEEKAFSPEVIPM (SEQ ID NO: 320)

Pool Hp3
8) EKAFSPEVIPMFSAL (SEQ ID NO: 322)

9) SPEVIPMFSALSEGA (SEQ ID NO: 323)

10) IPMFSALSEGATPQD (SEQ ID NO: 324)

Pool Hp4
11) SALSEGATPQDLNTM (SEQ ID NO: 325)

12) EGATPQDLNTMLNTV (SEQ ID NO: 326)

13) PQDLNTMLNTVGGHQ (SEQ ID NO: 327)

Pool Hp5
14) NTMLNTVGGHQAAMQ (SEQ ID NO: 328)

15) NTVGGHQAAMQMLKE (SEQ ID NO: 329)

16) GHQAAMQMLKETINE (SEQ ID NO: 330)

Pool Hp6
17) AMQMLKETINEEAAE (SEQ ID NO: 331)

18) LKETINEEAAEWDRL (SEQ ID NO: 332)

19) INEEAAEWDRLHPVH (SEQ ID NO: 333)

Pool Hp7
20) AAEWDRLHPVHAGPI (SEQ ID NO: 334)

21) DRLHPVHAGPIAPGQ (SEQ ID NO: 335)

22) PVHAGPIAPGQMREP (SEQ ID NO: 336)

Pool Hp8
23) GPIAPGQMREPRGSD (SEQ ID NO: 338)

24) PGQMREPRGSDIAGT (SEQ ID NO: 339)

25) REPRGSDIAGTTSTL (SEQ ID NO: 340)

Pool Hp9
26) GSDIAGTTSTLQEQI (SEQ ID NO: 341)

27) AGTTSTLQEQIGWMT (SEQ ID NO: 342)

28) STLQEQIGWMTNNPP (SEQ ID NO: 343)

Pool Hp10
29) EQIGWMTNNPPIPVG (SEQ ID NO: 344)

30) WMTNNPPIPVGEIYK (SEQ ID NO: 345)

31) NPPIPVGEIYKRWII (SEQ ID NO: 346)

Pool Hp11
32) PVGEIYKRWIILGLN (SEQ ID NO: 347)

33) IYKRWIILGLNKIVR (SEQ ID NO: 348)

34) WIILGLNKIVRMYSP (SEQ ID NO: 349)

Pool Hp12
35) GLNKIVRMYSPTSIL (SEQ ID NO: 350)

36) IVRMYSPTSILDIRQ (SEQ ID NO: 351)

37) YSPTSILDIRQGPKE (SEQ ID NO: 352)

Pool Hp13
38) SILDIRQGPKEPFRD (SEQ ID NO: 353)

39) IRQGPKEPFRDYVDR (SEQ ID NO: 354)

40) PKEPFRDYVDRFYKT (SEQ ID NO: 355)

-continued

```
Pool Hp14
41)    FRDYVDRFYKTLRAE       (SEQ ID NO: 356)

42)    VDRFYKTLRAEQASQ       (SEQ ID NO: 357)

43)    YKTLRAEQASQEVKN       (SEQ ID NO: 358)

Pool Hp15
44)    RAEQASQEVKNWMTE       (SEQ ID NO: 359)

45)    ASQEVKNWMTETLLV       (SEQ ID NO: 360)

46)    VKNWMTETLLVQNAN       (SEQ ID NO: 361)

Pool Hp16
47)    MTETLLVQNANPDCK       (SEQ ID NO: 362)

48)    LLVQNANPDCKTILK       (SEQ ID NO: 363)

49)    NANPDCKTILKALGP       (SEQ ID NO: 364)

Pool Hp17
50)    DCKTILKALGPAATL       (SEQ ID NO: 365)

51)    ILKALGPAATLEEMM       (SEQ ID NO: 366)

52)    LGPAATLEEMMTACQ       (SEQ ID NO: 367)

Pool Hp18
53)    ATLEEMMTACQGVGG       (SEQ ID NO: 368)

54)    EMMTACQGVGGPGHK       (SEQ ID NO: 369)

55)    ACQGVGGPGHKARVL       (SEQ ID NO: 370)
```

SIVmm251 RT

```
SRT1
1)     PIAKVEPVKVTLKR        (SEQ ID NO: 495)

2)     EPVKVTLKPGKVGPK       (SEQ ID NO: 496)

3)     KPGKVGPKLKQWPL        (SEQ ID NO: 497)

4)     PKLKQWPLSKEKIVA       (SEQ ID NO: 498)

SR2
5)     LSKEKIVALREICEK       (SEQ ID NO: 499)

6)     ALREICEKMEKDGQL       (SEQ ID NO: 500)

7)     KMEKDGQLEEAPPTNPY     (SEQ ID NO: 501)

8)     EAPPTNPYNTPTFAI       (SEQ ID NO: 502)

SRT3
9)     YNTPTFAIKKKDKNK       (SEQ ID NO: 503)

10)    IKKKDKNKWRMLIDF       (SEQ ID NO: 504)

11)    KWRMLIDFRELNRV        (SEQ ID NO: 505)

12)    DFRELNRVTQDFTEV       (SEQ ID NO: 506)

SRT4
13)    VTQDFTEVQLGIPH        (SEQ ID NO: 507)

14)    EVQLGIPHPAGLAKR       (SEQ ID NO: 508)

15)    HPAGLAKRKRITVL        (SEQ ID NO: 509)

SRT5
16)    KRKRITVLDIGDAYF       (SEQ ID NO: 510)

17)    DAYFSIPLDEEFR         (SEQ ID NO: 511)

18)    SIPLDEEFRQYTAF        (SEQ ID NO: 512)

SRT6
19)    EFRQYTAFTLPSV         (SEQ ID NO: 513)

20)    TAFTLPSVNNAEPGK       (SEQ ID NO: 514)

21)    VNNAEPGKRYIYKVL       (SEQ ID NO: 515)

22)    KRYIYKVLPQGWK         (SEQ ID NO: 516)

SRT7
23)    KVLPQGWKGSPAIFR       (SEQ ID NO: 517)

24)    WKGSPAIFQYTMRHV       (SEQ ID NO: 518)

25)    FQYTMRHVLEPFRKA       (SEQ ID NO: 519)

26)    RHVLEPFRKANPDV        (SEQ ID NO: 520)

SRT8
27)    FRKANPDVTLVQYM        (SEQ ID NO: 521)

28)    VQYMDDILIASDRR        (SEQ ID NO: 522)

29)    DILIASDRTDLEHDR       (SEQ ID NO: 523)

30)    RTDLEHDRVVLQLK        (SEQ ID NO: 524)

SRT9
31)    DLEHDRVVLQLKEL        (SEQ ID NO: 525)

32)    LKELLNSIGFSTPEEK      (SEQ ID NO: 526)

33)    GFSTPEEKFQKDPPF       (SEQ ID NO: 527)

34)    KFQKDPPFQWMGYEL       (SEQ ID NO: 528)

SRT10
35)    FQWMGYELWPTKWKL       (SEQ ID NO: 529)

36)    LWPTKWKLQKIEL         (SEQ ID NO: 530)

37)    WKLQKIELPQRETW        (SEQ ID NO: 531)

38)    ELPQRETWTVNDIQK       (SEQ ID NO: 532)

39)    VNDIQKLVGVLNRR        (SEQ ID NO: 533)

SRT11
40)    VGVLNWAAQIYRRR        (SEQ ID NO: 534)

41)    LNWAAQIYPGIKTKH       (SEQ ID NO: 535)

42)    YPGIKTKHLCRLIR        (SEQ ID NO: 536)

43)    KHLCRLIRGKMTL         (SEQ ID NO: 537)

SRT12
44)    LIRGKMTLTEEVQW        (SEQ ID NO: 538)

45)    TLTEEVQWTEMAEA        (SEQ ID NO: 539)

46)    VQWTEMAEAEYEENK       (SEQ ID NO: 540)

47)    EAEYEENKIILSQER       (SEQ ID NO: 541)

SRT13
48)    KIILSQEQEGCYY         (SEQ ID NO: 542)

49)    SQEQEGCYYQEGKPL       (SEQ ID NO: 543)

50)    YYQEGKPLEATVIK        (SEQ ID NO: 544)

51)    PLEATVIKSQDNQW        (SEQ ID NO: 545)

52)    IKSQDNQWSYKIH         (SEQ ID NO: 546)

SRT14
53)    NQWSYKIHQEDKILK       (SEQ ID NO: 547)

54)    HQEDKILKVGKFAKI       (SEQ ID NO: 548)
```

```
55)   KVGKFAKIKNTHTNGV         (SEQ ID NO: 549)

SRT15
56)   KNTHTNGVRLLAHVI          (SEQ ID NO: 550)

57)   RLLAHVIQKIGKEAR          (SEQ ID NO: 551)

58)   KIGKEAIVIWGQR            (SEQ ID NO: 552)

59)   WGQVPKFHLPV              (SEQ ID NO: 553)

SRT16
60)   VPKFHLPVERDVW            (SEQ ID NO: 554)

61)   LPVERDVWEQWWTDY          (SEQ ID NO: 555)

62)   WEQWWTDYWQVTWI           (SEQ ID NO: 556)

63)   DYWQVTWIPEWDFI           (SEQ ID NO: 557)

SRT17
64)   TWIPEWDFISTPPLVR         (SEQ ID NO: 558)

65)   STPPLVRLVFNRR            (SEQ ID NO: 559)

66)   RLVFNLVKDPIEGEETY        (SEQ ID NO: 560)

SIVmm251 p24

Pool Sp1
1)    PVQQIGGNYVHLPLSPR        (SEQ ID NO: 561)

2)    GNYVHLPLSPRTLNA          (SEQ ID NO: 562)

3)    SPRTLNAWVKLIEEKK         (SEQ ID NO: 563)

Pool Sp2
4)    LNAWVKLIEEKKFGA          (SEQ ID NO: 564)

5)    IEEKKFGAEVVPGF           (SEQ ID NO: 565)

Pool Sp3
6)    KKFGAEVVPGFQALSEGR       (SEQ ID NO: 566)

7)    FQALSEGCTPYDIR           (SEQ ID NO: 567)

Pool Sp4
8)    EGCTPYDINQMLNCV          (SEQ ID NO: 568)

9)    YDINQMLNCVGDHQA          (SEQ ID NO: 569)

Pool Sp5
10)   DHQAAMQIIRDIINEEA        (SEQ ID NO: 570)

11)   MQIIRDIINEEAADW          (SEQ ID NO: 571)

12)   INEEAADWDLQHPQPA         (SEQ ID NO: 572)

Pool Sp6
13)   DLQHPQPAPQQGQLR          (SEQ ID NO: 573)

Pool Sp7
14)   APQQGQLREPSGSDI          (SEQ ID NO: 574)

15)   REPSGSDIAGTTSSV          (SEQ ID NO: 575)

Pool Sp8
16)   IAGTTSSVDEQIQWM          (SEQ ID NO: 576)

17)   VDEQIQWMYRQQNPI          (SEQ ID NO: 577)

Pool Sp9
18)   MYRQQNPIPVGNIYR          (SEQ ID NO: 578)

19)   NPIPVGNIYRRWI            (SEQ ID NO: 579)

Pool Sp10
20)   RRWIQLGLQKCVRMY          (SEQ ID NO: 580)

21)   LQKCVRMYNPTNIL           (SEQ ID NO: 581)

Pool Sp11
22)   MYNPTNILDVKQGPK          (SEQ ID NO: 582)

Pool Sp12
23)   LDVKQGPKEPFQSYV          (SEQ ID NO: 583)

24)   KEPFQSYVDRFYKSL          (SEQ ID NO: 584)

Pool Sp13
25)   VDRFYKSLRAEQTDA          (SEQ ID NO: 585)

26)   LRAEQTDAAVKNWM           (SEQ ID NO: 586)

Pool Sp14
27)   TDAAVKNWMTQTL            (SEQ ID NO: 469)

Pool Sp15
28)   WMTQTLLIQNANPDCK         (SEQ ID NO: 587)

29)   IQNANPDCKLVLK            (SEQ ID NO: 588)

Pool Sp16
30)   KGLGVNPTLEEMLTAR         (SEQ ID NO: 589)

Pool Sp17
31)   NPTLEEMLTACQGVGGPGQK     (SEQ ID NO: 590)

32)   GVGGPGQKARLM             (SEQ ID NO: 591)
```

Peptides for Mapping MAB Epitopes

| Code | Peptide sequence | (aa-mer) | |
|---|---|---|---|
| Antibody FIV p24 Peptides (FB = Bangston; FC = FC1; FCS = only "PDCK" changed to FC1) | | | |
| FB1) | PIQTVNGAPQYVALDPKMVSIFMEKAREGL | (30) | (SEQ ID NO: 371) |
| FB2) | QYVALDPKMVSIFMEKAREGLGGEEVQL | (28) | (SEQ ID NO: 372) |
| FC2) | EVQLWFTAFSANLTPTDMATLIMAAP | (26) | (SEQ ID NO: 373) |
| FB3) | TLIMAAPGCAADKEILDESLKQLTAEYDR | (29) | (SEQ ID NO: 374) |
| FB4) | SLKQLTAEYDRTHPPDGPRPLPYFTAAEIM | (30) | (SEQ ID NO: 375) |
| FB5) | PLPYFTAAEIMGIGLTQEQQAEARFAPARM | (30) | (SEQ ID NO: 376) |
| FB6) | EQQAEARFAPARMQCRAWYLEALGKLAAIK | (30) | (SEQ ID NO: 377) |
| FB7) | LEALGKLAAIKAKSPRAVQLRQGAKEDY | (28) | (SEQ ID NO: 378) |

-continued

| Code | Peptide sequence | | |
|---|---|---|---|
| FB8) | VQLRQGAKEDYSSFIDRLFAQIDQEQNTA | (29) | (SEQ ID NO: 379) |
| FB9) | FAQIDQEQNTAEVKLYLKQSLSIANANA | (28) | (SEQ ID NO: 380) |
| FB10) | KQSLSIANANAECKKAMSHLKPESTLEEKL | (30) | (SEQ ID NO: 381) |
| FB11) | LKPESTLEEKLRACQEVGSPGYKMQLL | (28) | (SEQ ID NO: 382) |
| FCS12) | FAQIDQEQNTAEVKLYLKQSLSIANANPDCK | (31) | (SEQ ID NO: 383) |
| FCS13) | LSIANANPDCKRAMSHLKPESTLEEKLRA | (29) | (SEQ ID NO: 384) |

| | | (aa-mer) [Hydrophlicity] | |
|---|---|---|---|
| | FIV-Bang p24 (30-mer) | | |
| FBO1) | PIQTVNGAPQYVALDPKMVSIFMEKAREGL | (30) [-0.02] | (SEQ ID NO: 371) |
| FBO2) | PQYVALDPKMVSIFMEKAREGLGGEEVQ | (28) [-0.30] | (SEQ ID NO: 385) |
| FBO3) | IFMEKAREGLGGEEVQLWFTAFSANLTPTD | (30) [-0.12] | (SEQ ID NO: 386) |
| FBO4) | KAREGLGGEEVQLWFTAFSANLTPTDMA | (28) [-0.20] | (SEQ ID NO: 387) |
| FCO5) | NLTSTDMATLIMSAPGCAADKEILDETLKQ | (30) [-0.03] FC1 | (SEQ ID NO: 388) |
| FBO6) | TLIMAAPGCAADKEILDESLKQLTAEYDRT | (30) [-0.18] | (SEQ ID NO: 389) |
| FBO7) | AAPGCAADKEILDESLKQLTAEYDRTHPPD | (30) [-0.83] | (SEQ ID NO: 390) |
| FBO8) | CAADKEILDESLKQLTAEYDRTHPPDAPRP | (30) [-1.08] | (SEQ ID NO: 391) |
| FBO9) | SLKQLTAEYDRTHPPDAPRPLPYFTAAEIM | (30) [-0.64] | (SEQ ID NO: 392) |
| FBO10) | RTHPPDAPRPLPYFTAAEIMGIGLTQEQQA | (30) [-0.56] | (SEQ ID NO: 393) |
| FBO11) | LPYFTAAEIMGIGLTQEQQAEARFAPARMQ | (30) [-0.11] | (SEQ ID NO: 394) |
| FBO12) | GIGLTQEQQAEARFAPARMQCRAWYLEALG | (30) [-0.33] | (SEQ ID NO: 395) |
| FBO13) | EARFAPARMQCRAWYLEALGKLAAIKAKSP | (30) [-0.16] | (SEQ ID NO: 396) |
| FBO14) | CRAWYLEALGKLAAIKAKSPRAVQLRQGAK | (30) [-0.20] | (SEQ ID NO: 397) |
| FBO15) | KLAAIKAKSPRAVQLRQGAKEDYSSFIDRL | (30) [-0.53] | (SEQ ID NO: 398) |
| FBO16) | RAVQLRQGAKEDYSSFIDRLFAQIDQEQNT | (30) [-0.94] | (SEQ ID NO: 399) |
| FBO17) | EDYSSFIDRLFAQIDQEQNTAEVKLYLKQS | (30) [-0.76] | (SEQ ID NO: 400) |
| FBO18) | FAQIDQEQNTAEVKLYLKQSLSIANANAEC | (30) [-0.37] | (SEQ ID NO: 401) |
| FBO19) | AEVKLYLKQSLSIANANAECKKAMSHLKPE | (30) [-0.39] | (SEQ ID NO: 402) |
| FBO20) | LSIANANAECKKAMSHLKPESTLEEKLRAC | (30) [-0.45] | (SEQ ID NO: 403) |
| FBO21) | KKAMSHLKPESTLEEKLRACQEVGSPGYKM | (30) [-0.92] | (SEQ ID NO: 404) |
| FBO22) | STLEEKLRACQEVGSPGYKMQLL | (23) [-0.44] | (SEQ ID NO: 405) |
| | HIV-1-UCD1 p24 (22-30-mer) | | |
| HB1) | PVVQNLQGQMVHQPISPRTLNAWVKVVEEK | (30) [-0.34] | (SEQ ID NO: 406) |
| HB2) | QMVHQPISPRTLNAWVKVVEEKAFSPEVIP | (30) [-0.13] | (SEQ ID NO: 407) |
| HB3) | KVVEEKAFSPEVIPMFTALSEGATPQDLNT | (30) [-0.12] | (SEQ ID NO: 408) |
| HB4) | SPEVIPMFTALSEGATPQDLNTMLNTVGGH | (30) [-0.00] | (SEQ ID NO: 409) |
| HB5) | TALSEGATPQDLNTMLNTVGGHQAAMQMLK | (30) [-0.19] | (SEQ ID NO: 410) |
| HB6) | DLNTMLNTVGGHQAAMQMLKETINEEAAEW | (30) [-0.43] | (SEQ ID NO: 411) |
| HB7) | GHQAAMQMLKETINEEAAEWDRLHPVHAGP | (30) [-0.75] | (SEQ ID NO: 412) |

| Code | Peptide sequence | | | |
|---|---|---|---|---|
| HB8) | ETINEEAAEWDRLHPVHAGPIAPDQMREPR | (30) | [-1.12] | (SEQ ID NO: 413) |
| HB9) | DRLHPVHAGPIAPDQMREPRGSDIAGITST | (30) | [-0.64] | (SEQ ID NO: 414) |
| HB10) | IAPDQMREPRGSDIAGITSTLQEQIGWMTN | (30) | [-0.56] | (SEQ ID NO: 415) |
| HB11) | GSDIAGITSTLQEQIGWMTNNPPIPVGEIY | (30) | [-0.09] | (SEQ ID NO: 416) |
| HB12) | LQEQIGWMTNNPPIPVGEIYKRWIILGLNK | (30) | [-0.22] | (SEQ ID NO: 417) |
| HB13) | MTNNPPIPVGEIYKRWIILGLNKIVRMYSP | (30) | [-0.02] | (SEQ ID NO: 418) |
| HB14) | KRWIILGLNKIVRMYSPTSILDIRQGPKEP | (30) | [-0.31] | (SEQ ID NO: 419) |
| HB15) | IVRMYSPTSILDIRQGPKEPFRDYVDRFYK | (30) | [-0.72] | (SEQ ID NO: 420) |
| HB16) | ETINEEAAEWDRLHPVHAGPIAPDQMREPR | (30) | [-1.12] | (SEQ ID NO: 413) |
| HB17) | DRLHPVHAGPIAPDQMREPRGSDIAGITST | (30) | [-0.64] | (SEQ ID NO: 414) |
| HB18) | IAPDQMREPRGSDIAGITSTLQEQIGWMTN | (30) | [-0.56] | (SEQ ID NO: 415) |
| HB19) | GSDIAGITSTLQEQIGWMTNNPPIPVGEIY | (30) | [-0.09] | (SEQ ID NO: 416) |
| HB20) | LQEQIGWMTNNPPIPVGEIYKRWIILGLNK | (30) | [-0.22] | (SEQ ID NO: 417) |
| HB21) | MTNNPPIPVGEIYKRWIILGLNKIVRMYSP | (30) | [-0.02] | (SEQ ID NO: 418) |
| HB22) | KRWIILGLNKIVRMYSPTSILDIRQGPKEP | (30) | [-0.31] | (SEQ ID NO: 419) |
| HB23) | IVRMYSPTSILDIRQGPKEPFRDYVDRFYK | (30) | [-0.72] | (SEQ ID NO: 420) |
| HB24) | LDIRQGPKEPFRDYVDRFYKTLRAEQASQD | (30) | [-1.32] | (SEQ ID NO: 421) |
| HB25) | FRDYVDRFYKTLRAEQASQDVKNWMTETLL | (30) | [-0.83] | (SEQ ID NO: 422) |
| HB26) | TLRAEQASQDVKNWMTETLLVQNANPDCKT | (30) | [-0.79] | (SEQ ID NO: 423) |
| HB27) | VKNWMTETLLVQNANPDCKTILKALGPAAT | (30) | [-0.01] | (SEQ ID NO: 424) |
| HB28) | VQNANPDCKTILKALGPAATLEEMMTACQG | (30) | [-0.02] | (SEQ ID NO: 425) |
| HB29) | TLEEMMTACQGVGGPGHKARVL | (22) | [-0.04] | (SEQ ID NO: 426) |

Materials and Methods for Examples 5-11

Study population. Blood from HIV-1 infected subjects was obtained from the University of California at San Francisco (UCSF), the University of South Florida in Tampa, and the University of Florida Center for HIV/AIDS Research, Education and Service (UF CARES) in Jacksonville. These subjects are distributed into three groups according to the length of infection and the anti-retroviral therapy (ART) status (Table 9). The HIV-infected (HIV+) subjects consist of long-term survivors (LTS) who have been infected for more than 10 years and remain healthy without antiretroviral therapy (LTS/ART−); subjects with short-term infection without ART (ST/ART−) and subjects on ART for various amounts of time (ART+). T-cell counts and HIV-1 RNA levels were performed by clinical laboratories at UCSF Medical Center and UF Shands Medical Center (Gainesville, Fla.). Bloods from HIV seronegative (HIV−) samples were obtained from LifeSouth Community Blood Centers (Gainesville, Fla.) or randomly selected volunteers at UF. The blood collections were performed according to the policy and protocol approved by the Institutional Review Boards at UF and UCSF and processed in 2-30 hours after collection.

RT overlapping peptides. Overlapping peptides of subtype-B HIV-1UCD1 and subtype-B FIVFC1 RT proteins and selected peptides for epitope mapping were produced initially by SynPep (Dublin, Calif.) and later by RS Synthesis LLC (Louisville, Ky.) with similar findings. Four to five consecutive peptides (11-16 aa long with 8-10 aa overlap) were grouped into 21 pools: H1-H21 for HIV and counterparts F1-F21 for FIV. In addition, 9mer and 15-16mer peptides with modified sequences were also synthesized by RS Synthesis LLC and used for peptide epitope mapping as shown in Table 10.

ELISpot assays. Enzyme-linked immunosorbent spot assays (ELISpot) for IFNγ (R&D Systems, Minneapolis, Minn.) were performed with AIM V medium containing 5% heat-inactivated (56° C., 30 min) human serum as previously described (Abbott et al. (2012)). The PBMC from HIV+ subjects were stimulated with either peptide pool (4-5 consecutive peptides per pool at 5 μg per peptide) or individual peptide (15 μg/well). The peptides were 11-16 aa in length with 8-10 aa overlap. The results were analyzed with an ELISpot reader (MVS Pacific LLC, Minneapolis, Minn.) and adjusted to spot forming units (SFU) per $10^6$ cells, after subtraction of the average medium control for each subject. The PBMC from HIV+ subjects were stimulated with T-cell mitogen, phytohemaglutinin A (PHA, 5 μg/mL), as positive control. At a positive threshold of 70 SFU, HIV− subjects had no substantial IFNγ responses (>50 SFU) to HIV and FIV peptide pools.

Flow cytometry (FACS) for carboxyfluoresein diacetate succinimide ester (CFSE)-proliferation and intracellular cytotoxin staining (ICS). The CFSE-proliferation analysis was performed on PBMC according to the manufacturer's protocol (Invitrogen, Carlsbad, Calif.) and processed as previously described (Lichterfeld et al. (2004)). Modifications consisted of using $2.0$-$5.0 \times 10^5$ CFSE-labeled cells stimulated for 5 days (37° C., 5% $CO_2$) with 30 μg/well of total peptides in a pool (15 μg/well for individual peptide, Table 10) or 5 μg/mL PHA in AIM V medium containing 25 μg/mL of gentamycin and 10% heat-inactivated human serum. Subsequently these cells were harvested and labeled with the LIVE/DEAD fixable yellow dye (Invitrogen) and then treated 5 min with anti-CD16/CD32 antibody (Biolegend, San Diego, Calif.) for blocking non-specific binding before phenotype-specific antibodies. The following antibodies were used for the CFSE-proliferation analysis: anti-CD4 APC, anti-CD3 APC-H7, and anti-CD8 Pacific Blue (BD Biosciences, San Jose, Calif.).

The ICS analysis (Horton et al. (2007)) involved stimulating $0.5$-$1.0 \times 10^6$ freshly isolated PBMC for 6 h with the same peptide stimulant and culture conditions as the proliferation analysis in the presence of 1 μg/mL of Golgi transport inhibitor and monensin followed by labeling with LIVE/DEAD fixable yellow dye and then treatment with anti-CD16/CD32 antibody and T-cell phenotypic antibodies. The cells were subsequently fixed and permeabilized with Cytofix/Cytoperm solution (BD Biosciences) before reaction with anti-cytotoxin antibodies. The antibodies consisted of anti-CD3 APC-H7, anti-CD4 BD Horizon V450, and anti-CD8 FITC followed by anti-GrzB Alexa 700 and anti-GrzA PE (all from BD Biosciences), and anti-perforin PerCP (Abcam, Boston, Mass.).

In both analyses, $1.0$-$2.0 \times 10^4$ cells were fixed in phosphate-buffered saline (PBS) containing 2% paraformaldehyde and analyzed on BD LSRII using FACSDIVA Software (BD Biosciences), with a positive threshold of 3% $CFSE^{low}$ for CFSE-proliferation and 1% T cells expressing cytotoxin for ICS. The final value for each subject was derived after subtraction of the subject's medium control and the average value of peptide-stimulated cells from uninfected control subjects.

Statistics. Paired Student t-test with two-tailed distribution (SigmaPlot version 11.0, San Jose, Calif.) was used to evaluate the statistical differences between the results from two time points in FIG. 19. These results were considered statistically different when $p<0.05$.

Example 5

Screening for IFNγ-Inducing Epitopes on HIV-1 and FIV RT

As a first step towards identifying the CTL-associated reactive sites on HIV-1 and FIV RT proteins, the PBMC from HIV+ subjects and HIV− subjects were screened by ELISpot analysis for IFNγ responses to overlapping RT peptide pools of HIV-1 and FIV. NK cells, CD3+CD4+ T-helper cells, CD3+CD4+ CTLs, and CD3+CD8+ CTLs generally produce IFNγ responses to viral peptides (Abbas et al. (2010); Soghoian et al. (2012)). In this study, many HIV-1 pools induced IFNγ responses of high magnitudes above the threshold level (≥70 SFU) with the PBMC from HIV+ subjects (FIG. 17A) but none with the PBMC from HIV− subjects (data not shown). Therefore, the viral specificity of the IFNγ responses is associated with HIV-1 infection. The average responder frequency for all 21 pools was 25% (range, 4-54%) (FIG. 17E). Of all HIV peptide pools screened, pool H11 induced the highest and the most frequent IFNγ responses.

Figures 17A, 17B:
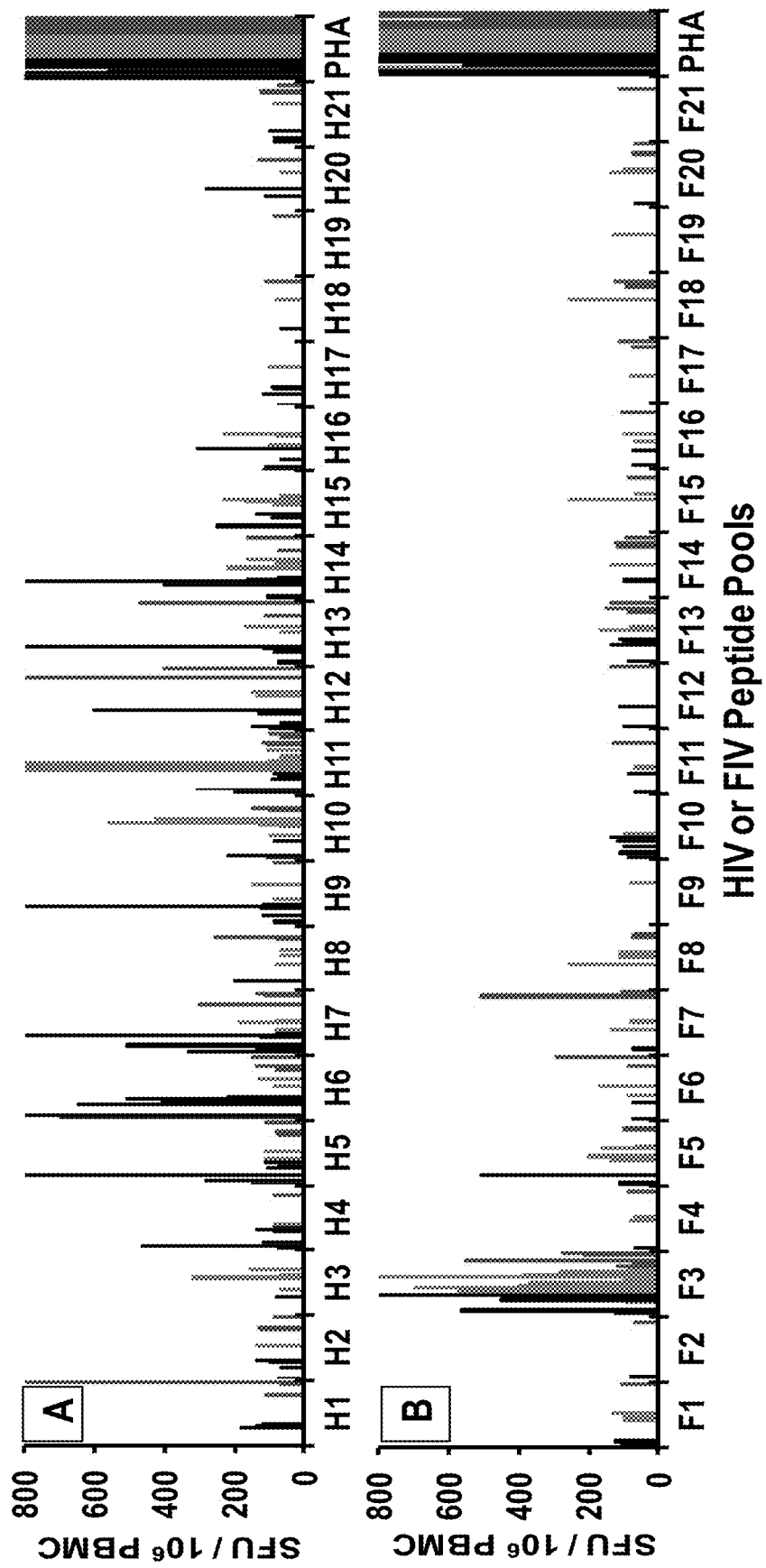
FIGS. 17A-17F. IFNγ and CD8+ T cell proliferation responses of HIV-infected subjects to HIV and FIV reverse transcriptase (RT) peptide pools. The IFNγ ELISpot (FIGS. 17A and 17B, n=32; 12 LTS, 12 ST, 8 ART+) and CD3+CD8+ T-cell proliferation (FIGS. 17C and 17D, n=26; 11 LTS, 7 ST, 8 ART+) responses to overlapping peptide pools of HIV RT (H1-H21.
Figures 17C, 17D:
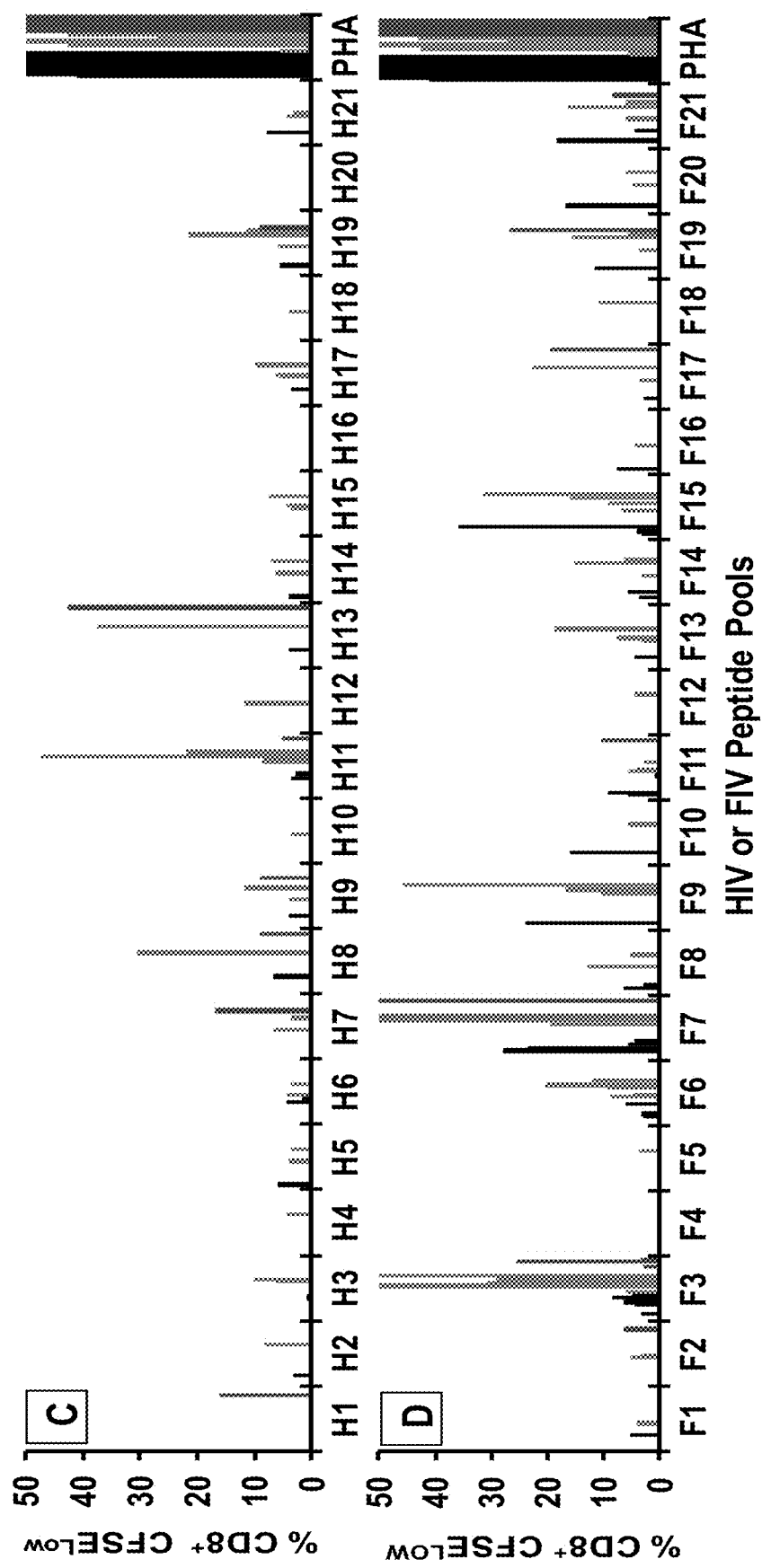
Figure 17E:
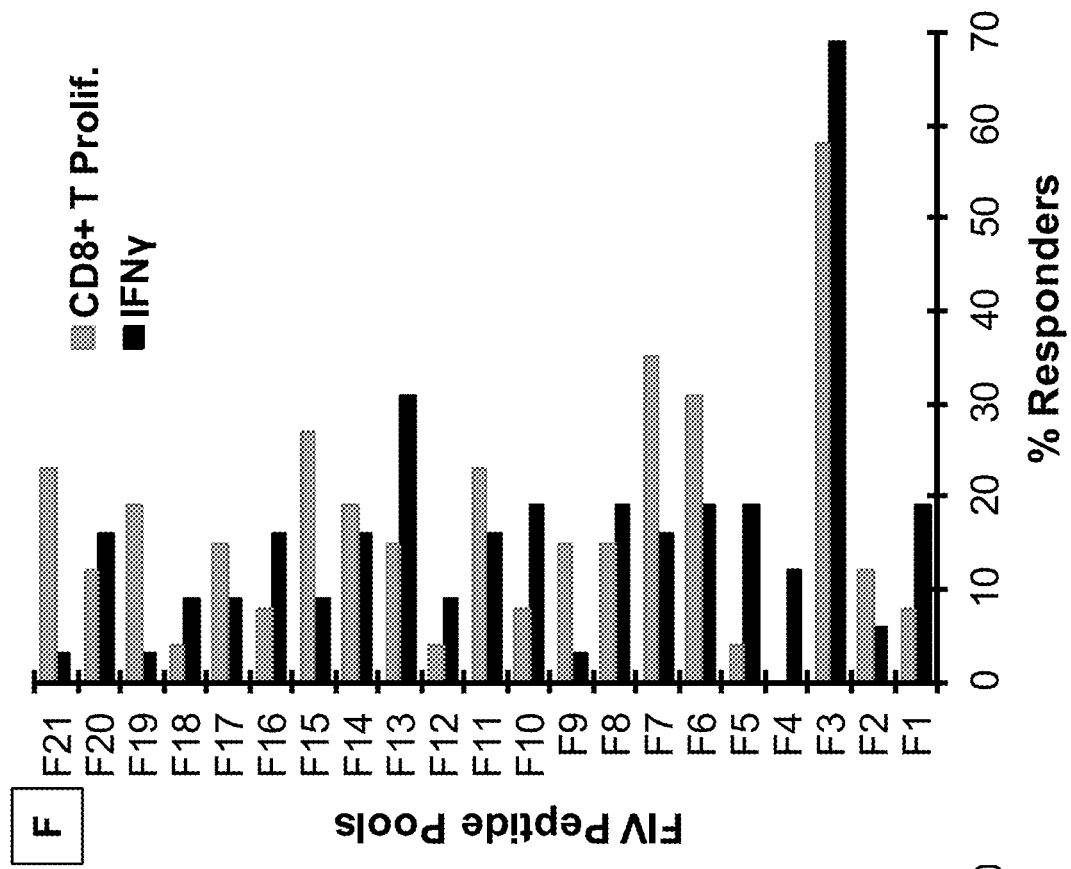
Figure 17F:
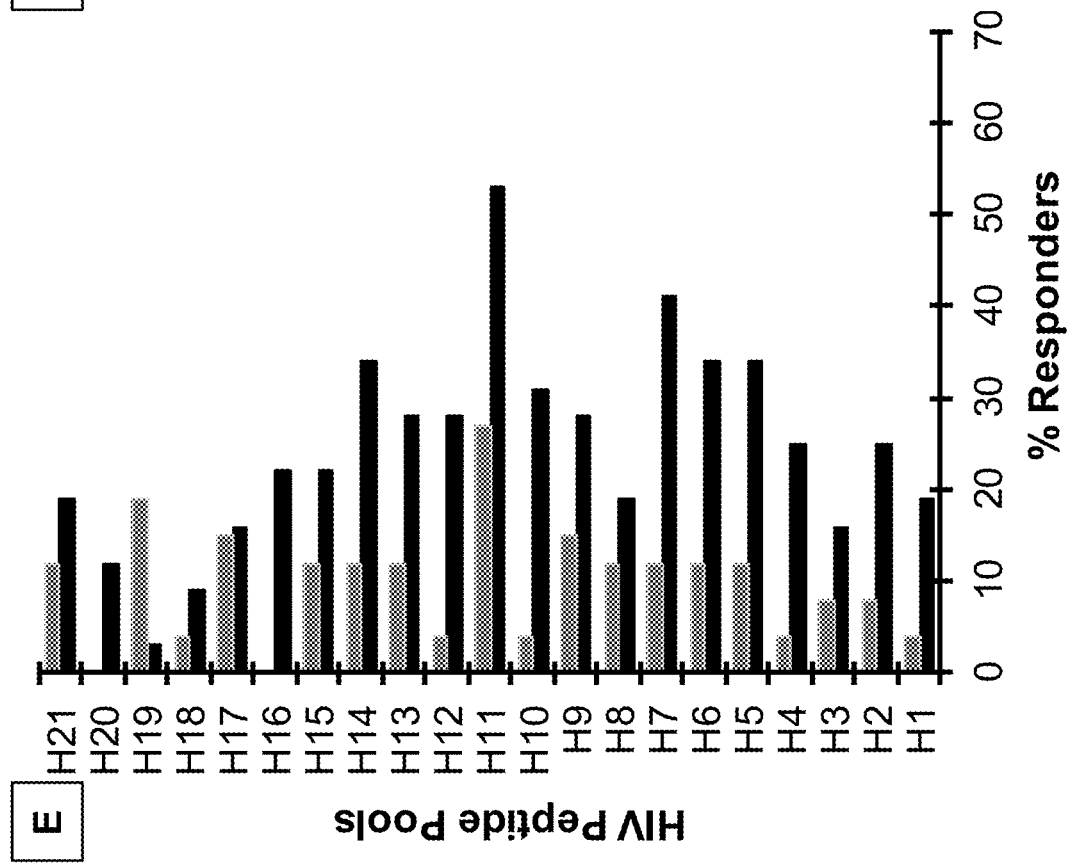

Compared to the HIV peptide-pool responses, the magnitude and the frequency of the IFNγ responses to the FIV peptide pools were much lower in the PBMC from HIV+ subjects (FIGS. 17B and 17F). The average responder frequency for all 21 pools was 17% (range, 4-69%) (FIG. 17F). A noticeable exception was observed with pool F3 which induced the highest and the most frequent cellular responses among the FIV pools (FIGS. 17B and 17F). PBMC from only five subjects (SF08, J08, J02, J09, TP01) responded to a counterpart pool H3 (grouped data only, FIG. 17A), and remarkably PBMC from four of these subjects responded to both F3 and H3 (grouped data only, FIGS. 17A and 17B). As expected, the PBMC of HIV− subjects had no IFNγ responses to the FIV pools (data not shown). Overall, HIV pools induced much higher and more frequent IFNγ responses than the FIV counterparts except for pool F3. However, only a few HIV and FIV counterparts were detected by the same individual (4-5 responders detected both: H3/F3, H6/F6, H7/F7, H11/F11, H13/F13).

The immune responses observed were present in all three clinical groups (LTS/ART−, ST/ART−, ART+). In addition these groups were not statistically different in terms of cell counts. However, it is noteworthy that 4 of 5 responders to pool H3 are in the ST group which may indicate that this response has been lost in the LTS and ART+ group, possibly due to HIV infection.

Example 6

Screening for T-Cell Proliferation Epitopes on HIV-1 and FIV RTs

The presence of strong T-cell proliferation responses to HIV antigen(s) has been associated with lower viral load and better disease outcome in HIV+ individuals (McKinnon et al. (2012)). In the current studies, CD3+CD4+ T cells (hereon CD4+ T cells) from HIV+ subjects (FIGS. 18A and 18B) had fewer proliferation responses than CD3+CD8+ T cells (CD8+ T cells) to both HIV and FIV pools (FIGS. 17C and 17D). The CD4+ T cells from only 5 of 26 HIV+ subjects responded to at least one HIV pool, whereas 9 of 26 HIV+ subjects responded to at least one FIV pool (FIGS. 18A and 18B). In contrast, the CD8+ T cells from 17 of 26 HIV+ subjects responded to the HIV pools, and 22 of 26 subjects responded to the FIV pools (FIGS. 17C and 17D).

The most striking result was the high magnitude and the high frequency of CD8+ T-cell proliferation to the FIV pools in comparison to HIV pools (FIGS. 17C and 17D). Furthermore, the average responder frequency to all FIV pools was 17% (range, 0-54%) (FIG. 17F), which is higher than the average of 10% (range, 0-24%) observed with the HIV pools (FIG. 17E). Only one of the HIV pools (H11) had a responder frequency of >20% (FIG. 17E), while the responder frequencies to the six FIV pools (F3, F6, F7, F11, F15, F21) were >20% (FIG. 17E). In addition, only a few HIV and FIV counterparts were detected by the same subject (2-4 responders detected both: H3/F3, H6/F6, H14/F14, H15/F15, H17/F17, H19/F19), but 43% (23 of 53) of the total positive proliferation responses to the HIV-1 pools were also positive to FIV counterparts.

The above results support the view that the CD8+ T-cell proliferative responses to FIV pools are more robust or possibly more intact than those to HIV pools. This finding is clearly opposite from the results of the IFNγ studies where the IFNγ responses were stronger against the HIV pools than the FIV pools (FIGS. 17A and 17B). These conflicting findings may be partially attributed to the difference in the cell types used (PBMC versus CD8+ T cells). Moreover, 12 of 15 responders showing CD8+ T-cell proliferation to the F3 pool also had robust IFNγ responses to the F3 pool (FIGS. 17B and 17D). These findings indicate that these subjects recognize peptide epitope(s) that induce both responses.

Example 7

The Persistence of IFNγ and Proliferation Responses to Selected HIV and FIV Peptide Pools Due to the ability of HIV to quickly escape from immunological pressure (Leslie et al. (2004); Troyer et al. (2009)), the PBMC from IFNγ responders (FIGS. 17A and 17B) were retested at least one year later for IFNγ responses to peptide pools H6, H11, and F3. The majority of the individuals tested retained positive IFNγ responses at the second time-point to H6 (8 of 11 responders) and to F3 (11 of 14 responders) but fewer to H11 (5 of 14 responders) (FIG. 19A). The cells from a few subjects were retested against H6 and F3 for a third time-point and demonstrated the persistence of the IFNγ responses to the F3 pool (4 of 5) but to a lesser extent to the H6 pool (2 of 4) after 3 years (FIG. 19A). More importantly, the persistence of the IFNγ responses to the F3 pool demonstrated the reproducibility of this activity even though no IFNγ responses were observed to the HIV-counterpart H3 by those who were tested after 2 years (Table 10, top for H3-3 peptide).

The CD4+ and CD8+ T-cell proliferation responses did not correlate with the IFNγ responses in general as only a low frequency of CD4+ T responses were observed. However, more CD4+ T-cell responses were observed in the production of cytotoxins. The lack of correlation between IFNγ ELISpot and CD8+ T-cell proliferation responses has been described before, with p24 proteins. In this case, the majority of responses (64%) were IFNγ+/proliferation− and only 30% of the responses were IFNα+/proliferation+ (Richmond et al. (2011)). Furthermore, the use of PBMC in the IFNγ analysis may have contributed to the lack of correlation between IFNγ and T-cell proliferation responses. Cells such as NK cells in PBMC are known to be high producer of IFNγ (Caligiuri (2008)) and could have also given the IFNγ responses.

In addition, the CD8+ T-cell proliferation responses to F3 pool (7 of 9 responders) persisted but not to H11 pool (2 of 5) and F6 pool (1 of 4) (FIG. 19B). Overall, these results suggest a major loss of HU-specific IFNγ and proliferation responses with maintenance of reactions to the F3 pool. Due to the strong persistent proliferation and IFNγ responses to the F3 pool, subsequent studies focused on the F3 peptide pool and its five individual peptide/epitopes.

Example 8

Identifying the Peptide Epitope(s) on F3 Region that Induces IFNγ and CD8+ T-Cell Proliferation Responses The finding that 69% and 58% of the HIV+ subjects responded to pool F3 with IFNγ production and CD8+ T-cell proliferation respectively (FIGS. 17E and 17F) suggested the potential that the F3 region contains multiple epitopes. The F3 peptide pool has five overlapping peptides of 13-15mers (F3-1, F3-2, F3-3, F3-4, F3-5). All ten F3 responders tested 1-2 years later had IFNγ responses to the F3-3 peptide, and one individual each had low IFNγ responses to individual peptides F3-1 and F3-4 (FIG. 20A). Furthermore, 4 of 22 F3 responders had IFNγ responses to the counterpart pool H3 in the first year (FIG. 17A), but all three of the H3 responders tested on or after the second year lost IFNγ responses to H3 and had no reactivity to any of the individual 13-15mer H3 peptides (Table 10, top; 0/3 IFNγ response to H3-3). As expected, all ten HIV-control subjects had no IFNγ responses to individual peptides of both pools F3 and H3 (data not shown).

Remarkably, the majority of IFNγ responses observed to pool F3 were specific for the F3-3 peptide, and the highest responder frequency of CD8+ T-cell proliferation was observed with F3-3 (5 of 8) as well; slightly lower reactions were noted with F3-2, F3-4, and F3-5 (3 of 8 each) (FIG. 20B). F3-3 is therefore the predominant FIV RT peptide that gives both IFNγ and T-cell proliferation responses.

Example 9

Characterization of CTL-Associated Activities Induced by the F3 Pool and F3-3 Peptide One of the most important CMI activities needed to control HIV infection is potent cytotoxicity (Betts et al. (1999)). Both CD4+ CTLs and CD8+ CTLs against HIV-1 have been detected in HIV+ subjects (McDermott et al. (2012)) and in HIV− individuals immunized with a candidate HIV-1 vaccine (de Souza et al. (2012)). Although activities to H6, H11, and F6 pools were demonstrated, our focus was on CTL-associated activities to F3 pool (FIGS. 21A-21C) and its five individual peptides (FIG. 21D). 100% (11 of 11) of the F3 responders expressed at least one cytotoxin (GrzA, GrzB, or perforin) in their CD4+ or CD8+ T cells similar to the 100% (8 of 8) of H11 responders but higher than the 75% (6 of 8) of H6 responders and 50% (3 of 6) of F6 responders. Hence, CTL-associated epitope(s) present on F3 and H11 were recognized by all the subjects tested. These findings suggest that multiple CTL epitopes may reside on each of these regions.

This study showed that all five individual F3 peptides induced GrzA, GrzB, and/or perforin in the CD4+ and/or CD8+ T cells of at least one or more HIV+ subjects tested (FIG. 21D). Based on this finding, different CTL-associated epitopes appear to be present within all five of the individual F3 peptides (data not shown).

Example 10

CMI Epitopes at H3-3 and F3-3 are Conserved Among Lentiviruses

According to LANL QuickAlign analysis, the H3 pool makes up a stretch of aa that is highly conserved among lentiviruses as it is identical to 47% of the HIV-1 RTs and 7% of the SIV RTs (hiv.lanl.gov/content/sequence/QUICK_A-LIGN/QuickAlign.html). AA sequence analysis of all HIV and FIV counterpart pairs determined that H3/F3 had the second highest aa identity of 66.7% (FIG. 22A). Furthermore, aa sequence analysis of the individual 13-15mer peptides shows high aa sequence identity and similarity between HIV and FIV (FIG. 22B). The HIV and FIV pair with the highest similarity was shown in order of the highest to the lowest: H3-1/F3-1 (92%), H3-2/F3-2 (81%), H3-3/F3-3 (75%), H3-4/F3-4 (71%), and H3-5/F3-5 (71%). Considerable similarities in sequences were observed when the H3 and F3 13-15mer peptides were compared to SIV and CAEV counterpart sequences. Based on aa sequence similarity, both the H3/F3 peptide-pool regions and their counterpart individual peptides are evolutionarily conserved (FIGS. 22A and 22B).

Due to the consistently higher CMI responses to F3-3 than to the other four individual F3 peptides (FIG. 20), subsequent studies focused on F3-3 and its HIV-counterpart H3-3. According to LANL QuickAlign analysis, H3-3 has an 83% and 35% aa identity with various HIV-1 and SIV sequences, respectively. H3-3 and F3-3 peptides have 69% identity and 75% similarity with two gaps (FIG. 22B; Table 10, top). Even with such sequence similarity, IFNγ and CD8+ T-cell proliferation responses greatly differed between these peptides (Table 10).

F3-3 differs from the H3-3 used in the current study (row 1 versus row 2, Table 10) by lacking one aa (Asp on position 4 of H3-3) and having four aa differences at the F3-3 positions 5, 9, 11, and 15. The combination of a D4 deletion and three changes at K10, V12, and E16 of H3-3 with aa identical to F3-3 resulted in IFNγ responses approaching F3-3 (Table 10, F3-3m6). The addition of D4 to F3-3 (16mer) (F3-3m2) also resulted in IFNγ responses approaching F3-3, whereas the removal of V16 from F3-3m2, giving 15mer F3-3m1, caused a major loss in IFNγ responses and also a modest loss in CD8+ T-cell proliferation responses. Furthermore, a single aa change at F3-3 positions 9 (M9→K9; F3-3m5), 11 (I11→V11; F3-3m3), or 15 (V15→E15; CAEV & MVV peptide) caused major losses in both IFNγ and CD8+ T-cell proliferation responses. Note that none of the modifications of H3-3 and the peptides tested in Table 10, induced IFNγ or T-cell proliferation responses in the PBMC or the T cells from HIV-control subjects (data not shown).

Peptide F3-3 has high degrees of aa identity to those of ungulate lentiviruses (93%, caprine arthritis-encephalitis virus [CAEV] and Maedi-Visna virus [MVV]) (Table 10). Thus, the F3-3 sequence is greatly conserved among lentiviruses. In this regard, the ungulate peptide counterpart of F3-3, induced IFNγ responses in the PBMC from 1 of 9 F3-3 responders tested (Table 10, top). The above results demonstrate that the F3-3 sequence contains evolutionarily-conserved epitope(s) that induces persistent CMI responses, including strong CTL-associated activity, even when the responses to the counterpart H3-3 are lost.

Example 11

In these studies, the CMI responses by the HIV+ subjects to FIV and HIV RT peptides or peptide pools resulted in three major observations: First, the CD8+ T-cell proliferation responses to FIV pools were more robust with higher frequency of responders than those induced by the HIV pools (FIGS. 17E and 17F). This observation was unexpected since higher levels of IFNγ responses were observed with HIV pools than with FIV pools. These proliferation responses to the FIV pools, especially to F3, persisted over a longer time period than those to the HIV pools tested (FIG. 19B). Thus, the few aa differences between these viruses may be sufficient for the CD8+ T cells to recognize the F3 but not the H3 peptides. In fact, three aa substitutions in the H3-3 aa sequence (V10→I10; K12→M12; E16→V16) with aa identical to F3-3 led to immunological responses more consistent with that of F3-3 (Table 10). This observation clearly supports our finding that only a few aa changes can substantially alter the responses to a peptide epitope.

The robust CD8+ T-cell responses by the HIV+ subjects to FIV peptide pools suggest that these peptide regions contain evolutionarily-conserved epitopes. Importantly, 23 of 53 (43%) total positive CD8+ T-cell proliferation responses and 40 of 166 (23%) total positive IFNγ responses to HIV pools were also positive for their counterpart FIV pools (FIG. 17). This observation suggests that the T-cell response measured by CD8+T-cell proliferation (43%) was more successful at screening for evolutionarily conserved peptide epitopes than by the IFNγ response (23%).

The second observation was the profound and persistent IFNγ and CD8+ T-cell proliferation responses to pool F3 which had more responders than to any HIV pool (FIG. 19). The pool F3 induced IFNγ responses in the PBMC from a large number (69%) of HIV+ subjects and CD8+ T-cell proliferation responses in a substantial number (58%) of these subjects. These results suggest the presence of multiple CD8+ T-cell epitopes in the F3 region. One to three F3 responders had IFNγ or CD8+ T-cell proliferation responses to F3-1 and F3-4, and both peptide epitopes induced CTL-associated activities (FIG. 21). In fact, the LANL database shows three CTL-associated epitopes (NTPVFAIKK, NK9 (SEQ ID NO:427); NTPVFAIKKK, NK10 (SEQ ID NO:428); and KLVDFRELNK, KK10 (SEQ ID NO:429)) on the counterpart H3. The NK9 and NK10 sequences are identical between FIV and HIV-1 and are found at the carboxy-end of both 13mer peptides F3-1 and H3-1. F3-1 only differs from H3-1 by having tryptophan (W3) instead of tyrosine (Y3) at position 3. This finding suggests that this single aa difference resulted in the CD8+ T-cell proliferation response to F3-1 but not to H3-1. In the case of KK10, this epitope resides on H3-4 and differs by three aa from its direct counterpart on F3-4 (mLiDFRvLNK (MK10) (SEQ ID NO:430); different aa indicated in lower case).

The third major observation was the robust IFNγ (100%, all ten F3 responders tested) and CD8+ T-cell proliferation (62%, 5 of 8) responses to the 15mer peptide F3-3 (FIG. 20). These unusually high frequencies of responders to the F3-3 epitope raised a question as to whether more than one CMI epitope resides on F3-3. In this regard, current studies, using modified epitopes, identified three CMI epitopes on F3-3, which were not previously described in LANL: KKKSGKWRMLIDFRV (KV15) (SEQ ID NO:63), WRMLIDFRV (WV9) (SEQ ID NO:431), and KWRMLIDFR (KR9) (SEQ ID NO:432) (Table 10, bottom). The largest of these epitopes (F3-3; KV15) induce cytotoxin expression, and thus, one or more of them most likely are CTL-associated epitopes. These epitopes are closely related in sequence and evolution to ungulate lentiviruses (Table 10, top). Therefore, these findings indicate that the F3-3 epitopes are also evolutionarily conserved.

The unique example of pools F3/H3 (FIG. 22) highlights the existence of evolutionarily conserved HIV RT epitope region that is less immunogenic than its FIV RT counterpart sequence based on pools F3/H3 and peptide F3-3/H3-3 analyses. The selection pressure against HIV in humans may explain the lack of responses against the HIV sequence; the same pressure may not exist in cats against FIV. The use of FIV approach shows that F3-3 region may be a great target for T-cell responses in an HIV vaccine, since both IFNγ and proliferation responses to peptide F3-3 by HIV+ subjects indicate that they have previously encountered such sequence or its variant. The approach of using FIV to identify conserved regions for an HIV vaccine is a tool that compliments most approaches for developing a T-cell-based vaccine as in mosaic vaccines (Corey et al. (2010); Barouch et al. (2010); Santra et al. (2012)). Computational analyses identify potential conserved epitopes that are later tested for relevant biological activity. These analyses have been used to select conserved HIV/FIV sequences such as the one described for HIV/FIV integrase (Sanou et al. (2012a)). The current FIV approach simultaneously compares both HIV/FIV epitope sequences and immunological responses.

This cross-recognition of the F3-3 epitope(s) by the HIV+ subjects demonstrates the polyfunctionality of the T-cell subsets tested. Three patterns with either PBMC or T cells were observed: 1) IFNγ production by PBMC (IFNγ/PBMC), CD8+ T-cell proliferation, and CD4+ or CD8+ (CD4+/CD8+) T-cell cytotoxin expression; 2) IFNγ/PBMC and CD4+/CD8+ T-cell cytotoxin expression; and 3) CD8+ T-cell proliferation and CD4+/CD8+ T-cell cytotoxin expression. These observations are important since polyfunctional T-cell epitopes are likely to be associated with an effective HIV vaccine (McDermott et al. (2012); Betts et al. (2006)). Although current studies have had minimal focus on CD4+ T-cell responses, 2 of 3 F3 responders showing CD4+ T-cell proliferation also had expressed CD8+ T-cell responses to F3-3 (FIG. 17D and FIG. 18B). Moreover, the CD4+ T cells from substantial numbers of F3 responders had CTL-associated cytotoxin activities in response to pool F3 (FIG. 21). A vaccine is generally administered to HIV-naïve subjects with normal CD4+ T-cell immunity. Therefore, the importance of the CD4+ T-cell responses to F3-3 should be considered when identifying CTL-associated epitopes for an HIV vaccine. The vaccine epitopes that induce both anti-HIV CD8+ and CD4+ T responses are likely to be needed for effective vaccine protection. These studies using FIV RT peptide pools suggest that evolutionarily-conserved immunologic epitopes could be important for an effective HIV vaccine.

TABLE 9

Population Characteristics

| Group | Subject[a] | Age | Gender | Race | HIV+[b] | CD4/μL | CD8/μL | Viral Load[c] |
|---|---|---|---|---|---|---|---|---|
| LTS/ART | J01 | 25 | F | Black | 11 | 699 | 935 | Undetectable |
| | J10 | 35 | F | Black | 12 | 897 | 659 | Undetectable |
| | J11 | 21 | F | Black | 21 | 564 | 829 | 932 |
| | J14 | 47 | M | Hispanic | 25 | 722 | 1421 | 6790 |
| | SF01 | 42 | M | White | 16 | 1021 | 996 | Undetectable |
| | SF02 | 44 | M | White | 12 | 528 | 394 | Undetectable |
| | SF03 | 59 | M | White | 24 | 567 | 1040 | 5500 |
| | SF08 | 48 | M | White | 31 | 529 | 920 | 3401 |
| | SF17[d] | 56 | M | White | 11 | 374 | 1037 | 2000 |
| | SF19 | 40 | M | White | 12 | 292 | 556 | 40000 |
| | SF23 | 39 | M | White | 10 | 784 | 1018 | 3160 |
| | SF24 | 50 | M | White | 11 | 675 | 213 | Undetectable |
| ST/ART | TP01 | 19 | F | Hispanic | <1 | 391 | 583 | 13400 |
| | TP02 | 28 | M | White | <1 | 1280 | 1375 | Undetectable |
| | J02 | 50 | F | Black | 9 mo | 639 | 1248 | 710 |
| | J03 | 27 | F | Black/Hispanic | 8 mo | 368 | 1254 | 25700 |
| | J04 | 22 | M | Black | 6 mo | 537 | 1907 | 1740 |
| | J05 | 32 | M | Black | 2 mo | 384 | 2202 | 691 |
| | J06 | 28 | M | White | 6 mo | 501 | 1110 | 134000 |
| | J07 | 26 | F | Black | 4 mo | 448 | 1306 | 5120 |
| | J08 | 19 | F | Black/Hispanic | 9 mo | 323 | 932 | 3040 |
| | J09 | 27 | M | White | 2 mo | 482 | 882 | 109168 |
| | J12 | 26 | M | Pacific Islander | 5 mo | 352 | 688 | 405000 |
| | J13 | 41 | F | Black | 2 mo | 513 | 632 | 22100 |
| ART+ | SF04 | 55 | M | White | 28 | 540 | 864 | Undetectable |
| | SF07 | 65 | M | White | 25 | 610 | 2170 | Undetectable |
| | SF16 | 50 | M | White | 8 | 827 | 1018 | Undetectable |
| | SF18 | 38 | M | White | 4 | 1082 | 1298 | 1500 |
| | SF20 | 53 | M | White | 23 | 76 | 1172 | Undetectable |
| | SF22 | 48 | M | White | 13 | 1205 | 517 | Undetectable |
| | J15 | 56 | F | Black | 17 | 291 | 1101 | Undetectable |
| | J16 | 48 | F | White | 21 | 1250 | NA[d] | Undetectable |
| HIV− | NB1 | NA[e] | M | Unknown | | | | |
| | NB2 | NA[e] | F | Unknown | | | | |
| | NB3 | NA[e] | F | Unknown | | | | |
| | N1 | 58 | F | Asian | | | | |
| | N2 | 27 | M | Black | | | | |
| | N3 | 27 | F | Hispanic | | | | |
| | N4 | 24 | M | Asian | | | | |
| | N5 | 36 | M | Black | | | | |
| | N6 | 19 | F | White | | | | |
| | N7 | 27 | F | Black/Hispanic | | | | |

Table 9 Footnote

[a]HIV+ subjects from UF at Jacksonville (J), UCSF (SF), and University of South Florida at Tampa (TP); normal blood from blood bank (NB); normal blood from UF (N).
[b]Number of years of HIV infection or in months (mo).
[c]Virus load shown as copies/mL; undetectable at either <50 or <75.
[d]Subject started ART during the study.
[e]NA: not available. See Materials and Methods for other abbreviations.

TABLE 10

Variation of H3-3/F3-3 aa sequences and immunological responses

| Virus (Subtype)[a] | 9mer or 15mer Sequence[b] | SEQ ID NO: | Average SFU of IFNγ [range] (positive/total)[c,d] | % CD8+ T Proliferation [range] (positive/total)[c,d] |
|---|---|---|---|---|
| Evolutionary epitopes: | | | | |
| HIV-1 H3-3 | KKKdStKWRkLvDFR | 165 | 0 [0] (0/3) | 0 [0] (0/1) |
| FIV F3-3 | KKK SGKWRMLIDFRV | 63 | 536 [105-2500] (13/13) | 5.4 [0-15] (6/9) |
| HIV-1 (C) | KKK StKWRkLvDFRe | 433 | 7 [0-37] (0/9) | 0 [0] (0/5) |
| HIV-1 (A, B, C, D, 01_AE) | KKn StKWRkLvDFRe | 434 | 0 [0] (0/9) | 0.9 [0-4] (1/5) |
| SIVcpz-$_{Pts}$ | KKKdStKWRkLvDFRe[e] | 435 | 0 [0] (0/4) | 0 [0] (0/4) |
| CAEV & MVV | KKK SGKWRMLIDFRe[f] | 436 | 28 [0-100] (1/9) | 0.2 [0-0.8] (0/5) |
| Modifications of F3-3:[g] | | | | |
| HIV-1 H3-3 | KKKdStKWRkLvDFR | 165 | 0 [0] (0/3) | 0 [0] (0/1) |
| FIV F3-3m1 | KKKdSGKWRMLIDFR | 437 | 11 [0-45] (0/9) | 0.7 [0-3.2] (1/5) |
| FIV F3-3m2 | KKKdSGKWRMLIDFRV[e] | 438 | 280 [0-1208] (7/9) | 2.0 [0-5.6] (2/5) |
| FIV F3-3m3 | KKK SGKWRMLvDFRV | 439 | 7 [0-22] (0/9) | 0 [0] (0/5) |
| FIV F3-3m4 | KKK StKWRkLIDFRV | 440 | 9 [0-60] (0/9) | 0.2 [0-0.9] (0/5) |
| FIV F3-3m5 | KKK SGKWRkLIDFRV | 441 | 20 [0-52] (0/9) | 0.3 [0-1.6] (0/5) |
| FIV F3-3m6 | KKK StKWRMLIDFRV | 442 | 251 [20-1254] (7/9) | 7.0 [0-29.1] (2/5) |
| FIV F3-3 | KKK SGKWRMLIDFRV | 63 | 536 [105-2500] (13/13) | 5.4 [0-15] (6/9) |
| Epitopes on F3-3:[h] | | | | |
| FIV F3-3 (KV15) | KKK SGKWRMLIDFRV | 63 | 536 [105-2500] (13/13) | 5.4 [0-15] (6/9) |
| FIV 3-3 (WV9) | WRMLIDFRV | 431 | 278 [0-1295] (8/11) | 1.3 [0-4.2] (1/6) |
| FIV 3-3 (KR9) | KWRMLIDFR | 432 | 20 [0-70] (1/9) | 0 [0] (0/6) |

Table 10 footnotes:

[a] Genbank numbers as follows: HIV-1 H3-3 (K03455.1); FIV F3-3 (DQ365597.1); HIV-1 (C) (FJ595343); HIV-1 (A, B, C, D, 01_AE) (AJ313415, HM035584, HQ012309, HQ586068, HE590997); SIVcpz-Pts (ACM63211); CAEV (AAG48629.1); MVV (CAC44543); HERV-K (ABA28284).

[b] Lower case letter aa different from FIV F3-3. Many HIV-1 strains have glutamate (E) immediately after the carboxyl end of H3-3.

[c] Used only responders from FIGS. 17-19; range of IFNγ responses in SFU [range]; positive responses over total tested (positive/total).

[d] Small total participant numbers due to the use of only the F3 or H3 responders who are still positive during the second or third time-point. Only cells from H3 responders were used to test peptide H3-3; while cells from F3 responders were used to test other peptides.

[e] Only 16mer sequences.

[f] Replacing V15 with E15 in modifications F3-3m3 to F3-3m6 resulted in almost total loss of both IFNγ and proliferation responses.

[g] Six modifications of 15-16mer F3-3 sequences (F3-3m1 to F3-3m6) with aa present on H3-3.

[j] Sequence designation shown in parenthesis with the first and the last aa followed by the number of aa.

FIV RT Peptide-Pool F3

NPWNTPVFAIKKKSGKWRMLIDFRVVLNKLTDKGA  (SEQ ID NO: 443)

NPYNTPVFAIKKKDSTKWRKLVDFRELNKRTQDFW  (SEQ ID NO: 23)

HIV RT Peptide-Pool H3

FIV RT peptides for Pool F3:
F3-1:
NPWNTPVFAIKKK (13 aa)  (SEQ ID NO: 61)

F3-2:
TPVFAIKKKSGKWRM (15)  (SEQ ID NO: 62)

F3-3:
KKKSGKWRMLIDFRV (15)  (SEQ ID NO: 63)

F3-4:
WRMLIDFRVLNKL (13)  (SEQ ID NO: 64)

F3-5:
IDFRVLNKLTDKGA (14)  (SEQ ID NO: 65)

HIV-1 RT peptides for Pool H3:
H3-1:
NPYNTPVFAIKKK (13)  (SEQ ID NO: 163)

H3-2:
TPVFAIKKKDSTKWR (15)  (SEQ ID NO: 164)

H3-3:
KKKDSTKWRKLVDFR (15)  (SEQ ID NO: 165)

H3-4:
KWRKLVDFRELNKR (14)  (SEQ ID NO: 166)

H3-5:
VDFRELNKRTQDFW (14)  (SEQ ID NO: 167)

Combine sequence of Pool F6 immediately below:
PDYAPYTAFTLPRKNNAGPGRRYVWCSL  (SEQ ID NO: 444)

FRKYTAFTIPSTNNETPGIRYQYNVLPQGWK  (SEQ ID NO: 445)

Combined sequence of Pool H6 immediately above:

Peptides in pool F6
F6-1:
PDYAPYTAFTLPRK (14)  (SEQ ID NO: 74)

F6-2:
YTAFTLPRKNNA (12)  (SEQ ID NO: 75)

F6-3:
FTLPRKNNAGPGRRY (15)  (SEQ ID NO: 76)

F6-4:
NNAGPGRRYVWCSL (14)  (SEQ ID NO: 77)

Peptides in pool H6
H6-1:
FRKYTAFTIPSI (12)  (SEQ ID NO: 176)

H6-2:
FTIPSTNNETPGIRY (15)  (SEQ ID NO: 177)

H6-3:
NNETPGIRYQYNVL (14)  (SEQ ID NO: 178)

H6-4:
GIRYQYNVLPQGWK (14)  (SEQ ID NO: 179)

Combine sequence of Pool F7 immediately below:
GRRYVWCSLPQGWVLSPLIYQSTLDNIL  (SEQ ID NO: 446)

YNVLPQGWKGSPAIFQSSMTKILEPFRKQNPDI  (SEQ ID NO: 447)

Combined sequence of Pool H7 immediately above:

Peptides in pool F7
F7-1:
GRRYVWCSLPQGWVL (15)  (SEQ ID NO: 78)

F7-2:
CSLPQGWVLSPLIY (14)  (SEQ ID NO: 79)

F7-3:
GWVLSPLIYQSTL (13)  (SEQ ID NO: 80)

F7-4:
SPLIYQSTLDNIL (13)  (SEQ ID NO: 81)

Peptides in pool H7
H7-1:
YNVLPQGWKGSPAIF (15)  (SEQ ID NO: 180)

H7-2:
GWKGSPAIFQSSMTK (15)  (SEQ ID NO: 181)

H7-3:
AIFQSSMTKILEPFR (15)  (SEQ ID NO: 182)

H7-4:
MTKILEPFRKQNPDI (15)  (SEQ ID NO: 183)

Combine sequence of Pool F15 immediately below:
GKMNRQKKKAENTCDIALRACYKIREESIIRIGKEPI  (SEQ ID NO: 448)

RGAHTNDVKQLTEAVQKIVTESIVIWGKTPKFKLPI  (SEQ ID NO: 449)

Combined sequence of Pool H15 immediately above:

Peptides for pool F15
F15-1:
GKMNRQKKKAENTCDI (16)  (SEQ ID NO: 117)

F15-2:
KKAENTCDIALRACY (15)  (SEQ ID NO: 118)

F15-3:
CDIALRACYKIR (12)  (SEQ ID NO: 119)

```
F15-4:
                                           (SEQ ID NO: 120)
ALRACYKIREESIIR (15)

F15-5:
                                           (SEQ ID NO: 121)
KIREESIIRIGKEPI (15)

Peptides for pool H15
H15-1:
                                           (SEQ ID NO: 219)
RGAHTNDVKQLTEAV (15)

H15-2:
                                           (SEQ ID NO: 220)
DVKQLTEAVQKIV (13)

H15-3:
                                           (SEQ ID NO: 221)
LTEAVQKIVTESIVI (15)

H15-4:
                                           (SEQ ID NO: 222)
KIVTESIVIWGKTPK (15)

H15-5:
                                           (SEQ ID NO: 223)
IVIWGKTPKFKLPI (14)
```

Materials and Methods for Examples 12-17

Study population. The blood samples of HIV+ subjects were obtained from the University of California at San Francisco (UCSF) and the University of Florida Center for HIV/AIDS Research, Education and Service (UF CARES) in Jacksonville using the protocol approved by the Institutional Review Board at UF. HIV+ subjects consisted of fourteen long-term survivors (LTS) who are not receiving ART, ten subjects with short-term infection (ST) not receiving ART, and eleven HIV+ subjects receiving ART. Age, gender, and race as well as the viral and immune status of the HIV+ subjects used in the current study are outlined in Table 11. The blood samples were processed within 48 hours of collection. T-cell phenotyping and HIV-1 load were performed by the clinical laboratories at the UCSF Medical Center and UF CARES. The samples from twenty-two healthy HIV seronegative (HIV) subjects were obtained from LifeSouth Community Blood Centers (Gainesville, Fla.) or from UF.

ELISpot assays. Human enzyme-linked immunosorbent spot assays (ELISpot) (R&D Systems, Cat #XEL285) which measure IFNγ production were performed (Abbott et al. 2011). The positive threshold for human IFNγ responses was >50 spot forming units (SFU)/$10^6$ cells. The final value for each subject was derived after subtracting the result of each HIV+ subject with the media control followed by subtraction with the average response of the HIV− subjects which was rarely more than 10 SFU.

Flow cytometry (FACS) for measuring CFSE-proliferation and intracellular cytokine staining (ICS). Carboxyfluorescein diacetate succinimide ester (CFSE)-proliferation analysis was performed according to the manufacturer's protocol (Invitrogen) and processed as previously described (Lichterfeld et al. 2004) using the following modification: $2.5$-$5.0 \times 10^5$ CFSE-labeled PBMC stimulated for 4-5 days (37° C., 5% $CO_2$) with 15-30 µg of peptides in culture media (AIM V medium, 25 µg/mL gentamycin, and 10% heat-inactivated fetal bovine serum). The ICS analysis was performed as previously described (Horton et al. 2007; Pattacini et al. 2012).

The antibodies used for the proliferation analysis consisted of anti-CD4 allophycocyanin (APC) anti-CD3 APC-H7, and anti-CD8 Pacific Blue, and those for ICS were anti-CD3 APC-H7, anti-CD4 BD Horizon V450, anti-CD8 FITC, anti-granzyme B (GrzB) Alexa 700, anti-granzyme A (GrzA) PE (BD Biosciences, Cat #555349, 560176, 558207, 560345, 555366, 560213, 558904), and anti-perforin PerCP (Abcam, Cat #ab86319). Both analyses were performed with BD LSRII and FACSDIVA™ Software (BD Biosciences), using a positive threshold of >1% $CFSE^{low}$ for CFSE-proliferation except for ICS studies with threshold of >0.1% T cells expressing cytotoxin. The final value for each subject was derived after subtracting the result of each HIV+ subject with the media control followed by subtraction with the average response of the media-control subtracted HIV− subjects.

Human leukocyte antigen (HLA) analyses. The affinity of peptide binding to HLA was determined by NetMHC version 3.2 for HLA class-I (cbs.dtu.dk/services/NetMHC/), NetMHCII version 2.2 for HLA class-II (cbs.dtu.dk/services/NetMHCII/), and NetCTL version 1.2 for CTL-associated epitopes (cbs.dtu.dk/services/NetCTL/). The LANL database for CD8+ and CD4+ epitopes are based on the HIV-1 HXB2 sequence and identifies the epitope-interacting HLA allele(s).

Statistical analysis. Statistically significant differences between the results from two time points were calculated using a paired Student t-test with a two-tailed distribution (SigmaPlot version 11.0) and were considered statistically significant when p<0.05.

Example 12

Determining Conserved Cell-Mediated Immune (CMI) Peptides Based on IFNγ Responses The PBMC from the 31 HIV+ subjects developed robust IFNγ responses to the full length HIV-1 p24 peptide pools (FIG. 23A, 144 total responses), whereas minimal to no responses were observed with the PBMC from HIV-negative (HIV) control subjects (range of 0-15 spot forming unit (SFU)). The highest responder frequencies were observed to human p24 peptide pool 3 (Hp3) (18 of 31; 58%) followed by Hp2, Hp10, and Hp15 (11 of 31 each; 35%). A lower number of subjects responded to Hp7 and Hp14 (10 of 31 each; 32%). In addition, PBMC from the HIV+ subjects produced IFNγ responses of low magnitudes and frequencies to all FIV p24 peptide pools (FIG. 23B, 53 total responses) except for feline p24 peptide pools (Fp)13 and Fp14 which correspond to HIV sequences within Hp14 and Hp15 peptide pools. The highest responder frequencies were observed to Fp14 (11 of 31; 35%) with lower responder frequency to Fp13 (5 of 31; 16%). These findings suggested that these FIV pools contain potential cross-reactive epitopes to HIV. In addition, overlapping SIV p24 peptide pool (Sp) analysis identified a moderate number of responses to the corresponding SIV peptide pool Sp14 (5 of 15; 33%) (FIG. 23C), the counterpart to Fp14 and Hp15. These results suggest that evolutionarily conserved, cross-reactive epitope(s) may reside on Hp15, Fp14, and Sp14.

Example 13

Conserved CMI Peptides Based on T-Cell Proliferation Responses

The CD8+ T cells of the HIV+ subjects proliferated more frequently and at higher magnitudes to the HIV p24 peptide pools (FIG. 24A) than to the CD4+ T cells (FIG. 24D) (36

CD8+ T-cell responses vs. 12 CD4+ T-cell responses). The highest frequency of CD8+ T-cell proliferation responses to HIV p24 was against pools Hp1 (6 of 27; 22%) and Hp10 (8 of 27; 30%) followed by Hp9 (4 of 27; 15%) (FIG. 24A). The same analysis performed on T cells from healthy HIV subjects indicated that their CD4+ and CD8+ T cells did not significantly recognize HIV p24 pools except for the Hp15 pool with a frequency of 42%. All results are shown after subtraction of the average result of the responders for each peptide pool or peptide. CD8+ T cells from 42% (5 of 12) of the HIV− subjects had a substantial response to the Hp15 peptide pool. The number of HIV+ responders to Hp15 is low due to a high average result (28% CFSE$^{low}$) of HIV responders to Hp15 that were subtracted from the HIV+ responses (FIG. 24A). Except for the Hp15 pool (the counterpart of the Fp14 pool), the Fp9 pool, the Hp15-3 peptide in Hp15 pool, and the Fp9-3 peptide in Fp9 pool with 25-51% of the value before subtraction, none of the other peptide pools or peptides induced substantial CD8+ or CD4+ T-cell proliferation in HIV subjects (0-20% of the value before subtraction).

Figures 24E, 24F:
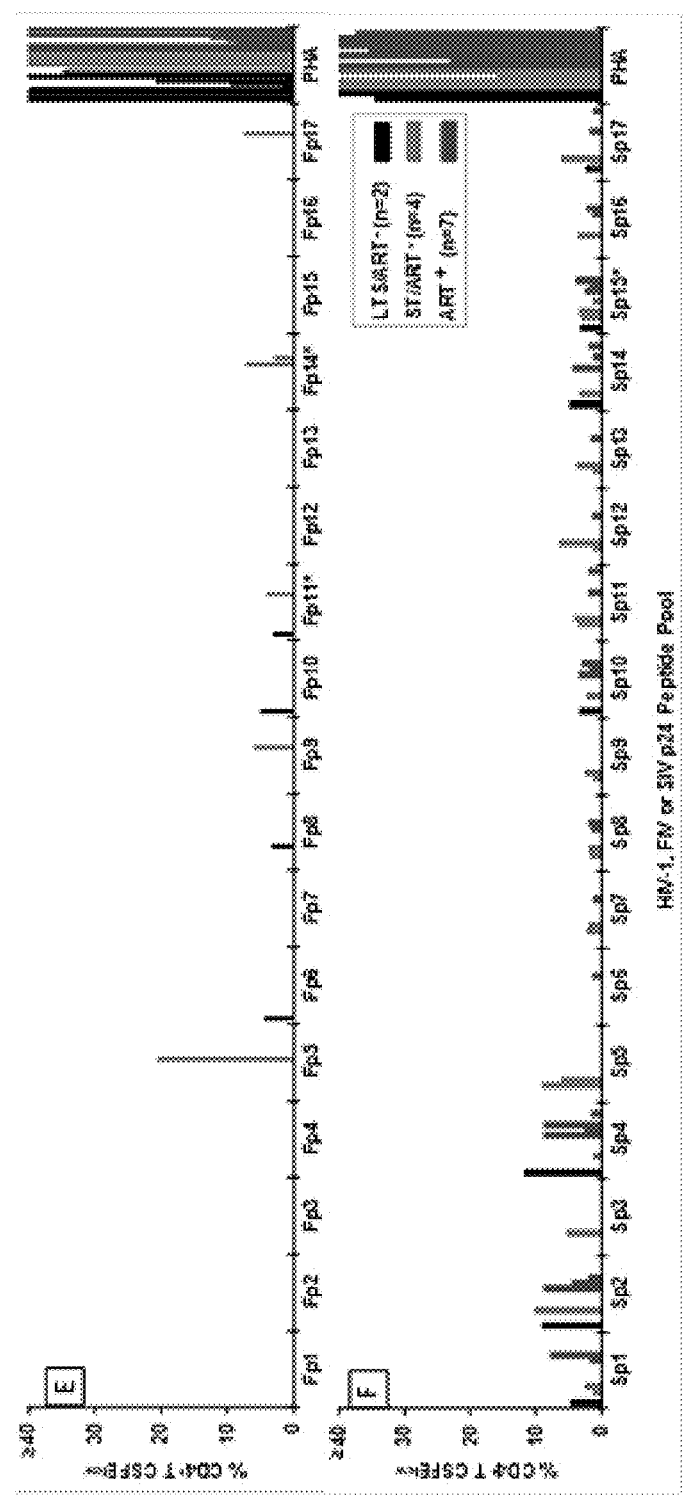

Twelve HIV+ subjects had CD8+ T-cell proliferation responses to FIV p24 pools (FIG. 24B) compared to only five subjects with CD4+ T-cell proliferation responses to the same peptide pools (FIG. 24E). Remarkably, substantial CD8+ T-cell proliferation responses were detected in HIV+ subjects to Fp9 (8 of 27; 30%) and to Fp14 (4 of 27; 15%) (FIG. 24B). A lower responder frequency at a lower magnitude was detected in HIV− subjects to Fp9 with a minimal response to Fp14. FIG. 24B shows HIV+ response after subtracting the average of HIV− responders. When compared with the SIV p24 pools, the Fp14-counterpart Sp14 pool, but not the Fp9-counterpart Sp9 pool, was recognized by CD8+ T cells from the HIV+ cohorts (FIG. 24C). In addition, CD8+ T cells from HIV+ subjects recognized multiple SIV peptide pools at a frequency of 38-54% (Sp1, Sp2, Sp4, Sp10, Sp14, Sp15) (FIG. 24C). However, Sp2, Sp4, Sp10, Sp14, and Sp15 were also recognized by CD8+ T cells from HIV subjects at a low frequency of 20-30%. FIG. 24C shows the HIV+ response after subtracting the average of HIV responders. Notably, both the Sp1 pool and its counterpart Hp1 pool were recognized by the CD8+ T cells from HIV+ subjects (FIGS. 24A and 24C).

Among the FIV peptide pools, the Fp9 pool induced strong CD8+ T-cell proliferation responses but few IFNγ responses, while the Fp14 pool induced both IFNγ and CD8+ T-cell proliferation responses (FIGS. 23B and 24B). As a result, subsequent studies focused on the Fp14 and Fp9 peptide pools and their HIV counterparts, Hp15 and Hp10, respectively.

Example 14

The Persistence of IFNγ Responses to Fp14 and CD8+ T-Cell Proliferation to Fp9

PBMC from 8 of 10 (80%) HIV+ subjects who initially responded to the Fp14 pool retained the IFNγ response for the duration of the 2-yr study period while 3 of 7 tested continued to respond in the 4th yr (FIG. 25A, left graph). Although there was no statistical difference between the IFNγ responses during the 1st yr and the 2nd yr of the seven HIV+ subjects monitored (t1 and t2, p=0.39), a statistically significant decrease in IFNγ response was detected when the levels were compared between the 2nd yr and 4th yr (t2 and t3, p=0.035) and between the initial time point and the 4th yr (t1 and t3, p=0.014). Similarly, the PBMC in 6 of 8 (75%) initial responders to Hp15, the counterpart for Fp14, remained responsive to Hp15 through the 2nd yr but showed a substantial declining trend in the magnitude of proliferation by the 4th yr (FIG. 25A, right graph).

CD8+ T cells from 7 of 9 (78%) initial Fp9 responders retained T-cell proliferation responses to Fp9 during the 2-yr monitoring period (FIG. 25B, left graph). Two of the seven subjects responding to the Fp9 pool (SF17, SF19) were treated with ART during or shortly after the 2nd yr time point (Table 11) leaving four subjects on ART and four subjects not on ART by yr 4. Three of 4 subjects on ART (SF17, SF19, SF20) maintained stable or increased levels of proliferation responses to Fp9, while one subject (SF18) continued to remain non-responsive. This finding suggests that the magnitude of response to Fp9 can improve in subjects (SF19, SF20) undergoing ART. In comparison, only 3 of 5 (60%) initial responders retained activity against Hp10, the counterpart of Fp9, through yr 2 (FIG. 25B, right graph). This response declined in magnitude by the 4th yr. A large majority of these responders had either a major decrease or a loss of response to the Hp10 peptide pool, while the response to pools Fp9, Fp14, and Hp15 persisted for at least 2 yr and some for as long as 4 yr. The Fp9 and Hp10 pools have very little sequence similarity (Table 12), and the response to Fp9, but not Hp10, was retained over time (FIG. 25B). Therefore, subsequent studies focused on the Fp9, Fp14, and Hp15 peptide pools. Due to the high frequency and magnitude of the response, Fp9 was selected for epitope mapping.

Example 15

Identifying the p24 Epitope(s) that Induce CMI Responses

The HIV Hp15 pool has three well-established CD8+ CTL epitopes described in LANL database that are present within the Hp15-1a, Hp15-1c, and Hp15-2/3a peptides (Table 12). These CTL epitopes have high sequence similarity to FIV Fp14-1b, Fp14-1a, and Fp14-3/4f respectively (Table 12). Furthermore, SIV Sp14-1b and Sp14-1a have sequence similarity to their direct counterparts Hp15-1a/Fp14-1b and Hp15-2/3a/Fp14-3/4f. Hence, these peptide epitopes show moderate to high conservation between species-specific lentiviruses.

Three to four overlapping 13-15mer peptides constitute each of the peptide pools Fp9 (Fp9-1, Fp9-2, Fp9-3), Fp14 (Fp14-1, Fp14-2, Fp14-3, Fp14-4), and Hp15 (Hp15-1, Hp15-2, Hp15-3). Fp9-3 and Hp10-3 have an aa sequence similarity of 29% and identity of 12% with four single aa differences due to gaps (Table 12). This low degree of sequence similarity and identity further supports the concept that epitope(s) on Fp9 are most likely not in the same location as those on Hp10. The analysis of individual 13-15mer peptides in the Fp9 pool indicates that the CD8+ T cells of the Fp9 responders proliferate predominantly in response to Fp9-3 (6 of 7) and to a lesser extent to Fp9-2 (3 of 7) (FIG. 26C). Based on this result, the 15mer Fp9-3 peptide was further evaluated to map specific proliferative epitope(s) using shorter (9mer) overlapping peptides.

When compared to Fp9 and Fp10 pools, Fp14 and Hp15 pools have a higher aa sequence similarity (65%) and identity (35%) with one aa difference due to a gap (Table 12). Based on aa sequence alignment analysis, the approximate counterpart for Hp15-1 and Hp15-2 peptides are Fp14-1 and Fp14-2 peptides respectively, whereas the Hp15-3 peptide contains regions that overlap both Fp14-3 and Fp14-4 peptides. Smaller regions have more similarity between Fp14-1 and Hp15-1 peptides (Table 12, section D) and between Fp14-4 and Hp15-3 peptides (Table 12, section B). PBMC from Fp14 responders had substantial IFNγ responses to peptide Fp14-3 (6 of 9 responders) followed by peptides Fp14-1 and Fp14-4 (both 3 of 9) (FIG. 26A). The majority of Hp15 responders had substantial IFNγ responses to Hp15-1 (7 of 9) and fewer responses to Hp15-3 (5 of 9) (FIG. 26B). Thus, Fp14-3 and Hp15-1 contain epitopes that induce significant IFNγ responses. These peptides are not counterpart FIV and HIV peptides based on aa sequence analysis and therefore are not expressing common epitope(s). However, PBMC from three LTS responded to both Fp14-3 and its counterpart Hp15-3, indicating a conserved CMI epitope within these peptides (FIGS. 26A and 26B; bars with *).

When specific epitope analyses of Fp9 and Fp14 regions were performed, two 9mer peptides (Fp9-3c and Fp9-3d) of the Fp9 region, differing by a single aa in carboxyl-end or amino-end, provided the highest frequency of a CD8$^+$ T-cell proliferation response (5/6 of 9) (Table 13) but at a low magnitude (<13% CFSE$^{low}$) (FIG. 27). Proliferation responses to Fp9-3c and Fp9-3d peptides were much lower than the levels of proliferation observed with the Fp9 pool (FIG. 27). Furthermore, this result is in stark contrast to the high frequency of responders (3 of 6, 50%) and the higher levels (average magnitude of 14% CFSE$^{low}$) of CD8$^+$ T-cell proliferation to the 15mer Fp9-3 peptide (FIG. 27A). Thus, the 15mer, but not the 9mer Fp9-3 peptides, appears to contain the epitope that induces the bulk of the proliferation responses of both CD8$^+$ and CD4$^+$ T cells (FIGS. 27A and 27C).

Figures 27E, 27F:
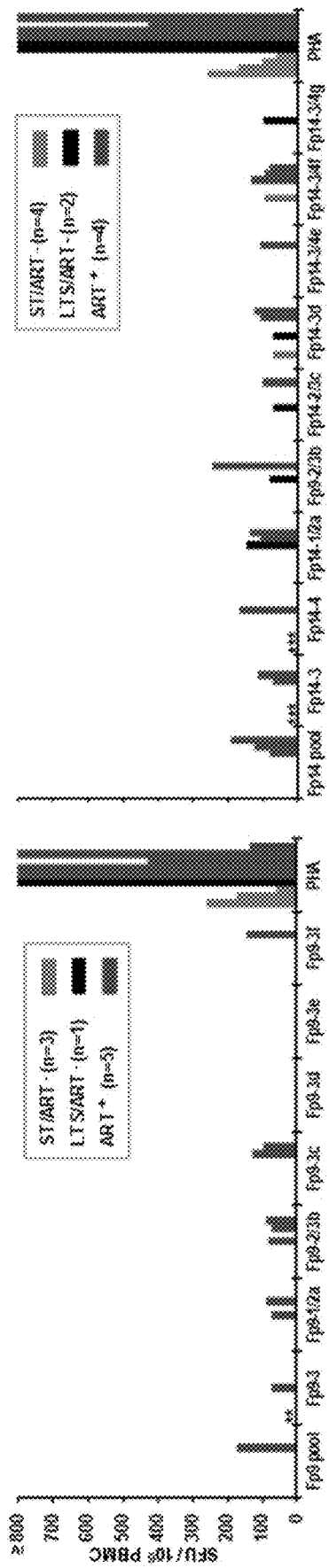

Similarly specific epitope analysis of the Fp14-3 region with an overlap with the Fp14-2 and Fp14-4 regions determined that a higher frequency of HIV$^+$ subjects respond to epitopes in Fp14-3 (Fp14-3d) and Fp14-4 (Fp14-3/4f, overlapping both Fp14-3 and Fp14-4) more than in Fp14-2, based on both CD8$^+$ T-cell proliferation and IFNγ responses (FIGS. 27B and 27F). Since the shorter sequence of 10mer Fp14-3/4f also resides in the larger 13mer Fp14-3d sequence (Table 13), it is still possible that both contain the same epitope (i.e., Fp14-3/4f). This observation is supported by in silico analysis using the HLA algorithm where the predicted HLA A2 supertype is common among all four responders for both Fp14-3d and Fp14-3/4f (Table 14). Thus, Fp14-3/4f contains the major epitope residing in Fp14-3 and Fp14-4 that is identified by the HLA A2 supertype.

Example 16

Characterization of CTL-Associated Activity Induced by Fp9, Fp14, and Hp15 Peptides In intracellular staining (ICS) analysis for cytotoxins, both CD8$^+$ and CD4$^+$ T cells expressed granzyme B (GrzB) most consistently in response to all three peptide pools tested (Fp9, Fp14, Hp15) (FIG. 28A). 40% (2 of 5) HIV$^+$ subjects had CD8$^+$ T cell GrzB expression to individual peptide pool Fp9, whereas 80% (4 of 5) responded to Fp14, and 80% (4 of 5) to Hp15 (FIG. 28A). Notably, GrzB was expressed by both CD4$^+$ and CD8$^+$ T cells from the same individuals although the overall expression magnitude of GzB, but not the frequency, was lower in the CD4$^+$ T cells (FIG. 28B). A few of the subjects who did not have GrzB responses did demonstrate either GrzA or perforin expression (FIG. 28A). When individual 13-15mer peptides from each pool were examined, CD8$^+$ T cells from all five HIV$^+$ subjects responded to Fp14-3, Fp14-4, and Hp15-1, whereas up to four HIV$^+$ subjects responded to Fp9-3 with the production of one or more cytotoxins. Hence, the majority of the Fp9, Fp14, and Hp15 peptides induced expression of one or more cytotoxins.

The short (9-13mer) peptides of Fp9-3, Fp14-3, and Fp14-4 from previous IFNγ and proliferation studies as well as a few additional short peptides (Table 13) were further tested with T cells from short-term HIV-infected subjects not on ART (ST/ART$^-$) for production of cytotoxins and expression of CD107a (FIGS. 28C and 28D), which are commonly expressed by CTLs. These short 9-13mer epitopes were produced based on the CTL algorithm of NetCTL 1.2 and HLA algorithm of NetMHC 3.4. The shortest peptides that predicted the highest CD8$^+$ T-cell responder frequency were 9mer peptides Fp9-3c (RMQCRAWYL) (SEQ ID NO:451) and Fp9-3d (ARMQCRAWY) (SEQ ID NO:452), 10mer peptide Fp14-3/4f (KLYLKQSLSI) (SEQ ID NO:453), and 13mer peptide Fp14-3d (AEVKLYLKQSLSI) (SEQ ID NO:454) (Table 13). Peptides Fp9-3, Fp9-3c and Fp9-3d induced very little cytotoxin expression in CD4$^+$ T cells (FIG. 28C). Among these peptides, Fp9-3 and Fp9-3d induced more cytotoxins in CD8$^+$ T cells from a slightly larger number of ST/ART$^-$ subjects (FIG. 28D). In comparison, Fp14-4 and Fp14-3/4f peptides followed by Fp14-1b and Fp14-3/4e induced a high frequency of cytotoxin expression in both CD4$^+$ and CD8$^+$ T cells from a majority of ST/ART$^-$ subjects (FIGS. 28C and 28D). Remarkably, the Fp14-4 and Fp14-3/4f peptides had a higher number of cytotoxin responses and a higher frequency of responders for both CD4$^+$ and CD8$^+$ T cells than their counterparts on HIV (Hp15-3; Hp15-2/3a) and SIV (Sp14-1; Sp14-1a).

When NetCTL and NetMHC predictions were compared to the responders' HLA class-I supertype(s), four responders to peptide Fp9-3c had the predicted responder HLA supertype A2 (Table 14). Three of them also had an additional HLA supertype (A1, A3, B27, or B62) predicted to have a strong binding affinity to Fp9-3c. The same analysis performed on Fp9-3d determined that 3 of 4 responders possessed supertype B44 while one responder had HLA supertype A1. Both supertypes are predicted to have a strong binding affinity to Fp9-3d. Similarly, Fp14-3/4f showed supertype A2 as the common HLA supertype correlating with all four responders. Moreover, three more subjects had additional HLA supertypes (A1, B27, or B58) with strong predicted binding affinity for Fp14-3/4f (Table 14). Hence, the ICS and the combined NetCTL/NetMHC analyses support the presence of CD8$^+$ T-cell epitopes on Fp9-3, Fp14-3, and Fp14-4 peptides.

Example 17

Based on IFNγ ELISpot and CFSE-proliferation analysis, the PBMC and T cells from HIV$^+$ subjects (Table 11) identified at least two cell-mediated immune (CMI) peptide epitopes in the FIV p24 pools Fp9 and Fp14 that could serve as potential T-cell immunogens (FIGS. 23 and 24). These peptides were effective in the majority of subjects that had a corresponding in silico predicted HLA and did not induce substantial responses in CD4$^+$ T cells from HIV subjects. Peptide pool Fp14 induced robust IFNγ production with a high frequency of responders (32%) and moderate CD8$^+$ T-cell proliferation responses (FIGS. 23B and 24B). In contrast, peptide pool Fp9 induced robust CD8$^+$ T-cell proliferation with a high frequency of responders (26%) and no IFNγ responses. Most notably, the immune activity induced by the Fp9 and Fp14 peptide pools was highly reproducible and persisted for up to 4 years (FIG. 25).

Unexpectedly, SIV p24 pools induced more CD4$^+$ and CD8$^+$ T-cell proliferation responses than the corresponding HIV p24 pools in HIV$^+$ subjects (FIGS. 24A and 24C). Moreover, the attenuated CD4$^+$ T-cell proliferation responses to the SIV pools were highly correlative to CD8$^+$ T-cell proliferation responses (FIG. 24F). In some cases, these CD4$^+$ T cells could be more sensitive to HIV-1 infection (see below). However, possibly the CD4$^+$ T cells that are cross-reactive to these peptides persist in HIV$^+$ subjects and can perhaps be stimulated by these conserved epitopes to enhance the CD8$^+$ T-cell responses against HIV.

In addition to high aa sequence similarity (Table 12), the peptide pools Hp15 and Fp14 induced IFNγ responses, notably, only in PBMC from HIV$^+$ subjects (FIGS. 26A and 26B). Furthermore, Fp14-3 and its HIV counterpart, Hp15-3, had a high frequency of IFNγ responders. When small 9-13mer peptides from the Fp14 region were evaluated (Table 13), two overlapping peptides within Fp14-3 and Fp14-4 (Fp14-3d, Fp14-3/4f) showed high CD8$^+$ and CD4$^+$ T-cell proliferation responses, low IFNγ responses in HIV$^+$ subjects (FIGS. 27B, 27D, 27F) and elicited no response in HIV$^-$ subjects (average of <10 SFU). Thus, the epitope(s) present in peptide pools Hp15 and Fp14 are specific and likely to be evolutionarily conserved.

Peptide analysis of the Fp9 region gave a high frequency of responders measured by CD8$^+$ T-cell proliferation to peptides Fp9-3c and Fp9-3d but higher CD8$^-$ T-cell proliferation responses to the 15mer peptide Fp9-3 (Table 13, FIGS. 27A and 27C). One concern regarding the Fp9-3 peptide is its ability to elicit non-specific CD8$^+$ and CD4$^+$ T-cell proliferation (mitogenic effect); mitogenic stimulation can serve as an activation signal and could enhance HIV-1 infection (Spina et al. 1997; Stevenson et al. 1990). However, Fp9-3 peptide is not a classical T-cell mitogen (compared to PHA and concanvalin A) because it does not induce IFNγ in T cells from either HIV$^+$ or HIV subjects (FIG. 27E). IFNγ production in some cases could enhance HIV-1 infection (Yamamoto et al. 1986; Roff et al. 2014). A percentage of CD8$^+$ T cells from HIV subjects proliferated in response to the Fp9 pool and the 15mer Fp9-3 peptide but not to Fp9-3c and Fp9-3d 9mer peptides. These less mitogenic peptides have a strong algorithmic prediction for CD8$^+$ T-cell activity with the most common HLA supertypes A2 and B44 (Table 14) (Marsh et al. 2000). Therefore, the less mitogenic Fp9-3c and Fp9-3d peptides are likely better candidates as vaccine immunogens.

In this report, the CTL epitopes Hp15-1c, Hp15-1a, and Hp15-2/3a were further evaluated for cytotoxin expression along with their counterpart in FIV Fp14-1a, Fp14-1b, and Fp14-3/4f, respectively (FIGS. 28C and 28D). In these studies, the HIV peptides and their FIV counterparts, Hp15-1c/Fp14-1a (blue box), Hp15-1a/Fp14-1b (purple box), and Hp15-2/3a/Fp14-3/4f (red box) had high cytotoxin and CD107a expression. The respective SIV counterparts Sp14-1c, Sp14-1b, and Sp14-1a had a slightly lower number of responses than either their FIV or HIV-1 counterpart (FIGS. 28C and 28D).

The CTL epitope within the Hp15-1 peptide described in LANL database is predicted to bind strongly to HLA supertype B44 (Kiepiela et al. 2007). The B44 supertype is associated with a lower incidence of HIV disease progression in study subjects in South Africa, Botswana, and Zimbabwe (Leslie et al. 2010; Carlson et al. 2012). The inducers of CD8$^+$ T-cell proliferation in HIV$^-$ subjects are epitopes within Hp15-3 and, to a lesser extent Hp15-2, but not in the Hp15-1 peptide (FIG. 29). Thus, two known CTL epitopes within Hp15-1c and Hp15-1a elicited substantial levels of cytotoxin and CD107a expression but not as high as the well characterized epitope Hp15-2/3a. Hp15-2/3a induced expression in both CD4$^+$ and CD8$^+$ T cells and did not stimulate T cells from HIV subjects. As a result, it should be a better candidate for use as a vaccine immunogen.

Among the three peptides in Fp9 pool, the 15mer Fp9-3 had the highest frequency of responders expressing one or more cytotoxins by ICS analysis (FIG. 28A and 28D). Based on NetCTL analysis, this peptide can mediate CD8$^+$ T-cell activity by expressing peptide-specific cytotoxin(s) and using multiple HLA supertypes (A2, B7, B8, B27, B62). This finding makes it a strong candidate as a HIV-1 vaccine immunogen (Table 14). Similarly, the epitopes in Fp14-4 and lesser extent in Fp14-3 (FIG. 28) had the highest frequency of responders expressing cytotoxin(s) with high binding affinity for supertypes A2 and/or B44 (Table 14). Since the HLA B44 supertype is associated with either control of HIV infection and/or slow progression to AIDS (Tang et al. 2011; Zhang et al. 2013; Goulder and Walker 2012) and the HLA A2 supertype is associated with low HIV transmission (MacDonald et al. 2001a; MacDonald et al. 2001b; Liu et al. 2003), targeting these supertypes are likely beneficial in the development of an effective vaccine. In addition, a recent study correlated HLA A2 alleles with vaccine efficacy in the RV144 HIV vaccine trial and highlighted the importance of HLA allotypes in developing an effective HIV vaccine (Gartland et al. 2014). Notably, the current observations indicate that the cross-reactive peptides Fp9-3, Fp9-3c, Fp9-3d, Fp14-3d, and Fp14-3/4f induce CMI responses in HIV$^+$ subjects and are predicted to bind with highly prevalent HLA supertypes A2 and/or B44 (Table 14) (Marsh et al. 2000; Gonzalez-Galarza et al. 2011; Allele Frequency Net Database, allelefrequencies.net, accessed Oct. 2, 2014).

Previously, we described evolutionarily conserved CD8$^+$ T-cell epitopes on the FIV reverse transcriptase (Sanou et al. 2013). In the current study, we have identified cross-reactive p24 epitopes that are found in both HIV and FIV peptide sequences. These results support the existence of an evolutionary lineage among essential proteins of inter-species lentiviruses. Being conserved, these sequences are most likely essential for viral fitness, and thus less likely to mutate (Sanou et al. 2012b).

In summary, by evaluating IFNγ production, CFSE proliferation, and ICS expression in both HIV$^+$ and HIV$^-$ subjects (FIG. 29), we can conclude that the large 13-15mer peptides, HIV Hp15-1 and FIV Fp14-4, and small 9-10mers Hp15-2/3a, Fp14-1b, Fp14-3/4e, and Fp14-3/4f induce robust CMI responses without mitogenic stimulation. Furthermore, since the Fp9 and Fp14 epitopes possess polyfunctional activity (a combination of IFNγ, T-cell proliferation and/or cytotoxin responses), they also merit consideration as potential immunogens for inclusion in an effective HIV-1 vaccine (de Souza et al. 2012; Almeida et al. 2007). Selectively targeting these conserved sequences and monitoring non-mitogenic, T-cell specific responses allow the identification of conserved FIV, HIV, and SIV immunogenic peptides that could be included in an HIV vaccine for prophylaxis and immunotherapy.

TABLE 11

Description of HIV+ Population

| Group | Subject [a] | Age | Gender [b] | Race | HIV+ [c] | CD4/μL | CD8/μL | Virus Load [d] |
|---|---|---|---|---|---|---|---|---|
| LTS/ART− | SF01 | 42 | M | White | 16 | 1021 | 996 | Undetectable |
| | SF02 | 44 | M | White | 12 | 528 | 394 | Undetectable |
| | SF03 | 59 | M | White | 24 | 567 | 1040 | 5500 |
| | SF05 | 49 | M | White | 22 | 483 | 1242 | Undetectable |
| | SF08 | 48 | M | White | 31 | 529 | 920 | 3401 |
| | SF17 [e,f] | 56 | M | White | 11 | 374 | 1037 | 2000 |
| | SF19 [e,f] | 40 | M | White | 12 | 292 | 556 | 40000 |
| | SF21 | 43 | M | White | 15 | 800 | 1375 | 3584 |
| | SF23 [f] | 39 | M | White | 10 | 784 | 1018 | 3160 |
| | SF24 [f] | 50 | M | White | 11 | 675 | 213 | Undetectable |
| | J01 | 25 | F | Black | 11 | 699 | 935 | Undetectable |
| | J10 | 35 | F | Black | 12 | 897 | 659 | Undetectable |
| | J11 | 21 | F | Black | 21 | 564 | 829 | 932 |
| | J14 | 47 | M | Hispanic | 25 | 722 | 1421 | 6790 |
| ST/ART− | J02 [f] | 50 | F | Black | 9 mo | 639 | 1248 | 710 |
| | J03 | 27 | F | Black/Hispanic | 8 mo | 368 | 1254 | 25700 |
| | J04 | 22 | M | Black | 6 mo | 537 | 1907 | 1740 |
| | J05 | 32 | M | Black | 2 mo | 384 | 2202 | 691 |
| | J06 [f] | 28 | M | White | 6 mo | 501 | 1110 | 134000 |
| | J07 | 26 | F | Black | 4 mo | 448 | 1306 | 5120 |
| | J08 | 19 | F | Black/Hispanic | 9 mo | 323 | 932 | 3040 |
| | J09 [f] | 27 | M | White | 2 mo | 482 | 882 | 109168 |
| | J12 [f] | 26 | M | Pacific Islander | 5 mo | 352 | 688 | 405000 |
| | J17 | 51 | F | Black | 2 mo | 375 | 1271 | 2140 |
| ART+ | SF04 | 55 | M | White | 28 | 540 | 864 | Undetectable |
| | SF07 | 65 | M | White | 25 | 610 | 2170 | Undetectable |
| | SF13 | 52 | M | White | 25 | 304 | 372 | Undetectable |
| | SF16 | 50 | M | White | 8 | 827 | 1018 | Undetectable |
| | SF18 [f] | 38 | M | White | 4 | 1082 | 1298 | 1500 |
| | SF20 [f] | 53 | M | White | 23 | 76 | 1172 | Undetectable |
| | SF22 | 48 | M | White | 13 | 1205 | 517 | Undetectable |
| | J16 | 48 | F | White | 21 | 1250 | NA [g] | Undetectable |
| | J22 | 36 | F | Black | 15 | 391 | 490 | Undetectable |
| | J23 | 50 | F | Black | 16 | 949 | 1261 | Undetectable |
| | J24 | 41 | M | Black | 23 | 202 | 1192 | Undetectable |

Table 11 Footnotes:
[a] SF prefix, HIV+ subject from the University of California, San Francisco. J prefix, HIV+ subject from the University of Florida at Jacksonville; for definition of subjects, see legend to FIG. 23. The results for virus load and CD4/CD8 T-cell counts are from the 1st sample obtained from patients (yr 1).
[b] M, male; F, female.
[c] Duration of known HIV infection (yr).
[d] Virus loads are shown as RNA copies/mL; undetectable ≤75 RNA copies/mL.
[e] HIV+ subject who was on ART starting at or shortly after yr 2.
[f] Subjects monitored for 4 yr (FIG. 25).
[g] NA, not available.

TABLE 12

Fp9/Fp9-3, Fp14/Fp14-3, and their counterpart aa sequences and CMI responses

| Peptide Pool & Individual Peptide [a] | AA Sequence (with gap) [b] | SEQ ID NO. | Compared Sequences [b] Similarity (Identity) [gap] |
|---|---|---|---|
| | A. Hp10/Hp10-3 vs. Fp9/Fp9-3: | | |
| Hp10 Pool | EQIGWMTNNPPIPVGEIYKRWII<br>** ---:: *. : * :-- | 455 | Hp10 & Fp9:<br>36% (16%) [5] |
| Fp9 Pool | EQQ---AEARFAPARMQCRAWYLEA | 456 | |
| Hp10-3 | NPPIPVGEIYKRWII<br>-- *. : * :-- | 346 | Hp10-3 & Fp9-3:<br>29% (12%) [4] |
| Fp9-3 | FAPARMQCRAWYLEA | 288 | |

TABLE 12-continued

Fp9/Fp9-3, Fp14/Fp14-3, and their counterpart aa sequences and CMI responses

| Peptide Pool & Individual Peptide [a] | AA Sequence (with gap) [b] | SEQ ID NO. | Compared Sequences [b] Similarity (Identity) [gap] |
|---|---|---|---|
| B. Hp15/Hp15-3 vs. Fp14/Fp14-3/Fp14-4: | | | |
| Hp15 Pool | RAEQASQEVKNWMTETLLVQNAN | 457 | Hp15 & Fp14: |
| | `** : *** ::.::* : **-` | | 65% (35%) [1] |
| Fp14 Pool | DQEQNTAEVKLYLKQSLSIANA | 458 | |
| Hp15-3 | VKNWMTETLLVQNAN | 361 | Hp15-3 & Fp14-3: |
| | `--** ::.::* : ---` | | 53% (18%) [5] |
| Fp14-3 | AEVKLYLKQSLSIA | 303 | |
| Hp15-3 | VKNWMTETLLVQNAN | 361 | Hp15-3 & Fp14-4: |
| | `-* ::.::* : **-` | | 67% (27%) [2] |
| Fp14-4 | KLYLKQSLSIANA | 304 | |
| C. 9mer Peptides of Fp14-3/4f vs. Hp15-2/3a vs. Sp14-1c: | | | |
| Fp14-3/4f | KLYLKQSLS | 459 | Hp15-2/3a & Fp14-3/4f: |
| | `-* ::.::*-` | | 70% (20%) [2] |
| Hp15-2/3a | VKNWMTETL | 460 | Hp15-2/3a & Sp14-1a: |
| | `****:` | | 100% (89%) [0] |
| Sp14-1a | VKNWMTQTL | 461 | |
| D. 10mer Peptides of Fp14-1a/b vs. Hp15-1c/a vs. Sp14-1c/b: | | | |
| Fp14-1a | QEQNTAEVKL | 462 | Hp15-1c & Fp14-1a: |
| | `** : ***` | | 60% (50%) [0] |
| Hp15-1c | AEQASQEVKN | 463 | Hp15-1c & Sp14-1b: |
| | `--*:. ***--` | | 50% (33%) [4] |
| Sp14-1b [c] | QTDAAVKNWM | 464 | |
| Sp14-1c | TDAAVKNWMT | 465 | |
| Fp14-1b | QNTAEVKLYL | 466 | Hp15-1a & Fp14-1b: |
| | `* : *** ::` | | 70% (40%) [0] |
| Hp15-1a | QASQEVKNWM | 467 | Hp15-1a & Sp14-1b: |
| | `*:. *****` | | 80% (60%) [0] |
| Sp14-1b [c] | QTDAAVKNWM | 468 | |

Table 12 Footnotes:
[a] Peptide pools are not hyphenated (e.g., Fp9) while the individual large peptides have a hyphen followed by a number (e.g., Fp9-3) indicating the number of the overlapping individual peptide starting from amino-end.
[b] Alignments denote identical amino acids (aa) as (*), aa with most similarity based on charge, polarity, acid/base, and hydrophilicity/hydrophobicity as (:), those with some similarity as (.), and each gap with a (-). The internal gaps are due to best alignment and the external gaps are due the length of the selected peptide or peptide pool. The percentage of aa sequence similarity and identity was determined from these alignment criteria.
[c] Note that Sp14 pool is a single 13mer peptide Sp14-1 (TDAAVKNWMTQTL) (SEQ ID NO: 469). As a result, Sp14-1c, the counterpart SIV Sp14-1 peptide for HIV Hp15-1 peptide, is a 10mer and did not include the first three aa (AEQ). Whereas Sp14-1b is a 10mer with glutamine (Q) added to amino-end and threonine (T) deleted from the carboxyl-end rather than a sequence of Sp14-1c.

TABLE 13

9-13mer T-cell epitope mapping of Fp9 and Fp14 sequences using responders to Fp9 or Fp14

| Peptide Code [a] (No. of aa) [b] | SEQ ID NO. | Peptide Sequence [a] | CD8+ T-cell Responder Frequency (%) [c] | CD4+ T-cell Responder Frequency (%) [c] |
|---|---|---|---|---|
| Fp9 Peptide Pool | | | | |
| Fp9-1 (13) | 286 | EQQAEARFAPARM | 1/7 (14) | 0/7 (0) |
| Fp9-1/2a (9) | 470 | EARFAPARM | 5/9 (56) | 0/9 (0) |
| Fp9-2 (15) | 287 | AEARFAPARMQCRAW | 3/7 (43) | 1/7 (14) |
| Fp9-2/3b (9) | 471 | APARMQCRA | 3/9 (33) | 0/9 (0) |

TABLE 13-continued 9-13mer T-cell epitope mapping of Fp9 and Fp14 sequences using responders to Fp9 or Fp14

| Peptide Code [a] (No. of aa) [b] | SEQ ID NO. | Peptide Sequence [a] | CD8+ T-cell Responder Frequency (%) [c] | | CD4+ T-cell Responder Frequency (%) [c] | |
|---|---|---|---|---|---|---|
| Fp9-3 (15) | 288 | FAPARMQCRAWYLEA | 6/7 | (86) | 1/7 | (14) |
| Fp9-3c (9) | 451 | RMQCRAWYL | 5/9 | (56) [d] | 4/9 | (44) [d] |
| Fp9-3d (9) | 452 | ARMQCRAWY | 6/9 | (67) [d] | 3/9 | (33) [d] |
| Fp9-3e (10) | 472 | ARMQCRAWYL | 3/9 | (33) | 1/9 | (11) |
| Fp9-3f (12) | 473 | APARMQCRAWYL | 4/9 | (44) | 1/9 | (11) |
| Fp14 Peptide Pool | | | | | | |
| Fp14-1 (14) | 301 | DQEQNTAEVKLYLK | 4/10 | (40) | 2/10 | (20) |
| Fp14-1a (10) | 474 | QEQNTAEVKL | 0/4 | (0) [e] | 1/4 | (25) [e] |
| Fp14-1b (10) | 466 | QNTAEVKLYL | 2/4 | (50) [e] | 1/4 | (25) [e] |
| Fp14-1/2a (9) | 476 | NTAEVKLYL | 4/10 | (40) | 1/10 | (10) |
| Fp14-2 (15) | 302 | EQNTAEVKLYLKQSL | 3/6 | (50) | 0/6 | (0) |
| Fp14-2/3b (9) | 477 | AEVKLYLKQ | 3/10 | (30) | 1/10 | (10) |
| Fp14-2/3c (11) | 478 | AEVKLYLKQSL | 9/10 | (90) | 5/10 | (50) |
| Fp14-3 (14) | 303 | AEVKLYLKQSLSIA | 5/6 | (83) | 0/6 | (0) |
| Fp14-3d (13) | 454 | AEVKLYLKQSLSI | 10/10 | (100) [d] | 7/10 | (70) [d] |
| Fp14-3/4e (9) | 479 | LYLKQSLSI | 9/10 | (90) | 6/10 | (60) |
| Fp14-3/4f (10) | 453 | KLYLKQSLSI | 10/10 | (100) [d] | 6/10 | (60) [d] |
| Fp14-3/4g (9) | 480 | YLKQSLSIA | 6/10 | (60) | 0/10 | (0) |
| Fp14-4 (13) | 304 | KLYLKQSLSIANA | 6/6 | (100) | 1/6 | (17) |

Table 13 Footnotes:
[a] The 13-15mer peptide designations used in the peptide pools and their corresponding aa sequences are in bold.
[b] Number of amino acids.
[c] The responder frequencies to the large peptides were derived from yr 2 and included only responders to either the Fp9 or Fp14 peptide pool via CFSE proliferation. The responder frequencies to the small 9-13mer peptides were obtained at yr 4 and included only responders to either the Fp9 or Fp14 peptide pool via both proliferation and IFNγ.
[d] The two highest frequency of responders to small peptides by both CD8+ and CD4+ T cells are highlighted in bold.
[e] Proliferation results are from small number of subjects tested (n = 4) but ICS results are from five subjects (FIG. 28).

TABLE 14

HLA supertypes of the responders to key short and long peptides

| Peptide Code (No. of aa) | NetCTL Prediction[a] | NetMHC Prediction[a] | Supertypes of Responder (HLA-A/B supertypes)[a] | Algorithm and Responder Common Supertype(s)[b] | Responder Frequency in % (magnitude) type[c] |
|---|---|---|---|---|---|
| Fp9-3 (15) | A2, B7, B8, B27, B62 | A2, B7, B8, B27 | SF17 (A1/A2, B7/B7) SF18 (A1/A1, B8/B44) SF19 (A2/A3, B44/B62) SF20 (A2/A2, B44/B58) | SF17 (A2, B7) SF18 (B8) SF19 (A2, B62) SF20 (A2) | 67% (X-high) CD8 Proliferation 83% (high) CD4 Proliferation 14% (medium) IFNγ High Cytotoxins |
| Fp9-3c (9) | A2, B8, B62 | A1, A2, A3, B8, B27 | SF17 (A1/A2, B7/B7) SF19 (A2/A3, B44/B62) SF20 (A2/A2, B44/B58) SF24 (A2, A3, B27/B44) | SF17 (A1, A2) SF19 (A2, B62) SF20 (A2) SF24 (A2, A3, B27) | 56% (low) CD8 Proliferation 44% (low) CD4 Proliferation 22% (low) IFNγ Extremely Low Cytotoxins |
| Fp9-3d (9) | B27 | A1, A3, B27, B44 | SF17 (A1/A2, B7/B7) SF19 (A2/A3, B44/B62) SF20 (A2/A2, B44/B58) SF24 (A2, A3, B27/B44) | SF17 (A1) SF19 (A3, B44) SF20 (B44) SF24 (A3, B27, B44) | 56% (low) CD8 Proliferation 33% (low) CD4 Proliferation 0% (none) IFNγ Moderate Cytotoxins (only CD8) |

TABLE 14-continued

HLA supertypes of the responders to key short and long peptides

| Peptide Code (No. of aa) | NetCTL Prediction[a] | NetMHC Prediction[a] | Supertypes of Responder (HLA-A/B supertypes)[a] | Algorithm and Responder Common Supertype(s)[b] | Responder Frequency in % (magnitude) type[c] |
|---|---|---|---|---|---|
| Fp14-3d (13) | A24, B44 | A1, A2, A24, B27, B44 | SF17 (A1/A2, B7/B7) SF19 (A2/A3, B44/B62) SF20 (A2/A2, B44/B58) SF24 (A2, A3, B27/B44) | SF17 (A1, A2) SF19 (A2, B44) SF20 (A2, B44) SF24 (A2, B27, B44) | 100% (high) CD8 Proliferation 70% (low) CD4 Proliferation 40% (low) IFNγ Low Cytotoxins (only CD8) |
| Fp14-3/4f (10) | A24 | A1, A2, A24, B27, B58 | SF17 (A1/A2, B7/B7) SF19 (A2/A3, B44/B62) SF20 (A2/A2, B44/B58) SF24 (A2, A3, B27/B44) | SF17 (A1, A2) SF19 (A2) SF20 (A2, B58) SF24 (A2, B27) | 100% (high) CD8 Proliferation 60% (low) CD4 Proliferation 40% (low) IFNγ High Cytotoxins |
| Fp14-1 (14) | A1, B39, B58 | A1, B44, B62 | SF17 (A1/A2, B7/B7) SF18 (A1/A3, B8/B44) SF20 (A2/A2, B44/B58) SF23 (A1/A3, B27/B44) | SF17 (A1) SF18 (A1, B44) SF20 (B44) SF23 (A1, B44) | 50% (low) CD8 Proliferation 37% (low) CD4 Proliferation 33% (medium) IFNγ High Cytototoxins |
| Hp15-1 (14) | B58 | B44, B58 | SF18 (A1/A1, B8/B44) SF19 (A2/A3, B44/B62) SF20 (A2/A2, B44/B58) SF24 (A2, A3, B27/B44) | SF18 (B44) SF19 (B44) SF20 (B44, B58) SF24 (B44) | 50% (low) CD8 Proliferation 0% (none) CD4 Proliferation 78% (medium) IFNγ High Cytotoxins |

Table 14 Footnotes:
[a]Four subjects who responded to the designated peptide were HLA class I typed, and their HLA alleles were compared to the HLA supertype(s) predicted for the designated peptide using the NetCTL 1.2 and NetMHC 3.2 algorithms. The HLA A and HLA B allotypes for the subjects are shown as HLA supertypes.
[b]The most common supertypes between subjects and the HLA algorithm predictions are shown. The bolded supertype represents the most common supertypes among the subjects.
[c]All results were from responders to either Fp9 or Fp14 peptide pools. The results for individual 9-11mer peptides were derived from FIG. 28. Those for 13-15mer peptides (Fp9-1, Fp14-1, Hp15-1) were derived from FIG. 5 and/or 7. The average positive values are considered low when the frequency of response is <15% CFSE or <125 SFU, and high when >30 CSFE or >300 SFU. The cytotoxin result is considered high when four or five subjects express one or more cytotoxins in the CD8+ T cells.

Example 18

Selection of Conserved FIV and HIV-1 p24 and RT Peptide Pools and Peptides.

In our recent studies, the PBMC and T cells from HIV+ subjects responded to two FIV p24 peptide-pools Fp9 and Fp14 (FIG. 30) (Roff et al. 2015) and one FIV RT peptide-pool FRT3 (Sanou et al. 2013). These peptide pools were identified by IFNγ ELISpot of PBMC and carboxyfluoresein diacetate succinimide ester (CFSE)-proliferation of CD3+ CD4+ and CD3+CD8+ T cells. FIV p24-pool Fp14 and RT-pool FRT3 induced both CD8+ T-cell proliferation and IFNγ responses but minimal CD4+ T-cell proliferation. In contrast, pool Fp9 induced predominantly CD8+ T-cell proliferation but minimal CD4+ T-cell proliferation or IFNγ responses. The p24-peptide Fp14-3 of pool Fp14 induced the most IFNγ responses followed by peptide Fp14-1, while the p24-peptide Fp9-3 of pool Fp9 induced CD8+ T-cell proliferation. The majority of the responses to RT-pool FRT3 were specific for peptide FRT3-3. However, intracellular cytokine/cytotoxin staining (ICS) analyses determined that peptides Fp14-3, Fp14-4, and FRT3-4 induced the highest frequency and levels of CD8+ CTL-associated activity followed by peptide Fp9-3, Fp14-1, and FRT3-1 (Fp14 peptides in FIGS. 31A-31B; FRT3 peptides in (Sanou et al. 2013)). The magnitude and frequency of CTL-associated cytotoxin (perforin, granzyme A, granzyme B) responses were much higher and more frequent in CD8+ T cells than CD4+ T cells (Roff et al. 2015; Sanou et al. 2013). This observation suggests that CD8+ CTLs are induced in responses to FIV peptides Fp9-3, Fp14-3, and Fp14-4, and also to the counterpart HIV-1 peptides Hp15-1 and Hp15-3. Our approach identified the HIV-1 peptides Hp15-1 and Hp15-3 to be the evolutionarily or lentivirally conserved epitopes which induced CTL-associated activity in T cells.

Remarkably, prototype FIV (IWV)-vaccinated cats (Coleman et al. 2014) also responded with high magnitude and/or frequency of T-cell proliferation to pools Fp9 and Fp14 (FIGS. 32A-32B). Hence, Fp9 and Fp14 pools are recognized by both HIV+ subjects and FIV-vaccinated cats and thus contain EC T-cell epitopes (FIGS. 30 and 32). Additional FIV-vaccinated semi-inbred and outbred cats were tested for Fp9 and Fp14 peptide pools with similar results as in FIG. 30 (FIG. 33A). However they induced more IFNγ responses to pools Fp9 and Fp14 than those induced by FIV-infected cats. Individual peptides Fp14-1, Fp14-2, and Fp14-3 induced consistently low levels (e.g., 50-200 SFU considered low levels) of IFNγ responses in FIV-vaccinated cats (FIG. 33C, left), whereas peptide Fp14-4 induced the most CD8+ T-cell proliferation responses followed by peptides Fp14-2 and Fp14-3 (FIG. 33C, right). Notably, peptides Fp14-1 and Fp14-2 induced the most CD4+ T-cell proliferation.

Evolutionarily Conserved (EC) or Lentivirally Conserved T-Cell Epitopes.

Above studies demonstrate that both HIV+ subjects and FIV-vaccinated cats recognized certain regions of FIV (e.g., Fp9 pool) or of both FIV and HIV-1 (e.g., Fp14 and Hp15 pools; FRT3 and HRT3 pools). Moderate to identical aa sequence similarities/identities are observed between HIV-1 and FIV or SIV at conserved regions (i.e., overlapping peptide pools) of Hp15/Sp14/Fp14 (Table 15) and at conserved epitope FRT3-3 (Table 16). Notably, there is high (100%) similarity and identity (87-96%) within HIV-1 subtypes at the Hp15 region (Table 15). 100% identity is observed among all HIV subtypes at the FRT3-3 epitope (Table 16). Thus, the Hp15/Fp14 region on p24 and HRT3-3/FRT3-3/SRT3-3 epitopes on RT are highly conserved epitopes and considered evolutionarily conserved (EC) epitopes. The high similarity between HIV-1 and SIV strongly suggests the existence of more EC epitopes between these lentiviruses that induce a high CD8+ T-cell responder frequency in PBMC from HIV+ subjects (HIV-1 pool Hp1 and SIV pool Sp1 FIGS. 30A, 30C) (Roff et al. 2015). Interestingly, our approach has identified additional non-conserved reactive epitopes including pool Fp9, which has minimal identity or similarity to the HIV and SIV counterparts and has the closest similarity to HIV Nef based on Los Alamos National Laboratory (LANL) QuickAlign program (53% similarity, 47% identity, 2 gaps). These additional identified non-conserved sequences including this 13mer Nef counterpart of Fp9 will also be evaluated as candidate peptide epitope for AIDS vaccine.

Sections A and C in Table 15 show the EC epitope selection methods for Hp15 peptides (Section A) and Fp14 peptides (Section C). EC peptides are first screened by IFNγ ELISpot analysis (IFN) and CFSE-based CD8$^+$ (8P) and CD4$^+$ (4P) T-cell proliferation analyses followed by CD8$^+$ T-cell ICS (8C), CD4$^+$ T-cell ICS (4C), and viral enhancing/inhibitory assay, and responses in HIV negative control subjects (NC).

Multiple Antigenic Peptide (MAP) Vaccine Study with EC Epitope Peptides.

Since peptide pools and individual peptides of Fp14 and FRT3 induced CTL-associate cytotoxin expression in T cells from HIV$^+$ subjects, an in vivo study was performed to test whether if vaccination with these EC epitope peptides of FIV p24 and RT can elicit protective immunity against FIV in laboratory cats. Eight semi-inbred cats that were primed 1× with the prototype vaccine and boosted 4×-6× with 200 μg of lipophylic (Pam, palmitate C16)-MAP. The three Pam-MAPs consisted of FIV p24-peptide Fp14-1 alone (MAP1b) or together with the FIV p24-peptide Fp4-3 (MAP1: Fp4-3/furin-sensitive-linker/14-1) and FIV RT peptides FRT3-3 overlapped with FRT3-4 (MAP2) and were administered SC/ID in FD-1 adjuvant with feline IL12 (FeIL12) (FIG. 34) (Table 17). Peptide Fp4-3 and peptide-pool Fp4 induced predominantly IFNγ, IL2, and CD4$^+$ T-cell proliferation responses (pool Fp4 in FIGS. 31A-31B; data not shown for Fp4-3), whereas peptide Fp14-1 induced IFNγ and CD4$^+$ T-cell proliferation responses in the PBMC from FIV-vaccinated cats (FIGS. 33A-33C). Using the same assay system, FRT3-3 and FRT3-4 induced strong IL2 and CD8$^+$ T-cell proliferation responses but modest IFNγ (FRT3-3) and negligible CD4$^+$ T-cell proliferation responses (data not shown). However in the T cells from HIV$^+$ subjects, Fp14-1, FRT3-3, and FRT3-4 stimulated IFNγ production, CD8$^+$ T-cell proliferation, and EC-CTL-associated activities (FIGS. 31A-31B) (Roff et al. 2015; Sanou et al. 2013), and is therefore an EC T-cell epitope. These peptides were chosen based on their ability to elicit FIV-specific immune responses in our FLA-defined semi-inbred cats. This pilot MAP study showed only moderate IFNγ responses and T-cell proliferation to individual peptide after the 2nd boost (Table 18). No adverse effects were observed throughout the study. More importantly, after 10 CID$_{50}$ of FIV$_{FC1}$ challenge, complete protection in 1 of 4 cats and partial protection in 2 of 4 cats were observed in the 4× MAP1/MAP2 boosted Group 1 with the second lowest amount of Fp4-3 peptide. All non-vaccinated control (Group 4, n=4) and 1× primed control (Group 3, n=3) groups were infected (Table 17). Partial protection consisted of a 3-6 wk delay in FIV detection and 2-log lower viral set point compared to the control group. However, only 1 of 2 cats with partial protection was observed in the 6× MAP1b/MAP1/MAP2 boosted Group 2b with the lowest amount of Fp4-3 peptide. The 6× MAP1/MAP2 boosted counterpart Group 2a with the most Fp4-3 peptide had no protection. Since Group 2b was immunized initially with MAP1 b instead of MAP1 and had one partially protected cat, this suggested that the non-EC peptide Fp4-3 may be blocking protection and instead enhancing infection.

To test the possibility that Fp4-3 peptide may be enhancing FIV infection, we performed an in vitro FIV enhancing/inhibitory analysis with all MAP peptides and immunogens. Most remarkably, significant enhancement of FIV infection was observed with peptide Fp4-3 (Fp4-3 vs. Positive Control, p<0.05), peptide FRT3-3 and MAP1, whereas peptide FRT3-4 (p<0.05) and MAP2 (p<0.01) significantly inhibited FIV infection (FIG. 35). Since peptide Fp14-1 and MAP1b had no significant in vitro effect, peptide Fp4-3 in the MAP1 is most likely the cause of the in vitro enhancement observed with MAP1. Another notable observation is that the most significant inhibition was observed with MAP2 which correlates with the strong inhibition observed with FRT3-4 (no difference between FRT3-4 vs MAP2, p=0.184). Since MAP2 consisted of peptides FRT3-3 and FRT3-4 with a natural overlap (FIG. 34), such overlap may have blocked the enhancing activity of peptide FRT3-3 while allowing the inhibitory activity of peptide FRT3-4. Hence, MAP2 was the most protective immunogen followed by MAP1b. Moreover, none of the MAP vaccinated cats had early detection or enhancement in viral load compared to the control cats. Perhaps, the strong immunity generated by the MAP2 has blocked the enhancing activity of the MAP1 when boosted together (Group 1, Table 3). To test this possibility, in vitro study is currently undergoing to evaluate whether MAP2 can block FIV enhancing activity of MAP1. Furthermore, more cats will be vaccinated with MAP 1b and MAP2 to determine the levels of cytotoxins generated to peptides Fp14-1, FRT3-3 and FRT3-4. Since these peptides have induced CTL-associated cytotoxin expression in T cells from HIV$^+$ subjects (FIGS. 31A-31B; FIG. 5 in (Sanou et al. 2013)), these EC peptides may also mediate their in vivo effects by inducing anti-FIV specific CTL activity. The in vitro results together with in vivo efficacy results further suggest that our in vitro tests (enhancing/inhibitory assay; cytotoxin/cytokine analyses) can select epitopes with potent antiviral activities which should decrease the number of protective EC epitopes needed to be tested in in vivo studies and more efficiently produce an effective T-cell based vaccine against FIV and HIV-1.

Evaluating the Direct Viral Enhancing or Inhibitory Effect of Fp9-3 and Hp15 Peptides.

Based on our FIV enhancing/inhibitory (E/I) assay, we have determined non-EC peptide Fp4-3 and EC peptide FRT3-3 significantly enhanced in vitro FIV infection. However, only peptide Fp4-3 correlated with the in vitro enhancement induced by MAP1. Since the in vitro E/I assay uses PBMC from naïve specific pathogen free (SPF) cats, it is unlikely that the in vitro stimulation of anti-FIV CTLs occurred in the culture and eliminated the infected cells. More likely, these enhancing or inhibitory peptides induced cytokines (enhancement: IFNγ, TNFα, GM-CSF; inhibition: IFNα, IL10), chemokines (inhibition: MIP1α, MIP1β, SDF-1, RANTES), or cellular restriction factors (inhibition: Trim5α, APOBEC3g) that either enhanced or inhibited FIV/HIV-1 infection. The two identified FIV-enhancing epitopes (Fp4-3 and FRT3-3 epitope peptides) (FIG. 35) also induced high levels of IFNγ production in the PBMC of FIV-vaccinated cats (data not shown) but moderate levels to FRT3-3 (Sanou et al. 2013) and modest levels to Fp4 pool (FIGS. 30A-30F) (Roff et al. 2015) in the PBMC of HIV$^+$ subjects. IFNγ has been shown to enhance in vitro FIV and HIV-1 infections of naïve cat and human PBMCs respectively (Tanabe and Yamamoto 2001; Yamamoto et al. 1986). IFNγ is produced during inflammatory responses to HIV-1 infection (Ipp and Zemlin 2013). Thus, high levels of antiviral cellular immune responses are needed while minimizing both non-specific and viral-specific activation of CD4$^+$ T cells which can enhance viral replication (Lane 2010). Removal of the enhancing epitopes on FIV and HIV-1 immunogens will be critical to produce an effective HIV-1 vaccine. To accomplish this goal, we will design a vaccine based on antiviral epitopes directed at inducing viral-specific CD4+ CTLs, CD8+ CTLs and polyfunctional T cells, and identifying viral enhancing epitopes to remove from vaccine candidates.

More importantly, our most recent in vitro studies demonstrated that EC epitope FRT3-4 directly inhibited the FIV infection. This observation is completely opposite of the FIV enhancement observed with EC epitope FRT3-3. Notably the enhancing epitope overlaps with the inhibitory epitope. Hence, careful epitope mapping must be performed to remove any enhancing epitopes from FIV vaccine immunogen. Similar to FIG. 36A, repeated in vitro E/I studies demonstrated that peptides Fp14-3 and Fp14-4 do not directly enhance or inhibit FIV infection. Therefore these EC T-cell peptides especially the Fp14-4 peptide, which induced strong $CD8^+$ T-cell proliferation in FIV-vaccinated cats (FIGS. 33A-33C), should be next tested for its ability to induce FIV-specific cytotoxin expression before in vivo challenge efficacy study. Its HIV-1 counterpart peptide Hp15-3 induced high levels and frequency of cytotoxin responses in T cells from $HIV^+$ subjects (FIGS. 31A-31B) (Roff et al. 2015). Similarly, Hp15-1, the HIV counterpart of Fp14-1, induced robust cytotoxin levels and responder frequencies in the $CD8^+$ T cells from $HIV^+$ subjects. Moreover, Hp15-1 strongly inhibited in vitro HIV-1 infection, whereas Hp15-3 had no direct effect on HIV-1 infection. Consequently, EC peptide Hp15-1 followed by peptide Hp15-3 should be included as the HIV-1 vaccine immunogens.

Another remarkable observation is that FIV p24 epitope peptide Fp9-3 inhibited in vitro infection of both FIV (FIG. 36A) and HIV-1 (FIG. 36B) but FRT3-4 inhibited only FIV. However these in vitro results indicate that FRT3-4 does not enhance FIV and HIV-1 infections and may be a promising T-cell epitope for vaccine since it induced CTL-associated cytotoxin expression in T cells from $HIV^+$ subjects (Sanou et al. 2013). If it also induces FIV-specific CTL activity in PBMC from FIV-vaccinated cats then this peptide will have direct and indirect modes of anti-FIV activities. In conclusion, we now have EC peptides Fp14-1, FRT3-4, and FRT3-3/3-4 as protective T-cell epitopes against FIV, and EC peptides Hp15-1 and Hp15-3 as protective T-cell epitopes against HIV-1, whereas cross-reactive Fp9-3 peptide may be useful against both FIV and HIV-1. We have also determined that palmitated MAP (Pam-MAP) is an excellent vehicle to deliver the peptide-based vaccine.

TABLE 15

Sequence conservation in EC p24 epitopes of Hp15/Fp14 pools

A. Subtype-B HIV-1 Hp15 Peptides

| | SEQ ID NO. | | IFN | 8P | 4P | 8C | 4C | E/I | NC |
|---|---|---|---|---|---|---|---|---|---|
| Hp15-1 | 359 | RAEQASQEVKNWMTE | + | + | + | + | + | ↓ | − |
| Hp15-2 | 360 | ASQEVKNWMTETLLV | + | − | − | + | + | n | − |
| Hp15-3 | 361 | VKNWMTETLLVQNAN | + | + | + | + | + | ↓ | + |

B. Subtypes/Strains

| | SEQ ID NO. | Fp14 Pool Counterparts | Compared to UCD1 | |
|---|---|---|---|---|
| HIV-1 UCD1 (B) | 457 | RAEQASQEVKNWMTETLLVQNAN<br>*****:****.************ | Identity | (Similarity) |
| HIV-1 (A) | 481 | RAEQATQEVKGWMTETLLVQNAN<br>*********************** | 91% | (100%) |
| HIV-1 (B) | 457 | RAEQASQEVKNWMTETLLVQNAN<br>*****:*:******:******** | 100% | (100%) |
| HIV-1 (C) | 482 | RAEQATQDVKNWMTDTLLVQNAN<br>*******:*************** | 87% | (100%) |
| HIV-1 (D) | 483 | RAEQASQDVKNWMTETLLVQNAN<br>**********:***:******** | 96% | (100%) |
| SIV CPZ | 484 | RAEQASQEVKTWMTDTLLVQNAN<br>****... ******.***:**** | 91% | (100%) |
| SIV Mac251/Mac239 | 485 | RAEQTDAAVKNWMTQTLLIQNAN<br> :  ::.::* : *** | 74% | (96%) |
| FIV (A, B, D) [Fp14] | 486 | DQEQNTAEVKLYLKQSLSIANAN<br> : ::.::* : *** | 39% | (70%) |
| FIV (C) | 487 | DQEQNTAEVKTYLKQSLSLANAN | 39% | (74%) |

TABLE 15-continued Sequence conservation in EC p24 epitopes of Hp15/Fp14 pools C. Subtype-B FIV Fp14 Peptides

| | SEQ ID NO. | | IFN | 8P | 4P | 8C | 4C | E/I | NC |
|---|---|---|---|---|---|---|---|---|---|
| Fp14-1 | 301 | DQEQNTAEVKLYLK | + | + | + | + | + | − | − |
| Fp14-2 | 302 | EQNTAEVKLYLKQSL | − | + | − | + | + | n | − |
| Fp14-3 | 303 | AEVKLYLKQSLSIA | + | + | + | + | + | − | − |
| Fp14-4 | 488 | KLYLKQSLSIANAN | + | + | + | + | + | − | − |

Sections A and C show positive (+) or negative (−) response for IFNγ (IFN); CD8+ T-cell proliferation (8P); CD4− T-cell proliferation (4P); CD8+ T-cell cytotoxins (8C); CD4+ T-cell cytotoxins (4C); or HIV enhancing or inhibitory (E/I) in HIV+ subjects when compared to those in HIV− control group (NC). Symbols: inhibitory (↓); identical aa (*); closely (:) or moderately (.) similar aa; not done (n); and bold aa residue differs from the one on HIV-1/UCD1.

TABLE 16

Sequence conservation in EC epitope FRT3-3

| Subtypes/ Strains | SEQ ID NO. | FRT3-3 Counterparts | Compared to UCD1 | |
|---|---|---|---|---|
| HIV-1 UCD1 (B) | 435 | KKKDSTKWRKLVDFRE *************** | Identity | (Similarity) |
| HIV-1 (A) | 435 | KKKDSTKWRKLVDFRE *************** | 100% | (100%) |
| HIV-1 (B) | 435 | KKKDSTKWRKLVDFRE *************** | 100% | (100%) |
| HIV-1 (C) | 435 | KKKDSTKWRKLVDFRE *************** | 100% | (100%) |
| HIV-1 (D) | 435 | KKKDSTKWRKLVDFRE *************** | 100% | (100%) |
| SIV CPZ | 435 | KKKDSTKWRKLVDFRE **..*.*:**** | 100% | (100%) |
| SIV MM | 489 | KKKDKNKWRMLIDFRE *** *:***.*:**** | 75% | (100%) |
| FIV (A, C) | 490 | KKK-SGKWRMLIDFRE *** *:***.*:*** | 75% | (94%) |
| FIV (B, D) [FRT3-3] | 63 | KKK-SGK<u>WRMLIDFRV</u> | 67% | (87%) |

Strong IFNγ and T-cell proliferation responses to FRT3-3 decreased to zero when the following aa's on the FRT3-3 peptide were changed with the corresponding ones on the HRT3-3 peptide: V15→E15, I11→V11, and M9→K9 (highest to lowest decrease) (Sanou et al. 2013). The underline shows an epitope which is also detected by HIV− subjects.

TABLE 17

Prototype Dual-Subtype FIV (IWV) Vaccine Prime and MAP Vaccine Boosts

| Group # [# of cats] | Prime | Boost-1 | Boost-2 | Boost-3 | Boost-4 | Boost-5 | Boost-6 | Full-to-Partial Protection |
|---|---|---|---|---|---|---|---|---|
| 1 [4] | 1x IWV → | MAP1 → | MAP1 + 2 → | MAP2 → | MAP1 + 2 | — | — | 3/4 (1 Full + 2 Partial) |
| 2a [2] | 1x IWV → | MAP1 → | MAP1 → | MAP1 → | MAP2 → | MAP2 → | MAP1 + 2 | 0/2 |
| 2b [2] | 1x IWV → | MAP1b → | MAP1b → | MAP1b → | MAP2 → | MAP2 → | MAP1 + 2 | 1/2 (Partial) |
| 3 [3] | 1x IWV | — | — | — | — | — | — | 0/3 |
| 4 [4] | PBS | PBS | PBS | PBS | PBS | — | — | 0/4 |

TABLE 18

Prototype Dual-Subtype FIV (IWV) Vaccine Prime and Post-SECOND MAP Boost

| | | | | IFNγ (SFU) | IL2 (SFU) | Proliferation (CFSE<sup>low</sup>) | |
|---|---|---|---|---|---|---|---|
| Cat ID | Prime | Boost-1 | Boost-2 | Fp4-3/Fp14-1 | Fp4-3/Fp14-1 | CD4+ T cells | CD8+ T cells |
| QVW | 1x IWV → | MAP1 → | MAP1 | 21/0 [0] | 0/0 [9] | 0/6 [7] | 0/5 [6] |
| DVD | 1x IWV → | MAP1 → | MAP1 | 132/37 [206] | 95/53 [296] | 3/0 [2] | 6/0 [9] |

TABLE 18-continued

Prototype Dual-Subtype FIV (IWV) Vaccine Prime and Post-SECOND MAP Boost

| | | | | IFNγ (SFU) | IL2 (SFU) | Proliferation (CFSE$^{low}$) | |
|---|---|---|---|---|---|---|---|
| Cat ID | Prime | Boost-1 | Boost-2 | Fp4-3/Fp14-1 | Fp4-3/Fp14-1 | CD4$^+$ T cells | CD8$^+$ T cells |
| QVQ | 1x IWV → | MAP1b → | MAP1b | 0/0 [43] | 0/12 [165] | 1/1 [7] | 0/6 [7] |
| DVB | 1x IWV → | MAP1b → | MAP1b | 0/0 [0] | 0/70 [76] | 0/2 [1] | 0/12 [10] |

Peptide Fp4-3 (left), peptide Fp14-1 (middle) and MAP1 [right] were culture stimulants. IL2 and IFNγ ELISpot results of >50 spot forming units (SFU/10$^6$ PBMC) and CFSE-proliferation of >2 are considered positive (bolded). The prime-boost vaccination induced IL2 responses in 3 of 4 cats and IFNγ response in one. Larger responses were induced by MAP1 than individual peptides in culture. These results demonstrate that both peptides in the MAP are recognized by the cats and MAP formulation may be more effective in delivering peptides into cells.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 5,530,101
U.S. Pat. No. 5,585,089
U.S. Pat. No. 5,693,762
U.S. Pat. No. 6,180,370
U.S. Pat. No. 6,407,213
Abbas A K, Lichtman A H, Pillai S (Eds). Cytokines. In: Cellular and molecular Immunology. Philadelphia, Pa.: Saunders Elsevier; 2010, p. 267-301.
Abbott J R, Pu R, Coleman J K, Yamamoto J K. 2012. Utilization of feline ELISPOT for mapping vaccine epitopes. Methods Mol. Biol. 792:47-63.
Abbott J R, Sanou M P, Coleman J K, Yamamoto J K. 2011. Evolutionarily conserved T-cell epitopes on FIV for designing an HIV/AIDS vaccine. Vet. Immunol. Immunopathol. 143:246-54.
Ackley, C. D., J. K. Yamamoto, N. B. Levy, N. C. Pedersen, M. D. Cooper (1990) "Immunologic abnormalities in pathogen-free cats experimentally infected with feline immunodeficiency virus," J. Virol. 64:5652-5655.
Allele Frequency Net Database, allelefrequencies.net/ Accessed Oct. 2, 2014.
Almeida, J. R., Price, D. A., Papagno, L., Arkoub, Z. A., Sauce, D., Bornstein, E., Asher, T. E., Samri, A., Schnuriger, A., Theodorou, I., Costagliola, D., Rouzioux, C., Agut, H., Marcelin, A. G., Douek, D., Autran, B., Appay, V., 2007. Superior control of HIV-1 replication by CD8+ T cells is reflected by their avidity, polyfunctionality, and clonal turnover. The Journal of experimental medicine 204, 2473-2485.
Altschul, S. F. (1990) "Basic Local Alignment Search Tool," J. Mol. Biol. 215:402-410.
Altschul, S. F. et al. (1997) "Gapped BLAST and PSI-BLAST: A New Generation of Protein Database Search Programs," Nucl. Acids Res. 25:3389-3402.
Ardito M, Fueyo J, Tassone R, et al. An integrated genomic and immunoinformatic approach to H. pylori vaccine design. Immunome Res 2011; 20; 7: 1.
Balla-Jhagjhoorsingh S S, Koopman G, Mooij P, Haaksma T G, Teeuwsen V J, Bontrop R E, Heeney J L. 1999. Conserved CTL epitopes shared between HIV-infected human long-term survivors and chimpanzees. J. Immunol. 162:2308-14.
Barouch D H, O'Brien K L, Simmons N L, et al. Mosaic HIV-1 vaccines expand the breadth and depth of cellular immune responses in rhesus monkeys. Nat Med 2010; 16: 319-23.
Belyakov I M, Ahlers J D. 2012. Mucosal immunity and HIV-1 infection: applications for mucosal AIDS vaccine development. Curr Top Microbiol Immunol 354:157-79.
Betts M R, Krowka J F, Kepler T B, Davidian M, Christopherson C, Kwok S, Louie L, Eron J, Sheppard H, Frelinger J A. 1999. Human immunodeficiency virus type 1-specific cytotoxic T lymphocyte activity is inversely correlated with HIV type 1 viral load in HIV type 1-infected long-term survivors. AIDS Res. Hum. Retroviruses 15:1219-28.
Betts M R, Nason M C, West S M, De Rosa S C, Migueles S A, Abraham J, Lederman M M, Benito J M, Goepfert P A, Connors M, Roederer M, Koup R A. 2006. HIV nonprogressors preferentially maintain highly functional HIV-specific CD8+ T cells. Blood 107: 4781-9.
Bhasin M, Raghava, GPS. Prediction of CTL epitopes using QM, SVM and ANN techniques. Vaccine 2004; 22: 3195-201.
Buchbinder S P, Mehrotra D V, Duerr A, Fitzgerald D W, Mogg R, Li D, Gilbert P B, Lama J R, Marmor M, Del Rio C, McElrath M J, Casimiro D R, Gottesdiener K M, Chodakewitz J A, Corey L, Robertson M N; Step Study Protocol Team. 2008. Efficacy assessment of a cell-mediated immunity HIV-1 vaccine (the Step Study): a double-blind, randomised, placebo-controlled, test-of-concept trial. Lancet 372:1881-93.
Caligiuri M A. Human natural killer cells. 2008. Blood 112:461-9. Review.
Cao H, Kanki P, Sankale J L, et al. Cytotoxic T-lymphocyte cross-reactivity among different human immunodeficiency virus type 1 clades: implications for vaccine development. J Virol 1997; 71: 8615-23.
Carlson, J. M., Listgarten, J., Pfeifer, N., Tan, V., Kadie, C., Walker, B. D., Ndung'u, T., Shapiro, R., Frater, J., Brumme, Z. L., Goulder, P. J., Heckerman, D., 2012. Widespread impact of HLA restriction on immune control and escape pathways of HIV-1. Journal of virology 86, 5230-5243. doi: 10.1128/JVI.06728-11.
Coleman J K, Pu R, Martin M, Sato E, Yamamoto J K. 2005. HIV-1 p24 vaccine protects cats against FIV. AIDS 19:1457-66.

Coleman J K, Pu R, Martin M M, Noon-Song E N, Zwijnenberg R, Yamamoto J K. Feline immunodeficiency virus (FIV) vaccine efficacy and FIV neutralizing antibodies. *Vaccine* 2014; 32:746-54.

Corey L, McElrath M J. 2010. HIV vaccines: mosaic approach to virus diversity. Nat. Med. 16:268-70.

De Groot A S, Rivera D S, McMurry J A, Buus S, Martin W. Identification of immunogenic HLA-B7 "Achilles' heel" epitopes within highly conserved regions of HIV. Vaccine 2008; 26: 3059-71.

de Souza M S, Ratto-Kim S, Chuenarom W, Schuetz A, Chantakulkij S, Nuntapinit B, Valencia-Micolta A, Thelian D, Nitayaphan S, Pitisuttithum P, Paris R M, Kaewkungwal J, Michael N L, Rerks-Ngarm S, Mathieson B, Marovich M, Currier J R, Kim J H; Ministry of Public Health—Thai AIDS Vaccine Evaluation Group Collaborators. 2012. The Thai phase III trial (RV144) vaccine regimen induces T cell responses that preferentially target epitopes within the V2 region of HIV-1 envelope. J Immunol. 188:5166-76.

Felgner, P. L., T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure," *Proc. Natl. Acad. Sci. USA* 84(21):7413-7417.

Flynn N M, Forthal D N, Harro C D, Judson F N, Mayer K H, Para M F, rgp120 HIV Vaccine Study Group. 2005. Placebo-controlled phase 3 trial of a recombinant glycoprotein 120 vaccine to prevent HIV-1 infection. J. Infect. Dis. 191:654-65.

Gartland, A. J., Li, S., McNevin, J., Tomaras, G. D., Gottardo, R., Janes, H., Fong, Y., Morris, D., Geraghty, D. E., Kijak, G. H., Edlefsen, P. T., Frahm, N., Larsen, B. B., Tovanabutra, S., Sanders-Buell, E., deCamp, A. C., Magaret, C. A., Ahmed, H., Goodridge, J. P., Chen, L., Konopa, P., Nariya, S., Stoddard, J. N., Wong, K., Zhao, H., Deng, W., Maust, B. S., Bose, M., Howell, S., Bates, A., Lazzaro, M., O'Sullivan, A., Lei, E., Bradfield, A., Ibitamuno, G., Assawadarachai, V., O'Connell, R. J., deSouza, M. S., Nitayaphan, S., Rerks-Ngarm, S., Robb, M. L., Sidney, J., Sette, A., Zolla-Pazner, S., Montefiori, D., McElrath, M. J., Mullins, J. I., Kim, J. H., Gilbert, P. B., Hertz, T., 2014. Analysis of HLA A*02 Association with Vaccine Efficacy in the RV144 HIV-1 Vaccine Trial. Journal of virology 88, 8242-8255.

Gonzalez-Galarza, F. F., Christmas, S., Middleton, D., Jones, A. R., 2011. Allele frequency net: a database and online repository for immune gene frequencies in worldwide populations. Nucleic acids research 39, D913-919. doi: 10.1093/nar/gkq1128.

Goulder P J, Watkins D I. 2008. Impact of MHC class I diversity on immune control of immunodeficiency virus replication. Nat. Rev. Immunol. 8:619-30.

Goulder, P. J., Walker, B. D., 2012. HIV and HLA class I: an evolving relationship. Immunity 37, 426-440. doi: 10.1016/j.immuni.2012.09.005.

Hanke T, McMichael A J, Dorrell L. 2007. Clinical experience with plasmid DNA- and modified vaccinia virus Ankara-vectored human immunodeficiency virus type 1 clade A vaccine focusing on T-cell induction. J. Gen. Virol. 8:1-12.

Horton H., E. P. Thomas, J. A. Stucky, I. Frank, Z. Moodie, Y. Huang, Y. Chiu, M. J. McElrath and S. C. De Rosa. 2007. Optimization and validation of an 8-color intracellular cytokine staining (ICS) assay to quantify antigen-specific T cells induced by vaccination. *J Immunol.* 323: 39-54.

Hosie, M. J., O. Jarrett (1990) "Serological responses of cats to feline immunodeficiency virus," *AIDS* 4:215-220.

Ipp H, Zemlin A. The paradox of the immune response in HIV infection: when inflammation becomes harmful. *Clin Chim Acta* 2013; 416:96-9.

Jenner E. An inquiry into the causes and effects of the Variolae Vaccinae, a disease discovered in some of the western counties of England, particularly Gloucestershire, and known by the name of the cow-pox. London: Sampson Low, 1798.

Johnson R P, Trocha A, Yang L, et al. HIV-1 gag-specific cytotoxic T lymphocytes recognize multiple highly conserved epitopes. Fine specificity of the gag-specific response defined by using unstimulated peripheral blood mononuclear cells and cloned effector cells. J Immunol 1991; 147: 1512-21.

Kakinuma, S., K. Motokawa, T. Hohdatsu, J. K. Yamamoto, H. Koyama, H. Hashimoto (1995) "Nucleotide Sequence of Feline Immunodeficiency Virus: Classification of Japanese Isolates into Two Subtypes Which Are Distinct from Non-Japanese Subtypes," *J. Virol.* 69(6):3639-3646.

Karlin, S. and Altschul, S. F. (1990) "Methods for Assessing the Statistical Significance of Molecular Sequence Features by Using General Scoring Schemes," *Proc. Natl. Acad. Sci. USA* 87:2264-2268.

Karlin, S. and Altschul, S. F. (1993) "Applications and Statistics for Multiple High-Scoring Segments in Molecular Sequences," *Proc. Natl. Acad. Sci. USA* 90:5873-5877.

Kiepiela P, Kholiswa N, Thobakgale C, et al. $CD8^+$ T-cell responses to different HIV proteins have discordant associations with viral load. *Nature Med* 2007; 13: 46-53.

Koff W C. 2010. HIV vaccine development: Challenges and opportunities towards solving the HIV vaccine-neutralizing antibody problem. Vaccine 30:4310-5.

Kohler, G., C. Milstein (1975) "Continuous cultures of fused cells secreting antibody of predefined specificity" *Nature* 256(5517):495-497.

Korber B T, Letvin N L, Haynes B F. T-cell vaccine strategies for human immunodeficiency virus, the virus with a thousand faces. J Virol 2009; 83: 8300-14.

Kotterman M A, Schaffer D V. Engineering adeno-associated viruses for clinical gene therapy. *Nat Rev Gene* 2014; 15:445-51. Review.

Kowalczyk W, Monsó M, de la Torre B G, Andreu D. Synthesis of multiple antigenic peptides (MAPs)—strategies and limitations. J. Pept. Sci., 2011, 17:247-251 (published online 30 Nov. 2010).

Lane H C. Pathogenesis of HIV infection: total $CD4^+$ T-cell pool, immune activation, and inflammation. *Top HIV Med* 2010; 18:2-6.

Larsen M V, Lundegaard C, Lamberth K, Buus S, Lund O, Nielsen M. Large-scale validation of methods for cytotoxic T-lymphocyte epitope prediction. BMC Bioinform 2007; 8:424.

Leslie A J, Pfafferott K J, Chetty P, Draenert R, Addo M M, Feeney M, Tang Y, Holmes E C, Allen T, Prado J G, Altfeld M, Brander C, Dixon C, Ramduth D, Jeena P, Thomas S A, St John A, Roach T A, Kupfer B, Luzzi G, Edwards A, Taylor G, Lyall H, Tudor-Williams G, Novelli V, Martinez-Picado J, Kiepiela P, 494 Walker B D, Goulder P J. 2004. HIV evolution: CTL escape mutation and reversion after transmission. Nat. Med. 10:282-9.

Leslie, A., Matthews, P. C., Listgarten, J., Carlson, J. M., Kadie, C., Ndung'u, T., Brander, C., Coovadia, H., Walker, B. D., Heckerman, D., Goulder, P. J., 2010. Additive contribution of HLA class I alleles in the immune control of HIV-1 infection. Journal of virology 84, 9879-9888. doi: 10.1128/JVI.00320-10.

Li F, Finnefrock A C, Dubey S A, Korber B T, Szinger J, Cole S, McElrath M J, Shiver J W, Casimiro D R, Corey L, Self S G. 2011. Mapping HIV-1 vaccine induced T-cell responses: bias towards less-conserved regions and potential impact on vaccine efficacy in the Step study. PloS One. 6:e20479. doi:10.1371/journal.pone.0020479.

Li F, Horton H, Gilbert P B, McElrath J M, Corey L, Self S G. HIV-1 CTL-based vaccine immunogen selection: antigen diversity and cellular response features. Curr HIV Res 2007; 5: 97-107.

Lichterfeld M, Kaufmann D E, Yu X G, Mui S K, Addo M M, Johnston M N, Cohen D, Robbins G K, Pae E, Alter G, Wurcel A, Stone D, Rosenberg E S, Walker B D, Altfeld M. 2004. Loss of HIV-1-specific CD8+ T cell proliferation after acute HIV-1 infection and restoration by vaccine-induced HIV-1-specific CD4+ T cells. J. Exp. Med. 200:701-12.

Liu, C., Carrington, M., Kaslow, R. A., Gao, X., Rinaldo, C. R., Jacobson, L. P., Margolick, J. B., Phair, J., O'Brien, S. J., Detels, R., 2003. Association of polymorphisms in human leukocyte antigen class I and transporter associated with antigen processing genes with resistance to human immunodeficiency virus type 1 infection. The Journal of infectious diseases 187, 1404-1410.

Llano A, Frahm N, Brander C. 2009. How to optimally define optimal cytotoxic T lymphocyte epitopes in HIV infection? In Yusim K (ed), HIV Molecular Immunology 2009. Los Alamos National Laboratory, Los Alamos, N. Mex.

Los Alamos National Laboratory. HIV molecular immunology database: Best-defined CTL/CD8+ Epitope Summary: (hiv.lanl.gov/content/immunology/tables/optimal_ctl_summary.html)

Louwagie, J., F. E. McCutchan, M. Peeters, T. P. Brennan, E. Sanders-Buell, G. A. Eddy, G. van den Grosen, K. Fransen, G. M. Gershy-Damet, R. Deleys, D. S. Burke (1993) "Phylogenetic analysis of gag genes from 70 international HIV-1 isolates provides evidence for multiple genotypes," AIDS 7:769-780.

Lundegaard C, Lamberth K, Harndahl M, Buus S, Lund O, Nielsen M. NetMHC-3.0: Accurate web accessible predictions of Human, Mouse, and Monkey MEW class I affinities for peptides of length 8-11. NAR 2008; 36: 50912.

MacDonald, K. S., Embree, J. E., Nagelkerke, N. J., Castillo, J., Ramhadin, S., Njenga, S., Oyug, J., Ndinya-Achola, J., Barber, B. H., Bwayo, J. J., Plummer, F. A., 2001. The HLA A2/6802 supertype is associated with reduced risk of perinatal human immunodeficiency virus type 1 transmission. The Journal of infectious diseases 183, 503-506.

MacDonald, K. S., Matukas, L., Embree, J. E., Fowke, K., Kimani, J., Nagelkerke, N. J., Oyugi, J., Kiama, P., Kaul, R., Luscher, M. A., Rowland-Jones, S., Ndinya-Achola, J., Ngugi, E., Bwayo, J. J., Plummer, F. A., 2001. Human leucocyte antigen supertypes and immune susceptibility to HIV-1, implications for vaccine design. Immunology letters 79, 151-157.

Marsh S. G., Parham P., Barber L. D. 2000. The HLA Class I and Class II Loci. In Marsh S. G., Parham P., Barber L. D. (eds), The HLA Facts Book. London: Academy Press; p. 93-272.

McDermott A B, Koup R A. 2012. CD8+ T cells in preventing HIV infection and disease. AIDS 26:1281-92.

McKinnon L R, Kaul R, Kimani J, Nagelkerke N J, Wachihi C, Fowke K R, Ball T B, Plummer F A. 2012. HIV-specific CD8+ T-cell proliferation is prospectively associated with delayed disease progression. Immunol. Cell Biol. 90:346-51.

Moss S F, Moise L, Lee D S, et al. HelicoVax: epitope-based therapeutic *Helicobacter pylori* vaccination in a mouse model. Vaccine 2011; 29:2085-91.

Mothe B, Liano A, Ibarrondo J, Daniels M, Miranda C, Zamarreño J, Bach V, Zuniga R, Pérez-Álvarez S, Berger C T, Puertas M C, Martinez-Picado J, Rolland M, Farfan M, Szinger J J, Hildebrand W H, Yang O O, Sanchez-Merino V, Brumme C J, Brumme Z L, Heckerman D, Allen T M, Mullins J I, Gómez G, Goulder P J, Walker B D, Gatell J M, Clotet B, Korber B T, Sanchez J, Brander C. 2011. Definition of the viral targets of protective HIV-1-specific T cell responses. J. Transl. Med. 9:208.

Murphy, F., D. W. Kingsbury (1990) "Virus Taxonomy," In *Fields Virology*, 2nd Ed., B. N. Fields, D. M. Knipe et al., eds, Raven Press, New York, Chapter 2, pp. 9-36.

Nakayama K. Furin: a mammalian subtilisin/Kex2p-like endoprotease involved in processing of a wide variety of precursor proteins. Biochem J1997; 327:625-35.

Ogg G S, Jin X, Bonhoeffer S, Dunbar P R, Nowak M A, Monard S, Segal J P, Cao Y, Rowland-Jones S L, Cerundolo V, Hurley A, Markowitz M, Ho D D, Nixon D F, McMichael A J. 1998. Quantitation of HIV-1-specific cytotoxic T lymphocytes and plasma load of viral RNA. Science 279:2103-6.

Olmsted, R. A., A. K. Barnes, J. K. Yamamoto, V. M. Hirsch, R. H. Purcell, P. R. Johnson (1989a) "Molecular cloning of feline immunodeficiency virus," *Proc. Nat. Acad. Sci. USA* 86:2448-2452.

Olmsted, R. A., V. M. Hirsch, R. H. Purcell, P. R. Johnson (1989b) "Nucleotide sequence analysis of feline immunodeficiency virus: Genome organization and relationship to other lentivirus," *Proc. Natl. Acad. Sci. USA* 86:8088-8092.

Pattacini, L., Mize, G. J., Graham, J. B., Fluharty, T. R., Graham, T. M., Lingnau, K., Wizel, B., Perdiguero, B., Esteban, M., Pantaleo, G., Shen, M., Spies, G. A., McElrath, M. J., Lund, J. M., 2012. A novel HIV vaccine adjuvanted by IC31 induces robust and persistent humoral and cellular immunity. PloS one 7, e42163. doi:10.1371/journal.pone.0042163.

Pedersen, N. C., E. W. Ho, M. L. Brown, J. K. Yamamoto (1987) "Isolation of a T-lymphotropic virus from domestic cats with an immunodeficiency-like syndrome," *Science* 235:790-793.

Pitisuttithum P, Gilbert P, Gurwith M, Heyward W, Martin M, van Griensven F,5 Hu D, Tappero J W, Choopanya K, Bangkok Vaccine Evaluation Group. 2006. Randomized, double-blind, placebo-controlled efficacy trial of a bivalent recombinant glycoprotein 120 HIV-1 vaccine among injection drug users in Bangkok, Thailand. J. Infect. Dis. 194:1661-71.

Plotkin S A. 2008. Vaccines: correlates of vaccine-induced immunity. Clin. Infect. Dis. 47:401-09.

Posnett, D. N. et al. (1988) "A Novel Method for Producing Anti-peptide Antibodies," *J. Biol. Chem.* 263(4):1719-1725.

Rerks-Ngarm S, Pitisuttithum P, Nitayaphan S, Kaewkungwal J, Chiu J, Paris R, Premsri N, Namwat C, de Souza M, Adams E, Benenson M, Gurunathan S, Tartaglia J, McNeil J G, Francis D P, Stablein D, Birx D L, Chunsuttiwat S, Khamboonruang C, Thongcharoen P, Robb M L, Michael N L, Kunasol P, Kim J H, MOPH-TAVEG Investigators. 2009. Vaccination with ALVAC and AIDSVAX to prevent HIV-1 infection in Thailand. N. Engl. J. Med. 361:2209-20.

Richmond M, McKinnon L R, Kiazyk S A, Wachihi C, Kimani M, Kimani J, Plummer F A, Ball T B. 2011. Epitope mapping of HIV-specific CD8+ T cell responses by multiple immunological readouts reveals distinct specificities defined by function. J Virol. 85:1275-86.

Rigby, M. A., E. C. Holmes, M. Pistello, A. Mackay, A. J. Leigh-Brown, J. C. Neil (1993) "Evolution of structural proteins of feline immunodeficiency virus: molecular epidemiology and evidence of selection for change," *J. Gen. Virol.* 74:425-436.

Roff S R, Sanou M P, Rathore M H, Levy J A, Yamamoto J K. Conserved epitopes on HIV-1, FIV and SIV p24 proteins are recognized by HIV-1-infected subjects. *Hum Vac Immunother* (submitted, under revision) 2015.

Roff, S. R., Noon-Song, E. N., Yamamoto, J. K., 2014. The Significance of Interferon-gamma in HIV-1 Pathogenesis, Therapy, and Prophylaxis. Frontiers in immunology 4, 498. doi: 10.3389/fimmu.2013.00498.

Rolland M, Nickle D C, Mullins J I. 2007. HIV-1 Group M Conserved Elements Vaccine. PLoS Pathog. 3:e157. doi: 10.1371/journal.ppat.0030157.

Rowland-Jones S L, Dong T, Fowke K R, et al. Cytotoxic T cell responses to multiple conserved HIV epitopes in HIV-resistant prostitutes in Nairobi. J Clin Invest 1998; 102: 1758-65.

Rowland-Jones, S., J. Sutton, K. Ariyoshi, T. Dong, F. Gotch, S. McAdam, et al. (1995) "HIV-specific cytotoxic T-cells in HIV-exposed but uninfected Gambian women," *Nat. Med.* 1:59-64.

Salmon-Ceron D, Durier C, Desaint C. Cuzin L, Surenaud M, Hamouda N B, Leliévre J D, Bonnet B, Pialoux G, Poizot-Martin I, Aboulker J P, Levy Y, Launay O, ANRS VAC18 trial group. 2010. Immunogenicity and safety of an HIV-1 lipopeptide vaccine in healthy adults: a phase 2 placebo-controlled ANRS trial. AIDS 24:2211-23.

Sanou M P, De Groot A S, Murphy-Corb M, Levy J A, Yamamoto J K. 2012a. HIV-1 Vaccine Trials: Evolving Concepts and Designs. Open AIDS J. 6:246-260.

Sanou, M. P., De Groot, A. S., Murphey-Corb, M., Levy, J. A., Yamamoto, J. K., 2012b. HIV-1 Vaccine Trials: Evolving Concepts and Designs. The open AIDS journal 6, 274-288.

Sanou, M. P., Roff, S. R., Mennella, A., Sleasman, J. W., Rathore, M. H., Yamamoto, J. K., Levy, J. A., 2013. Evolutionarily conserved epitopes on human immunodeficiency virus type 1 (HIV-1) and feline immunodeficiency virus reverse transcriptases detected by HIV-1-infected subjects. Journal of virology 87, 10004-10015.doi: 10.1128/JVI.00359-13.

Santra S, Liao H X, Zhang R, et al. Mosaic vaccines elicit CD8+ T lymphocyte responses that confer enhanced immune coverage of diverse HIV strains in monkeys. Nat Med 2010; 16: 324-8.

Santra S, Muldoon M, Watson S, Buzby A, Balachandran H, Carlson K R, Mach L, Kong W P, McKee K, Yang Z Y, Rao S S, Mascola J R, Nabel G J, Korber B T, Letvin N L. 2012. Breadth of cellular and humoral immune responses elicited in rhesus monkeys by multi-valent mosaic and consensus immunogens. Virology 428:121-7.

Saunders K O, Rudicell R S, Nabel G J. 2012. The design and evaluation of HIV-1 vaccines. AIDS 26:1293-1302.

Smith S M. HIV CTL escape: at what cost? Retrovirology 2004; 1: 8.

Sodora, D. L., E. G. Shpaer, B. E. Kitchell, S. W. Dow, E. A. Hoover, J. I. Mullins (1994) "Identification of three feline immunodeficiency virus (FIV) env gene subtype and comparison of the FIV and human immunodeficiency virus type 1 evolutionary patterns," *J. Virol.* 68:2230-2238.

Soghoian D Z, Jessen H, Flanders M, Sierra-Davidson K, Cutler S, Pertel T, Ranasinghe S, Lindqvist M, Davis I, Lane K, Rychert J, Rosenberg E S, Piechocka-Trocha A, Brass A L, Brenchley J M, Walker B D, Streeck H. 2012. HIV-specific cytolytic CD4 T cell responses during acute HIV infection predict disease outcome. Sci. Transl. Med. 4:123ra25. doi:10.1126/scitranslmed.3003165.

Spina, C. A., Prince, H. E., Richman, D. D., 1997. Preferential replication of HIV-1 in the CD45RO memory cell subset of primary CD4 lymphocytes in vitro. The Journal of clinical investigation 99, 1774-1785.

Stamatatos L. 2012. HIV vaccine design: the neutralizing antibody conundrum. Curr. Opin. Immunol. 24:316-23.

Stevenson, M., Stanwick, T. L., Dempsey, M. P., Lamonica, C. A., 1990. HIV-1 replication is controlled at the level of T cell activation and proviral integration. The EMBO journal 9, 1551-1560.

Stranzl T, Larsen M V, Lundegaard C, Nielsen M. NetCTLpan: pan-specific MHC class I pathway epitope predictions. Immunogenetics 2010; 62: 357-68.

Talbott, R. L., E. E. Sparger, K. M. Lovelace, W. M. Fitch, N. C. Pedersen, P. A. Luciw, J. H. Elder (1989) "Nucleotide sequence and genomic organization of feline immunodeficiency virus," *Proc. Natl. Acad. Sci. USA* 86:5743-5747.

Tam, J. P. (1988) "Synthetic Peptide Vaccine Design: Synthesis and Properties of a High-Density Multiple Antigenic Peptide System," *Proc. Nat. Acad. Sci. USA* 85(15): 5409-5413.

Tanabe T, Yamamoto J K. Feline immunodeficiency virus lacks sensitivity to the antiviral activity of feline IFN-gamma. *J Interferon Cytokine Res* 2001; 21:1039-46.

Tang, J., Cormier, E., Gilmour, J., Price, M. A., Prentice, H. A., Song, W., Kamali, A., Karita, E., Lakhi, S., Sanders, E. J., Anzala, O., Amornkul, P. N., Allen, S., Hunter, E., Kaslow, R. A., Network, I. A. H. R., 2011. Human leukocyte antigen variants B*44 and B*57 are consistently favorable during two distinct phases of primary HIV-1 infection in sub-Saharan Africans with several viral subtypes. Journal of virology 85, 8894-8902. doi: 10.1128/JVI.00439-11.

Troyer R M, McNevin J, Liu Y, Zhang S C, Krizan R W, Abraha A, Tebit D M, Zhao H, Avila S, Lobritz M A, McElrath M J, Le Gall S, Mullins J I, Arts E J. 2009. Variable fitness impact of HIV-1 escape mutations to cytotoxic T lymphocyte (CTL) response. PLoS Pathog. 5:e1000365. doi:10.1371/journal.ppat.1000365.

Walker B D, Flexner C, Paradis T J, Fuller T C, Hirsch M S, Schooley R T, Moss B. 1988. HIV-1 reverse transcriptase is a target for cytotoxic T lymphocytes in infected individuals. Science 240:64-6.

Walther-Jallow L, Nilsson C, Soderlund J, ten Haaft P, Mäkitalo B, Biberfeld P, Böttiger P, Heeney J, Biberfeld G, Thorstensson R. 2001. Cross-protection against mucosal simian immunodeficiency virus (SIVsm) challenge in human immunodeficiency virus type 2-vaccinated cynomolgus monkeys. J. Gen. Virol. 82:1601-12.

Wang Y E, Li B, Carlson J M. Protective HLA class I alleles that restrict acute-phase CD8+ T-cell responses are associated with viral escape mutations located in highly conserved regions of human immunodeficiency virus type-1. J Virol 2009; 83: 1845-55.

Yamamoto J K, Pu R, Sato E, Hohdatsu T. Feline immunodeficiency virus pathogenesis and development of a dual-subtype feline-immunodeficiency-virus vaccine. AIDS 2007; 21: 547-63.

Yamamoto J K, Sanou M P, Abbott J R, Coleman J K. Feline immunodeficiency virus model for designing HIV/AIDS vaccines. Curr HIV Res 2010; 8:14-25.

Yamamoto, J. K., B. A. Tones, R. Pu (2002) "Development of the dual-subtype FIV vaccine," *AIDScience April* 2002, 2(8), website at aidscience.org/Articles/AIDScience020.asp/ Accessed 25 Dec. 2004.

Yamamoto, J. K., Barre-Sinoussi, F., Bolton, V., Pedersen, N. C., Gardner, M. B., 1986. Human alpha- and beta-interferon but not gamma-suppress the in vitro replication of LAV, HTLV-III, and ARV-2. Journal of interferon research 6, 143-152.

Yamamoto, J. K., E. Sparger, E. W. Ho, P. H. Andersen, T. P. O'Connor, C. P. Mandell, L. Lowenstine, N. C. Pedersen (1988b) "Pathogenesis of experimentally induced feline immunodeficiency virus infection in cats," *Am. J Vet. Res.* 49:1246-1258.

Yamamoto, J. K., N. C. Pedersen, E. W. Ho, T. Okuda, G. H. Theilen (1988a) "Feline immunodeficiency syndrome—a comparison between feline T-lymphotropic lentivirus and feline leukemia virus," Leukemia, December Supplement 2:204S-215S Yongqun H, Rappuoli R, De Groot A S, Chen R T. Emerging Vaccine Informatics. J Biomed Biotechnol 2010; 2010: 218590.

Yusim K, Kesmir C, Gaschen B, et al. Clustering patterns of cytotoxic T-lymphocyte epitopes in human immunodeficiency virus type 1 (HIV-1) proteins reveal imprints of immune evasion on HIV-1 global variation. J Virol 2002; 76:8757-68.

Zhang, X., Huang, X., Xia, W., Li, W., Zhang, T., Wu, H., Xu, X., Yan, H., 2013. HLA-B*44 is associated with a lower viral set point and slow CD4 decline in a cohort of Chinese homosexual men acutely infected with HIV-1. Clinical and vaccine immunology: CVI 20, 1048-1054. doi: 10.1128/CVI.00015-13.

Mwau M I, Cebere J, Sutton P, et al. A human immunodeficiency virus 1 (HIV-1) clade A vaccine in clinical trials: stimulation of HIV-specific T-cell responses by DNA and recombinant modified vaccinia virus Ankara (MVA) vaccines in humans. J Gen Virol 2004; 85: 911-9.

Cebere I, Dorrell L, McShane H, et al. Phase I clinical trial safety of DNA- and modified virus Ankara-vectored human immunodeficiency virus type 1 (HIV-1) vaccines administered alone and in a prime-boost regime to healthy HIV-1-uninfected volunteers. Vaccine 2006; 24: 417-25.

Jaoko W, Nakwagala F N, Anzala O, et al. Safety and immunogenicity of recombinant low-dosage HIV-1 A vaccine candidates vectored by plasmid pTHr DNA or modified vaccinia virus Ankara (MVA) in humans in East Africa. Vaccine 2008; 26: 2788-95.

Hanke T, McMichael A J, Dorrell L. Clinical experience with plasmid DNA- and modified vaccinia virus Ankara-vectored human immunodeficiency virus type 1 clade A vaccine focusing on T-cell induction. J Gen Virol 2007; 88: 1-12.

Goonetilleke N, Moore S, Dally L, et al. Induction of multifunctional human immunodeficiency virus type 1 (HIV-1)-specific T cells capable of proliferation in healthy subjects by using a prime-boost regimen of DNA- and modified vaccinia virus Ankara-vectored vaccines expressing HIV-1 Gag coupled to CD8+ T-cell epitopes. J Virol 2006; 80: 4717-28.

Gorse G J, Baden L R, Wecker M, et al. Safety and immunogenicity of cytotoxic T-lymphocyte poly-epitope, DNA plasmid (EP HIV-1090) vaccine in healthy, human immunodeficiency virus type 1 (HIV-1)-uninfected adults. Vaccine 2008; 26: 215-23.

Spearman P, Kalams S, Elizaga M, Metch B, Chiu Y L, et al. Safety and immunogenicity of a CTL multiepitope peptide vaccine for HIV with or without GM-CSF in a phase I trial. Vaccine 2009; 27: 243-9.

Salmon-Ceron D, Durier C, Desaint C. et al. Immunogenicity and safety of an HIV-1 lipopeptide vaccine in healthy adults: a phase 2 placebo-controlled ANRS trial. AIDS 2010; 24: 2211-23.

SEQUENCE LISTING

```
<160> NUMBER OF SEQ ID NOS: 591

<210> SEQ ID NO 1
<211> LENGTH: 9
<212> TYPE: PRT
<213> ORGANISM: Human immunodeficiency virus

<400> SEQUENCE: 1

Leu Pro Pro Ile Val Ala Lys Glu Ile
1               5

<210> SEQ ID NO 2
<211> LENGTH: 9
<212> TYPE: PRT
<213> ORGANISM: Human immunodeficiency virus

<400> SEQUENCE: 2

Thr His Leu Glu Gly Lys Ile Ile Leu
1               5

<210> SEQ ID NO 3
<211> LENGTH: 10
```

-continued

<212> TYPE: PRT
<213> ORGANISM: Human immunodeficiency virus

<400> SEQUENCE: 3

Ser Thr Thr Val Lys Ala Ala Cys Trp Trp
1 5 10

<210> SEQ ID NO 4
<211> LENGTH: 9
<212> TYPE: PRT
<213> ORGANISM: Human immunodeficiency virus

<400> SEQUENCE: 4

Ile Gln Gln Glu Phe Gly Ile Pro Tyr
1 5

<210> SEQ ID NO 5
<211> LENGTH: 8
<212> TYPE: PRT
<213> ORGANISM: Human immunodeficiency virus

<400> SEQUENCE: 5

Val Arg Asp Gln Ala Glu His Leu
1 5

<210> SEQ ID NO 6
<211> LENGTH: 9
<212> TYPE: PRT
<213> ORGANISM: Human immunodeficiency virus

<400> SEQUENCE: 6

Lys Thr Ala Val Gln Met Ala Val Phe
1 5

<210> SEQ ID NO 7
<211> LENGTH: 10
<212> TYPE: PRT
<213> ORGANISM: Human immunodeficiency virus

<400> SEQUENCE: 7

Ala Val Phe Ile His Asn Phe Lys Arg Lys
1 5 10

<210> SEQ ID NO 8
<211> LENGTH: 10
<212> TYPE: PRT
<213> ORGANISM: Human immunodeficiency virus

<400> SEQUENCE: 8

Phe Lys Arg Lys Gly Gly Ile Gly Gly Tyr
1 5 10

<210> SEQ ID NO 9
<211> LENGTH: 9
<212> TYPE: PRT
<213> ORGANISM: Human immunodeficiency virus

<400> SEQUENCE: 9

Lys Arg Lys Gly Gly Ile Gly Gly Tyr
1 5

<210> SEQ ID NO 10
<211> LENGTH: 9
<212> TYPE: PRT
<213> ORGANISM: Human immunodeficiency virus

```
<400> SEQUENCE: 10

Ile Ile Ala Thr Asp Ile Gln Thr Lys
1               5

<210> SEQ ID NO 11
<211> LENGTH: 9
<212> TYPE: PRT
<213> ORGANISM: Human immunodeficiency virus

<400> SEQUENCE: 11

Lys Ile Gln Asn Phe Arg Val Tyr Tyr
1               5

<210> SEQ ID NO 12
<211> LENGTH: 9
<212> TYPE: PRT
<213> ORGANISM: Human immunodeficiency virus

<400> SEQUENCE: 12

Val Pro Arg Arg Lys Ala Lys Ile Ile
1               5

<210> SEQ ID NO 13
<211> LENGTH: 9
<212> TYPE: PRT
<213> ORGANISM: Human immunodeficiency virus

<400> SEQUENCE: 13

Arg Lys Ala Lys Ile Ile Arg Asp Tyr
1               5

<210> SEQ ID NO 14
<211> LENGTH: 9
<212> TYPE: PRT
<213> ORGANISM: Human immunodeficiency virus

<400> SEQUENCE: 14

Thr His Leu Glu Gly Lys Ile Ile Ile
1               5

<210> SEQ ID NO 15
<211> LENGTH: 9
<212> TYPE: PRT
<213> ORGANISM: Human immunodeficiency virus

<400> SEQUENCE: 15

Thr His Phe Asn Gly Lys Ile Ile Ile
1               5

<210> SEQ ID NO 16
<211> LENGTH: 9
<212> TYPE: PRT
<213> ORGANISM: Human immunodeficiency virus

<400> SEQUENCE: 16

Met Ala Val Phe Ile His Asn Phe Lys
1               5

<210> SEQ ID NO 17
<211> LENGTH: 9
<212> TYPE: PRT
<213> ORGANISM: Human immunodeficiency virus

<400> SEQUENCE: 17
```

```
Met Ala Val His Cys Met Asn Phe Lys
1               5

<210> SEQ ID NO 18
<211> LENGTH: 9
<212> TYPE: PRT
<213> ORGANISM: Human immunodeficiency virus

<400> SEQUENCE: 18

Leu Ala Leu Tyr Cys Leu Asn Phe Lys
1               5

<210> SEQ ID NO 19
<211> LENGTH: 9
<212> TYPE: PRT
<213> ORGANISM: Human immunodeficiency virus

<400> SEQUENCE: 19

Val Pro Arg Arg His Ile Arg Arg Val
1               5

<210> SEQ ID NO 20
<211> LENGTH: 9
<212> TYPE: PRT
<213> ORGANISM: Human immunodeficiency virus

<400> SEQUENCE: 20

Ile Leu Ala Thr Asp Ile Gln Thr Thr
1               5

<210> SEQ ID NO 21
<211> LENGTH: 9
<212> TYPE: PRT
<213> ORGANISM: Human immunodeficiency virus

<400> SEQUENCE: 21

Gln Glu Ser Leu Arg Ile Gln Asp Tyr
1               5

<210> SEQ ID NO 22
<211> LENGTH: 9
<212> TYPE: PRT
<213> ORGANISM: Human immunodeficiency virus

<400> SEQUENCE: 22

Ile Val Ala Glu Glu Ile Lys Arg Lys
1               5

<210> SEQ ID NO 23
<211> LENGTH: 35
<212> TYPE: PRT
<213> ORGANISM: Human immunodeficiency virus

<400> SEQUENCE: 23

Asn Pro Tyr Asn Thr Pro Val Phe Ala Ile Lys Lys Lys Asp Ser Thr
1               5                   10                  15

Lys Trp Arg Lys Leu Val Asp Phe Arg Glu Leu Asn Lys Arg Thr Gln
            20                  25                  30

Asp Phe Trp
            35

<210> SEQ ID NO 24
<211> LENGTH: 34
```

```
<212> TYPE: PRT
<213> ORGANISM: Feline immunodeficiency virus

<400> SEQUENCE: 24

Asn Pro Trp Asn Thr Pro Val Phe Ala Ile Lys Lys Ser Gly Lys
1               5                   10                  15

Trp Arg Met Leu Ile Asp Phe Arg Val Leu Asn Lys Leu Thr Asp Lys
            20                  25                  30

Gly Ala

<210> SEQ ID NO 25
<211> LENGTH: 31
<212> TYPE: PRT
<213> ORGANISM: Human immunodeficiency virus

<400> SEQUENCE: 25

Phe Arg Lys Tyr Thr Ala Phe Thr Ile Pro Ser Ile Asn Asn Glu Thr
1               5                   10                  15

Pro Gly Ile Arg Tyr Gln Tyr Asn Val Leu Pro Gln Gly Trp Lys
            20                  25                  30

<210> SEQ ID NO 26
<211> LENGTH: 29
<212> TYPE: PRT
<213> ORGANISM: Feline immunodeficiency virus

<400> SEQUENCE: 26

Pro Asp Tyr Ala Pro Tyr Thr Ala Phe Thr Leu Pro Arg Lys Asn Asn
1               5                   10                  15

Ala Gly Pro Gly Arg Arg Tyr Val Trp Cys Ser Leu Pro
            20                  25

<210> SEQ ID NO 27
<211> LENGTH: 34
<212> TYPE: PRT
<213> ORGANISM: Human immunodeficiency virus

<400> SEQUENCE: 27

Asn Asp Ile Gln Lys Leu Val Gly Lys Leu Asn Trp Ala Ser Gln Ile
1               5                   10                  15

Tyr Pro Gly Ile Lys Val Arg Gln Leu Cys Lys Leu Leu Arg Gly Thr
            20                  25                  30

Lys Ala

<210> SEQ ID NO 28
<211> LENGTH: 37
<212> TYPE: PRT
<213> ORGANISM: Feline immunodeficiency virus

<400> SEQUENCE: 28

Ile Gln Gln Lys Gln Leu Glu Ile Pro Glu Arg Pro Thr Leu Asn Glu
1               5                   10                  15

Leu Gln Lys Leu Val Gly Lys Ile Asn Trp Ala Ser Gln Thr Ile Pro
            20                  25                  30

Asp Leu Ser Ile Lys
        35

<210> SEQ ID NO 29
<211> LENGTH: 36
<212> TYPE: PRT
<213> ORGANISM: Human immunodeficiency virus
```

-continued

<400> SEQUENCE: 29

Arg Glu Ile Leu Lys Glu Pro Val His Gly Val Tyr Tyr Asp Pro Ser
1               5                   10                  15

Lys Asp Leu Ile Ala Glu Ile Gln Lys Gln Gly Gln Gly Gln Trp Thr
            20                  25                  30

Tyr Gln Ile Tyr
        35

<210> SEQ ID NO 30
<211> LENGTH: 35
<212> TYPE: PRT
<213> ORGANISM: Feline immunodeficiency virus

<400> SEQUENCE: 30

Thr Glu Ala Lys Lys Glu Val Gln Lys Ala Lys Glu Ala Ile Glu Thr
1               5                   10                  15

Gln Ala Gln Leu Lys Tyr Tyr Asp Pro Ser Arg Glu Leu Tyr Ala Lys
            20                  25                  30

Leu Ser Leu
        35

<210> SEQ ID NO 31
<211> LENGTH: 35
<212> TYPE: PRT
<213> ORGANISM: Simian immunodeficiency virus

<400> SEQUENCE: 31

Asn Pro Tyr Asn Thr Pro Thr Phe Ala Ile Lys Lys Lys Asp Lys Asn
1               5                   10                  15

Lys Trp Arg Met Leu Ile Asp Phe Arg Glu Leu Asn Arg Val Thr Gln
            20                  25                  30

Asp Phe Thr
        35

<210> SEQ ID NO 32
<211> LENGTH: 31
<212> TYPE: PRT
<213> ORGANISM: Simian immunodeficiency virus

<400> SEQUENCE: 32

Phe Arg Gln Tyr Thr Ala Phe Thr Leu Pro Ser Val Asn Asn Ala Glu
1               5                   10                  15

Pro Gly Lys Arg Tyr Ile Tyr Lys Val Leu Pro Gln Gly Trp Lys
            20                  25                  30

<210> SEQ ID NO 33
<211> LENGTH: 34
<212> TYPE: PRT
<213> ORGANISM: Simian immunodeficiency virus

<400> SEQUENCE: 33

Asn Asp Ile Gln Lys Leu Val Gly Val Leu Asn Trp Ala Ala Gln Ile
1               5                   10                  15

Tyr Pro Gly Ile Lys Thr Lys His Leu Cys Arg Leu Ile Arg Gly Lys
            20                  25                  30

Met Thr

<210> SEQ ID NO 34
<211> LENGTH: 36

-continued

```
<212> TYPE: PRT
<213> ORGANISM: Simian immunodeficiency virus

<400> SEQUENCE: 34

Lys Ile Ile Leu Ser Gln Glu Gln Glu Gly Cys Tyr Tyr Gln Glu Gly
1               5                   10                  15

Lys Pro Leu Glu Ala Thr Val Ile Lys Ser Gln Asp Asn Gln Trp Ser
            20                  25                  30

Tyr Lys Ile His
        35

<210> SEQ ID NO 35
<211> LENGTH: 23
<212> TYPE: PRT
<213> ORGANISM: Feline immunodeficiency virus

<400> SEQUENCE: 35

Gln Glu Gln Gln Ala Glu Ala Arg Phe Ala Pro Ala Arg Met Gln Cys
1               5                   10                  15

Arg Ala Trp Tyr Leu Glu Ala
            20

<210> SEQ ID NO 36
<211> LENGTH: 24
<212> TYPE: PRT
<213> ORGANISM: Simian immunodeficiency virus

<400> SEQUENCE: 36

Glu Gln Ile Gln Trp Met Tyr Arg Gln Gln Asn Pro Ile Pro Val Gly
1               5                   10                  15

Asn Ile Tyr Arg Arg Trp Ile Gln
            20

<210> SEQ ID NO 37
<211> LENGTH: 22
<212> TYPE: PRT
<213> ORGANISM: Feline immunodeficiency virus

<400> SEQUENCE: 37

Asp Gln Glu Gln Asn Thr Ala Glu Val Lys Leu Tyr Leu Lys Gln Ser
1               5                   10                  15

Leu Ser Ile Ala Asn Ala
            20

<210> SEQ ID NO 38
<211> LENGTH: 23
<212> TYPE: PRT
<213> ORGANISM: Simian immunodeficiency virus

<400> SEQUENCE: 38

Arg Ala Glu Gln Thr Asp Ala Ala Val Lys Asn Trp Met Thr Gln Thr
1               5                   10                  15

Leu Leu Ile Gln Asn Ala Asn
            20

<210> SEQ ID NO 39
<211> LENGTH: 23
<212> TYPE: PRT
<213> ORGANISM: Human immunodeficiency virus

<400> SEQUENCE: 39

Glu Gln Ile Gly Trp Met Thr Asn Asn Pro Pro Ile Pro Val Gly Glu
```

```
            1               5                  10                 15
Ile Tyr Lys Arg Trp Ile Ile
                 20

<210> SEQ ID NO 40
<211> LENGTH: 23
<212> TYPE: PRT
<213> ORGANISM: Human immunodeficiency virus

<400> SEQUENCE: 40

Arg Ala Glu Gln Ala Ser Gln Glu Val Lys Asn Trp Met Thr Glu Thr
1               5                   10                  15

Leu Leu Val Gln Asn Ala Asn
                 20

<210> SEQ ID NO 41
<211> LENGTH: 1377
<212> TYPE: DNA
<213> ORGANISM: Artificial sequence
<220> FEATURE:
<223> OTHER INFORMATION: chimera polynucleotide comprising sequences of
      HIV and FIV (Petaluma)

<400> SEQUENCE: 41
atggggaatg acaggggcg agattggaaa atggccatta agagatgtag taatgttgct        60
gtaggagtag gggggaagag taaaaaattt ggagaaggga atttcagatg gccattaga      120 atggctaatg tatctacagg acgagaacct ggtgatatac cagagacttt agatcaacta      180
tggttggtta tttgcgattt acaagaaaga agagaaaaat ttggatctag caaagaaatt      240
gatatggcaa ttgtgacatt gaaagtcttt gcggtagcag acttttttaaa tatgacggtg    300 tctactgctg ctgcagctga aaatatgtat tctctaatgg gattagacac taggccatct      360
atgaaagaag caggtggaaa agaggaaggc cctccacagg catatcctgt agtgcagaac      420
ctccaggggc aaatggtaca tcagcccata tcacctagaa ctttaaatgc atgggtaaag      480
gtagtagaag agaaggcttt cagcccagaa gtaatacccat gtttacagc attatcagaa     540 ggagccaccc cacaagattt aaacaccatg ctaaacacag tgggggggaca tcaagcagcc     600 atgcaaatgt taaaagagac catcaatgag gaagctgcag aatgggatag attgcatcca      660
gtgcatgcag ggcctattgc accagaccag atgagagaac caaggggaag tgacatagca     720
ggaattacta gtacccttca ggaacaaata ggatggatga caaataatcc acctatccca      780
gtaggagaaa tctataaaag atggataatc ctgggattaa ataaaatagt aagaatgtat      840
agccctacca gcattctgga cataagacaa ggaccaaagg aacccttttag agactatgta    900 gaccggttct ataaaactct aagagccgag caagcttcac aggatgtaaa aaattggatg      960
acagaaacct tgttggtcca aaatgcaaac ccagattgta gactattttt aaaagcattg    1020
ggaccagcag ctacactaga agaaatgatg acagcatgtc agggagtggg gggacccgga     1080
cataaagcaa gagttttggc agaagctctt acaaaagttc aagtagtgca atcaaaagga    1140
tcaggaccag tgtgttttaa ttgtaaaaaa ccaggacatc tagcaagaca atgtagagaa     1200
gtgaaaaaat gtaataaatg tggaaaacct ggtcatctag ctgccaaatg ttggcaagga    1260
aatagaaaga attcgggaaa ctggaaggcg gggcgagctg cagccccagt gaatcaagtg    1320
cagcaagcag taatgccatc tgcacctcca atggaggaga aactattgga tttataa      1377

<210> SEQ ID NO 42
<211> LENGTH: 1374
```

<212> TYPE: DNA
<213> ORGANISM: Artificial sequence
<220> FEATURE:
<223> OTHER INFORMATION: chimera polynucleotide comprising sequences of
      HIV and FIV (Shizouka)

<400> SEQUENCE: 42

| | | | | | |
|---|---|---|---|---|---|
| atggggaatg | gacaggggcg | agattggaaa | acggccataa | agagatgtag | taatgttgct | 60 |
| gtaggtacgg | gacaacgaag | taagaagttc | ggggaaggaa | attttagatg | ggccttgaga | 120 |
| atggccaatg | taactacagg | acgtgaacct | ggtgatatac | cagagacctt | agatcaactg | 180 |
| agagtactta | tctgtgattt | acaggaaaga | agggagaagt | ttggatctag | caaagaactt | 240 |
| gatatggcaa | tcctcactct | aaaagttttt | gcagtagcag | gagtcttaaa | tatgtctgta | 300 |
| tctactgcta | ctgccgctga | aaatatgtat | gctcagatgg | gattagatac | tagaccatct | 360 |
| ttaaaggagg | caggaggaaa | ggtagaggag | cctccacagg | catatcctgt | agtgcagaac | 420 |
| ctccagggc | aaatggtaca | tcagcccata | tcacctagaa | ctttaaatgc | atgggtaaag | 480 |
| gtagtagaag | agaaggcttt | cagcccagaa | gtaataccca | tgtttacagc | attatcagaa | 540 |
| ggagccaccc | cacaagattt | aaacaccatg | ctaaacacag | tggggggaca | tcaagcagcc | 600 |
| atgcaaatgt | taaaagagac | catcaatgag | gaagctgcga | atgggataga | attgcatcca | 660 |
| gtgcatgcag | ggcctattgc | accagaccag | atgagagaac | caaggggaag | tgacatagca | 720 |
| ggaattacta | gtacccttca | ggaacaaata | ggatggatga | caataatcc | acctatccca | 780 |
| gtaggagaaa | tctataaaag | atggataatc | ctgggattaa | ataaaatagt | aagaatgtat | 840 |
| agccctacca | gcattctgga | cataagacaa | ggaccaaagg | aacccttag | agactatgta | 900 |
| gaccggttct | ataaaactct | aagagccgag | caagcttcac | aggatgtaaa | aaattggatg | 960 |
| acagaaacct | gttggtcca | aaatgcaaac | ccagattgta | agactatttt | aaaagcattg | 1020 |
| ggaccagcag | ctacactaga | agaaatgatg | acagcatgtc | agggagtggg | gggacccgga | 1080 |
| cataaagcaa | gagttttggc | agaagctctt | acaaaagttc | aaacagttca | agcaaaagga | 1140 |
| ccaaaaccag | tatgttttaa | ttgtaaaaaa | ccagggcatc | tagctagaca | atgtagagat | 1200 |
| gtgaaaagat | gtaataaatg | tggaaagcct | ggccatttgg | ctgccaaatg | ttggcaagga | 1260 |
| agcagaaatg | cttcgggaaa | cgggaagatg | gggcgagctg | cagccccagt | aaaccaagtg | 1320 |
| cagcaagcag | tgccatctgc | tcctccagtg | aagagaagt | tgttagattt | ataa | 1374 |

<210> SEQ ID NO 43
<211> LENGTH: 458
<212> TYPE: PRT
<213> ORGANISM: Artificial sequence
<220> FEATURE:
<223> OTHER INFORMATION: chimera polypeptide comprising sequences of HIV
      and FIV (Petaluma)

<400> SEQUENCE: 43

Met Gly Asn Gly Gln Gly Arg Asp Trp Lys Met Ala Ile Lys Arg Cys
1               5                   10                  15

Ser Asn Val Ala Val Gly Val Gly Gly Lys Ser Lys Lys Phe Gly Glu
            20                  25                  30

Gly Asn Phe Arg Trp Ala Ile Arg Met Ala Asn Val Ser Thr Gly Arg
        35                  40                  45

Glu Pro Gly Asp Ile Pro Glu Thr Leu Asp Gln Leu Trp Leu Val Ile
    50                  55                  60

Cys Asp Leu Gln Glu Arg Arg Glu Lys Phe Gly Ser Ser Lys Glu Ile
65                  70                  75                  80

```
Asp Met Ala Ile Val Thr Leu Lys Val Phe Ala Val Ala Gly Leu Leu
                85                  90                  95
Asn Met Thr Val Ser Thr Ala Ala Ala Glu Asn Met Tyr Ser Leu
            100                 105                 110
Met Gly Leu Asp Thr Arg Pro Ser Met Lys Glu Ala Gly Gly Lys Glu
        115                 120                 125
Glu Gly Pro Pro Gln Ala Tyr Pro Val Gln Asn Leu Gln Gly Gln
    130                 135                 140
Met Val His Gln Pro Ile Ser Pro Arg Thr Leu Asn Ala Trp Val Lys
145                 150                 155                 160
Val Val Glu Glu Lys Ala Phe Ser Pro Glu Val Ile Pro Met Phe Thr
                165                 170                 175
Ala Leu Ser Glu Gly Ala Thr Pro Gln Asp Leu Asn Thr Met Leu Asn
            180                 185                 190
Thr Val Gly Gly His Gln Ala Ala Met Gln Met Leu Lys Glu Thr Ile
        195                 200                 205
Asn Glu Glu Ala Ala Glu Trp Asp Arg Leu His Pro Val His Ala Gly
    210                 215                 220
Pro Ile Ala Pro Asp Gln Met Arg Glu Pro Arg Gly Ser Asp Ile Ala
225                 230                 235                 240
Gly Ile Thr Ser Thr Leu Gln Glu Gln Ile Gly Trp Met Thr Asn Asn
                245                 250                 255
Pro Pro Ile Pro Val Gly Glu Ile Tyr Lys Arg Trp Ile Ile Leu Gly
            260                 265                 270
Leu Asn Lys Ile Val Arg Met Tyr Ser Pro Thr Ser Ile Leu Asp Ile
        275                 280                 285
Arg Gln Gly Pro Lys Glu Pro Phe Arg Asp Tyr Val Asp Arg Phe Tyr
    290                 295                 300
Lys Thr Leu Arg Ala Glu Gln Ala Ser Gln Asp Val Lys Asn Trp Met
305                 310                 315                 320
Thr Glu Thr Leu Leu Val Gln Asn Ala Asn Pro Asp Cys Lys Thr Ile
                325                 330                 335
Leu Lys Ala Leu Gly Pro Ala Ala Thr Leu Glu Glu Met Met Thr Ala
            340                 345                 350
Cys Gln Gly Val Gly Gly Pro Gly His Lys Ala Arg Val Leu Ala Glu
        355                 360                 365
Ala Leu Thr Lys Val Gln Val Val Gln Ser Lys Gly Ser Gly Pro Val
    370                 375                 380
Cys Phe Asn Cys Lys Lys Pro Gly His Leu Ala Arg Gln Cys Arg Glu
385                 390                 395                 400
Val Lys Lys Cys Asn Lys Cys Gly Lys Pro Gly His Leu Ala Ala Lys
                405                 410                 415
Cys Trp Gln Gly Asn Arg Lys Asn Ser Gly Asn Trp Lys Ala Gly Arg
            420                 425                 430
Ala Ala Ala Pro Val Asn Gln Val Gln Gln Ala Val Met Pro Ser Ala
        435                 440                 445
Pro Pro Met Glu Glu Lys Leu Leu Asp Leu
    450                 455

<210> SEQ ID NO 44
<211> LENGTH: 457
<212> TYPE: PRT
<213> ORGANISM: Artificial sequence
<220> FEATURE:
```

<223> OTHER INFORMATION: chimera polypeptide comprising sequences of HIV and FIV (Shizouka)

<400> SEQUENCE: 44

```
Met Gly Asn Gly Gln Gly Arg Asp Trp Lys Thr Ala Ile Lys Arg Cys
1               5                   10                  15

Ser Asn Val Ala Val Gly Thr Gly Gln Arg Ser Lys Lys Phe Gly Glu
            20                  25                  30

Gly Asn Phe Arg Trp Ala Leu Arg Met Ala Asn Val Thr Thr Gly Arg
        35                  40                  45

Glu Pro Gly Asp Ile Pro Glu Thr Leu Asp Gln Leu Arg Val Leu Ile
    50                  55                  60

Cys Asp Leu Gln Glu Arg Arg Glu Lys Phe Gly Ser Ser Lys Glu Leu
65                  70                  75                  80

Asp Met Ala Ile Leu Thr Leu Lys Val Phe Ala Val Ala Gly Val Leu
                85                  90                  95

Asn Met Ser Val Ser Thr Ala Thr Ala Ala Glu Asn Met Tyr Ala Gln
            100                 105                 110

Met Gly Leu Asp Thr Arg Pro Ser Leu Lys Glu Ala Gly Gly Lys Val
        115                 120                 125

Glu Glu Pro Pro Gln Ala Tyr Pro Val Val Gln Asn Leu Gln Gly Gln
    130                 135                 140

Met Val His Gln Pro Ile Ser Pro Arg Thr Leu Asn Ala Trp Val Lys
145                 150                 155                 160

Val Val Glu Glu Lys Ala Phe Ser Pro Glu Val Ile Pro Met Phe Thr
                165                 170                 175

Ala Leu Ser Glu Gly Ala Thr Pro Gln Asp Leu Asn Thr Met Leu Asn
            180                 185                 190

Thr Val Gly Gly His Gln Ala Ala Met Gln Met Leu Lys Glu Thr Ile
        195                 200                 205

Asn Glu Glu Ala Ala Glu Trp Asp Arg Leu His Pro Val His Ala Gly
    210                 215                 220

Pro Ile Ala Pro Asp Gln Met Arg Glu Pro Arg Gly Ser Asp Ile Ala
225                 230                 235                 240

Gly Ile Thr Ser Thr Leu Gln Glu Gln Ile Gly Trp Met Thr Asn Asn
                245                 250                 255

Pro Pro Ile Pro Val Gly Glu Ile Tyr Lys Arg Trp Ile Ile Leu Gly
            260                 265                 270

Leu Asn Lys Ile Val Arg Met Tyr Ser Pro Thr Ser Ile Leu Asp Ile
        275                 280                 285

Arg Gln Gly Pro Lys Glu Pro Phe Arg Asp Tyr Val Asp Arg Phe Tyr
    290                 295                 300

Lys Thr Leu Arg Ala Glu Gln Ala Ser Gln Asp Val Lys Asn Trp Met
305                 310                 315                 320

Thr Glu Thr Leu Leu Val Gln Asn Ala Asn Pro Asp Cys Lys Thr Ile
                325                 330                 335

Leu Lys Ala Leu Gly Pro Ala Ala Thr Leu Glu Glu Met Met Thr Ala
            340                 345                 350

Cys Gln Gly Val Gly Gly Pro Gly His Lys Ala Arg Val Leu Ala Glu
        355                 360                 365

Ala Leu Thr Lys Val Gln Thr Val Gln Ala Lys Gly Pro Lys Pro Val
    370                 375                 380

Cys Phe Asn Cys Lys Lys Pro Gly His Leu Ala Arg Gln Cys Arg Asp
385                 390                 395                 400
```

```
Val Lys Arg Cys Asn Lys Cys Lys Pro Gly His Leu Ala Ala Lys
            405                 410                 415

Cys Trp Gln Gly Ser Arg Asn Ala Ser Gly Asn Gly Lys Met Gly Arg
        420                 425                 430

Ala Ala Ala Pro Val Asn Gln Val Gln Gln Ala Val Pro Ser Ala Pro
            435                 440                 445

Pro Val Glu Lys Leu Leu Asp Leu
    450                 455

<210> SEQ ID NO 45
<211> LENGTH: 441
<212> TYPE: PRT
<213> ORGANISM: Human immunodeficiency virus

<400> SEQUENCE: 45

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Glu Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
```

-continued

```
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Thr Arg Gly Ala His Thr Asn Asp Val Lys Gln Leu
        355                 360                 365

Thr Glu Ala Val Gln Lys Ile Thr Thr Glu Ser Ile Val Ile Trp Gly
    370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
            420                 425                 430

Pro Ile Val Gly Ala Glu Thr Phe Tyr
        435                 440

<210> SEQ ID NO 46
<211> LENGTH: 445
<212> TYPE: PRT
<213> ORGANISM: Feline immunodeficiency virus

<400> SEQUENCE: 46

Ala Gln Ile Ser Glu Lys Ile Pro Ile Val Lys Val Arg Met Lys Asp
1               5                   10                  15

Pro Thr Gln Gly Pro Gln Val Lys Gln Trp Pro Leu Ser Asn Glu Lys
            20                  25                  30

Ile Glu Ala Leu Thr Asp Ile Val Glu Arg Leu Glu Leu Glu Gly Lys
        35                  40                  45

Val Lys Arg Ala Asp Pro Asn Asn Pro Trp Asn Thr Pro Val Phe Ala
    50                  55                  60

Ile Lys Lys Lys Ser Gly Lys Trp Arg Met Leu Ile Asp Phe Arg Val
65                  70                  75                  80

Leu Asn Lys Leu Thr Asp Lys Gly Ala Glu Val Gln Leu Gly Leu Pro
                85                  90                  95

His Pro Ala Gly Leu Lys Met Arg Lys Gln Val Thr Val Leu Asp Ile
            100                 105                 110

Gly Asp Ala Tyr Phe Thr Ile Pro Leu Asp Pro Asp Tyr Ala Pro Tyr
        115                 120                 125

Thr Ala Phe Thr Leu Pro Arg Lys Asn Asn Ala Gly Pro Gly Arg Arg
    130                 135                 140

Tyr Val Trp Cys Ser Leu Pro Gln Gly Trp Val Leu Ser Pro Leu Ile
145                 150                 155                 160

Tyr Gln Ser Thr Leu Asp Asn Ile Leu Gln Pro Phe Ile Arg Gln Asn
                165                 170                 175

Pro Glu Leu Asp Ile Tyr Gln Tyr Met Asp Asp Ile Tyr Ile Gly Ser
            180                 185                 190

Asp Leu Asn Lys Lys Glu His Lys Gln Lys Val Glu Glu Leu Arg Lys
        195                 200                 205

Leu Leu Leu Trp Trp Gly Phe Glu Thr Pro Glu Asp Lys Leu Gln Glu
    210                 215                 220

Glu Pro Pro Tyr Lys Trp Met Gly Tyr Glu Leu His Pro Leu Thr Trp
225                 230                 235                 240
```

```
Ser Ile Gln Gln Lys Gln Leu Glu Ile Pro Glu Arg Pro Thr Leu Asn
                245                 250                 255

Glu Leu Gln Lys Leu Val Gly Lys Ile Asn Trp Ala Ser Gln Thr Ile
            260                 265                 270

Pro Asp Leu Ser Ile Lys Glu Leu Thr Thr Met Met Arg Gly Asp Gln
        275                 280                 285

Arg Leu Asp Ser Ile Arg Glu Trp Thr Thr Glu Ala Lys Lys Glu Val
    290                 295                 300

Gln Lys Ala Lys Glu Ala Ile Glu Thr Gln Ala Gln Leu Lys Tyr Tyr
305                 310                 315                 320

Asp Pro Ser Arg Glu Leu Tyr Ala Lys Leu Ser Leu Val Gly Pro His
                325                 330                 335

Gln Ile Cys Tyr Gln Val Tyr His Lys Asn Pro Glu His Val Leu Trp
            340                 345                 350

Tyr Gly Lys Met Asn Arg Gln Lys Lys Lys Ala Glu Asn Thr Cys Asp
        355                 360                 365

Ile Ala Leu Arg Ala Cys Tyr Lys Ile Arg Glu Glu Ser Ile Ile Arg
    370                 375                 380

Ile Gly Lys Glu Pro Ile Tyr Glu Ile Pro Ala Ser Arg Glu Ala Trp
385                 390                 395                 400

Glu Ser Asn Leu Ile Arg Ser Pro Tyr Leu Lys Ala Pro Pro Pro Glu
                405                 410                 415

Val Glu Phe Ile His Ala Ala Leu Asn Ile Lys Arg Ala Leu Ser Met
            420                 425                 430

Ile Gln Asp Thr Pro Ile Leu Gly Ala Glu Thr Trp Tyr
        435                 440                 445

<210> SEQ ID NO 47
<211> LENGTH: 439
<212> TYPE: PRT
<213> ORGANISM: Simian immunodeficiency virus

<400> SEQUENCE: 47

Pro Ile Ala Lys Val Glu Pro Val Lys Val Thr Leu Lys Pro Gly Lys
1               5                   10                  15

Val Gly Pro Lys Leu Lys Gln Trp Pro Leu Ser Lys Glu Lys Ile Val
            20                  25                  30

Ala Leu Arg Glu Ile Cys Glu Lys Met Glu Lys Asp Gly Gln Leu Glu
        35                  40                  45

Glu Ala Pro Pro Thr Asn Pro Tyr Asn Thr Pro Thr Phe Ala Ile Lys
    50                  55                  60

Lys Lys Asp Lys Asn Lys Trp Arg Met Leu Ile Asp Phe Arg Glu Leu
65                  70                  75                  80

Asn Arg Val Thr Gln Asp Phe Thr Glu Val Gln Leu Gly Ile Pro His
                85                  90                  95

Pro Ala Gly Leu Ala Lys Arg Lys Arg Ile Thr Val Leu Asp Ile Gly
            100                 105                 110

Asp Ala Tyr Phe Ser Ile Pro Leu Asp Glu Glu Phe Arg Gln Tyr Thr
        115                 120                 125

Ala Phe Thr Leu Pro Ser Val Asn Asn Ala Glu Pro Gly Lys Arg Tyr
    130                 135                 140

Ile Tyr Lys Val Leu Pro Gln Gly Trp Lys Gly Ser Pro Ala Ile Phe
145                 150                 155                 160

Gln Tyr Thr Met Arg His Val Leu Glu Pro Phe Arg Lys Ala Asn Pro
                165                 170                 175
```

```
Asp Val Thr Leu Val Gln Tyr Met Asp Asp Ile Leu Ile Ala Ser Asp
            180                 185                 190

Arg Thr Asp Leu Glu His Asp Arg Val Val Leu Gln Leu Lys Glu Leu
            195                 200                 205

Leu Asn Ser Ile Gly Phe Ser Thr Pro Glu Lys Phe Gln Lys Asp
        210                 215                 220

Pro Pro Phe Gln Trp Met Gly Tyr Glu Leu Trp Pro Thr Lys Trp Lys
225                 230                 235                 240

Leu Gln Lys Ile Glu Leu Pro Gln Arg Glu Thr Trp Thr Val Asn Asp
            245                 250                 255

Ile Gln Lys Leu Val Gly Val Leu Asn Trp Ala Ala Gln Ile Tyr Pro
            260                 265                 270

Gly Ile Lys Thr Lys His Leu Cys Arg Leu Ile Arg Gly Lys Met Thr
            275                 280                 285

Leu Thr Glu Glu Val Gln Trp Thr Glu Met Ala Glu Ala Glu Tyr Glu
            290                 295                 300

Glu Asn Lys Ile Ile Leu Ser Gln Glu Gln Glu Gly Cys Tyr Tyr Gln
305                 310                 315                 320

Glu Gly Lys Pro Leu Glu Ala Thr Val Ile Lys Ser Gln Asp Asn Gln
            325                 330                 335

Trp Ser Tyr Lys Ile His Gln Glu Asp Lys Ile Leu Lys Val Gly Lys
            340                 345                 350

Phe Ala Lys Ile Lys Asn Thr His Thr Asn Gly Val Arg Leu Leu Ala
            355                 360                 365

His Val Ile Gln Lys Ile Gly Lys Glu Ala Ile Val Ile Trp Gly Gln
            370                 375                 380

Val Pro Lys Phe His Leu Pro Val Glu Arg Asp Val Trp Glu Gln Trp
385                 390                 395                 400

Trp Thr Asp Tyr Trp Gln Val Thr Trp Ile Pro Glu Trp Asp Phe Ile
            405                 410                 415

Ser Thr Pro Pro Leu Val Arg Leu Val Phe Asn Leu Val Lys Asp Pro
            420                 425                 430

Ile Glu Gly Glu Glu Thr Tyr
            435

<210> SEQ ID NO 48
<211> LENGTH: 223
<212> TYPE: PRT
<213> ORGANISM: Feline immunodeficiency virus

<400> SEQUENCE: 48

Pro Ile Gln Thr Val Asn Gly Val Pro Gln Tyr Val Ala Leu Asp Pro
1               5                   10                  15

Lys Met Val Ser Ile Phe Met Glu Lys Ala Arg Glu Gly Leu Gly Gly
            20                  25                  30

Glu Glu Val Gln Leu Trp Phe Thr Ala Phe Ser Ala Asn Leu Thr Pro
        35                  40                  45

Thr Asp Met Ala Thr Leu Ile Met Ala Ala Pro Gly Cys Ala Ala Asp
    50                  55                  60

Lys Glu Ile Leu Asp Glu Ser Leu Lys Gln Leu Thr Ala Glu Tyr Asp
65                  70                  75                  80

Arg Thr His Pro Pro Asp Ala Pro Arg Pro Leu Pro Tyr Phe Thr Ala
            85                  90                  95

Ala Glu Ile Met Gly Ile Gly Leu Thr Gln Glu Gln Gln Ala Glu Ala
```

```
                 100                 105                 110
Arg Phe Ala Pro Ala Arg Met Gln Cys Arg Ala Trp Tyr Leu Glu Ala
            115                 120                 125

Leu Gly Lys Leu Ala Ala Ile Lys Ala Lys Ser Pro Arg Ala Val Gln
        130                 135                 140

Leu Arg Gln Gly Ala Lys Glu Asp Tyr Ser Ser Phe Ile Asp Arg Leu
145                 150                 155                 160

Phe Ala Gln Ile Asp Gln Glu Gln Asn Thr Ala Glu Val Lys Leu Tyr
                165                 170                 175

Leu Lys Gln Ser Leu Ser Ile Ala Asn Ala Asn Ala Asp Cys Lys Lys
            180                 185                 190

Ala Met Ser His Leu Lys Pro Glu Ser Thr Leu Glu Glu Lys Leu Arg
        195                 200                 205

Ala Cys Gln Glu Ile Gly Ser Pro Gly Tyr Lys Met Gln Leu Leu
    210                 215                 220

<210> SEQ ID NO 49
<211> LENGTH: 228
<212> TYPE: PRT
<213> ORGANISM: Simian immunodeficiency virus

<400> SEQUENCE: 49

Pro Val Gln Gln Ile Gly Gly Asn Tyr Val His Leu Pro Leu Ser Pro
1               5                   10                  15

Arg Thr Leu Asp Ala Trp Val Lys Leu Ile Glu Glu Lys Lys Phe Gly
            20                  25                  30

Ala Glu Val Val Pro Gly Phe Gln Ala Leu Ser Glu Gly Cys Thr Pro
        35                  40                  45

Tyr Asp Ile Asn Gln Met Leu Asn Cys Val Gly Asp His Gln Ala Ala
    50                  55                  60

Met Gln Ile Ile Arg Asp Ile Ile Asn Glu Glu Ala Ala Asp Trp Asp
65                  70                  75                  80

Leu Gln His Pro Gln Pro Ala Pro Gln Gln Gly Gln Leu Arg Glu Pro
                85                  90                  95

Ser Gly Ser Asp Ile Ala Gly Thr Thr Ser Ser Val Asp Glu Gln Ile
            100                 105                 110

Gln Trp Met Tyr Arg Gln Gln Asn Pro Ile Pro Val Gly Asn Ile Tyr
        115                 120                 125

Arg Arg Trp Ile Gln Leu Gly Leu Gln Arg Cys Val Arg Met Tyr Asn
    130                 135                 140

Pro Thr Asn Ile Leu Asp Val Lys Gln Gly Pro Lys Glu Pro Phe Gln
145                 150                 155                 160

Ser Tyr Val Asp Arg Phe Tyr Lys Ser Leu Arg Ala Glu Gln Thr Asp
                165                 170                 175

Ala Ala Val Lys Asn Trp Met Thr Gln Thr Leu Leu Ile Gln Asn Ala
            180                 185                 190

Asn Pro Asp Cys Lys Leu Val Leu Lys Gly Leu Gly Val Asn Pro Thr
        195                 200                 205

Leu Glu Glu Met Leu Thr Ala Cys Gln Gly Val Glu Gly Pro Gly Gln
    210                 215                 220

Lys Ala Arg Leu
225

<210> SEQ ID NO 50
<211> LENGTH: 231
```

<212> TYPE: PRT
<213> ORGANISM: Human immunodeficiency virus

<400> SEQUENCE: 50

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 51
<211> LENGTH: 13
<212> TYPE: PRT
<213> ORGANISM: Feline immunodeficiency virus

<400> SEQUENCE: 51

Val Glu Arg Leu Glu Leu Glu Gly Lys Val Lys Arg Ala
1               5                   10

<210> SEQ ID NO 52
<211> LENGTH: 15
<212> TYPE: PRT
<213> ORGANISM: Feline immunodeficiency virus

<400> SEQUENCE: 52

Ala Gln Ile Ser Glu Lys Ile Pro Ile Val Lys Val Arg Met Lys
1               5                   10                  15

<210> SEQ ID NO 53
<211> LENGTH: 17
<212> TYPE: PRT
<213> ORGANISM: Feline immunodeficiency virus

<400> SEQUENCE: 53

Ile Pro Ile Val Lys Val Arg Met Lys Asp Pro Thr Gln Gly Pro Gln
1               5                   10                  15

Val

<210> SEQ ID NO 54
<211> LENGTH: 14
<212> TYPE: PRT
<213> ORGANISM: Feline immunodeficiency virus

<400> SEQUENCE: 54

Lys Asp Pro Thr Gln Gly Pro Gln Val Lys Gln Trp Pro Leu
1               5                   10

<210> SEQ ID NO 55
<211> LENGTH: 14
<212> TYPE: PRT
<213> ORGANISM: Feline immunodeficiency virus

<400> SEQUENCE: 55

Gly Pro Gln Val Lys Gln Trp Pro Leu Ser Asn Glu Lys Ile
1               5                   10

<210> SEQ ID NO 56
<211> LENGTH: 13
<212> TYPE: PRT
<213> ORGANISM: Feline immunodeficiency virus

<400> SEQUENCE: 56

Lys Gln Trp Pro Leu Ser Asn Glu Lys Ile Glu Ala Leu
1               5                   10

<210> SEQ ID NO 57
<211> LENGTH: 15
<212> TYPE: PRT
<213> ORGANISM: Feline immunodeficiency virus

<400> SEQUENCE: 57

Leu Ser Asn Glu Lys Ile Glu Ala Leu Thr Asp Ile Val Glu Arg
1               5                   10                  15

<210> SEQ ID NO 58
<211> LENGTH: 15
<212> TYPE: PRT
<213> ORGANISM: Feline immunodeficiency virus

<400> SEQUENCE: 58

Glu Ala Leu Thr Asp Ile Val Glu Arg Leu Glu Leu Glu Gly Lys
1               5                   10                  15

<210> SEQ ID NO 59
<211> LENGTH: 15
<212> TYPE: PRT
<213> ORGANISM: Feline immunodeficiency virus

<400> SEQUENCE: 59

Glu Leu Glu Gly Lys Val Lys Arg Ala Asp Pro Asn Asn Pro Trp
1               5                   10                  15

<210> SEQ ID NO 60
<211> LENGTH: 15
<212> TYPE: PRT
<213> ORGANISM: Feline immunodeficiency virus

<400> SEQUENCE: 60

```
Lys Arg Ala Asp Pro Asn Asn Pro Trp Asn Thr Pro Val Phe Ala
1               5                   10                  15

<210> SEQ ID NO 61
<211> LENGTH: 13
<212> TYPE: PRT
<213> ORGANISM: Feline immunodeficiency virus

<400> SEQUENCE: 61

Asn Pro Trp Asn Thr Pro Val Phe Ala Ile Lys Lys Lys
1               5                   10

<210> SEQ ID NO 62
<211> LENGTH: 15
<212> TYPE: PRT
<213> ORGANISM: Feline immunodeficiency virus

<400> SEQUENCE: 62

Thr Pro Val Phe Ala Ile Lys Lys Lys Ser Gly Lys Trp Arg Met
1               5                   10                  15

<210> SEQ ID NO 63
<211> LENGTH: 15
<212> TYPE: PRT
<213> ORGANISM: Feline immunodeficiency virus

<400> SEQUENCE: 63

Lys Lys Lys Ser Gly Lys Trp Arg Met Leu Ile Asp Phe Arg Val
1               5                   10                  15

<210> SEQ ID NO 64
<211> LENGTH: 13
<212> TYPE: PRT
<213> ORGANISM: Feline immunodeficiency virus

<400> SEQUENCE: 64

Trp Arg Met Leu Ile Asp Phe Arg Val Leu Asn Lys Leu
1               5                   10

<210> SEQ ID NO 65
<211> LENGTH: 14
<212> TYPE: PRT
<213> ORGANISM: Feline immunodeficiency virus

<400> SEQUENCE: 65

Ile Asp Phe Arg Val Leu Asn Lys Leu Thr Asp Lys Gly Ala
1               5                   10

<210> SEQ ID NO 66
<211> LENGTH: 15
<212> TYPE: PRT
<213> ORGANISM: Feline immunodeficiency virus

<400> SEQUENCE: 66

Leu Asn Lys Leu Thr Asp Lys Gly Ala Glu Val Gln Leu Gly Leu
1               5                   10                  15

<210> SEQ ID NO 67
<211> LENGTH: 15
<212> TYPE: PRT
<213> ORGANISM: Feline immunodeficiency virus

<400> SEQUENCE: 67

Lys Gly Ala Glu Val Gln Leu Gly Leu Pro His Pro Ala Gly Leu
```

-continued

```
1               5                   10                  15

<210> SEQ ID NO 68
<211> LENGTH: 15
<212> TYPE: PRT
<213> ORGANISM: Feline immunodeficiency virus

<400> SEQUENCE: 68

Leu Gly Leu Pro His Pro Ala Gly Leu Lys Met Arg Lys Gln Val
1               5                   10                  15

<210> SEQ ID NO 69
<211> LENGTH: 14
<212> TYPE: PRT
<213> ORGANISM: Feline immunodeficiency virus

<400> SEQUENCE: 69

Ala Gly Leu Lys Met Arg Lys Gln Val Thr Val Leu Asp Ile
1               5                   10

<210> SEQ ID NO 70
<211> LENGTH: 14
<212> TYPE: PRT
<213> ORGANISM: Feline immunodeficiency virus

<400> SEQUENCE: 70

Arg Lys Gln Val Thr Val Leu Asp Ile Gly Asp Ala Tyr Phe
1               5                   10

<210> SEQ ID NO 71
<211> LENGTH: 13
<212> TYPE: PRT
<213> ORGANISM: Feline immunodeficiency virus

<400> SEQUENCE: 71

Val Leu Asp Ile Gly Asp Ala Tyr Phe Thr Ile Pro Leu
1               5                   10

<210> SEQ ID NO 72
<211> LENGTH: 14
<212> TYPE: PRT
<213> ORGANISM: Feline immunodeficiency virus

<400> SEQUENCE: 72

Gly Asp Ala Tyr Phe Thr Ile Pro Leu Asp Pro Asp Tyr Ala
1               5                   10

<210> SEQ ID NO 73
<211> LENGTH: 14
<212> TYPE: PRT
<213> ORGANISM: Feline immunodeficiency virus

<400> SEQUENCE: 73

Thr Ile Pro Leu Asp Pro Asp Tyr Ala Pro Tyr Thr Ala Phe
1               5                   10

<210> SEQ ID NO 74
<211> LENGTH: 14
<212> TYPE: PRT
<213> ORGANISM: Feline immunodeficiency virus

<400> SEQUENCE: 74

Pro Asp Tyr Ala Pro Tyr Thr Ala Phe Thr Leu Pro Arg Lys
1               5                   10
```

<210> SEQ ID NO 75
<211> LENGTH: 12
<212> TYPE: PRT
<213> ORGANISM: Feline immunodeficiency virus

<400> SEQUENCE: 75

Tyr Thr Ala Phe Thr Leu Pro Arg Lys Asn Asn Ala
1               5                   10

<210> SEQ ID NO 76
<211> LENGTH: 15
<212> TYPE: PRT
<213> ORGANISM: Feline immunodeficiency virus

<400> SEQUENCE: 76

Phe Thr Leu Pro Arg Lys Asn Asn Ala Gly Pro Gly Arg Arg Tyr
1               5                   10                  15

<210> SEQ ID NO 77
<211> LENGTH: 14
<212> TYPE: PRT
<213> ORGANISM: Feline immunodeficiency virus

<400> SEQUENCE: 77

Asn Asn Ala Gly Pro Gly Arg Arg Tyr Val Trp Cys Ser Leu
1               5                   10

<210> SEQ ID NO 78
<211> LENGTH: 15
<212> TYPE: PRT
<213> ORGANISM: Feline immunodeficiency virus

<400> SEQUENCE: 78

Gly Arg Arg Tyr Val Trp Cys Ser Leu Pro Gln Gly Trp Val Leu
1               5                   10                  15

<210> SEQ ID NO 79
<211> LENGTH: 14
<212> TYPE: PRT
<213> ORGANISM: Feline immunodeficiency virus

<400> SEQUENCE: 79

Cys Ser Leu Pro Gln Gly Trp Val Leu Ser Pro Leu Ile Tyr
1               5                   10

<210> SEQ ID NO 80
<211> LENGTH: 13
<212> TYPE: PRT
<213> ORGANISM: Feline immunodeficiency virus

<400> SEQUENCE: 80

Gly Trp Val Leu Ser Pro Leu Ile Tyr Gln Ser Thr Leu
1               5                   10

<210> SEQ ID NO 81
<211> LENGTH: 13
<212> TYPE: PRT
<213> ORGANISM: Feline immunodeficiency virus

<400> SEQUENCE: 81

Ser Pro Leu Ile Tyr Gln Ser Thr Leu Asp Asn Ile Leu
1               5                   10

<210> SEQ ID NO 82

-continued

```
<211> LENGTH: 14
<212> TYPE: PRT
<213> ORGANISM: Feline immunodeficiency virus

<400> SEQUENCE: 82

Tyr Gln Ser Thr Leu Asp Asn Ile Leu Gln Pro Phe Ile Arg
1               5                   10

<210> SEQ ID NO 83
<211> LENGTH: 14
<212> TYPE: PRT
<213> ORGANISM: Feline immunodeficiency virus

<400> SEQUENCE: 83

Asp Asn Ile Leu Gln Pro Phe Ile Arg Gln Asn Pro Glu Leu
1               5                   10

<210> SEQ ID NO 84
<211> LENGTH: 15
<212> TYPE: PRT
<213> ORGANISM: Feline immunodeficiency virus

<400> SEQUENCE: 84

Pro Phe Ile Arg Gln Asn Pro Glu Leu Asp Ile Tyr Gln Tyr Met
1               5                   10                  15

<210> SEQ ID NO 85
<211> LENGTH: 14
<212> TYPE: PRT
<213> ORGANISM: Feline immunodeficiency virus

<400> SEQUENCE: 85

Pro Glu Leu Asp Ile Tyr Gln Tyr Met Asp Asp Ile Tyr Ile
1               5                   10

<210> SEQ ID NO 86
<211> LENGTH: 15
<212> TYPE: PRT
<213> ORGANISM: Feline immunodeficiency virus

<400> SEQUENCE: 86

Tyr Gln Tyr Met Asp Asp Ile Tyr Ile Gly Ser Asp Leu Asn Lys
1               5                   10                  15

<210> SEQ ID NO 87
<211> LENGTH: 15
<212> TYPE: PRT
<213> ORGANISM: Feline immunodeficiency virus

<400> SEQUENCE: 87

Ile Tyr Ile Gly Ser Asp Leu Asn Lys Lys Glu His Lys Gln Lys
1               5                   10                  15

<210> SEQ ID NO 88
<211> LENGTH: 15
<212> TYPE: PRT
<213> ORGANISM: Feline immunodeficiency virus

<400> SEQUENCE: 88

Leu Asn Lys Lys Glu His Lys Gln Lys Val Glu Glu Leu Arg Lys
1               5                   10                  15

<210> SEQ ID NO 89
<211> LENGTH: 14
<212> TYPE: PRT
```

<213> ORGANISM: Feline immunodeficiency virus

<400> SEQUENCE: 89

Lys Gln Lys Val Glu Glu Leu Arg Lys Leu Leu Leu Trp Trp
1 5 10

<210> SEQ ID NO 90
<211> LENGTH: 17
<212> TYPE: PRT
<213> ORGANISM: Feline immunodeficiency virus

<400> SEQUENCE: 90

Glu Leu Arg Lys Leu Leu Leu Trp Trp Gly Phe Glu Thr Pro Glu Asp
1 5 10 15

Lys

<210> SEQ ID NO 91
<211> LENGTH: 16
<212> TYPE: PRT
<213> ORGANISM: Feline immunodeficiency virus

<400> SEQUENCE: 91

Trp Gly Phe Glu Thr Pro Glu Asp Lys Leu Gln Glu Glu Pro Pro Tyr
1 5 10 15

<210> SEQ ID NO 92
<211> LENGTH: 14
<212> TYPE: PRT
<213> ORGANISM: Feline immunodeficiency virus

<400> SEQUENCE: 92

Asp Lys Leu Gln Glu Glu Pro Pro Tyr Lys Trp Met Gly Tyr
1 5 10

<210> SEQ ID NO 93
<211> LENGTH: 14
<212> TYPE: PRT
<213> ORGANISM: Feline immunodeficiency virus

<400> SEQUENCE: 93

Glu Pro Pro Tyr Lys Trp Met Gly Tyr Glu Leu His Pro Leu
1 5 10

<210> SEQ ID NO 94
<211> LENGTH: 13
<212> TYPE: PRT
<213> ORGANISM: Feline immunodeficiency virus

<400> SEQUENCE: 94

Trp Met Gly Tyr Glu Leu His Pro Leu Thr Trp Ser Ile
1 5 10

<210> SEQ ID NO 95
<211> LENGTH: 14
<212> TYPE: PRT
<213> ORGANISM: Feline immunodeficiency virus

<400> SEQUENCE: 95

Glu Leu His Pro Leu Thr Trp Ser Ile Gln Gln Lys Gln Leu
1 5 10

<210> SEQ ID NO 96
<211> LENGTH: 14
<212> TYPE: PRT

<213> ORGANISM: Feline immunodeficiency virus

<400> SEQUENCE: 96

Thr Trp Ser Ile Gln Gln Lys Gln Leu Glu Ile Pro Glu Arg
1               5                   10

<210> SEQ ID NO 97
<211> LENGTH: 14
<212> TYPE: PRT
<213> ORGANISM: Feline immunodeficiency virus

<400> SEQUENCE: 97

Ile Gln Gln Lys Gln Leu Glu Ile Pro Glu Arg Pro Thr Leu
1               5                   10

<210> SEQ ID NO 98
<211> LENGTH: 15
<212> TYPE: PRT
<213> ORGANISM: Feline immunodeficiency virus

<400> SEQUENCE: 98

Leu Glu Ile Pro Glu Arg Pro Thr Leu Asn Glu Leu Gln Lys Leu
1               5                   10                  15

<210> SEQ ID NO 99
<211> LENGTH: 15
<212> TYPE: PRT
<213> ORGANISM: Feline immunodeficiency virus

<400> SEQUENCE: 99

Pro Thr Leu Asn Glu Leu Gln Lys Leu Val Gly Lys Ile Asn Trp
1               5                   10                  15

<210> SEQ ID NO 100
<211> LENGTH: 15
<212> TYPE: PRT
<213> ORGANISM: Feline immunodeficiency virus

<400> SEQUENCE: 100

Leu Gln Lys Leu Val Gly Lys Ile Asn Trp Ala Ser Gln Thr Ile
1               5                   10                  15

<210> SEQ ID NO 101
<211> LENGTH: 15
<212> TYPE: PRT
<213> ORGANISM: Feline immunodeficiency virus

<400> SEQUENCE: 101

Lys Ile Asn Trp Ala Ser Gln Thr Ile Pro Asp Leu Ser Ile Lys
1               5                   10                  15

<210> SEQ ID NO 102
<211> LENGTH: 15
<212> TYPE: PRT
<213> ORGANISM: Feline immunodeficiency virus

<400> SEQUENCE: 102

Ser Gln Thr Ile Pro Asp Leu Ser Ile Lys Glu Leu Thr Thr Met
1               5                   10                  15

<210> SEQ ID NO 103
<211> LENGTH: 15
<212> TYPE: PRT
<213> ORGANISM: Feline immunodeficiency virus

<400> SEQUENCE: 103

Leu Ser Ile Lys Glu Leu Thr Thr Met Met Arg Gly Asp Gln Arg
1               5                   10                  15

<210> SEQ ID NO 104
<211> LENGTH: 14
<212> TYPE: PRT
<213> ORGANISM: Feline immunodeficiency virus

<400> SEQUENCE: 104

Thr Thr Met Met Arg Gly Asp Gln Arg Leu Asp Ser Ile Arg
1               5                   10

<210> SEQ ID NO 105
<211> LENGTH: 15
<212> TYPE: PRT
<213> ORGANISM: Feline immunodeficiency virus

<400> SEQUENCE: 105

Gly Asp Gln Arg Leu Asp Ser Ile Arg Glu Trp Thr Thr Glu Ala
1               5                   10                  15

<210> SEQ ID NO 106
<211> LENGTH: 15
<212> TYPE: PRT
<213> ORGANISM: Feline immunodeficiency virus

<400> SEQUENCE: 106

Ser Ile Arg Glu Trp Thr Thr Glu Ala Lys Lys Glu Val Gln Lys
1               5                   10                  15

<210> SEQ ID NO 107
<211> LENGTH: 14
<212> TYPE: PRT
<213> ORGANISM: Feline immunodeficiency virus

<400> SEQUENCE: 107

Thr Glu Ala Lys Lys Glu Val Gln Lys Ala Lys Glu Ala Ile
1               5                   10

<210> SEQ ID NO 108
<211> LENGTH: 15
<212> TYPE: PRT
<213> ORGANISM: Feline immunodeficiency virus

<400> SEQUENCE: 108

Glu Val Gln Lys Ala Lys Glu Ala Ile Glu Thr Gln Ala Gln Leu
1               5                   10                  15

<210> SEQ ID NO 109
<211> LENGTH: 12
<212> TYPE: PRT
<213> ORGANISM: Feline immunodeficiency virus

<400> SEQUENCE: 109

Glu Ala Ile Glu Thr Gln Ala Gln Leu Lys Tyr Tyr
1               5                   10

<210> SEQ ID NO 110
<211> LENGTH: 15
<212> TYPE: PRT
<213> ORGANISM: Feline immunodeficiency virus

<400> SEQUENCE: 110

Glu Thr Gln Ala Gln Leu Lys Tyr Tyr Asp Pro Ser Arg Glu Leu
1               5                   10                  15

<210> SEQ ID NO 111
<211> LENGTH: 15
<212> TYPE: PRT
<213> ORGANISM: Feline immunodeficiency virus

<400> SEQUENCE: 111

Lys Tyr Tyr Asp Pro Ser Arg Glu Leu Tyr Ala Lys Leu Ser Leu
1               5                   10                  15

<210> SEQ ID NO 112
<211> LENGTH: 15
<212> TYPE: PRT
<213> ORGANISM: Feline immunodeficiency virus

<400> SEQUENCE: 112

Arg Glu Leu Tyr Ala Lys Leu Ser Leu Val Gly Pro His Gln Ile
1               5                   10                  15

<210> SEQ ID NO 113
<211> LENGTH: 15
<212> TYPE: PRT
<213> ORGANISM: Feline immunodeficiency virus

<400> SEQUENCE: 113

Leu Ser Leu Val Gly Pro His Gln Ile Cys Tyr Gln Val Tyr His
1               5                   10                  15

<210> SEQ ID NO 114
<211> LENGTH: 15
<212> TYPE: PRT
<213> ORGANISM: Feline immunodeficiency virus

<400> SEQUENCE: 114

His Gln Ile Cys Tyr Gln Val Tyr His Lys Asn Pro Glu His Val
1               5                   10                  15

<210> SEQ ID NO 115
<211> LENGTH: 15
<212> TYPE: PRT
<213> ORGANISM: Feline immunodeficiency virus

<400> SEQUENCE: 115

Val Tyr His Lys Asn Pro Glu His Val Leu Trp Tyr Gly Lys Met
1               5                   10                  15

<210> SEQ ID NO 116
<211> LENGTH: 15
<212> TYPE: PRT
<213> ORGANISM: Feline immunodeficiency virus

<400> SEQUENCE: 116

Glu His Val Leu Trp Tyr Gly Lys Met Asn Arg Gln Lys Lys Lys
1               5                   10                  15

<210> SEQ ID NO 117
<211> LENGTH: 16
<212> TYPE: PRT
<213> ORGANISM: Feline immunodeficiency virus

<400> SEQUENCE: 117

Gly Lys Met Asn Arg Gln Lys Lys Lys Ala Glu Asn Thr Cys Asp Ile
1               5                   10                  15

```
<210> SEQ ID NO 118
<211> LENGTH: 15
<212> TYPE: PRT
<213> ORGANISM: Feline immunodeficiency virus

<400> SEQUENCE: 118

Lys Lys Ala Glu Asn Thr Cys Asp Ile Ala Leu Arg Ala Cys Tyr
1               5                   10                  15

<210> SEQ ID NO 119
<211> LENGTH: 12
<212> TYPE: PRT
<213> ORGANISM: Feline immunodeficiency virus

<400> SEQUENCE: 119

Cys Asp Ile Ala Leu Arg Ala Cys Tyr Lys Ile Arg
1               5                   10

<210> SEQ ID NO 120
<211> LENGTH: 15
<212> TYPE: PRT
<213> ORGANISM: Feline immunodeficiency virus

<400> SEQUENCE: 120

Ala Leu Arg Ala Cys Tyr Lys Ile Arg Glu Glu Ser Ile Ile Arg
1               5                   10                  15

<210> SEQ ID NO 121
<211> LENGTH: 15
<212> TYPE: PRT
<213> ORGANISM: Feline immunodeficiency virus

<400> SEQUENCE: 121

Lys Ile Arg Glu Glu Ser Ile Ile Arg Ile Gly Lys Glu Pro Ile
1               5                   10                  15

<210> SEQ ID NO 122
<211> LENGTH: 14
<212> TYPE: PRT
<213> ORGANISM: Feline immunodeficiency virus

<400> SEQUENCE: 122

Ile Ile Arg Ile Gly Lys Glu Pro Ile Tyr Glu Ile Pro Ala
1               5                   10

<210> SEQ ID NO 123
<211> LENGTH: 14
<212> TYPE: PRT
<213> ORGANISM: Feline immunodeficiency virus

<400> SEQUENCE: 123

Lys Glu Pro Ile Tyr Glu Ile Pro Ala Ser Arg Glu Ala Trp
1               5                   10

<210> SEQ ID NO 124
<211> LENGTH: 15
<212> TYPE: PRT
<213> ORGANISM: Feline immunodeficiency virus

<400> SEQUENCE: 124

Glu Ile Pro Ala Ser Arg Glu Ala Trp Glu Ser Asn Leu Ile Arg
1               5                   10                  15
```

```
<210> SEQ ID NO 125
<211> LENGTH: 15
<212> TYPE: PRT
<213> ORGANISM: Feline immunodeficiency virus

<400> SEQUENCE: 125

Glu Ala Trp Glu Ser Asn Leu Ile Arg Ser Pro Tyr Leu Lys Ala
1               5                   10                  15

<210> SEQ ID NO 126
<211> LENGTH: 14
<212> TYPE: PRT
<213> ORGANISM: Feline immunodeficiency virus

<400> SEQUENCE: 126

Leu Ile Arg Ser Pro Tyr Leu Lys Ala Pro Pro Glu Val
1               5                   10

<210> SEQ ID NO 127
<211> LENGTH: 15
<212> TYPE: PRT
<213> ORGANISM: Feline immunodeficiency virus

<400> SEQUENCE: 127

Tyr Leu Lys Ala Pro Pro Pro Glu Val Glu Phe Ile His Ala Ala
1               5                   10                  15

<210> SEQ ID NO 128
<211> LENGTH: 15
<212> TYPE: PRT
<213> ORGANISM: Feline immunodeficiency virus

<400> SEQUENCE: 128

Pro Glu Val Glu Phe Ile His Ala Ala Leu Asn Ile Lys Arg Ala
1               5                   10                  15

<210> SEQ ID NO 129
<211> LENGTH: 13
<212> TYPE: PRT
<213> ORGANISM: Feline immunodeficiency virus

<400> SEQUENCE: 129

His Ala Ala Leu Asn Ile Lys Arg Ala Leu Ser Met Ile
1               5                   10

<210> SEQ ID NO 130
<211> LENGTH: 15
<212> TYPE: PRT
<213> ORGANISM: Feline immunodeficiency virus

<400> SEQUENCE: 130

Asn Ile Lys Arg Ala Leu Ser Met Ile Gln Asp Thr Pro Ile Leu
1               5                   10                  15

<210> SEQ ID NO 131
<211> LENGTH: 15
<212> TYPE: PRT
<213> ORGANISM: Feline immunodeficiency virus

<400> SEQUENCE: 131

Ser Met Ile Gln Asp Thr Pro Ile Leu Gly Ala Glu Thr Trp Tyr
1               5                   10                  15

<210> SEQ ID NO 132
<211> LENGTH: 15
```

-continued

<212> TYPE: PRT
<213> ORGANISM: Feline immunodeficiency virus

<400> SEQUENCE: 132

Pro Ile Leu Gly Ala Glu Thr Trp Tyr Ile Asp Gly Gly Arg Lys
1               5                   10                  15

<210> SEQ ID NO 133
<211> LENGTH: 15
<212> TYPE: PRT
<213> ORGANISM: Feline immunodeficiency virus

<400> SEQUENCE: 133

Thr Trp Tyr Ile Asp Gly Gly Arg Lys Gln Gly Lys Ala Ala Arg
1               5                   10                  15

<210> SEQ ID NO 134
<211> LENGTH: 13
<212> TYPE: PRT
<213> ORGANISM: Feline immunodeficiency virus

<400> SEQUENCE: 134

Gly Arg Lys Gln Gly Lys Ala Ala Arg Ala Ala Tyr Trp
1               5                   10

<210> SEQ ID NO 135
<211> LENGTH: 15
<212> TYPE: PRT
<213> ORGANISM: Feline immunodeficiency virus

<400> SEQUENCE: 135

Gly Lys Ala Ala Arg Ala Ala Tyr Trp Thr Asp Thr Gly Lys Trp
1               5                   10                  15

<210> SEQ ID NO 136
<211> LENGTH: 14
<212> TYPE: PRT
<213> ORGANISM: Feline immunodeficiency virus

<400> SEQUENCE: 136

Ala Tyr Trp Thr Asp Thr Gly Lys Trp Gln Val Met Glu Ile
1               5                   10

<210> SEQ ID NO 137
<211> LENGTH: 15
<212> TYPE: PRT
<213> ORGANISM: Feline immunodeficiency virus

<400> SEQUENCE: 137

Thr Gly Lys Trp Gln Val Met Glu Ile Glu Gly Ser Asn Gln Lys
1               5                   10                  15

<210> SEQ ID NO 138
<211> LENGTH: 15
<212> TYPE: PRT
<213> ORGANISM: Feline immunodeficiency virus

<400> SEQUENCE: 138

Met Glu Ile Glu Gly Ser Asn Gln Lys Ala Glu Val Gln Ala Leu
1               5                   10                  15

<210> SEQ ID NO 139
<211> LENGTH: 15
<212> TYPE: PRT
<213> ORGANISM: Feline immunodeficiency virus

<400> SEQUENCE: 139

Asn Gln Lys Ala Glu Val Gln Ala Leu Leu Ala Leu Gln Ala
1               5                   10                  15

<210> SEQ ID NO 140
<211> LENGTH: 15
<212> TYPE: PRT
<213> ORGANISM: Feline immunodeficiency virus

<400> SEQUENCE: 140

Val Gln Ala Leu Leu Leu Ala Leu Gln Ala Gly Pro Glu Glu Met
1               5                   10                  15

<210> SEQ ID NO 141
<211> LENGTH: 12
<212> TYPE: PRT
<213> ORGANISM: Feline immunodeficiency virus

<400> SEQUENCE: 141

Ala Leu Gln Ala Gly Pro Glu Glu Met Asn Ile Ile
1               5                   10

<210> SEQ ID NO 142
<211> LENGTH: 15
<212> TYPE: PRT
<213> ORGANISM: Feline immunodeficiency virus

<400> SEQUENCE: 142

Ala Gly Pro Glu Glu Met Asn Ile Ile Thr Asp Ser Gln Tyr Ile
1               5                   10                  15

<210> SEQ ID NO 143
<211> LENGTH: 13
<212> TYPE: PRT
<213> ORGANISM: Feline immunodeficiency virus

<400> SEQUENCE: 143

Asn Ile Ile Thr Asp Ser Gln Tyr Ile Leu Asn Ile Ile
1               5                   10

<210> SEQ ID NO 144
<211> LENGTH: 15
<212> TYPE: PRT
<213> ORGANISM: Feline immunodeficiency virus

<400> SEQUENCE: 144

Asp Ser Gln Tyr Ile Leu Asn Ile Ile Thr Gln Gln Pro Asp Leu
1               5                   10                  15

<210> SEQ ID NO 145
<211> LENGTH: 14
<212> TYPE: PRT
<213> ORGANISM: Feline immunodeficiency virus

<400> SEQUENCE: 145

Asn Ile Ile Thr Gln Gln Pro Asp Leu Met Glu Gly Leu Trp
1               5                   10

<210> SEQ ID NO 146
<211> LENGTH: 15
<212> TYPE: PRT
<213> ORGANISM: Feline immunodeficiency virus

<400> SEQUENCE: 146

```
Thr Gln Gln Pro Asp Leu Met Glu Gly Leu Trp Gln Glu Val Leu
1               5                   10                  15

<210> SEQ ID NO 147
<211> LENGTH: 15
<212> TYPE: PRT
<213> ORGANISM: Feline immunodeficiency virus

<400> SEQUENCE: 147

Met Glu Gly Leu Trp Gln Glu Val Leu Glu Met Glu Lys Lys
1               5                   10                  15

<210> SEQ ID NO 148
<211> LENGTH: 14
<212> TYPE: PRT
<213> ORGANISM: Feline immunodeficiency virus

<400> SEQUENCE: 148

Glu Val Leu Glu Glu Met Glu Lys Lys Ile Ala Ile Phe Ile
1               5                   10

<210> SEQ ID NO 149
<211> LENGTH: 15
<212> TYPE: PRT
<213> ORGANISM: Feline immunodeficiency virus

<400> SEQUENCE: 149

Met Glu Lys Lys Ile Ala Ile Phe Ile Asp Trp Val Pro Gly His
1               5                   10                  15

<210> SEQ ID NO 150
<211> LENGTH: 12
<212> TYPE: PRT
<213> ORGANISM: Feline immunodeficiency virus

<400> SEQUENCE: 150

Ile Phe Ile Asp Trp Val Pro Gly His Lys Gly Ile
1               5                   10

<210> SEQ ID NO 151
<211> LENGTH: 15
<212> TYPE: PRT
<213> ORGANISM: Feline immunodeficiency virus

<400> SEQUENCE: 151

Asp Trp Val Pro Gly His Lys Gly Ile Pro Gly Asn Glu Glu Val
1               5                   10                  15

<210> SEQ ID NO 152
<211> LENGTH: 16
<212> TYPE: PRT
<213> ORGANISM: Feline immunodeficiency virus

<400> SEQUENCE: 152

Lys Gly Ile Pro Gly Asn Glu Glu Val Asp Lys Leu Cys Gln Thr Met
1               5                   10                  15

<210> SEQ ID NO 153
<211> LENGTH: 13
<212> TYPE: PRT
<213> ORGANISM: Human immunodeficiency virus

<400> SEQUENCE: 153

Pro Ile Ser Pro Ile Glu Thr Val Pro Val Lys Leu Lys
```

```
<210> SEQ ID NO 154
<211> LENGTH: 12
<212> TYPE: PRT
<213> ORGANISM: Human immunodeficiency virus

<400> SEQUENCE: 154

Ile Glu Thr Val Pro Val Lys Leu Lys Pro Gly Met
1               5                   10

<210> SEQ ID NO 155
<211> LENGTH: 15
<212> TYPE: PRT
<213> ORGANISM: Human immunodeficiency virus

<400> SEQUENCE: 155

Val Pro Val Lys Leu Lys Pro Gly Met Asp Gly Pro Lys Val Lys
1               5                   10                  15

<210> SEQ ID NO 156
<211> LENGTH: 13
<212> TYPE: PRT
<213> ORGANISM: Human immunodeficiency virus

<400> SEQUENCE: 156

Pro Gly Met Asp Gly Pro Lys Val Lys Gln Trp Pro Leu
1               5                   10

<210> SEQ ID NO 157
<211> LENGTH: 15
<212> TYPE: PRT
<213> ORGANISM: Human immunodeficiency virus

<400> SEQUENCE: 157

Gly Pro Lys Val Lys Gln Trp Pro Leu Thr Glu Glu Lys Ile Lys
1               5                   10                  15

<210> SEQ ID NO 158
<211> LENGTH: 14
<212> TYPE: PRT
<213> ORGANISM: Human immunodeficiency virus

<400> SEQUENCE: 158

Trp Pro Leu Thr Glu Glu Lys Ile Lys Ala Leu Ile Glu Ile
1               5                   10

<210> SEQ ID NO 159
<211> LENGTH: 15
<212> TYPE: PRT
<213> ORGANISM: Human immunodeficiency virus

<400> SEQUENCE: 159

Glu Lys Ile Lys Ala Leu Ile Glu Ile Cys Thr Glu Met Glu Lys
1               5                   10                  15

<210> SEQ ID NO 160
<211> LENGTH: 15
<212> TYPE: PRT
<213> ORGANISM: Human immunodeficiency virus

<400> SEQUENCE: 160

Ile Glu Ile Cys Thr Glu Met Glu Lys Glu Gly Lys Ile Ser Lys
1               5                   10                  15
```

<210> SEQ ID NO 161
<211> LENGTH: 16
<212> TYPE: PRT
<213> ORGANISM: Human immunodeficiency virus

<400> SEQUENCE: 161

Met Glu Lys Glu Gly Lys Ile Ser Lys Ile Gly Pro Glu Asn Pro Tyr
1               5                   10                  15

<210> SEQ ID NO 162
<211> LENGTH: 15
<212> TYPE: PRT
<213> ORGANISM: Human immunodeficiency virus

<400> SEQUENCE: 162

Ser Lys Ile Gly Pro Glu Asn Pro Tyr Asn Thr Pro Val Phe Ala
1               5                   10                  15

<210> SEQ ID NO 163
<211> LENGTH: 13
<212> TYPE: PRT
<213> ORGANISM: Human immunodeficiency virus

<400> SEQUENCE: 163

Asn Pro Tyr Asn Thr Pro Val Phe Ala Ile Lys Lys Lys
1               5                   10

<210> SEQ ID NO 164
<211> LENGTH: 15
<212> TYPE: PRT
<213> ORGANISM: Human immunodeficiency virus

<400> SEQUENCE: 164

Thr Pro Val Phe Ala Ile Lys Lys Lys Asp Ser Thr Lys Trp Arg
1               5                   10                  15

<210> SEQ ID NO 165
<211> LENGTH: 15
<212> TYPE: PRT
<213> ORGANISM: Human immunodeficiency virus

<400> SEQUENCE: 165

Lys Lys Lys Asp Ser Thr Lys Trp Arg Lys Leu Val Asp Phe Arg
1               5                   10                  15

<210> SEQ ID NO 166
<211> LENGTH: 14
<212> TYPE: PRT
<213> ORGANISM: Human immunodeficiency virus

<400> SEQUENCE: 166

Lys Trp Arg Lys Leu Val Asp Phe Arg Glu Leu Asn Lys Arg
1               5                   10

<210> SEQ ID NO 167
<211> LENGTH: 14
<212> TYPE: PRT
<213> ORGANISM: Human immunodeficiency virus

<400> SEQUENCE: 167

Val Asp Phe Arg Glu Leu Asn Lys Arg Thr Gln Asp Phe Trp
1               5                   10

<210> SEQ ID NO 168

```
<211> LENGTH: 15
<212> TYPE: PRT
<213> ORGANISM: Human immunodeficiency virus

<400> SEQUENCE: 168

Leu Asn Lys Arg Thr Gln Asp Phe Trp Glu Val Gln Leu Gly Ile
1               5                   10                  15

<210> SEQ ID NO 169
<211> LENGTH: 15
<212> TYPE: PRT
<213> ORGANISM: Human immunodeficiency virus

<400> SEQUENCE: 169

Asp Phe Trp Glu Val Gln Leu Gly Ile Pro His Pro Ala Gly Leu
1               5                   10                  15

<210> SEQ ID NO 170
<211> LENGTH: 15
<212> TYPE: PRT
<213> ORGANISM: Human immunodeficiency virus

<400> SEQUENCE: 170

Leu Gly Ile Pro His Pro Ala Gly Leu Lys Lys Lys Ser Val
1               5                   10                  15

<210> SEQ ID NO 171
<211> LENGTH: 14
<212> TYPE: PRT
<213> ORGANISM: Human immunodeficiency virus

<400> SEQUENCE: 171

Ala Gly Leu Lys Lys Lys Lys Ser Val Thr Val Leu Asp Val
1               5                   10

<210> SEQ ID NO 172
<211> LENGTH: 14
<212> TYPE: PRT
<213> ORGANISM: Human immunodeficiency virus

<400> SEQUENCE: 172

Lys Lys Ser Val Thr Val Leu Asp Val Gly Asp Ala Tyr Phe
1               5                   10

<210> SEQ ID NO 173
<211> LENGTH: 15
<212> TYPE: PRT
<213> ORGANISM: Human immunodeficiency virus

<400> SEQUENCE: 173

Val Leu Asp Val Gly Asp Ala Tyr Phe Ser Val Pro Leu Asp Lys
1               5                   10                  15

<210> SEQ ID NO 174
<211> LENGTH: 14
<212> TYPE: PRT
<213> ORGANISM: Human immunodeficiency virus

<400> SEQUENCE: 174

Ala Tyr Phe Ser Val Pro Leu Asp Lys Asp Phe Arg Lys Tyr
1               5                   10

<210> SEQ ID NO 175
<211> LENGTH: 14
<212> TYPE: PRT
```

```
<213> ORGANISM: Human immunodeficiency virus

<400> SEQUENCE: 175

Pro Leu Asp Lys Asp Phe Arg Lys Tyr Thr Ala Phe Thr Ile
1               5                   10

<210> SEQ ID NO 176
<211> LENGTH: 12
<212> TYPE: PRT
<213> ORGANISM: Human immunodeficiency virus

<400> SEQUENCE: 176

Phe Arg Lys Tyr Thr Ala Phe Thr Ile Pro Ser Ile
1               5                   10

<210> SEQ ID NO 177
<211> LENGTH: 15
<212> TYPE: PRT
<213> ORGANISM: Human immunodeficiency virus

<400> SEQUENCE: 177

Phe Thr Ile Pro Ser Thr Asn Asn Glu Thr Pro Gly Ile Arg Tyr
1               5                   10                  15

<210> SEQ ID NO 178
<211> LENGTH: 14
<212> TYPE: PRT
<213> ORGANISM: Human immunodeficiency virus

<400> SEQUENCE: 178

Asn Asn Glu Thr Pro Gly Ile Arg Tyr Gln Tyr Asn Val Leu
1               5                   10

<210> SEQ ID NO 179
<211> LENGTH: 14
<212> TYPE: PRT
<213> ORGANISM: Human immunodeficiency virus

<400> SEQUENCE: 179

Gly Ile Arg Tyr Gln Tyr Asn Val Leu Pro Gln Gly Trp Lys
1               5                   10

<210> SEQ ID NO 180
<211> LENGTH: 15
<212> TYPE: PRT
<213> ORGANISM: Human immunodeficiency virus

<400> SEQUENCE: 180

Tyr Asn Val Leu Pro Gln Gly Trp Lys Gly Ser Pro Ala Ile Phe
1               5                   10                  15

<210> SEQ ID NO 181
<211> LENGTH: 15
<212> TYPE: PRT
<213> ORGANISM: Human immunodeficiency virus

<400> SEQUENCE: 181

Gly Trp Lys Gly Ser Pro Ala Ile Phe Gln Ser Ser Met Thr Lys
1               5                   10                  15

<210> SEQ ID NO 182
<211> LENGTH: 15
<212> TYPE: PRT
<213> ORGANISM: Human immunodeficiency virus
```

```
<400> SEQUENCE: 182

Ala Ile Phe Gln Ser Ser Met Thr Lys Ile Leu Glu Pro Phe Arg
1               5                   10                  15

<210> SEQ ID NO 183
<211> LENGTH: 15
<212> TYPE: PRT
<213> ORGANISM: Human immunodeficiency virus

<400> SEQUENCE: 183

Met Thr Lys Ile Leu Glu Pro Phe Arg Lys Gln Asn Pro Asp Ile
1               5                   10                  15

<210> SEQ ID NO 184
<211> LENGTH: 15
<212> TYPE: PRT
<213> ORGANISM: Human immunodeficiency virus

<400> SEQUENCE: 184

Pro Phe Arg Lys Gln Asn Pro Asp Ile Val Ile Tyr Gln Tyr Met
1               5                   10                  15

<210> SEQ ID NO 185
<211> LENGTH: 14
<212> TYPE: PRT
<213> ORGANISM: Human immunodeficiency virus

<400> SEQUENCE: 185

Pro Asp Ile Val Ile Tyr Gln Tyr Met Asp Asp Leu Tyr Val
1               5                   10

<210> SEQ ID NO 186
<211> LENGTH: 15
<212> TYPE: PRT
<213> ORGANISM: Human immunodeficiency virus

<400> SEQUENCE: 186

Tyr Gln Tyr Met Asp Asp Leu Tyr Val Gly Ser Asp Leu Glu Ile
1               5                   10                  15

<210> SEQ ID NO 187
<211> LENGTH: 15
<212> TYPE: PRT
<213> ORGANISM: Human immunodeficiency virus

<400> SEQUENCE: 187

Leu Tyr Val Gly Ser Asp Leu Glu Ile Gly Gln His Arg Thr Lys
1               5                   10                  15

<210> SEQ ID NO 188
<211> LENGTH: 14
<212> TYPE: PRT
<213> ORGANISM: Human immunodeficiency virus

<400> SEQUENCE: 188

Leu Glu Ile Gly Gln His Arg Thr Lys Ile Glu Glu Leu Arg
1               5                   10

<210> SEQ ID NO 189
<211> LENGTH: 15
<212> TYPE: PRT
<213> ORGANISM: Human immunodeficiency virus

<400> SEQUENCE: 189
```

```
His Arg Thr Lys Ile Glu Glu Leu Arg Gln His Leu Leu Arg Trp
1               5                   10                  15

<210> SEQ ID NO 190
<211> LENGTH: 16
<212> TYPE: PRT
<213> ORGANISM: Human immunodeficiency virus

<400> SEQUENCE: 190

Glu Leu Arg Gln His Leu Leu Arg Trp Gly Phe Thr Thr Pro Asp Lys
1               5                   10                  15

<210> SEQ ID NO 191
<211> LENGTH: 13
<212> TYPE: PRT
<213> ORGANISM: Human immunodeficiency virus

<400> SEQUENCE: 191

Arg Trp Gly Phe Thr Thr Pro Asp Lys His Gln Lys
1               5                   10

<210> SEQ ID NO 192
<211> LENGTH: 15
<212> TYPE: PRT
<213> ORGANISM: Human immunodeficiency virus

<400> SEQUENCE: 192

Thr Thr Pro Asp Lys Lys His Gln Lys Glu Pro Pro Phe Leu Trp
1               5                   10                  15

<210> SEQ ID NO 193
<211> LENGTH: 15
<212> TYPE: PRT
<213> ORGANISM: Human immunodeficiency virus

<400> SEQUENCE: 193

His Gln Lys Glu Pro Pro Phe Leu Trp Met Gly Tyr Glu Leu His
1               5                   10                  15

<210> SEQ ID NO 194
<211> LENGTH: 15
<212> TYPE: PRT
<213> ORGANISM: Human immunodeficiency virus

<400> SEQUENCE: 194

Phe Leu Trp Met Gly Tyr Glu Leu His Pro Asp Lys Trp Thr Val
1               5                   10                  15

<210> SEQ ID NO 195
<211> LENGTH: 14
<212> TYPE: PRT
<213> ORGANISM: Human immunodeficiency virus

<400> SEQUENCE: 195

Glu Leu His Pro Asp Lys Trp Thr Val Gln Pro Ile Met Leu
1               5                   10

<210> SEQ ID NO 196
<211> LENGTH: 15
<212> TYPE: PRT
<213> ORGANISM: Human immunodeficiency virus

<400> SEQUENCE: 196

Lys Trp Thr Val Gln Pro Ile Met Leu Pro Glu Lys Asp Ser Trp
1               5                   10                  15
```

<210> SEQ ID NO 197
<211> LENGTH: 14
<212> TYPE: PRT
<213> ORGANISM: Human immunodeficiency virus

<400> SEQUENCE: 197

Ile Met Leu Pro Glu Lys Asp Ser Trp Thr Val Asn Asp Ile
1               5                   10

<210> SEQ ID NO 198
<211> LENGTH: 15
<212> TYPE: PRT
<213> ORGANISM: Human immunodeficiency virus

<400> SEQUENCE: 198

Lys Asp Ser Trp Thr Val Asn Asp Ile Gln Lys Leu Val Gly Lys
1               5                   10                  15

<210> SEQ ID NO 199
<211> LENGTH: 13
<212> TYPE: PRT
<213> ORGANISM: Human immunodeficiency virus

<400> SEQUENCE: 199

Asn Asp Ile Gln Lys Leu Val Gly Lys Leu Asn Trp Ala
1               5                   10

<210> SEQ ID NO 200
<211> LENGTH: 14
<212> TYPE: PRT
<213> ORGANISM: Human immunodeficiency virus

<400> SEQUENCE: 200

Lys Leu Val Gly Lys Leu Asn Trp Ala Ser Gln Ile Tyr Ala
1               5                   10

<210> SEQ ID NO 201
<211> LENGTH: 14
<212> TYPE: PRT
<213> ORGANISM: Human immunodeficiency virus

<400> SEQUENCE: 201

Leu Asn Trp Ala Ser Gln Ile Tyr Ala Gly Ile Lys Val Arg
1               5                   10

<210> SEQ ID NO 202
<211> LENGTH: 15
<212> TYPE: PRT
<213> ORGANISM: Human immunodeficiency virus

<400> SEQUENCE: 202

Ser Gln Ile Tyr Ala Gly Ile Lys Val Arg Gln Leu Cys Lys Leu
1               5                   10                  15

<210> SEQ ID NO 203
<211> LENGTH: 15
<212> TYPE: PRT
<213> ORGANISM: Human immunodeficiency virus

<400> SEQUENCE: 203

Ile Lys Val Arg Gln Leu Cys Lys Leu Leu Arg Gly Ala Lys Ala
1               5                   10                  15

-continued

```
<210> SEQ ID NO 204
<211> LENGTH: 14
<212> TYPE: PRT
<213> ORGANISM: Human immunodeficiency virus

<400> SEQUENCE: 204

Cys Lys Leu Leu Arg Gly Ala Lys Ala Leu Thr Glu Val Ile
1               5                   10

<210> SEQ ID NO 205
<211> LENGTH: 15
<212> TYPE: PRT
<213> ORGANISM: Human immunodeficiency virus

<400> SEQUENCE: 205

Gly Ala Lys Ala Leu Thr Glu Val Ile Pro Leu Thr Lys Glu Ala
1               5                   10                  15

<210> SEQ ID NO 206
<211> LENGTH: 14
<212> TYPE: PRT
<213> ORGANISM: Human immunodeficiency virus

<400> SEQUENCE: 206

Glu Val Ile Pro Leu Thr Lys Glu Ala Glu Leu Glu Leu Ala
1               5                   10

<210> SEQ ID NO 207
<211> LENGTH: 15
<212> TYPE: PRT
<213> ORGANISM: Human immunodeficiency virus

<400> SEQUENCE: 207

Thr Lys Glu Ala Glu Leu Glu Leu Ala Glu Asn Arg Glu Ile Leu
1               5                   10                  15

<210> SEQ ID NO 208
<211> LENGTH: 14
<212> TYPE: PRT
<213> ORGANISM: Human immunodeficiency virus

<400> SEQUENCE: 208

Glu Leu Ala Glu Asn Arg Glu Ile Leu Lys Glu Pro Val His
1               5                   10

<210> SEQ ID NO 209
<211> LENGTH: 13
<212> TYPE: PRT
<213> ORGANISM: Human immunodeficiency virus

<400> SEQUENCE: 209

Arg Glu Ile Leu Lys Glu Pro Val His Gly Val Tyr Tyr
1               5                   10

<210> SEQ ID NO 210
<211> LENGTH: 15
<212> TYPE: PRT
<213> ORGANISM: Human immunodeficiency virus

<400> SEQUENCE: 210

Lys Glu Pro Val His Gly Val Tyr Tyr Asp Pro Ser Lys Asp Leu
1               5                   10                  15

<210> SEQ ID NO 211
<211> LENGTH: 15
```

```
<212> TYPE: PRT
<213> ORGANISM: Human immunodeficiency virus

<400> SEQUENCE: 211

Val Tyr Tyr Asp Pro Ser Lys Asp Leu Ile Ala Glu Ile Gln Lys
1               5                   10                  15

<210> SEQ ID NO 212
<211> LENGTH: 15
<212> TYPE: PRT
<213> ORGANISM: Human immunodeficiency virus

<400> SEQUENCE: 212

Lys Asp Leu Ile Ala Glu Ile Gln Lys Gln Gly Gln Gly Gln Trp
1               5                   10                  15

<210> SEQ ID NO 213
<211> LENGTH: 14
<212> TYPE: PRT
<213> ORGANISM: Human immunodeficiency virus

<400> SEQUENCE: 213

Ile Gln Lys Gln Gly Gln Gly Gln Trp Thr Tyr Gln Ile Tyr
1               5                   10

<210> SEQ ID NO 214
<211> LENGTH: 15
<212> TYPE: PRT
<213> ORGANISM: Human immunodeficiency virus

<400> SEQUENCE: 214

Gly Gln Gly Gln Trp Thr Tyr Gln Ile Tyr Gln Glu Pro Phe Lys
1               5                   10                  15

<210> SEQ ID NO 215
<211> LENGTH: 15
<212> TYPE: PRT
<213> ORGANISM: Human immunodeficiency virus

<400> SEQUENCE: 215

Tyr Gln Ile Tyr Gln Glu Pro Phe Lys Asn Leu Lys Thr Gly Lys
1               5                   10                  15

<210> SEQ ID NO 216
<211> LENGTH: 14
<212> TYPE: PRT
<213> ORGANISM: Human immunodeficiency virus

<400> SEQUENCE: 216

Pro Phe Lys Asn Leu Lys Thr Gly Lys Tyr Ala Arg Met Arg
1               5                   10

<210> SEQ ID NO 217
<211> LENGTH: 12
<212> TYPE: PRT
<213> ORGANISM: Human immunodeficiency virus

<400> SEQUENCE: 217

Lys Thr Gly Lys Tyr Ala Arg Met Arg Gly Ala His
1               5                   10

<210> SEQ ID NO 218
<211> LENGTH: 14
<212> TYPE: PRT
<213> ORGANISM: Human immunodeficiency virus
```

<400> SEQUENCE: 218

Lys Tyr Ala Arg Met Arg Gly Ala His Thr Asn Asp Val Lys
1               5                   10

<210> SEQ ID NO 219
<211> LENGTH: 15
<212> TYPE: PRT
<213> ORGANISM: Human immunodeficiency virus

<400> SEQUENCE: 219

Arg Gly Ala His Thr Asn Asp Val Lys Gln Leu Thr Glu Ala Val
1               5                   10                  15

<210> SEQ ID NO 220
<211> LENGTH: 13
<212> TYPE: PRT
<213> ORGANISM: Human immunodeficiency virus

<400> SEQUENCE: 220

Asp Val Lys Gln Leu Thr Glu Ala Val Gln Lys Ile Val
1               5                   10

<210> SEQ ID NO 221
<211> LENGTH: 15
<212> TYPE: PRT
<213> ORGANISM: Human immunodeficiency virus

<400> SEQUENCE: 221

Leu Thr Glu Ala Val Gln Lys Ile Val Thr Glu Ser Ile Val Ile
1               5                   10                  15

<210> SEQ ID NO 222
<211> LENGTH: 15
<212> TYPE: PRT
<213> ORGANISM: Human immunodeficiency virus

<400> SEQUENCE: 222

Lys Ile Val Thr Glu Ser Ile Val Ile Trp Gly Lys Thr Pro Lys
1               5                   10                  15

<210> SEQ ID NO 223
<211> LENGTH: 14
<212> TYPE: PRT
<213> ORGANISM: Human immunodeficiency virus

<400> SEQUENCE: 223

Ile Val Ile Trp Gly Lys Thr Pro Lys Phe Lys Leu Pro Ile
1               5                   10

<210> SEQ ID NO 224
<211> LENGTH: 14
<212> TYPE: PRT
<213> ORGANISM: Human immunodeficiency virus

<400> SEQUENCE: 224

Lys Thr Pro Lys Phe Lys Leu Pro Ile Gln Lys Glu Thr Trp
1               5                   10

<210> SEQ ID NO 225
<211> LENGTH: 13
<212> TYPE: PRT
<213> ORGANISM: Human immunodeficiency virus

<400> SEQUENCE: 225

```
Lys Leu Pro Ile Gln Lys Glu Thr Trp Glu Ala Trp Trp
1               5                   10
```

<210> SEQ ID NO 226
<211> LENGTH: 14
<212> TYPE: PRT
<213> ORGANISM: Human immunodeficiency virus

<400> SEQUENCE: 226

```
Ile Gln Lys Glu Thr Trp Glu Ala Trp Trp Thr Glu Tyr Trp
1               5                   10
```

<210> SEQ ID NO 227
<211> LENGTH: 14
<212> TYPE: PRT
<213> ORGANISM: Human immunodeficiency virus

<400> SEQUENCE: 227

```
Trp Glu Ala Trp Trp Thr Glu Tyr Trp Gln Ala Thr Trp Ile
1               5                   10
```

<210> SEQ ID NO 228
<211> LENGTH: 15
<212> TYPE: PRT
<213> ORGANISM: Human immunodeficiency virus

<400> SEQUENCE: 228

```
Thr Glu Tyr Trp Gln Ala Thr Trp Ile Pro Glu Trp Glu Leu Val
1               5                   10                  15
```

<210> SEQ ID NO 229
<211> LENGTH: 15
<212> TYPE: PRT
<213> ORGANISM: Human immunodeficiency virus

<400> SEQUENCE: 229

```
Thr Trp Ile Pro Glu Trp Glu Leu Val Asn Thr Pro Pro Leu Val
1               5                   10                  15
```

<210> SEQ ID NO 230
<211> LENGTH: 15
<212> TYPE: PRT
<213> ORGANISM: Human immunodeficiency virus

<400> SEQUENCE: 230

```
Glu Leu Val Asn Thr Pro Pro Leu Val Lys Leu Trp Tyr Gln Leu
1               5                   10                  15
```

<210> SEQ ID NO 231
<211> LENGTH: 14
<212> TYPE: PRT
<213> ORGANISM: Human immunodeficiency virus

<400> SEQUENCE: 231

```
Pro Leu Val Lys Leu Trp Tyr Gln Leu Glu Lys Glu Pro Ile
1               5                   10
```

<210> SEQ ID NO 232
<211> LENGTH: 15
<212> TYPE: PRT
<213> ORGANISM: Human immunodeficiency virus

<400> SEQUENCE: 232

```
Trp Tyr Gln Leu Glu Lys Glu Pro Ile Glu Gly Ala Glu Thr Phe
```

-continued

```
1               5                   10                  15

<210> SEQ ID NO 233
<211> LENGTH: 15
<212> TYPE: PRT
<213> ORGANISM: Human immunodeficiency virus

<400> SEQUENCE: 233

Glu Pro Ile Glu Gly Ala Glu Thr Phe Tyr Val Asp Gly Ala Ala
1               5                   10                  15

<210> SEQ ID NO 234
<211> LENGTH: 15
<212> TYPE: PRT
<213> ORGANISM: Human immunodeficiency virus

<400> SEQUENCE: 234

Glu Thr Phe Tyr Val Asp Gly Ala Ala Asn Arg Glu Thr Lys Leu
1               5                   10                  15

<210> SEQ ID NO 235
<211> LENGTH: 15
<212> TYPE: PRT
<213> ORGANISM: Human immunodeficiency virus

<400> SEQUENCE: 235

Gly Ala Ala Asn Arg Glu Thr Lys Leu Gly Lys Ala Gly Tyr Val
1               5                   10                  15

<210> SEQ ID NO 236
<211> LENGTH: 14
<212> TYPE: PRT
<213> ORGANISM: Human immunodeficiency virus

<400> SEQUENCE: 236

Thr Lys Leu Gly Lys Ala Gly Tyr Val Thr Asn Arg Gly Arg
1               5                   10

<210> SEQ ID NO 237
<211> LENGTH: 15
<212> TYPE: PRT
<213> ORGANISM: Human immunodeficiency virus

<400> SEQUENCE: 237

Ala Gly Tyr Val Thr Asn Arg Gly Arg Gln Lys Val Val Pro Leu
1               5                   10                  15

<210> SEQ ID NO 238
<211> LENGTH: 12
<212> TYPE: PRT
<213> ORGANISM: Human immunodeficiency virus

<400> SEQUENCE: 238

Arg Gly Arg Gln Lys Val Val Pro Leu Thr Asp Ala
1               5                   10

<210> SEQ ID NO 239
<211> LENGTH: 14
<212> TYPE: PRT
<213> ORGANISM: Human immunodeficiency virus

<400> SEQUENCE: 239

Arg Gln Lys Val Val Pro Leu Thr Asp Ala Thr Asn Gln Lys
1               5                   10
```

<210> SEQ ID NO 240
<211> LENGTH: 15
<212> TYPE: PRT
<213> ORGANISM: Human immunodeficiency virus

<400> SEQUENCE: 240

Pro Leu Thr Asp Ala Thr Asn Gln Lys Thr Glu Leu Glu Ala Ile
1               5                   10                  15

<210> SEQ ID NO 241
<211> LENGTH: 13
<212> TYPE: PRT
<213> ORGANISM: Human immunodeficiency virus

<400> SEQUENCE: 241

Asn Gln Lys Thr Glu Leu Glu Ala Ile His Leu Ala Leu
1               5                   10

<210> SEQ ID NO 242
<211> LENGTH: 14
<212> TYPE: PRT
<213> ORGANISM: Human immunodeficiency virus

<400> SEQUENCE: 242

Glu Leu Glu Ala Ile His Leu Ala Leu Gln Asp Ser Gly Leu
1               5                   10

<210> SEQ ID NO 243
<211> LENGTH: 14
<212> TYPE: PRT
<213> ORGANISM: Human immunodeficiency virus

<400> SEQUENCE: 243

His Leu Ala Leu Gln Asp Ser Gly Leu Glu Val Asn Ile Val
1               5                   10

<210> SEQ ID NO 244
<211> LENGTH: 15
<212> TYPE: PRT
<213> ORGANISM: Human immunodeficiency virus

<400> SEQUENCE: 244

Asp Ser Gly Leu Glu Val Asn Ile Val Thr Asp Ser Gln Tyr Ala
1               5                   10                  15

<210> SEQ ID NO 245
<211> LENGTH: 15
<212> TYPE: PRT
<213> ORGANISM: Human immunodeficiency virus

<400> SEQUENCE: 245

Asn Ile Val Thr Asp Ser Gln Tyr Ala Leu Gly Ile Ile Gln Ala
1               5                   10                  15

<210> SEQ ID NO 246
<211> LENGTH: 14
<212> TYPE: PRT
<213> ORGANISM: Human immunodeficiency virus

<400> SEQUENCE: 246

Ser Gln Tyr Ala Leu Gly Ile Ile Gln Ala Gln Pro Asp Lys
1               5                   10

<210> SEQ ID NO 247

-continued

```
<211> LENGTH: 15
<212> TYPE: PRT
<213> ORGANISM: Human immunodeficiency virus

<400> SEQUENCE: 247

Gly Ile Ile Gln Ala Gln Pro Asp Lys Ser Glu Ser Glu Leu Val
1               5                   10                  15

<210> SEQ ID NO 248
<211> LENGTH: 13
<212> TYPE: PRT
<213> ORGANISM: Human immunodeficiency virus

<400> SEQUENCE: 248

Pro Asp Lys Ser Glu Ser Glu Leu Val Ser Gln Ile Ile
1               5                   10

<210> SEQ ID NO 249
<211> LENGTH: 15
<212> TYPE: PRT
<213> ORGANISM: Human immunodeficiency virus

<400> SEQUENCE: 249

Glu Ser Glu Leu Val Ser Gln Ile Ile Glu Gln Leu Ile Lys Lys
1               5                   10                  15

<210> SEQ ID NO 250
<211> LENGTH: 15
<212> TYPE: PRT
<213> ORGANISM: Human immunodeficiency virus

<400> SEQUENCE: 250

Ser Gln Ile Ile Glu Gln Leu Ile Lys Lys Glu Lys Val Tyr Leu
1               5                   10                  15

<210> SEQ ID NO 251
<211> LENGTH: 15
<212> TYPE: PRT
<213> ORGANISM: Human immunodeficiency virus

<400> SEQUENCE: 251

Leu Ile Lys Lys Glu Lys Val Tyr Leu Ala Trp Val Pro Ala His
1               5                   10                  15

<210> SEQ ID NO 252
<211> LENGTH: 12
<212> TYPE: PRT
<213> ORGANISM: Human immunodeficiency virus

<400> SEQUENCE: 252

Val Tyr Leu Ala Trp Val Pro Ala His Lys Gly Ile
1               5                   10

<210> SEQ ID NO 253
<211> LENGTH: 15
<212> TYPE: PRT
<213> ORGANISM: Human immunodeficiency virus

<400> SEQUENCE: 253

Ala Trp Val Pro Ala His Lys Gly Ile Gly Gly Asn Glu Gln Val
1               5                   10                  15

<210> SEQ ID NO 254
<211> LENGTH: 13
<212> TYPE: PRT
```

```
<213> ORGANISM: Human immunodeficiency virus

<400> SEQUENCE: 254

Lys Gly Ile Gly Gly Asn Glu Gln Val Asp Lys Leu Val
1               5                   10

<210> SEQ ID NO 255
<211> LENGTH: 15
<212> TYPE: PRT
<213> ORGANISM: Human immunodeficiency virus

<400> SEQUENCE: 255

Gly Asn Glu Gln Val Asp Lys Leu Val Ser Ser Gly Ile Arg Lys
1               5                   10                  15

<210> SEQ ID NO 256
<211> LENGTH: 11
<212> TYPE: PRT
<213> ORGANISM: Human immunodeficiency virus

<400> SEQUENCE: 256

Lys Leu Val Ser Ser Gly Ile Arg Lys Val Leu
1               5                   10

<210> SEQ ID NO 257
<211> LENGTH: 12
<212> TYPE: PRT
<213> ORGANISM: Feline immunodeficiency virus

<400> SEQUENCE: 257

Val Gln Leu Trp Phe Thr Ala Phe Ser Ala Asn Leu
1               5                   10

<210> SEQ ID NO 258
<211> LENGTH: 14
<212> TYPE: PRT
<213> ORGANISM: Feline immunodeficiency virus

<400> SEQUENCE: 258

Pro Ile Gln Thr Val Asn Gly Ala Pro Gln Tyr Val Ala Leu
1               5                   10

<210> SEQ ID NO 259
<211> LENGTH: 15
<212> TYPE: PRT
<213> ORGANISM: Feline immunodeficiency virus

<400> SEQUENCE: 259

Thr Val Asn Gly Ala Pro Gln Tyr Val Ala Leu Asp Pro Lys Met
1               5                   10                  15

<210> SEQ ID NO 260
<211> LENGTH: 15
<212> TYPE: PRT
<213> ORGANISM: Feline immunodeficiency virus

<400> SEQUENCE: 260

Ala Pro Gln Tyr Val Ala Leu Asp Pro Lys Met Val Ser Ile Phe
1               5                   10                  15

<210> SEQ ID NO 261
<211> LENGTH: 15
<212> TYPE: PRT
<213> ORGANISM: Feline immunodeficiency virus
```

-continued

<400> SEQUENCE: 261

Val Ala Leu Asp Pro Lys Met Val Ser Ile Phe Met Glu Lys Ala
1               5                   10                  15

<210> SEQ ID NO 262
<211> LENGTH: 15
<212> TYPE: PRT
<213> ORGANISM: Feline immunodeficiency virus

<400> SEQUENCE: 262

Pro Lys Met Val Ser Ile Phe Met Glu Lys Ala Arg Glu Gly Leu
1               5                   10                  15

<210> SEQ ID NO 263
<211> LENGTH: 16
<212> TYPE: PRT
<213> ORGANISM: Feline immunodeficiency virus

<400> SEQUENCE: 263

Ser Ile Phe Met Glu Lys Ala Arg Glu Gly Leu Gly Gly Glu Glu Val
1               5                   10                  15

<210> SEQ ID NO 264
<211> LENGTH: 15
<212> TYPE: PRT
<213> ORGANISM: Feline immunodeficiency virus

<400> SEQUENCE: 264

Ile Phe Met Glu Lys Ala Arg Glu Gly Leu Gly Gly Glu Glu Val
1               5                   10                  15

<210> SEQ ID NO 265
<211> LENGTH: 15
<212> TYPE: PRT
<213> ORGANISM: Feline immunodeficiency virus

<400> SEQUENCE: 265

Lys Ala Arg Glu Gly Leu Gly Gly Glu Glu Val Gln Leu Trp Phe
1               5                   10                  15

<210> SEQ ID NO 266
<211> LENGTH: 14
<212> TYPE: PRT
<213> ORGANISM: Feline immunodeficiency virus

<400> SEQUENCE: 266

Gly Leu Gly Gly Glu Glu Val Gln Leu Trp Phe Thr Ala Phe
1               5                   10

<210> SEQ ID NO 267
<211> LENGTH: 15
<212> TYPE: PRT
<213> ORGANISM: Feline immunodeficiency virus

<400> SEQUENCE: 267

Gly Glu Glu Val Gln Leu Trp Phe Thr Ala Phe Ser Ala Asn Leu
1               5                   10                  15

<210> SEQ ID NO 268
<211> LENGTH: 15
<212> TYPE: PRT
<213> ORGANISM: Feline immunodeficiency virus

<400> SEQUENCE: 268

```
Leu Trp Phe Thr Ala Phe Ser Ala Asn Leu Thr Pro Thr Asp Met
1               5                   10                  15

<210> SEQ ID NO 269
<211> LENGTH: 15
<212> TYPE: PRT
<213> ORGANISM: Feline immunodeficiency virus

<400> SEQUENCE: 269

Ala Phe Ser Ala Asn Leu Thr Pro Thr Asp Met Ala Thr Leu Ile
1               5                   10                  15

<210> SEQ ID NO 270
<211> LENGTH: 14
<212> TYPE: PRT
<213> ORGANISM: Feline immunodeficiency virus

<400> SEQUENCE: 270

Asn Leu Thr Pro Thr Asp Met Ala Thr Leu Ile Met Ala Ala
1               5                   10

<210> SEQ ID NO 271
<211> LENGTH: 15
<212> TYPE: PRT
<213> ORGANISM: Feline immunodeficiency virus

<400> SEQUENCE: 271

Pro Thr Asp Met Ala Thr Leu Ile Met Ala Ala Pro Gly Cys Ala
1               5                   10                  15

<210> SEQ ID NO 272
<211> LENGTH: 14
<212> TYPE: PRT
<213> ORGANISM: Feline immunodeficiency virus

<400> SEQUENCE: 272

Ala Thr Leu Ile Met Ala Ala Pro Gly Cys Ala Ala Asp Lys
1               5                   10

<210> SEQ ID NO 273
<211> LENGTH: 14
<212> TYPE: PRT
<213> ORGANISM: Feline immunodeficiency virus

<400> SEQUENCE: 273

Ile Met Ala Ala Pro Gly Cys Ala Ala Asp Lys Glu Ile Leu
1               5                   10

<210> SEQ ID NO 274
<211> LENGTH: 15
<212> TYPE: PRT
<213> ORGANISM: Feline immunodeficiency virus

<400> SEQUENCE: 274

Ala Pro Gly Cys Ala Ala Asp Lys Glu Ile Leu Asp Glu Ser Leu
1               5                   10                  15

<210> SEQ ID NO 275
<211> LENGTH: 14
<212> TYPE: PRT
<213> ORGANISM: Feline immunodeficiency virus

<400> SEQUENCE: 275

Ala Ala Asp Lys Glu Ile Leu Asp Glu Ser Leu Lys Gln Leu
1               5                   10
```

<210> SEQ ID NO 276
<211> LENGTH: 15
<212> TYPE: PRT
<213> ORGANISM: Feline immunodeficiency virus

<400> SEQUENCE: 276

Lys Glu Ile Leu Asp Glu Ser Leu Lys Gln Leu Thr Ala Glu Tyr
1               5                   10                  15

<210> SEQ ID NO 277
<211> LENGTH: 15
<212> TYPE: PRT
<213> ORGANISM: Feline immunodeficiency virus

<400> SEQUENCE: 277

Asp Glu Ser Leu Lys Gln Leu Thr Ala Glu Tyr Asp Arg Thr His
1               5                   10                  15

<210> SEQ ID NO 278
<211> LENGTH: 17
<212> TYPE: PRT
<213> ORGANISM: Feline immunodeficiency virus

<400> SEQUENCE: 278

Lys Gln Leu Thr Ala Glu Tyr Asp Arg Thr His Pro Pro Asp Gly Pro
1               5                   10                  15

Arg

<210> SEQ ID NO 279
<211> LENGTH: 15
<212> TYPE: PRT
<213> ORGANISM: Feline immunodeficiency virus

<400> SEQUENCE: 279

Tyr Asp Arg Thr His Pro Pro Asp Gly Pro Arg Pro Leu Pro Tyr
1               5                   10                  15

<210> SEQ ID NO 280
<211> LENGTH: 15
<212> TYPE: PRT
<213> ORGANISM: Feline immunodeficiency virus

<400> SEQUENCE: 280

His Pro Pro Asp Gly Pro Arg Pro Leu Pro Tyr Phe Thr Ala Ala
1               5                   10                  15

<210> SEQ ID NO 281
<211> LENGTH: 14
<212> TYPE: PRT
<213> ORGANISM: Feline immunodeficiency virus

<400> SEQUENCE: 281

Gly Pro Arg Pro Leu Pro Tyr Phe Thr Ala Ala Glu Ile Met
1               5                   10

<210> SEQ ID NO 282
<211> LENGTH: 15
<212> TYPE: PRT
<213> ORGANISM: Feline immunodeficiency virus

<400> SEQUENCE: 282

Pro Leu Pro Tyr Phe Thr Ala Ala Glu Ile Met Gly Ile Gly Leu
1               5                   10                  15

<210> SEQ ID NO 283
<211> LENGTH: 17
<212> TYPE: PRT
<213> ORGANISM: Feline immunodeficiency virus

<400> SEQUENCE: 283

Phe Thr Ala Ala Glu Ile Met Gly Ile Gly Leu Thr Gln Glu Gln Gln
1               5                   10                  15

Ala

<210> SEQ ID NO 284
<211> LENGTH: 15
<212> TYPE: PRT
<213> ORGANISM: Feline immunodeficiency virus

<400> SEQUENCE: 284

Met Gly Ile Gly Leu Thr Gln Glu Gln Gln Ala Glu Ala Arg Phe
1               5                   10                  15

<210> SEQ ID NO 285
<211> LENGTH: 15
<212> TYPE: PRT
<213> ORGANISM: Feline immunodeficiency virus

<400> SEQUENCE: 285

Leu Thr Gln Glu Gln Gln Ala Glu Ala Arg Phe Ala Pro Ala Arg
1               5                   10                  15

<210> SEQ ID NO 286
<211> LENGTH: 13
<212> TYPE: PRT
<213> ORGANISM: Feline immunodeficiency virus

<400> SEQUENCE: 286

Glu Gln Gln Ala Glu Ala Arg Phe Ala Pro Ala Arg Met
1               5                   10

<210> SEQ ID NO 287
<211> LENGTH: 15
<212> TYPE: PRT
<213> ORGANISM: Feline immunodeficiency virus

<400> SEQUENCE: 287

Ala Glu Ala Arg Phe Ala Pro Ala Arg Met Gln Cys Arg Ala Trp
1               5                   10                  15

<210> SEQ ID NO 288
<211> LENGTH: 15
<212> TYPE: PRT
<213> ORGANISM: Feline immunodeficiency virus

<400> SEQUENCE: 288

Phe Ala Pro Ala Arg Met Gln Cys Arg Ala Trp Tyr Leu Glu Ala
1               5                   10                  15

<210> SEQ ID NO 289
<211> LENGTH: 15
<212> TYPE: PRT
<213> ORGANISM: Feline immunodeficiency virus

<400> SEQUENCE: 289

Arg Met Gln Cys Arg Ala Trp Tyr Leu Glu Ala Leu Gly Lys Leu
1               5                   10                  15

<210> SEQ ID NO 290
<211> LENGTH: 15
<212> TYPE: PRT
<213> ORGANISM: Feline immunodeficiency virus

<400> SEQUENCE: 290

Arg Ala Trp Tyr Leu Glu Ala Leu Gly Lys Leu Ala Ala Ile Lys
1               5                   10                  15

<210> SEQ ID NO 291
<211> LENGTH: 13
<212> TYPE: PRT
<213> ORGANISM: Feline immunodeficiency virus

<400> SEQUENCE: 291

Leu Glu Ala Leu Gly Lys Leu Ala Ala Ile Lys Ala Lys
1               5                   10

<210> SEQ ID NO 292
<211> LENGTH: 15
<212> TYPE: PRT
<213> ORGANISM: Feline immunodeficiency virus

<400> SEQUENCE: 292

Ala Leu Gly Lys Leu Ala Ala Ile Lys Ala Lys Ser Pro Arg Ala
1               5                   10                  15

<210> SEQ ID NO 293
<211> LENGTH: 15
<212> TYPE: PRT
<213> ORGANISM: Feline immunodeficiency virus

<400> SEQUENCE: 293

Leu Ala Ala Ile Lys Ala Lys Ser Pro Arg Ala Val Gln Leu Arg
1               5                   10                  15

<210> SEQ ID NO 294
<211> LENGTH: 15
<212> TYPE: PRT
<213> ORGANISM: Feline immunodeficiency virus

<400> SEQUENCE: 294

Lys Ala Lys Ser Pro Arg Ala Val Gln Leu Arg Gln Gly Ala Lys
1               5                   10                  15

<210> SEQ ID NO 295
<211> LENGTH: 14
<212> TYPE: PRT
<213> ORGANISM: Feline immunodeficiency virus

<400> SEQUENCE: 295

Pro Arg Ala Val Gln Leu Arg Gln Gly Ala Lys Glu Asp Tyr
1               5                   10

<210> SEQ ID NO 296
<211> LENGTH: 15
<212> TYPE: PRT
<213> ORGANISM: Feline immunodeficiency virus

<400> SEQUENCE: 296

Val Gln Leu Arg Gln Gly Ala Lys Glu Asp Tyr Ser Ser Phe Ile
1               5                   10                  15

<210> SEQ ID NO 297
<211> LENGTH: 15
<212> TYPE: PRT
<213> ORGANISM: Feline immunodeficiency virus

<400> SEQUENCE: 297

Arg Gln Gly Ala Lys Glu Asp Tyr Ser Ser Phe Ile Asp Arg Leu
1               5                   10                  15

<210> SEQ ID NO 298
<211> LENGTH: 15
<212> TYPE: PRT
<213> ORGANISM: Feline immunodeficiency virus

<400> SEQUENCE: 298

Lys Glu Asp Tyr Ser Ser Phe Ile Asp Arg Leu Phe Ala Gln Ile
1               5                   10                  15

<210> SEQ ID NO 299
<211> LENGTH: 14
<212> TYPE: PRT
<213> ORGANISM: Feline immunodeficiency virus

<400> SEQUENCE: 299

Asp Arg Leu Phe Ala Gln Ile Asp Gln Glu Gln Asn Thr Ala
1               5                   10

<210> SEQ ID NO 300
<211> LENGTH: 15
<212> TYPE: PRT
<213> ORGANISM: Feline immunodeficiency virus

<400> SEQUENCE: 300

Phe Ala Gln Ile Asp Gln Glu Gln Asn Thr Ala Glu Val Lys Leu
1               5                   10                  15

<210> SEQ ID NO 301
<211> LENGTH: 14
<212> TYPE: PRT
<213> ORGANISM: Feline immunodeficiency virus

<400> SEQUENCE: 301

Asp Gln Glu Gln Asn Thr Ala Glu Val Lys Leu Tyr Leu Lys
1               5                   10

<210> SEQ ID NO 302
<211> LENGTH: 15
<212> TYPE: PRT
<213> ORGANISM: Feline immunodeficiency virus

<400> SEQUENCE: 302

Glu Gln Asn Thr Ala Glu Val Lys Leu Tyr Leu Lys Gln Ser Leu
1               5                   10                  15

<210> SEQ ID NO 303
<211> LENGTH: 14
<212> TYPE: PRT
<213> ORGANISM: Feline immunodeficiency virus

<400> SEQUENCE: 303

Ala Glu Val Lys Leu Tyr Leu Lys Gln Ser Leu Ser Ile Ala
1               5                   10

<210> SEQ ID NO 304
<211> LENGTH: 13

<210> SEQ ID NO 304
<211> LENGTH: 11 (not shown; inferred)
<212> TYPE: PRT
<213> ORGANISM: Feline immunodeficiency virus

<400> SEQUENCE: 304

Lys Leu Tyr Leu Lys Gln Ser Leu Ser Ile Ala Asn Ala
1               5                   10

<210> SEQ ID NO 305
<211> LENGTH: 16
<212> TYPE: PRT
<213> ORGANISM: Feline immunodeficiency virus

<400> SEQUENCE: 305

Tyr Leu Lys Gln Ser Leu Ser Ile Ala Asn Ala Asn Pro Asp Cys Lys
1               5                   10                  15

<210> SEQ ID NO 306
<211> LENGTH: 14
<212> TYPE: PRT
<213> ORGANISM: Feline immunodeficiency virus

<400> SEQUENCE: 306

Leu Ser Ile Ala Asn Ala Asn Pro Asp Cys Lys Arg Ala Met
1               5                   10

<210> SEQ ID NO 307
<211> LENGTH: 15
<212> TYPE: PRT
<213> ORGANISM: Feline immunodeficiency virus

<400> SEQUENCE: 307

Ala Asn Ala Asn Pro Asp Cys Lys Arg Ala Met Ser His Leu Lys
1               5                   10                  15

<210> SEQ ID NO 308
<211> LENGTH: 16
<212> TYPE: PRT
<213> ORGANISM: Feline immunodeficiency virus

<400> SEQUENCE: 308

Pro Asp Cys Lys Arg Ala Met Ser His Leu Lys Pro Glu Ser Thr Leu
1               5                   10                  15

<210> SEQ ID NO 309
<211> LENGTH: 15
<212> TYPE: PRT
<213> ORGANISM: Feline immunodeficiency virus

<400> SEQUENCE: 309

Ala Met Ser His Leu Lys Pro Glu Ser Thr Leu Glu Glu Lys Leu
1               5                   10                  15

<210> SEQ ID NO 310
<211> LENGTH: 13
<212> TYPE: PRT
<213> ORGANISM: Feline immunodeficiency virus

<400> SEQUENCE: 310

Leu Lys Pro Glu Ser Thr Leu Glu Glu Lys Leu Arg Ala
1               5                   10

<210> SEQ ID NO 311
<211> LENGTH: 15
<212> TYPE: PRT
<213> ORGANISM: Feline immunodeficiency virus

<400> SEQUENCE: 311

Pro Glu Ser Thr Leu Glu Glu Lys Leu Arg Ala Cys Gln Glu Val
1               5                   10                  15

<210> SEQ ID NO 312
<211> LENGTH: 16
<212> TYPE: PRT
<213> ORGANISM: Feline immunodeficiency virus

<400> SEQUENCE: 312

Leu Glu Glu Lys Leu Arg Ala Cys Gln Glu Val Gly Ser Pro Gly Tyr
1               5                   10                  15

<210> SEQ ID NO 313
<211> LENGTH: 16
<212> TYPE: PRT
<213> ORGANISM: Feline immunodeficiency virus

<400> SEQUENCE: 313

Arg Ala Cys Gln Glu Val Gly Ser Pro Gly Tyr Lys Met Gln Leu Leu
1               5                   10                  15

<210> SEQ ID NO 314
<211> LENGTH: 15
<212> TYPE: PRT
<213> ORGANISM: Human immunodeficiency virus

<400> SEQUENCE: 314

Pro Ile Val Gln Asn Leu Gln Gly Gln Met Val His Gln Ala Ile
1               5                   10                  15

<210> SEQ ID NO 315
<211> LENGTH: 15
<212> TYPE: PRT
<213> ORGANISM: Human immunodeficiency virus

<400> SEQUENCE: 315

Asn Leu Gln Gly Gln Met Val His Gln Ala Ile Ser Pro Arg Thr
1               5                   10                  15

<210> SEQ ID NO 316
<211> LENGTH: 15
<212> TYPE: PRT
<213> ORGANISM: Human immunodeficiency virus

<400> SEQUENCE: 316

Gln Met Val His Gln Ala Ile Ser Pro Arg Thr Leu Asn Ala Trp
1               5                   10                  15

<210> SEQ ID NO 317
<211> LENGTH: 15
<212> TYPE: PRT
<213> ORGANISM: Human immunodeficiency virus

<400> SEQUENCE: 317

Gln Ala Ile Ser Pro Arg Thr Leu Asn Ala Trp Val Lys Val Val
1               5                   10                  15

<210> SEQ ID NO 318
<211> LENGTH: 15
<212> TYPE: PRT
<213> ORGANISM: Human immunodeficiency virus

<400> SEQUENCE: 318

```
Pro Arg Thr Leu Asn Ala Trp Val Lys Val Val Glu Glu Lys Ala
1               5                   10                  15

<210> SEQ ID NO 319
<211> LENGTH: 15
<212> TYPE: PRT
<213> ORGANISM: Human immunodeficiency virus

<400> SEQUENCE: 319

Asn Ala Trp Val Lys Val Val Glu Glu Lys Ala Phe Ser Pro Glu
1               5                   10                  15

<210> SEQ ID NO 320
<211> LENGTH: 15
<212> TYPE: PRT
<213> ORGANISM: Human immunodeficiency virus

<400> SEQUENCE: 320

Lys Val Val Glu Glu Lys Ala Phe Ser Pro Glu Val Ile Pro Met
1               5                   10                  15

<210> SEQ ID NO 321
<211> LENGTH: 16
<212> TYPE: PRT
<213> ORGANISM: Human immunodeficiency virus

<400> SEQUENCE: 321

Lys Val Val Glu Glu Lys Ala Phe Ser Pro Glu Val Ile Pro Met His
1               5                   10                  15

<210> SEQ ID NO 322
<211> LENGTH: 15
<212> TYPE: PRT
<213> ORGANISM: Human immunodeficiency virus

<400> SEQUENCE: 322

Glu Lys Ala Phe Ser Pro Glu Val Ile Pro Met Phe Ser Ala Leu
1               5                   10                  15

<210> SEQ ID NO 323
<211> LENGTH: 15
<212> TYPE: PRT
<213> ORGANISM: Human immunodeficiency virus

<400> SEQUENCE: 323

Ser Pro Glu Val Ile Pro Met Phe Ser Ala Leu Ser Glu Gly Ala
1               5                   10                  15

<210> SEQ ID NO 324
<211> LENGTH: 15
<212> TYPE: PRT
<213> ORGANISM: Human immunodeficiency virus

<400> SEQUENCE: 324

Ile Pro Met Phe Ser Ala Leu Ser Glu Gly Ala Thr Pro Gln Asp
1               5                   10                  15

<210> SEQ ID NO 325
<211> LENGTH: 15
<212> TYPE: PRT
<213> ORGANISM: Human immunodeficiency virus

<400> SEQUENCE: 325

Ser Ala Leu Ser Glu Gly Ala Thr Pro Gln Asp Leu Asn Thr Met
```

<210> SEQ ID NO 326
<211> LENGTH: 15
<212> TYPE: PRT
<213> ORGANISM: Human immunodeficiency virus

<400> SEQUENCE: 326

Glu Gly Ala Thr Pro Gln Asp Leu Asn Thr Met Leu Asn Thr Val
1               5                   10                  15

<210> SEQ ID NO 327
<211> LENGTH: 15
<212> TYPE: PRT
<213> ORGANISM: Human immunodeficiency virus

<400> SEQUENCE: 327

Pro Gln Asp Leu Asn Thr Met Leu Asn Thr Val Gly Gly His Gln
1               5                   10                  15

<210> SEQ ID NO 328
<211> LENGTH: 15
<212> TYPE: PRT
<213> ORGANISM: Human immunodeficiency virus

<400> SEQUENCE: 328

Asn Thr Met Leu Asn Thr Val Gly Gly His Gln Ala Ala Met Gln
1               5                   10                  15

<210> SEQ ID NO 329
<211> LENGTH: 15
<212> TYPE: PRT
<213> ORGANISM: Human immunodeficiency virus

<400> SEQUENCE: 329

Asn Thr Val Gly Gly His Gln Ala Ala Met Gln Met Leu Lys Glu
1               5                   10                  15

<210> SEQ ID NO 330
<211> LENGTH: 15
<212> TYPE: PRT
<213> ORGANISM: Human immunodeficiency virus

<400> SEQUENCE: 330

Gly His Gln Ala Ala Met Gln Met Leu Lys Glu Thr Ile Asn Glu
1               5                   10                  15

<210> SEQ ID NO 331
<211> LENGTH: 15
<212> TYPE: PRT
<213> ORGANISM: Human immunodeficiency virus

<400> SEQUENCE: 331

Ala Met Gln Met Leu Lys Glu Thr Ile Asn Glu Glu Ala Ala Glu
1               5                   10                  15

<210> SEQ ID NO 332
<211> LENGTH: 15
<212> TYPE: PRT
<213> ORGANISM: Human immunodeficiency virus

<400> SEQUENCE: 332

Leu Lys Glu Thr Ile Asn Glu Glu Ala Ala Glu Trp Asp Arg Leu
1               5                   10                  15

<210> SEQ ID NO 333
<211> LENGTH: 15
<212> TYPE: PRT
<213> ORGANISM: Human immunodeficiency virus

<400> SEQUENCE: 333

Ile Asn Glu Glu Ala Ala Glu Trp Asp Arg Leu His Pro Val His
1               5                   10                  15

<210> SEQ ID NO 334
<211> LENGTH: 15
<212> TYPE: PRT
<213> ORGANISM: Human immunodeficiency virus

<400> SEQUENCE: 334

Ala Ala Glu Trp Asp Arg Leu His Pro Val His Ala Gly Pro Ile
1               5                   10                  15

<210> SEQ ID NO 335
<211> LENGTH: 15
<212> TYPE: PRT
<213> ORGANISM: Human immunodeficiency virus

<400> SEQUENCE: 335

Asp Arg Leu His Pro Val His Ala Gly Pro Ile Ala Pro Gly Gln
1               5                   10                  15

<210> SEQ ID NO 336
<211> LENGTH: 15
<212> TYPE: PRT
<213> ORGANISM: Human immunodeficiency virus

<400> SEQUENCE: 336

Pro Val His Ala Gly Pro Ile Ala Pro Gly Gln Met Arg Glu Pro
1               5                   10                  15

<210> SEQ ID NO 337
<211> LENGTH: 16
<212> TYPE: PRT
<213> ORGANISM: Human immunodeficiency virus

<400> SEQUENCE: 337

Pro Val His Ala Gly Pro Ile Ala Pro Gly Gln Met Arg Glu Pro His
1               5                   10                  15

<210> SEQ ID NO 338
<211> LENGTH: 15
<212> TYPE: PRT
<213> ORGANISM: Human immunodeficiency virus

<400> SEQUENCE: 338

Gly Pro Ile Ala Pro Gly Gln Met Arg Glu Pro Arg Gly Ser Asp
1               5                   10                  15

<210> SEQ ID NO 339
<211> LENGTH: 15
<212> TYPE: PRT
<213> ORGANISM: Human immunodeficiency virus

<400> SEQUENCE: 339

Pro Gly Gln Met Arg Glu Pro Arg Gly Ser Asp Ile Ala Gly Thr
1               5                   10                  15

<210> SEQ ID NO 340

```
<211> LENGTH: 15
<212> TYPE: PRT
<213> ORGANISM: Human immunodeficiency virus

<400> SEQUENCE: 340

Arg Glu Pro Arg Gly Ser Asp Ile Ala Gly Thr Thr Ser Thr Leu
1               5                   10                  15

<210> SEQ ID NO 341
<211> LENGTH: 15
<212> TYPE: PRT
<213> ORGANISM: Human immunodeficiency virus

<400> SEQUENCE: 341

Gly Ser Asp Ile Ala Gly Thr Thr Ser Thr Leu Gln Glu Gln Ile
1               5                   10                  15

<210> SEQ ID NO 342
<211> LENGTH: 15
<212> TYPE: PRT
<213> ORGANISM: Human immunodeficiency virus

<400> SEQUENCE: 342

Ala Gly Thr Thr Ser Thr Leu Gln Glu Gln Ile Gly Trp Met Thr
1               5                   10                  15

<210> SEQ ID NO 343
<211> LENGTH: 15
<212> TYPE: PRT
<213> ORGANISM: Human immunodeficiency virus

<400> SEQUENCE: 343

Ser Thr Leu Gln Glu Gln Ile Gly Trp Met Thr Asn Asn Pro Pro
1               5                   10                  15

<210> SEQ ID NO 344
<211> LENGTH: 15
<212> TYPE: PRT
<213> ORGANISM: Human immunodeficiency virus

<400> SEQUENCE: 344

Glu Gln Ile Gly Trp Met Thr Asn Asn Pro Pro Ile Pro Val Gly
1               5                   10                  15

<210> SEQ ID NO 345
<211> LENGTH: 15
<212> TYPE: PRT
<213> ORGANISM: Human immunodeficiency virus

<400> SEQUENCE: 345

Trp Met Thr Asn Asn Pro Pro Ile Pro Val Gly Glu Ile Tyr Lys
1               5                   10                  15

<210> SEQ ID NO 346
<211> LENGTH: 15
<212> TYPE: PRT
<213> ORGANISM: Human immunodeficiency virus

<400> SEQUENCE: 346

Asn Pro Pro Ile Pro Val Gly Glu Ile Tyr Lys Arg Trp Ile Ile
1               5                   10                  15

<210> SEQ ID NO 347
<211> LENGTH: 15
<212> TYPE: PRT
```

<213> ORGANISM: Human immunodeficiency virus

<400> SEQUENCE: 347

Pro Val Gly Glu Ile Tyr Lys Arg Trp Ile Ile Leu Gly Leu Asn
1               5                   10                  15

<210> SEQ ID NO 348
<211> LENGTH: 15
<212> TYPE: PRT
<213> ORGANISM: Human immunodeficiency virus

<400> SEQUENCE: 348

Ile Tyr Lys Arg Trp Ile Ile Leu Gly Leu Asn Lys Ile Val Arg
1               5                   10                  15

<210> SEQ ID NO 349
<211> LENGTH: 15
<212> TYPE: PRT
<213> ORGANISM: Human immunodeficiency virus

<400> SEQUENCE: 349

Trp Ile Ile Leu Gly Leu Asn Lys Ile Val Arg Met Tyr Ser Pro
1               5                   10                  15

<210> SEQ ID NO 350
<211> LENGTH: 15
<212> TYPE: PRT
<213> ORGANISM: Human immunodeficiency virus

<400> SEQUENCE: 350

Gly Leu Asn Lys Ile Val Arg Met Tyr Ser Pro Thr Ser Ile Leu
1               5                   10                  15

<210> SEQ ID NO 351
<211> LENGTH: 15
<212> TYPE: PRT
<213> ORGANISM: Human immunodeficiency virus

<400> SEQUENCE: 351

Ile Val Arg Met Tyr Ser Pro Thr Ser Ile Leu Asp Ile Arg Gln
1               5                   10                  15

<210> SEQ ID NO 352
<211> LENGTH: 15
<212> TYPE: PRT
<213> ORGANISM: Human immunodeficiency virus

<400> SEQUENCE: 352

Tyr Ser Pro Thr Ser Ile Leu Asp Ile Arg Gln Gly Pro Lys Glu
1               5                   10                  15

<210> SEQ ID NO 353
<211> LENGTH: 15
<212> TYPE: PRT
<213> ORGANISM: Human immunodeficiency virus

<400> SEQUENCE: 353

Ser Ile Leu Asp Ile Arg Gln Gly Pro Lys Glu Pro Phe Arg Asp
1               5                   10                  15

<210> SEQ ID NO 354
<211> LENGTH: 15
<212> TYPE: PRT
<213> ORGANISM: Human immunodeficiency virus -continued

<400> SEQUENCE: 354

Ile Arg Gln Gly Pro Lys Glu Pro Phe Arg Asp Tyr Val Asp Arg
1               5                   10                  15

<210> SEQ ID NO 355
<211> LENGTH: 15
<212> TYPE: PRT
<213> ORGANISM: Human immunodeficiency virus

<400> SEQUENCE: 355

Pro Lys Glu Pro Phe Arg Asp Tyr Val Asp Arg Phe Tyr Lys Thr
1               5                   10                  15

<210> SEQ ID NO 356
<211> LENGTH: 15
<212> TYPE: PRT
<213> ORGANISM: Human immunodeficiency virus

<400> SEQUENCE: 356

Phe Arg Asp Tyr Val Asp Arg Phe Tyr Lys Thr Leu Arg Ala Glu
1               5                   10                  15

<210> SEQ ID NO 357
<211> LENGTH: 15
<212> TYPE: PRT
<213> ORGANISM: Human immunodeficiency virus

<400> SEQUENCE: 357

Val Asp Arg Phe Tyr Lys Thr Leu Arg Ala Glu Gln Ala Ser Gln
1               5                   10                  15

<210> SEQ ID NO 358
<211> LENGTH: 15
<212> TYPE: PRT
<213> ORGANISM: Human immunodeficiency virus

<400> SEQUENCE: 358

Tyr Lys Thr Leu Arg Ala Glu Gln Ala Ser Gln Glu Val Lys Asn
1               5                   10                  15

<210> SEQ ID NO 359
<211> LENGTH: 15
<212> TYPE: PRT
<213> ORGANISM: Human immunodeficiency virus

<400> SEQUENCE: 359

Arg Ala Glu Gln Ala Ser Gln Glu Val Lys Asn Trp Met Thr Glu
1               5                   10                  15

<210> SEQ ID NO 360
<211> LENGTH: 15
<212> TYPE: PRT
<213> ORGANISM: Human immunodeficiency virus

<400> SEQUENCE: 360

Ala Ser Gln Glu Val Lys Asn Trp Met Thr Glu Thr Leu Leu Val
1               5                   10                  15

<210> SEQ ID NO 361
<211> LENGTH: 15
<212> TYPE: PRT
<213> ORGANISM: Human immunodeficiency virus

<400> SEQUENCE: 361

-continued

Val Lys Asn Trp Met Thr Glu Thr Leu Leu Val Gln Asn Ala Asn
1               5                   10                  15

<210> SEQ ID NO 362
<211> LENGTH: 15
<212> TYPE: PRT
<213> ORGANISM: Human immunodeficiency virus

<400> SEQUENCE: 362

Met Thr Glu Thr Leu Leu Val Gln Asn Ala Asn Pro Asp Cys Lys
1               5                   10                  15

<210> SEQ ID NO 363
<211> LENGTH: 15
<212> TYPE: PRT
<213> ORGANISM: Human immunodeficiency virus

<400> SEQUENCE: 363

Leu Leu Val Gln Asn Ala Asn Pro Asp Cys Lys Thr Ile Leu Lys
1               5                   10                  15

<210> SEQ ID NO 364
<211> LENGTH: 15
<212> TYPE: PRT
<213> ORGANISM: Human immunodeficiency virus

<400> SEQUENCE: 364

Asn Ala Asn Pro Asp Cys Lys Thr Ile Leu Lys Ala Leu Gly Pro
1               5                   10                  15

<210> SEQ ID NO 365
<211> LENGTH: 15
<212> TYPE: PRT
<213> ORGANISM: Human immunodeficiency virus

<400> SEQUENCE: 365

Asp Cys Lys Thr Ile Leu Lys Ala Leu Gly Pro Ala Ala Thr Leu
1               5                   10                  15

<210> SEQ ID NO 366
<211> LENGTH: 15
<212> TYPE: PRT
<213> ORGANISM: Human immunodeficiency virus

<400> SEQUENCE: 366

Ile Leu Lys Ala Leu Gly Pro Ala Ala Thr Leu Glu Glu Met Met
1               5                   10                  15

<210> SEQ ID NO 367
<211> LENGTH: 15
<212> TYPE: PRT
<213> ORGANISM: Human immunodeficiency virus

<400> SEQUENCE: 367

Leu Gly Pro Ala Ala Thr Leu Glu Glu Met Met Thr Ala Cys Gln
1               5                   10                  15

<210> SEQ ID NO 368
<211> LENGTH: 15
<212> TYPE: PRT
<213> ORGANISM: Human immunodeficiency virus

<400> SEQUENCE: 368

Ala Thr Leu Glu Glu Met Met Thr Ala Cys Gln Gly Val Gly Gly
1               5                   10                  15

<210> SEQ ID NO 369
<211> LENGTH: 15
<212> TYPE: PRT
<213> ORGANISM: Human immunodeficiency virus

<400> SEQUENCE: 369

Glu Met Met Thr Ala Cys Gln Gly Val Gly Gly Pro Gly His Lys
1               5                   10                  15

<210> SEQ ID NO 370
<211> LENGTH: 15
<212> TYPE: PRT
<213> ORGANISM: Human immunodeficiency virus

<400> SEQUENCE: 370

Ala Cys Gln Gly Val Gly Gly Pro Gly His Lys Ala Arg Val Leu
1               5                   10                  15

<210> SEQ ID NO 371
<211> LENGTH: 30
<212> TYPE: PRT
<213> ORGANISM: Feline immunodeficiency virus

<400> SEQUENCE: 371

Pro Ile Gln Thr Val Asn Gly Ala Pro Gln Tyr Val Ala Leu Asp Pro
1               5                   10                  15

Lys Met Val Ser Ile Phe Met Glu Lys Ala Arg Glu Gly Leu
            20                  25                  30

<210> SEQ ID NO 372
<211> LENGTH: 28
<212> TYPE: PRT
<213> ORGANISM: Feline immunodeficiency virus

<400> SEQUENCE: 372

Gln Tyr Val Ala Leu Asp Pro Lys Met Val Ser Ile Phe Met Glu Lys
1               5                   10                  15

Ala Arg Glu Gly Leu Gly Gly Glu Glu Val Gln Leu
            20                  25

<210> SEQ ID NO 373
<211> LENGTH: 26
<212> TYPE: PRT
<213> ORGANISM: Feline immunodeficiency virus

<400> SEQUENCE: 373

Glu Val Gln Leu Trp Phe Thr Ala Phe Ser Ala Asn Leu Thr Pro Thr
1               5                   10                  15

Asp Met Ala Thr Leu Ile Met Ala Ala Pro
            20                  25

<210> SEQ ID NO 374
<211> LENGTH: 29
<212> TYPE: PRT
<213> ORGANISM: Feline immunodeficiency virus

<400> SEQUENCE: 374

Thr Leu Ile Met Ala Ala Pro Gly Cys Ala Ala Asp Lys Glu Ile Leu
1               5                   10                  15

Asp Glu Ser Leu Lys Gln Leu Thr Ala Glu Tyr Asp Arg
            20                  25

<210> SEQ ID NO 375
<211> LENGTH: 30
<212> TYPE: PRT
<213> ORGANISM: Feline immunodeficiency virus

<400> SEQUENCE: 375

Ser Leu Lys Gln Leu Thr Ala Glu Tyr Asp Arg Thr His Pro Pro Asp
1               5                   10                  15

Gly Pro Arg Pro Leu Pro Tyr Phe Thr Ala Ala Glu Ile Met
            20                  25                  30

<210> SEQ ID NO 376
<211> LENGTH: 30
<212> TYPE: PRT
<213> ORGANISM: Feline immunodeficiency virus

<400> SEQUENCE: 376

Pro Leu Pro Tyr Phe Thr Ala Ala Glu Ile Met Gly Ile Gly Leu Thr
1               5                   10                  15

Gln Glu Gln Gln Ala Glu Ala Arg Phe Ala Pro Ala Arg Met
            20                  25                  30

<210> SEQ ID NO 377
<211> LENGTH: 30
<212> TYPE: PRT
<213> ORGANISM: Feline immunodeficiency virus

<400> SEQUENCE: 377

Glu Gln Gln Ala Glu Ala Arg Phe Ala Pro Ala Arg Met Gln Cys Arg
1               5                   10                  15

Ala Trp Tyr Leu Glu Ala Leu Gly Lys Leu Ala Ala Ile Lys
            20                  25                  30

<210> SEQ ID NO 378
<211> LENGTH: 28
<212> TYPE: PRT
<213> ORGANISM: Feline immunodeficiency virus

<400> SEQUENCE: 378

Leu Glu Ala Leu Gly Lys Leu Ala Ala Ile Lys Ala Lys Ser Pro Arg
1               5                   10                  15

Ala Val Gln Leu Arg Gln Gly Ala Lys Glu Asp Tyr
            20                  25

<210> SEQ ID NO 379
<211> LENGTH: 29
<212> TYPE: PRT
<213> ORGANISM: Feline immunodeficiency virus

<400> SEQUENCE: 379

Val Gln Leu Arg Gln Gly Ala Lys Glu Asp Tyr Ser Ser Phe Ile Asp
1               5                   10                  15

Arg Leu Phe Ala Gln Ile Asp Gln Glu Gln Asn Thr Ala
            20                  25

<210> SEQ ID NO 380
<211> LENGTH: 28
<212> TYPE: PRT
<213> ORGANISM: Feline immunodeficiency virus

<400> SEQUENCE: 380

Phe Ala Gln Ile Asp Gln Glu Gln Asn Thr Ala Glu Val Lys Leu Tyr

```
                1               5                   10                  15
Leu Lys Gln Ser Leu Ser Ile Ala Asn Ala Asn Ala
                20                  25

<210> SEQ ID NO 381
<211> LENGTH: 30
<212> TYPE: PRT
<213> ORGANISM: Feline immunodeficiency virus

<400> SEQUENCE: 381

Lys Gln Ser Leu Ser Ile Ala Asn Ala Asn Ala Glu Cys Lys Lys Ala
1               5                   10                  15

Met Ser His Leu Lys Pro Glu Ser Thr Leu Glu Glu Lys Leu
                20                  25                  30

<210> SEQ ID NO 382
<211> LENGTH: 27
<212> TYPE: PRT
<213> ORGANISM: Feline immunodeficiency virus

<400> SEQUENCE: 382

Leu Lys Pro Glu Ser Thr Leu Glu Glu Lys Leu Arg Ala Cys Gln Glu
1               5                   10                  15

Val Gly Ser Pro Gly Tyr Lys Met Gln Leu Leu
                20                  25

<210> SEQ ID NO 383
<211> LENGTH: 31
<212> TYPE: PRT
<213> ORGANISM: Feline immunodeficiency virus

<400> SEQUENCE: 383

Phe Ala Gln Ile Asp Gln Glu Gln Asn Thr Ala Glu Val Lys Leu Tyr
1               5                   10                  15

Leu Lys Gln Ser Leu Ser Ile Ala Asn Ala Asn Pro Asp Cys Lys
                20                  25                  30

<210> SEQ ID NO 384
<211> LENGTH: 29
<212> TYPE: PRT
<213> ORGANISM: Feline immunodeficiency virus

<400> SEQUENCE: 384

Leu Ser Ile Ala Asn Ala Asn Pro Asp Cys Lys Arg Ala Met Ser His
1               5                   10                  15

Leu Lys Pro Glu Ser Thr Leu Glu Glu Lys Leu Arg Ala
                20                  25

<210> SEQ ID NO 385
<211> LENGTH: 28
<212> TYPE: PRT
<213> ORGANISM: Feline immunodeficiency virus

<400> SEQUENCE: 385

Pro Gln Tyr Val Ala Leu Asp Pro Lys Met Val Ser Ile Phe Met Glu
1               5                   10                  15

Lys Ala Arg Glu Gly Leu Gly Gly Glu Glu Val Gln
                20                  25

<210> SEQ ID NO 386
<211> LENGTH: 30
<212> TYPE: PRT
```

```
<213> ORGANISM: Feline immunodeficiency virus

<400> SEQUENCE: 386

Ile Phe Met Glu Lys Ala Arg Glu Gly Leu Gly Gly Glu Glu Val Gln
1               5                   10                  15

Leu Trp Phe Thr Ala Phe Ser Ala Asn Leu Thr Pro Thr Asp
            20                  25                  30

<210> SEQ ID NO 387
<211> LENGTH: 28
<212> TYPE: PRT
<213> ORGANISM: Feline immunodeficiency virus

<400> SEQUENCE: 387

Lys Ala Arg Glu Gly Leu Gly Gly Glu Glu Val Gln Leu Trp Phe Thr
1               5                   10                  15

Ala Phe Ser Ala Asn Leu Thr Pro Thr Asp Met Ala
            20                  25

<210> SEQ ID NO 388
<211> LENGTH: 30
<212> TYPE: PRT
<213> ORGANISM: Feline immunodeficiency virus

<400> SEQUENCE: 388

Asn Leu Thr Ser Thr Asp Met Ala Thr Leu Ile Met Ser Ala Pro Gly
1               5                   10                  15

Cys Ala Ala Asp Lys Glu Ile Leu Asp Glu Thr Leu Lys Gln
            20                  25                  30

<210> SEQ ID NO 389
<211> LENGTH: 30
<212> TYPE: PRT
<213> ORGANISM: Feline immunodeficiency virus

<400> SEQUENCE: 389

Thr Leu Ile Met Ala Ala Pro Gly Cys Ala Ala Asp Lys Glu Ile Leu
1               5                   10                  15

Asp Glu Ser Leu Lys Gln Leu Thr Ala Glu Tyr Asp Arg Thr
            20                  25                  30

<210> SEQ ID NO 390
<211> LENGTH: 30
<212> TYPE: PRT
<213> ORGANISM: Feline immunodeficiency virus

<400> SEQUENCE: 390

Ala Ala Pro Gly Cys Ala Ala Asp Lys Glu Ile Leu Asp Glu Ser Leu
1               5                   10                  15

Lys Gln Leu Thr Ala Glu Tyr Asp Arg Thr His Pro Pro Asp
            20                  25                  30

<210> SEQ ID NO 391
<211> LENGTH: 30
<212> TYPE: PRT
<213> ORGANISM: Feline immunodeficiency virus

<400> SEQUENCE: 391

Cys Ala Ala Asp Lys Glu Ile Leu Asp Glu Ser Leu Lys Gln Leu Thr
1               5                   10                  15

Ala Glu Tyr Asp Arg Thr His Pro Pro Asp Ala Pro Arg Pro
            20                  25                  30
```

<210> SEQ ID NO 392
<211> LENGTH: 30
<212> TYPE: PRT
<213> ORGANISM: Feline immunodeficiency virus

<400> SEQUENCE: 392

Ser Leu Lys Gln Leu Thr Ala Glu Tyr Asp Arg Thr His Pro Pro Asp
1               5                   10                  15

Ala Pro Arg Pro Leu Pro Tyr Phe Thr Ala Ala Glu Ile Met
            20                  25                  30

<210> SEQ ID NO 393
<211> LENGTH: 30
<212> TYPE: PRT
<213> ORGANISM: Feline immunodeficiency virus

<400> SEQUENCE: 393

Arg Thr His Pro Pro Asp Ala Pro Arg Pro Leu Pro Tyr Phe Thr Ala
1               5                   10                  15

Ala Glu Ile Met Gly Ile Gly Leu Thr Gln Glu Gln Gln Ala
            20                  25                  30

<210> SEQ ID NO 394
<211> LENGTH: 30
<212> TYPE: PRT
<213> ORGANISM: Feline immunodeficiency virus

<400> SEQUENCE: 394

Leu Pro Tyr Phe Thr Ala Ala Glu Ile Met Gly Ile Gly Leu Thr Gln
1               5                   10                  15

Glu Gln Gln Ala Glu Ala Arg Phe Ala Pro Ala Arg Met Gln
            20                  25                  30

<210> SEQ ID NO 395
<211> LENGTH: 30
<212> TYPE: PRT
<213> ORGANISM: Feline immunodeficiency virus

<400> SEQUENCE: 395

Gly Ile Gly Leu Thr Gln Glu Gln Gln Ala Glu Ala Arg Phe Ala Pro
1               5                   10                  15

Ala Arg Met Gln Cys Arg Ala Trp Tyr Leu Glu Ala Leu Gly
            20                  25                  30

<210> SEQ ID NO 396
<211> LENGTH: 30
<212> TYPE: PRT
<213> ORGANISM: Feline immunodeficiency virus

<400> SEQUENCE: 396

Glu Ala Arg Phe Ala Pro Ala Arg Met Gln Cys Arg Ala Trp Tyr Leu
1               5                   10                  15

Glu Ala Leu Gly Lys Leu Ala Ala Ile Lys Ala Lys Ser Pro
            20                  25                  30

<210> SEQ ID NO 397
<211> LENGTH: 30
<212> TYPE: PRT
<213> ORGANISM: Feline immunodeficiency virus

<400> SEQUENCE: 397

Cys Arg Ala Trp Tyr Leu Glu Ala Leu Gly Lys Leu Ala Ala Ile Lys
1               5                   10                  15

Ala Lys Ser Pro Arg Ala Val Gln Leu Arg Gln Gly Ala Lys
            20                  25                  30

<210> SEQ ID NO 398
<211> LENGTH: 30
<212> TYPE: PRT
<213> ORGANISM: Feline immunodeficiency virus

<400> SEQUENCE: 398

Lys Leu Ala Ala Ile Lys Ala Lys Ser Pro Arg Ala Val Gln Leu Arg
1               5                   10                  15

Gln Gly Ala Lys Glu Asp Tyr Ser Ser Phe Ile Asp Arg Leu
            20                  25                  30

<210> SEQ ID NO 399
<211> LENGTH: 30
<212> TYPE: PRT
<213> ORGANISM: Feline immunodeficiency virus

<400> SEQUENCE: 399

Arg Ala Val Gln Leu Arg Gln Gly Ala Lys Glu Asp Tyr Ser Ser Phe
1               5                   10                  15

Ile Asp Arg Leu Phe Ala Gln Ile Asp Gln Glu Gln Asn Thr
            20                  25                  30

<210> SEQ ID NO 400
<211> LENGTH: 30
<212> TYPE: PRT
<213> ORGANISM: Feline immunodeficiency virus

<400> SEQUENCE: 400

Glu Asp Tyr Ser Ser Phe Ile Asp Arg Leu Phe Ala Gln Ile Asp Gln
1               5                   10                  15

Glu Gln Asn Thr Ala Glu Val Lys Leu Tyr Leu Lys Gln Ser
            20                  25                  30

<210> SEQ ID NO 401
<211> LENGTH: 30
<212> TYPE: PRT
<213> ORGANISM: Feline immunodeficiency virus

<400> SEQUENCE: 401

Phe Ala Gln Ile Asp Gln Glu Gln Asn Thr Ala Glu Val Lys Leu Tyr
1               5                   10                  15

Leu Lys Gln Ser Leu Ser Ile Ala Asn Ala Asn Ala Glu Cys
            20                  25                  30

<210> SEQ ID NO 402
<211> LENGTH: 30
<212> TYPE: PRT
<213> ORGANISM: Feline immunodeficiency virus

<400> SEQUENCE: 402

Ala Glu Val Lys Leu Tyr Leu Lys Gln Ser Leu Ser Ile Ala Asn Ala
1               5                   10                  15

Asn Ala Glu Cys Lys Lys Ala Met Ser His Leu Lys Pro Glu
            20                  25                  30

<210> SEQ ID NO 403
<211> LENGTH: 30

```
<212> TYPE: PRT
<213> ORGANISM: Feline immunodeficiency virus

<400> SEQUENCE: 403

Leu Ser Ile Ala Asn Ala Asn Ala Glu Cys Lys Lys Ala Met Ser His
1               5                   10                  15

Leu Lys Pro Glu Ser Thr Leu Glu Glu Lys Leu Arg Ala Cys
            20                  25                  30

<210> SEQ ID NO 404
<211> LENGTH: 30
<212> TYPE: PRT
<213> ORGANISM: Feline immunodeficiency virus

<400> SEQUENCE: 404

Lys Lys Ala Met Ser His Leu Lys Pro Glu Ser Thr Leu Glu Glu Lys
1               5                   10                  15

Leu Arg Ala Cys Gln Glu Val Gly Ser Pro Gly Tyr Lys Met
            20                  25                  30

<210> SEQ ID NO 405
<211> LENGTH: 23
<212> TYPE: PRT
<213> ORGANISM: Feline immunodeficiency virus

<400> SEQUENCE: 405

Ser Thr Leu Glu Glu Lys Leu Arg Ala Cys Gln Glu Val Gly Ser Pro
1               5                   10                  15

Gly Tyr Lys Met Gln Leu Leu
            20

<210> SEQ ID NO 406
<211> LENGTH: 30
<212> TYPE: PRT
<213> ORGANISM: Human immunodeficiency virus

<400> SEQUENCE: 406

Pro Val Val Gln Asn Leu Gln Gly Gln Met Val His Gln Pro Ile Ser
1               5                   10                  15

Pro Arg Thr Leu Asn Ala Trp Val Lys Val Val Glu Glu Lys
            20                  25                  30

<210> SEQ ID NO 407
<211> LENGTH: 30
<212> TYPE: PRT
<213> ORGANISM: Human immunodeficiency virus

<400> SEQUENCE: 407

Gln Met Val His Gln Pro Ile Ser Pro Arg Thr Leu Asn Ala Trp Val
1               5                   10                  15

Lys Val Val Glu Glu Lys Ala Phe Ser Pro Glu Val Ile Pro
            20                  25                  30

<210> SEQ ID NO 408
<211> LENGTH: 30
<212> TYPE: PRT
<213> ORGANISM: Human immunodeficiency virus

<400> SEQUENCE: 408

Lys Val Val Glu Glu Lys Ala Phe Ser Pro Glu Val Ile Pro Met Phe
1               5                   10                  15

Thr Ala Leu Ser Glu Gly Ala Thr Pro Gln Asp Leu Asn Thr
```

<210> SEQ ID NO 409
<211> LENGTH: 30
<212> TYPE: PRT
<213> ORGANISM: Human immunodeficiency virus

<400> SEQUENCE: 409

Ser Pro Glu Val Ile Pro Met Phe Thr Ala Leu Ser Glu Gly Ala Thr
1               5                   10                  15

Pro Gln Asp Leu Asn Thr Met Leu Asn Thr Val Gly Gly His
            20                  25                  30

<210> SEQ ID NO 410
<211> LENGTH: 30
<212> TYPE: PRT
<213> ORGANISM: Human immunodeficiency virus

<400> SEQUENCE: 410

Thr Ala Leu Ser Glu Gly Ala Thr Pro Gln Asp Leu Asn Thr Met Leu
1               5                   10                  15

Asn Thr Val Gly Gly His Gln Ala Ala Met Gln Met Leu Lys
            20                  25                  30

<210> SEQ ID NO 411
<211> LENGTH: 30
<212> TYPE: PRT
<213> ORGANISM: Human immunodeficiency virus

<400> SEQUENCE: 411

Asp Leu Asn Thr Met Leu Asn Thr Val Gly Gly His Gln Ala Ala Met
1               5                   10                  15

Gln Met Leu Lys Glu Thr Ile Asn Glu Glu Ala Ala Glu Trp
            20                  25                  30

<210> SEQ ID NO 412
<211> LENGTH: 30
<212> TYPE: PRT
<213> ORGANISM: Human immunodeficiency virus

<400> SEQUENCE: 412

Gly His Gln Ala Ala Met Gln Met Leu Lys Glu Thr Ile Asn Glu Glu
1               5                   10                  15

Ala Ala Glu Trp Asp Arg Leu His Pro Val His Ala Gly Pro
            20                  25                  30

<210> SEQ ID NO 413
<211> LENGTH: 30
<212> TYPE: PRT
<213> ORGANISM: Human immunodeficiency virus

<400> SEQUENCE: 413

Glu Thr Ile Asn Glu Glu Ala Ala Glu Trp Asp Arg Leu His Pro Val
1               5                   10                  15

His Ala Gly Pro Ile Ala Pro Asp Gln Met Arg Glu Pro Arg
            20                  25                  30

<210> SEQ ID NO 414
<211> LENGTH: 30
<212> TYPE: PRT
<213> ORGANISM: Human immunodeficiency virus

<400> SEQUENCE: 414

```
Asp Arg Leu His Pro Val His Ala Gly Pro Ile Ala Pro Asp Gln Met
1               5                   10                  15

Arg Glu Pro Arg Gly Ser Asp Ile Ala Gly Ile Thr Ser Thr
            20                  25                  30
```

<210> SEQ ID NO 415
<211> LENGTH: 30
<212> TYPE: PRT
<213> ORGANISM: Human immunodeficiency virus

<400> SEQUENCE: 415

```
Ile Ala Pro Asp Gln Met Arg Glu Pro Arg Gly Ser Asp Ile Ala Gly
1               5                   10                  15

Ile Thr Ser Thr Leu Gln Glu Gln Ile Gly Trp Met Thr Asn
            20                  25                  30
```

<210> SEQ ID NO 416
<211> LENGTH: 30
<212> TYPE: PRT
<213> ORGANISM: Human immunodeficiency virus

<400> SEQUENCE: 416

```
Gly Ser Asp Ile Ala Gly Ile Thr Ser Thr Leu Gln Glu Gln Ile Gly
1               5                   10                  15

Trp Met Thr Asn Asn Pro Pro Ile Pro Val Gly Glu Ile Tyr
            20                  25                  30
```

<210> SEQ ID NO 417
<211> LENGTH: 30
<212> TYPE: PRT
<213> ORGANISM: Human immunodeficiency virus

<400> SEQUENCE: 417

```
Leu Gln Glu Gln Ile Gly Trp Met Thr Asn Asn Pro Pro Ile Pro Val
1               5                   10                  15

Gly Glu Ile Tyr Lys Arg Trp Ile Ile Leu Gly Leu Asn Lys
            20                  25                  30
```

<210> SEQ ID NO 418
<211> LENGTH: 30
<212> TYPE: PRT
<213> ORGANISM: Human immunodeficiency virus

<400> SEQUENCE: 418

```
Met Thr Asn Asn Pro Pro Ile Pro Val Gly Glu Ile Tyr Lys Arg Trp
1               5                   10                  15

Ile Ile Leu Gly Leu Asn Lys Ile Val Arg Met Tyr Ser Pro
            20                  25                  30
```

<210> SEQ ID NO 419
<211> LENGTH: 30
<212> TYPE: PRT
<213> ORGANISM: Human immunodeficiency virus

<400> SEQUENCE: 419

```
Lys Arg Trp Ile Ile Leu Gly Leu Asn Lys Ile Val Arg Met Tyr Ser
1               5                   10                  15

Pro Thr Ser Ile Leu Asp Ile Arg Gln Gly Pro Lys Glu Pro
            20                  25                  30
```

<210> SEQ ID NO 420

```
<211> LENGTH: 30
<212> TYPE: PRT
<213> ORGANISM: Human immunodeficiency virus

<400> SEQUENCE: 420

Ile Val Arg Met Tyr Ser Pro Thr Ser Ile Leu Asp Ile Arg Gln Gly
1               5                   10                  15

Pro Lys Glu Pro Phe Arg Asp Tyr Val Asp Arg Phe Tyr Lys
            20                  25                  30

<210> SEQ ID NO 421
<211> LENGTH: 30
<212> TYPE: PRT
<213> ORGANISM: Human immunodeficiency virus

<400> SEQUENCE: 421

Leu Asp Ile Arg Gln Gly Pro Lys Glu Pro Phe Arg Asp Tyr Val Asp
1               5                   10                  15

Arg Phe Tyr Lys Thr Leu Arg Ala Glu Gln Ala Ser Gln Asp
            20                  25                  30

<210> SEQ ID NO 422
<211> LENGTH: 30
<212> TYPE: PRT
<213> ORGANISM: Human immunodeficiency virus

<400> SEQUENCE: 422

Phe Arg Asp Tyr Val Asp Arg Phe Tyr Lys Thr Leu Arg Ala Glu Gln
1               5                   10                  15

Ala Ser Gln Asp Val Lys Asn Trp Met Thr Glu Thr Leu Leu
            20                  25                  30

<210> SEQ ID NO 423
<211> LENGTH: 30
<212> TYPE: PRT
<213> ORGANISM: Human immunodeficiency virus

<400> SEQUENCE: 423

Thr Leu Arg Ala Glu Gln Ala Ser Gln Asp Val Lys Asn Trp Met Thr
1               5                   10                  15

Glu Thr Leu Leu Val Gln Asn Ala Asn Pro Asp Cys Lys Thr
            20                  25                  30

<210> SEQ ID NO 424
<211> LENGTH: 30
<212> TYPE: PRT
<213> ORGANISM: Human immunodeficiency virus

<400> SEQUENCE: 424

Val Lys Asn Trp Met Thr Glu Thr Leu Leu Val Gln Asn Ala Asn Pro
1               5                   10                  15

Asp Cys Lys Thr Ile Leu Lys Ala Leu Gly Pro Ala Ala Thr
            20                  25                  30

<210> SEQ ID NO 425
<211> LENGTH: 30
<212> TYPE: PRT
<213> ORGANISM: Human immunodeficiency virus

<400> SEQUENCE: 425

Val Gln Asn Ala Asn Pro Asp Cys Lys Thr Ile Leu Lys Ala Leu Gly
1               5                   10                  15
```

Pro Ala Ala Thr Leu Glu Glu Met Met Thr Ala Cys Gln Gly
            20                  25                  30

<210> SEQ ID NO 426
<211> LENGTH: 22
<212> TYPE: PRT
<213> ORGANISM: Human immunodeficiency virus

<400> SEQUENCE: 426

Thr Leu Glu Glu Met Met Thr Ala Cys Gln Gly Val Gly Gly Pro Gly
1               5                   10                  15

His Lys Ala Arg Val Leu
            20

<210> SEQ ID NO 427
<211> LENGTH: 9
<212> TYPE: PRT
<213> ORGANISM: Human immunodeficiency virus

<400> SEQUENCE: 427

Asn Thr Pro Val Phe Ala Ile Lys Lys
1               5

<210> SEQ ID NO 428
<211> LENGTH: 10
<212> TYPE: PRT
<213> ORGANISM: Human immunodeficiency virus

<400> SEQUENCE: 428

Asn Thr Pro Val Phe Ala Ile Lys Lys Lys
1               5                   10

<210> SEQ ID NO 429
<211> LENGTH: 10
<212> TYPE: PRT
<213> ORGANISM: Human immunodeficiency virus

<400> SEQUENCE: 429

Lys Leu Val Asp Phe Arg Glu Leu Asn Lys
1               5                   10

<210> SEQ ID NO 430
<211> LENGTH: 10
<212> TYPE: PRT
<213> ORGANISM: Feline immunodeficiency virus

<400> SEQUENCE: 430

Met Leu Ile Asp Phe Arg Val Leu Asn Lys
1               5                   10

<210> SEQ ID NO 431
<211> LENGTH: 9
<212> TYPE: PRT
<213> ORGANISM: Feline immunodeficiency virus

<400> SEQUENCE: 431

Trp Arg Met Leu Ile Asp Phe Arg Val
1               5

<210> SEQ ID NO 432
<211> LENGTH: 9
<212> TYPE: PRT
<213> ORGANISM: Feline immunodeficiency virus

<400> SEQUENCE: 432

```
Lys Trp Arg Met Leu Ile Asp Phe Arg
1               5
```

<210> SEQ ID NO 433
<211> LENGTH: 15
<212> TYPE: PRT
<213> ORGANISM: Human immunodeficiency virus

<400> SEQUENCE: 433

```
Lys Lys Lys Ser Thr Lys Trp Arg Lys Leu Val Asp Phe Arg Glu
1               5                   10                  15
```

<210> SEQ ID NO 434
<211> LENGTH: 15
<212> TYPE: PRT
<213> ORGANISM: Human immunodeficiency virus

<400> SEQUENCE: 434

```
Lys Lys Asn Ser Thr Lys Trp Arg Lys Leu Val Asp Phe Arg Glu
1               5                   10                  15
```

<210> SEQ ID NO 435
<211> LENGTH: 16
<212> TYPE: PRT
<213> ORGANISM: Simian immunodeficiency virus

<400> SEQUENCE: 435

```
Lys Lys Lys Asp Ser Thr Lys Trp Arg Lys Leu Val Asp Phe Arg Glu
1               5                   10                  15
```

<210> SEQ ID NO 436
<211> LENGTH: 15
<212> TYPE: PRT
<213> ORGANISM: Caprine arthritis-encephalitis virus/Maedi-Visna virus

<400> SEQUENCE: 436

```
Lys Lys Lys Ser Gly Lys Trp Arg Met Leu Ile Asp Phe Arg Glu
1               5                   10                  15
```

<210> SEQ ID NO 437
<211> LENGTH: 15
<212> TYPE: PRT
<213> ORGANISM: Feline immunodeficiency virus

<400> SEQUENCE: 437

```
Lys Lys Lys Asp Ser Gly Lys Trp Arg Met Leu Ile Asp Phe Arg
1               5                   10                  15
```

<210> SEQ ID NO 438
<211> LENGTH: 16
<212> TYPE: PRT
<213> ORGANISM: Feline immunodeficiency virus

<400> SEQUENCE: 438

```
Lys Lys Lys Asp Ser Gly Lys Trp Arg Met Leu Ile Asp Phe Arg Val
1               5                   10                  15
```

<210> SEQ ID NO 439
<211> LENGTH: 15
<212> TYPE: PRT
<213> ORGANISM: Feline immunodeficiency virus

<400> SEQUENCE: 439

```
Lys Lys Lys Ser Gly Lys Trp Arg Met Leu Val Asp Phe Arg Val
```

-continued

```
                1               5                   10                  15
```

<210> SEQ ID NO 440
<211> LENGTH: 15
<212> TYPE: PRT
<213> ORGANISM: Feline immunodeficiency virus

<400> SEQUENCE: 440

```
Lys Lys Lys Ser Thr Lys Trp Arg Lys Leu Ile Asp Phe Arg Val
1               5                   10                  15
```

<210> SEQ ID NO 441
<211> LENGTH: 15
<212> TYPE: PRT
<213> ORGANISM: Feline immunodeficiency virus

<400> SEQUENCE: 441

```
Lys Lys Lys Ser Gly Lys Trp Arg Lys Leu Ile Asp Phe Arg Val
1               5                   10                  15
```

<210> SEQ ID NO 442
<211> LENGTH: 15
<212> TYPE: PRT
<213> ORGANISM: Feline immunodeficiency virus

<400> SEQUENCE: 442

```
Lys Lys Lys Ser Thr Lys Trp Arg Met Leu Ile Asp Phe Arg Val
1               5                   10                  15
```

<210> SEQ ID NO 443
<211> LENGTH: 35
<212> TYPE: PRT
<213> ORGANISM: Feline immunodeficiency virus

<400> SEQUENCE: 443

```
Asn Pro Trp Asn Thr Pro Val Phe Ala Ile Lys Lys Lys Ser Gly Lys
1               5                   10                  15

Trp Arg Met Leu Ile Asp Phe Arg Val Val Leu Asn Lys Leu Thr Asp
                20                  25                  30

Lys Gly Ala
        35
```

<210> SEQ ID NO 444
<211> LENGTH: 28
<212> TYPE: PRT
<213> ORGANISM: Feline immunodeficiency virus

<400> SEQUENCE: 444

```
Pro Asp Tyr Ala Pro Tyr Thr Ala Phe Thr Leu Pro Arg Lys Asn Asn
1               5                   10                  15

Ala Gly Pro Gly Arg Arg Tyr Val Trp Cys Ser Leu
                20                  25
```

<210> SEQ ID NO 445
<211> LENGTH: 31
<212> TYPE: PRT
<213> ORGANISM: Human immunodeficiency virus

<400> SEQUENCE: 445

```
Phe Arg Lys Tyr Thr Ala Phe Thr Ile Pro Ser Thr Asn Asn Glu Thr
1               5                   10                  15

Pro Gly Ile Arg Tyr Gln Tyr Asn Val Leu Pro Gln Gly Trp Lys
                20                  25                  30
```

```
<210> SEQ ID NO 446
<211> LENGTH: 28
<212> TYPE: PRT
<213> ORGANISM: Feline immunodeficiency virus

<400> SEQUENCE: 446

Gly Arg Arg Tyr Val Trp Cys Ser Leu Pro Gln Gly Trp Val Leu Ser
1               5                   10                  15

Pro Leu Ile Tyr Gln Ser Thr Leu Asp Asn Ile Leu
            20                  25

<210> SEQ ID NO 447
<211> LENGTH: 33
<212> TYPE: PRT
<213> ORGANISM: Human immunodeficiency virus

<400> SEQUENCE: 447

Tyr Asn Val Leu Pro Gln Gly Trp Lys Gly Ser Pro Ala Ile Phe Gln
1               5                   10                  15

Ser Ser Met Thr Lys Ile Leu Glu Pro Phe Arg Lys Gln Asn Pro Asp
            20                  25                  30

Ile

<210> SEQ ID NO 448
<211> LENGTH: 37
<212> TYPE: PRT
<213> ORGANISM: Feline immunodeficiency virus

<400> SEQUENCE: 448

Gly Lys Met Asn Arg Gln Lys Lys Ala Glu Asn Thr Cys Asp Ile
1               5                   10                  15

Ala Leu Arg Ala Cys Tyr Lys Ile Arg Glu Glu Ser Ile Ile Arg Ile
            20                  25                  30

Gly Lys Glu Pro Ile
        35

<210> SEQ ID NO 449
<211> LENGTH: 36
<212> TYPE: PRT
<213> ORGANISM: Human immunodeficiency virus

<400> SEQUENCE: 449

Arg Gly Ala His Thr Asn Asp Val Lys Gln Leu Thr Glu Ala Val Gln
1               5                   10                  15

Lys Ile Val Thr Glu Ser Ile Val Ile Trp Gly Lys Thr Pro Lys Phe
            20                  25                  30

Lys Leu Pro Ile
        35

<210> SEQ ID NO 450
<211> LENGTH: 9
<212> TYPE: PRT
<213> ORGANISM: Simian immunodeficiency virus

<400> SEQUENCE: 450

Trp Arg Lys Leu Val Asp Phe Arg Glu
1               5

<210> SEQ ID NO 451
<211> LENGTH: 9
```

```
<212> TYPE: PRT
<213> ORGANISM: Feline immunodeficiency virus

<400> SEQUENCE: 451

Arg Met Gln Cys Arg Ala Trp Tyr Leu
1               5

<210> SEQ ID NO 452
<211> LENGTH: 9
<212> TYPE: PRT
<213> ORGANISM: Feline immunodeficiency virus

<400> SEQUENCE: 452

Ala Arg Met Gln Cys Arg Ala Trp Tyr
1               5

<210> SEQ ID NO 453
<211> LENGTH: 10
<212> TYPE: PRT
<213> ORGANISM: Feline immunodeficiency virus

<400> SEQUENCE: 453

Lys Leu Tyr Leu Lys Gln Ser Leu Ser Ile
1               5                   10

<210> SEQ ID NO 454
<211> LENGTH: 13
<212> TYPE: PRT
<213> ORGANISM: Feline immunodeficiency virus

<400> SEQUENCE: 454

Ala Glu Val Lys Leu Tyr Leu Lys Gln Ser Leu Ser Ile
1               5                   10

<210> SEQ ID NO 455
<211> LENGTH: 23
<212> TYPE: PRT
<213> ORGANISM: Human immunodeficiency virus

<400> SEQUENCE: 455

Glu Gln Ile Gly Trp Met Thr Asn Asn Pro Pro Ile Pro Val Gly Glu
1               5                   10                  15

Ile Tyr Lys Arg Trp Ile Ile
            20

<210> SEQ ID NO 456
<211> LENGTH: 22
<212> TYPE: PRT
<213> ORGANISM: Feline immunodeficiency virus

<400> SEQUENCE: 456

Glu Gln Gln Ala Glu Ala Arg Phe Ala Pro Ala Arg Met Gln Cys Arg
1               5                   10                  15

Ala Trp Tyr Leu Glu Ala
            20

<210> SEQ ID NO 457
<211> LENGTH: 23
<212> TYPE: PRT
<213> ORGANISM: Human immunodeficiency virus

<400> SEQUENCE: 457

Arg Ala Glu Gln Ala Ser Gln Glu Val Lys Asn Trp Met Thr Glu Thr
1               5                   10                  15
```

Leu Leu Val Gln Asn Ala Asn
            20

<210> SEQ ID NO 458
<211> LENGTH: 22
<212> TYPE: PRT
<213> ORGANISM: Feline immunodeficiency virus

<400> SEQUENCE: 458

Asp Gln Glu Gln Asn Thr Ala Glu Val Lys Leu Tyr Leu Lys Gln Ser
1               5                   10                  15

Leu Ser Ile Ala Asn Ala
            20

<210> SEQ ID NO 459
<211> LENGTH: 9
<212> TYPE: PRT
<213> ORGANISM: Feline immunodeficiency virus

<400> SEQUENCE: 459

Lys Leu Tyr Leu Lys Gln Ser Leu Ser
1               5

<210> SEQ ID NO 460
<211> LENGTH: 9
<212> TYPE: PRT
<213> ORGANISM: Human immunodeficiency virus

<400> SEQUENCE: 460

Val Lys Asn Trp Met Thr Glu Thr Leu
1               5

<210> SEQ ID NO 461
<211> LENGTH: 9
<212> TYPE: PRT
<213> ORGANISM: Simian immunodeficiency virus

<400> SEQUENCE: 461

Val Lys Asn Trp Met Thr Gln Thr Leu
1               5

<210> SEQ ID NO 462
<211> LENGTH: 10
<212> TYPE: PRT
<213> ORGANISM: Feline immunodeficiency virus

<400> SEQUENCE: 462

Gln Glu Gln Asn Thr Ala Glu Val Lys Leu
1               5                   10

<210> SEQ ID NO 463
<211> LENGTH: 10
<212> TYPE: PRT
<213> ORGANISM: Human immunodeficiency virus

<400> SEQUENCE: 463

Ala Glu Gln Ala Ser Gln Glu Val Lys Asn
1               5                   10

<210> SEQ ID NO 464
<211> LENGTH: 10
<212> TYPE: PRT
<213> ORGANISM: Simian immunodeficiency virus

```
<400> SEQUENCE: 464

Gln Thr Asp Ala Ala Val Lys Asn Trp Met
1               5                  10

<210> SEQ ID NO 465
<211> LENGTH: 10
<212> TYPE: PRT
<213> ORGANISM: Simian immunodeficiency virus

<400> SEQUENCE: 465

Thr Asp Ala Ala Val Lys Asn Trp Met Thr
1               5                  10

<210> SEQ ID NO 466
<211> LENGTH: 10
<212> TYPE: PRT
<213> ORGANISM: Feline immunodeficiency virus

<400> SEQUENCE: 466

Gln Asn Thr Ala Glu Val Lys Leu Tyr Leu
1               5                  10

<210> SEQ ID NO 467
<211> LENGTH: 10
<212> TYPE: PRT
<213> ORGANISM: Human immunodeficiency virus

<400> SEQUENCE: 467

Gln Ala Ser Gln Glu Val Lys Asn Trp Met
1               5                  10

<210> SEQ ID NO 468
<211> LENGTH: 10
<212> TYPE: PRT
<213> ORGANISM: Simian immunodeficiency virus

<400> SEQUENCE: 468

Gln Thr Asp Ala Ala Val Lys Asn Trp Met
1               5                  10

<210> SEQ ID NO 469
<211> LENGTH: 13
<212> TYPE: PRT
<213> ORGANISM: Simian immunodeficiency virus

<400> SEQUENCE: 469

Thr Asp Ala Ala Val Lys Asn Trp Met Thr Gln Thr Leu
1               5                  10

<210> SEQ ID NO 470
<211> LENGTH: 9
<212> TYPE: PRT
<213> ORGANISM: Feline immunodeficiency virus

<400> SEQUENCE: 470

Glu Ala Arg Phe Ala Pro Ala Arg Met
1               5

<210> SEQ ID NO 471
<211> LENGTH: 9
<212> TYPE: PRT
<213> ORGANISM: Feline immunodeficiency virus

<400> SEQUENCE: 471
```

Ala Pro Ala Arg Met Gln Cys Arg Ala
1               5

<210> SEQ ID NO 472
<211> LENGTH: 10
<212> TYPE: PRT
<213> ORGANISM: Feline immunodeficiency virus

<400> SEQUENCE: 472

Ala Arg Met Gln Cys Arg Ala Trp Tyr Leu
1               5                   10

<210> SEQ ID NO 473
<211> LENGTH: 12
<212> TYPE: PRT
<213> ORGANISM: Feline immunodeficiency virus

<400> SEQUENCE: 473

Ala Pro Ala Arg Met Gln Cys Arg Ala Trp Tyr Leu
1               5                   10

<210> SEQ ID NO 474
<211> LENGTH: 10
<212> TYPE: PRT
<213> ORGANISM: Feline immunodeficiency virus

<400> SEQUENCE: 474

Gln Glu Gln Asn Thr Ala Glu Val Lys Leu
1               5                   10

<210> SEQ ID NO 475

<400> SEQUENCE: 475

000

<210> SEQ ID NO 476
<211> LENGTH: 9
<212> TYPE: PRT
<213> ORGANISM: Feline immunodeficiency virus

<400> SEQUENCE: 476

Asn Thr Ala Glu Val Lys Leu Tyr Leu
1               5

<210> SEQ ID NO 477
<211> LENGTH: 9
<212> TYPE: PRT
<213> ORGANISM: Feline immunodeficiency virus

<400> SEQUENCE: 477

Ala Glu Val Lys Leu Tyr Leu Lys Gln
1               5

<210> SEQ ID NO 478
<211> LENGTH: 11
<212> TYPE: PRT
<213> ORGANISM: Feline immunodeficiency virus

<400> SEQUENCE: 478

Ala Glu Val Lys Leu Tyr Leu Lys Gln Ser Leu
1               5                   10

<210> SEQ ID NO 479
<211> LENGTH: 9

```
<212> TYPE: PRT
<213> ORGANISM: Feline immunodeficiency virus

<400> SEQUENCE: 479

Leu Tyr Leu Lys Gln Ser Leu Ser Ile
1               5

<210> SEQ ID NO 480
<211> LENGTH: 9
<212> TYPE: PRT
<213> ORGANISM: Feline immunodeficiency virus

<400> SEQUENCE: 480

Tyr Leu Lys Gln Ser Leu Ser Ile Ala
1               5

<210> SEQ ID NO 481
<211> LENGTH: 23
<212> TYPE: PRT
<213> ORGANISM: Human immunodeficiency virus

<400> SEQUENCE: 481

Arg Ala Glu Gln Ala Thr Gln Glu Val Lys Gly Trp Met Thr Glu Thr
1               5                   10                  15

Leu Leu Val Gln Asn Ala Asn
            20

<210> SEQ ID NO 482
<211> LENGTH: 23
<212> TYPE: PRT
<213> ORGANISM: Human immunodeficiency virus

<400> SEQUENCE: 482

Arg Ala Glu Gln Ala Thr Gln Asp Val Lys Asn Trp Met Thr Asp Thr
1               5                   10                  15

Leu Leu Val Gln Asn Ala Asn
            20

<210> SEQ ID NO 483
<211> LENGTH: 23
<212> TYPE: PRT
<213> ORGANISM: Human immunodeficiency virus

<400> SEQUENCE: 483

Arg Ala Glu Gln Ala Ser Gln Asp Val Lys Asn Trp Met Thr Glu Thr
1               5                   10                  15

Leu Leu Val Gln Asn Ala Asn
            20

<210> SEQ ID NO 484
<211> LENGTH: 23
<212> TYPE: PRT
<213> ORGANISM: Simian immunodeficiency virus

<400> SEQUENCE: 484

Arg Ala Glu Gln Ala Ser Gln Glu Val Lys Thr Trp Met Thr Asp Thr
1               5                   10                  15

Leu Leu Val Gln Asn Ala Asn
            20

<210> SEQ ID NO 485
<211> LENGTH: 23
<212> TYPE: PRT
```

<213> ORGANISM: Simian immunodeficiency virus

<400> SEQUENCE: 485

Arg Ala Glu Gln Thr Asp Ala Ala Val Lys Asn Trp Met Thr Gln Thr
1 5 10 15

Leu Leu Ile Gln Asn Ala Asn
20

<210> SEQ ID NO 486
<211> LENGTH: 23
<212> TYPE: PRT
<213> ORGANISM: Feline immunodeficiency virus

<400> SEQUENCE: 486

Asp Gln Glu Gln Asn Thr Ala Glu Val Lys Leu Tyr Leu Lys Gln Ser
1 5 10 15

Leu Ser Ile Ala Asn Ala Asn
20

<210> SEQ ID NO 487
<211> LENGTH: 23
<212> TYPE: PRT
<213> ORGANISM: Feline immunodeficiency virus

<400> SEQUENCE: 487

Asp Gln Glu Gln Asn Thr Ala Glu Val Lys Thr Tyr Leu Lys Gln Ser
1 5 10 15

Leu Ser Leu Ala Asn Ala Asn
20

<210> SEQ ID NO 488
<211> LENGTH: 14
<212> TYPE: PRT
<213> ORGANISM: Feline immunodeficiency virus

<400> SEQUENCE: 488

Lys Leu Tyr Leu Lys Gln Ser Leu Ser Ile Ala Asn Ala Asn
1 5 10

<210> SEQ ID NO 489
<211> LENGTH: 16
<212> TYPE: PRT
<213> ORGANISM: Simian immunodeficiency virus

<400> SEQUENCE: 489

Lys Lys Lys Asp Lys Asn Lys Trp Arg Met Leu Ile Asp Phe Arg Glu
1 5 10 15

<210> SEQ ID NO 490
<211> LENGTH: 15
<212> TYPE: PRT
<213> ORGANISM: Feline immunodeficiency virus

<400> SEQUENCE: 490

Lys Lys Lys Ser Gly Lys Trp Arg Met Leu Ile Asp Phe Arg Glu
1 5 10 15

<210> SEQ ID NO 491
<211> LENGTH: 19
<212> TYPE: PRT
<213> ORGANISM: Feline immunodeficiency virus

<400> SEQUENCE: 491

```
Lys Lys Lys Ser Gly Lys Trp Arg Leu Leu Ile Asp Phe Arg Val Leu
1               5                   10                  15

Asn Lys Leu

<210> SEQ ID NO 492
<211> LENGTH: 19
<212> TYPE: PRT
<213> ORGANISM: Feline immunodeficiency virus

<400> SEQUENCE: 492

Lys Lys Lys Ser Gly Lys Trp Arg Leu Leu Ile Asp Phe Arg Val Leu
1               5                   10                  15

Asn Lys Leu

<210> SEQ ID NO 493
<211> LENGTH: 33
<212> TYPE: PRT
<213> ORGANISM: Feline immunodeficiency virus

<400> SEQUENCE: 493

Pro Thr Asp Leu Ala Thr Leu Ile Leu Ala Ala Pro Gly Ser Ala Arg
1               5                   10                  15

Val Lys Arg Asp Gln Glu Gln Asn Thr Ala Glu Val Lys Leu Tyr Leu
            20                  25                  30

Lys

<210> SEQ ID NO 494
<211> LENGTH: 4
<212> TYPE: PRT
<213> ORGANISM: Artificial sequence
<220> FEATURE:
<223> OTHER INFORMATION: furin-sensitive linker sequence

<400> SEQUENCE: 494

Arg Val Lys Arg
1

<210> SEQ ID NO 495
<211> LENGTH: 14
<212> TYPE: PRT
<213> ORGANISM: Simian immunodeficiency virus

<400> SEQUENCE: 495

Pro Ile Ala Lys Val Glu Pro Val Lys Val Thr Leu Lys Arg
1               5                   10

<210> SEQ ID NO 496
<211> LENGTH: 15
<212> TYPE: PRT
<213> ORGANISM: Simian immunodeficiency virus

<400> SEQUENCE: 496

Glu Pro Val Lys Val Thr Leu Lys Pro Gly Lys Val Gly Pro Lys
1               5                   10                  15

<210> SEQ ID NO 497
<211> LENGTH: 14
<212> TYPE: PRT
<213> ORGANISM: Simian immunodeficiency virus

<400> SEQUENCE: 497

Lys Pro Gly Lys Val Gly Pro Lys Leu Lys Gln Trp Pro Leu
1               5                   10
```

<210> SEQ ID NO 498
<211> LENGTH: 15
<212> TYPE: PRT
<213> ORGANISM: Simian immunodeficiency virus

<400> SEQUENCE: 498

Pro Lys Leu Lys Gln Trp Pro Leu Ser Lys Glu Lys Ile Val Ala
1               5                   10                  15

<210> SEQ ID NO 499
<211> LENGTH: 15
<212> TYPE: PRT
<213> ORGANISM: Simian immunodeficiency virus

<400> SEQUENCE: 499

Leu Ser Lys Glu Lys Ile Val Ala Leu Arg Glu Ile Cys Glu Lys
1               5                   10                  15

<210> SEQ ID NO 500
<211> LENGTH: 15
<212> TYPE: PRT
<213> ORGANISM: Simian immunodeficiency virus

<400> SEQUENCE: 500

Ala Leu Arg Glu Ile Cys Glu Lys Met Glu Lys Asp Gly Gln Leu
1               5                   10                  15

<210> SEQ ID NO 501
<211> LENGTH: 17
<212> TYPE: PRT
<213> ORGANISM: Simian immunodeficiency virus

<400> SEQUENCE: 501

Lys Met Glu Lys Asp Gly Gln Leu Glu Glu Ala Pro Pro Thr Asn Pro
1               5                   10                  15

Tyr

<210> SEQ ID NO 502
<211> LENGTH: 15
<212> TYPE: PRT
<213> ORGANISM: Simian immunodeficiency virus

<400> SEQUENCE: 502

Glu Ala Pro Pro Thr Asn Pro Tyr Asn Thr Pro Thr Phe Ala Ile
1               5                   10                  15

<210> SEQ ID NO 503
<211> LENGTH: 15
<212> TYPE: PRT
<213> ORGANISM: Simian immunodeficiency virus

<400> SEQUENCE: 503

Tyr Asn Thr Pro Thr Phe Ala Ile Lys Lys Asp Lys Asn Lys
1               5                   10                  15

<210> SEQ ID NO 504
<211> LENGTH: 15
<212> TYPE: PRT
<213> ORGANISM: Simian immunodeficiency virus

<400> SEQUENCE: 504

Ile Lys Lys Lys Asp Lys Asn Lys Trp Arg Met Leu Ile Asp Phe
1               5                   10                  15

<210> SEQ ID NO 505
<211> LENGTH: 14
<212> TYPE: PRT
<213> ORGANISM: Simian immunodeficiency virus

<400> SEQUENCE: 505

Lys Trp Arg Met Leu Ile Asp Phe Arg Glu Leu Asn Arg Val
1               5                   10

<210> SEQ ID NO 506
<211> LENGTH: 15
<212> TYPE: PRT
<213> ORGANISM: Simian immunodeficiency virus

<400> SEQUENCE: 506

Asp Phe Arg Glu Leu Asn Arg Val Thr Gln Asp Phe Thr Glu Val
1               5                   10                  15

<210> SEQ ID NO 507
<211> LENGTH: 14
<212> TYPE: PRT
<213> ORGANISM: Simian immunodeficiency virus

<400> SEQUENCE: 507

Val Thr Gln Asp Phe Thr Glu Val Gln Leu Gly Ile Pro His
1               5                   10

<210> SEQ ID NO 508
<211> LENGTH: 15
<212> TYPE: PRT
<213> ORGANISM: Simian immunodeficiency virus

<400> SEQUENCE: 508

Glu Val Gln Leu Gly Ile Pro His Pro Ala Gly Leu Ala Lys Arg
1               5                   10                  15

<210> SEQ ID NO 509
<211> LENGTH: 14
<212> TYPE: PRT
<213> ORGANISM: Simian immunodeficiency virus

<400> SEQUENCE: 509

His Pro Ala Gly Leu Ala Lys Arg Lys Arg Ile Thr Val Leu
1               5                   10

<210> SEQ ID NO 510
<211> LENGTH: 15
<212> TYPE: PRT
<213> ORGANISM: Simian immunodeficiency virus

<400> SEQUENCE: 510

Lys Arg Lys Arg Ile Thr Val Leu Asp Ile Gly Asp Ala Tyr Phe
1               5                   10                  15

<210> SEQ ID NO 511
<211> LENGTH: 13
<212> TYPE: PRT
<213> ORGANISM: Simian immunodeficiency virus

<400> SEQUENCE: 511

Asp Ala Tyr Phe Ser Ile Pro Leu Asp Glu Glu Phe Arg
1               5                   10

```
<210> SEQ ID NO 512
<211> LENGTH: 14
<212> TYPE: PRT
<213> ORGANISM: Simian immunodeficiency virus

<400> SEQUENCE: 512

Ser Ile Pro Leu Asp Glu Glu Phe Arg Gln Tyr Thr Ala Phe
1               5                   10

<210> SEQ ID NO 513
<211> LENGTH: 13
<212> TYPE: PRT
<213> ORGANISM: Simian immunodeficiency virus

<400> SEQUENCE: 513

Glu Phe Arg Gln Tyr Thr Ala Phe Thr Leu Pro Ser Val
1               5                   10

<210> SEQ ID NO 514
<211> LENGTH: 15
<212> TYPE: PRT
<213> ORGANISM: Simian immunodeficiency virus

<400> SEQUENCE: 514

Thr Ala Phe Thr Leu Pro Ser Val Asn Asn Ala Glu Pro Gly Lys
1               5                   10                  15

<210> SEQ ID NO 515
<211> LENGTH: 15
<212> TYPE: PRT
<213> ORGANISM: Simian immunodeficiency virus

<400> SEQUENCE: 515

Val Asn Asn Ala Glu Pro Gly Lys Arg Tyr Ile Tyr Lys Val Leu
1               5                   10                  15

<210> SEQ ID NO 516
<211> LENGTH: 13
<212> TYPE: PRT
<213> ORGANISM: Simian immunodeficiency virus

<400> SEQUENCE: 516

Lys Arg Tyr Ile Tyr Lys Val Leu Pro Gln Gly Trp Lys
1               5                   10

<210> SEQ ID NO 517
<211> LENGTH: 15
<212> TYPE: PRT
<213> ORGANISM: Simian immunodeficiency virus

<400> SEQUENCE: 517

Lys Val Leu Pro Gln Gly Trp Lys Gly Ser Pro Ala Ile Phe Arg
1               5                   10                  15

<210> SEQ ID NO 518
<211> LENGTH: 15
<212> TYPE: PRT
<213> ORGANISM: Simian immunodeficiency virus

<400> SEQUENCE: 518

Trp Lys Gly Ser Pro Ala Ile Phe Gln Tyr Thr Met Arg His Val
1               5                   10                  15

<210> SEQ ID NO 519
<211> LENGTH: 15
```

```
<212> TYPE: PRT
<213> ORGANISM: Simian immunodeficiency virus

<400> SEQUENCE: 519

Phe Gln Tyr Thr Met Arg His Val Leu Glu Pro Phe Arg Lys Ala
1               5                   10                  15

<210> SEQ ID NO 520
<211> LENGTH: 14
<212> TYPE: PRT
<213> ORGANISM: Simian immunodeficiency virus

<400> SEQUENCE: 520

Arg His Val Leu Glu Pro Phe Arg Lys Ala Asn Pro Asp Val
1               5                   10

<210> SEQ ID NO 521
<211> LENGTH: 14
<212> TYPE: PRT
<213> ORGANISM: Simian immunodeficiency virus

<400> SEQUENCE: 521

Phe Arg Lys Ala Asn Pro Asp Val Thr Leu Val Gln Tyr Met
1               5                   10

<210> SEQ ID NO 522
<211> LENGTH: 14
<212> TYPE: PRT
<213> ORGANISM: Simian immunodeficiency virus

<400> SEQUENCE: 522

Val Gln Tyr Met Asp Asp Ile Leu Ile Ala Ser Asp Arg Arg
1               5                   10

<210> SEQ ID NO 523
<211> LENGTH: 15
<212> TYPE: PRT
<213> ORGANISM: Simian immunodeficiency virus

<400> SEQUENCE: 523

Asp Ile Leu Ile Ala Ser Asp Arg Thr Asp Leu Glu His Asp Arg
1               5                   10                  15

<210> SEQ ID NO 524
<211> LENGTH: 14
<212> TYPE: PRT
<213> ORGANISM: Simian immunodeficiency virus

<400> SEQUENCE: 524

Arg Thr Asp Leu Glu His Asp Arg Val Val Leu Gln Leu Lys
1               5                   10

<210> SEQ ID NO 525
<211> LENGTH: 14
<212> TYPE: PRT
<213> ORGANISM: Simian immunodeficiency virus

<400> SEQUENCE: 525

Asp Leu Glu His Asp Arg Val Val Leu Gln Leu Lys Glu Leu
1               5                   10

<210> SEQ ID NO 526
<211> LENGTH: 16
<212> TYPE: PRT
<213> ORGANISM: Simian immunodeficiency virus
```

```
<400> SEQUENCE: 526

Leu Lys Glu Leu Leu Asn Ser Ile Gly Phe Ser Thr Pro Glu Glu Lys
1               5                   10                  15

<210> SEQ ID NO 527
<211> LENGTH: 15
<212> TYPE: PRT
<213> ORGANISM: Simian immunodeficiency virus

<400> SEQUENCE: 527

Gly Phe Ser Thr Pro Glu Glu Lys Phe Gln Lys Asp Pro Pro Phe
1               5                   10                  15

<210> SEQ ID NO 528
<211> LENGTH: 15
<212> TYPE: PRT
<213> ORGANISM: Simian immunodeficiency virus

<400> SEQUENCE: 528

Lys Phe Gln Lys Asp Pro Pro Phe Gln Trp Met Gly Tyr Glu Leu
1               5                   10                  15

<210> SEQ ID NO 529
<211> LENGTH: 15
<212> TYPE: PRT
<213> ORGANISM: Simian immunodeficiency virus

<400> SEQUENCE: 529

Phe Gln Trp Met Gly Tyr Glu Leu Trp Pro Thr Lys Trp Lys Leu
1               5                   10                  15

<210> SEQ ID NO 530
<211> LENGTH: 13
<212> TYPE: PRT
<213> ORGANISM: Simian immunodeficiency virus

<400> SEQUENCE: 530

Leu Trp Pro Thr Lys Trp Lys Leu Gln Lys Ile Glu Leu
1               5                   10

<210> SEQ ID NO 531
<211> LENGTH: 14
<212> TYPE: PRT
<213> ORGANISM: Simian immunodeficiency virus

<400> SEQUENCE: 531

Trp Lys Leu Gln Lys Ile Glu Leu Pro Gln Arg Glu Thr Trp
1               5                   10

<210> SEQ ID NO 532
<211> LENGTH: 15
<212> TYPE: PRT
<213> ORGANISM: Simian immunodeficiency virus

<400> SEQUENCE: 532

Glu Leu Pro Gln Arg Glu Thr Trp Thr Val Asn Asp Ile Gln Lys
1               5                   10                  15

<210> SEQ ID NO 533
<211> LENGTH: 14
<212> TYPE: PRT
<213> ORGANISM: Simian immunodeficiency virus

<400> SEQUENCE: 533
```

Val Asn Asp Ile Gln Lys Leu Val Gly Val Leu Asn Arg Arg
1               5                   10

<210> SEQ ID NO 534
<211> LENGTH: 14
<212> TYPE: PRT
<213> ORGANISM: Simian immunodeficiency virus

<400> SEQUENCE: 534

Val Gly Val Leu Asn Trp Ala Ala Gln Ile Tyr Arg Arg Arg
1               5                   10

<210> SEQ ID NO 535
<211> LENGTH: 15
<212> TYPE: PRT
<213> ORGANISM: Simian immunodeficiency virus

<400> SEQUENCE: 535

Leu Asn Trp Ala Ala Gln Ile Tyr Pro Gly Ile Lys Thr Lys His
1               5                   10                  15

<210> SEQ ID NO 536
<211> LENGTH: 14
<212> TYPE: PRT
<213> ORGANISM: Simian immunodeficiency virus

<400> SEQUENCE: 536

Tyr Pro Gly Ile Lys Thr Lys His Leu Cys Arg Leu Ile Arg
1               5                   10

<210> SEQ ID NO 537
<211> LENGTH: 13
<212> TYPE: PRT
<213> ORGANISM: Simian immunodeficiency virus

<400> SEQUENCE: 537

Lys His Leu Cys Arg Leu Ile Arg Gly Lys Met Thr Leu
1               5                   10

<210> SEQ ID NO 538
<211> LENGTH: 14
<212> TYPE: PRT
<213> ORGANISM: Simian immunodeficiency virus

<400> SEQUENCE: 538

Leu Ile Arg Gly Lys Met Thr Leu Thr Glu Glu Val Gln Trp
1               5                   10

<210> SEQ ID NO 539
<211> LENGTH: 14
<212> TYPE: PRT
<213> ORGANISM: Simian immunodeficiency virus

<400> SEQUENCE: 539

Thr Leu Thr Glu Glu Val Gln Trp Thr Glu Met Ala Glu Ala
1               5                   10

<210> SEQ ID NO 540
<211> LENGTH: 15
<212> TYPE: PRT
<213> ORGANISM: Simian immunodeficiency virus

<400> SEQUENCE: 540

Val Gln Trp Thr Glu Met Ala Glu Ala Glu Tyr Glu Glu Asn Lys

```
1               5               10              15
```

<210> SEQ ID NO 541
<211> LENGTH: 15
<212> TYPE: PRT
<213> ORGANISM: Simian immunodeficiency virus

<400> SEQUENCE: 541

```
Glu Ala Glu Tyr Glu Glu Asn Lys Ile Ile Leu Ser Gln Glu Arg
1               5               10              15
```

<210> SEQ ID NO 542
<211> LENGTH: 13
<212> TYPE: PRT
<213> ORGANISM: Simian immunodeficiency virus

<400> SEQUENCE: 542

```
Lys Ile Ile Leu Ser Gln Glu Gln Glu Gly Cys Tyr Tyr
1               5               10
```

<210> SEQ ID NO 543
<211> LENGTH: 15
<212> TYPE: PRT
<213> ORGANISM: Simian immunodeficiency virus

<400> SEQUENCE: 543

```
Ser Gln Glu Gln Glu Gly Cys Tyr Tyr Gln Glu Gly Lys Pro Leu
1               5               10              15
```

<210> SEQ ID NO 544
<211> LENGTH: 14
<212> TYPE: PRT
<213> ORGANISM: Simian immunodeficiency virus

<400> SEQUENCE: 544

```
Tyr Tyr Gln Glu Gly Lys Pro Leu Glu Ala Thr Val Ile Lys
1               5               10
```

<210> SEQ ID NO 545
<211> LENGTH: 14
<212> TYPE: PRT
<213> ORGANISM: Simian immunodeficiency virus

<400> SEQUENCE: 545

```
Pro Leu Glu Ala Thr Val Ile Lys Ser Gln Asp Asn Gln Trp
1               5               10
```

<210> SEQ ID NO 546
<211> LENGTH: 13
<212> TYPE: PRT
<213> ORGANISM: Simian immunodeficiency virus

<400> SEQUENCE: 546

```
Ile Lys Ser Gln Asp Asn Gln Trp Ser Tyr Lys Ile His
1               5               10
```

<210> SEQ ID NO 547
<211> LENGTH: 15
<212> TYPE: PRT
<213> ORGANISM: Simian immunodeficiency virus

<400> SEQUENCE: 547

```
Asn Gln Trp Ser Tyr Lys Ile His Gln Glu Asp Lys Ile Leu Lys
1               5               10              15
```

<210> SEQ ID NO 548
<211> LENGTH: 15
<212> TYPE: PRT
<213> ORGANISM: Simian immunodeficiency virus

<400> SEQUENCE: 548

His Gln Glu Asp Lys Ile Leu Lys Val Gly Lys Phe Ala Lys Ile
1               5                   10                  15

<210> SEQ ID NO 549
<211> LENGTH: 16
<212> TYPE: PRT
<213> ORGANISM: Simian immunodeficiency virus

<400> SEQUENCE: 549

Lys Val Gly Lys Phe Ala Lys Ile Lys Asn Thr His Thr Asn Gly Val
1               5                   10                  15

<210> SEQ ID NO 550
<211> LENGTH: 15
<212> TYPE: PRT
<213> ORGANISM: Simian immunodeficiency virus

<400> SEQUENCE: 550

Lys Asn Thr His Thr Asn Gly Val Arg Leu Leu Ala His Val Ile
1               5                   10                  15

<210> SEQ ID NO 551
<211> LENGTH: 15
<212> TYPE: PRT
<213> ORGANISM: Simian immunodeficiency virus

<400> SEQUENCE: 551

Arg Leu Leu Ala His Val Ile Gln Lys Ile Gly Lys Glu Ala Arg
1               5                   10                  15

<210> SEQ ID NO 552
<211> LENGTH: 13
<212> TYPE: PRT
<213> ORGANISM: Simian immunodeficiency virus

<400> SEQUENCE: 552

Lys Ile Gly Lys Glu Ala Ile Val Ile Trp Gly Gln Arg
1               5                   10

<210> SEQ ID NO 553
<211> LENGTH: 11
<212> TYPE: PRT
<213> ORGANISM: Simian immunodeficiency virus

<400> SEQUENCE: 553

Trp Gly Gln Val Pro Lys Phe His Leu Pro Val
1               5                   10

<210> SEQ ID NO 554
<211> LENGTH: 13
<212> TYPE: PRT
<213> ORGANISM: Simian immunodeficiency virus

<400> SEQUENCE: 554

Val Pro Lys Phe His Leu Pro Val Glu Arg Asp Val Trp
1               5                   10

<210> SEQ ID NO 555

```
<211> LENGTH: 15
<212> TYPE: PRT
<213> ORGANISM: Simian immunodeficiency virus

<400> SEQUENCE: 555

Leu Pro Val Glu Arg Asp Val Trp Glu Gln Trp Trp Thr Asp Tyr
1               5                   10                  15

<210> SEQ ID NO 556
<211> LENGTH: 14
<212> TYPE: PRT
<213> ORGANISM: Simian immunodeficiency virus

<400> SEQUENCE: 556

Trp Glu Gln Trp Trp Thr Asp Tyr Trp Gln Val Thr Trp Ile
1               5                   10

<210> SEQ ID NO 557
<211> LENGTH: 14
<212> TYPE: PRT
<213> ORGANISM: Simian immunodeficiency virus

<400> SEQUENCE: 557

Asp Tyr Trp Gln Val Thr Trp Ile Pro Glu Trp Asp Phe Ile
1               5                   10

<210> SEQ ID NO 558
<211> LENGTH: 16
<212> TYPE: PRT
<213> ORGANISM: Simian immunodeficiency virus

<400> SEQUENCE: 558

Thr Trp Ile Pro Glu Trp Asp Phe Ile Ser Thr Pro Pro Leu Val Arg
1               5                   10                  15

<210> SEQ ID NO 559
<211> LENGTH: 13
<212> TYPE: PRT
<213> ORGANISM: Simian immunodeficiency virus

<400> SEQUENCE: 559

Ser Thr Pro Pro Leu Val Arg Leu Val Phe Asn Arg Arg
1               5                   10

<210> SEQ ID NO 560
<211> LENGTH: 17
<212> TYPE: PRT
<213> ORGANISM: Simian immunodeficiency virus

<400> SEQUENCE: 560

Arg Leu Val Phe Asn Leu Val Lys Asp Pro Ile Glu Gly Glu Glu Thr
1               5                   10                  15

Tyr

<210> SEQ ID NO 561
<211> LENGTH: 17
<212> TYPE: PRT
<213> ORGANISM: Simian immunodeficiency virus

<400> SEQUENCE: 561

Pro Val Gln Gln Ile Gly Gly Asn Tyr Val His Leu Pro Leu Ser Pro
1               5                   10                  15

Arg
```

```
<210> SEQ ID NO 562
<211> LENGTH: 15
<212> TYPE: PRT
<213> ORGANISM: Simian immunodeficiency virus

<400> SEQUENCE: 562

Gly Asn Tyr Val His Leu Pro Leu Ser Pro Arg Thr Leu Asn Ala
1               5                   10                  15

<210> SEQ ID NO 563
<211> LENGTH: 16
<212> TYPE: PRT
<213> ORGANISM: Simian immunodeficiency virus

<400> SEQUENCE: 563

Ser Pro Arg Thr Leu Asn Ala Trp Val Lys Leu Ile Glu Glu Lys Lys
1               5                   10                  15

<210> SEQ ID NO 564
<211> LENGTH: 15
<212> TYPE: PRT
<213> ORGANISM: Simian immunodeficiency virus

<400> SEQUENCE: 564

Leu Asn Ala Trp Val Lys Leu Ile Glu Glu Lys Lys Phe Gly Ala
1               5                   10                  15

<210> SEQ ID NO 565
<211> LENGTH: 14
<212> TYPE: PRT
<213> ORGANISM: Simian immunodeficiency virus

<400> SEQUENCE: 565

Ile Glu Glu Lys Lys Phe Gly Ala Glu Val Val Pro Gly Phe
1               5                   10

<210> SEQ ID NO 566
<211> LENGTH: 18
<212> TYPE: PRT
<213> ORGANISM: Simian immunodeficiency virus

<400> SEQUENCE: 566

Lys Lys Phe Gly Ala Glu Val Val Pro Gly Phe Gln Ala Leu Ser Glu
1               5                   10                  15

Gly Arg

<210> SEQ ID NO 567
<211> LENGTH: 14
<212> TYPE: PRT
<213> ORGANISM: Simian immunodeficiency virus

<400> SEQUENCE: 567

Phe Gln Ala Leu Ser Glu Gly Cys Thr Pro Tyr Asp Ile Arg
1               5                   10

<210> SEQ ID NO 568
<211> LENGTH: 15
<212> TYPE: PRT
<213> ORGANISM: Simian immunodeficiency virus

<400> SEQUENCE: 568

Glu Gly Cys Thr Pro Tyr Asp Ile Asn Gln Met Leu Asn Cys Val
1               5                   10                  15
```

```
<210> SEQ ID NO 569
<211> LENGTH: 15
<212> TYPE: PRT
<213> ORGANISM: Simian immunodeficiency virus

<400> SEQUENCE: 569

Tyr Asp Ile Asn Gln Met Leu Asn Cys Val Gly Asp His Gln Ala
1               5                   10                  15

<210> SEQ ID NO 570
<211> LENGTH: 17
<212> TYPE: PRT
<213> ORGANISM: Simian immunodeficiency virus

<400> SEQUENCE: 570

Asp His Gln Ala Ala Met Gln Ile Ile Arg Asp Ile Ile Asn Glu Glu
1               5                   10                  15

Ala

<210> SEQ ID NO 571
<211> LENGTH: 15
<212> TYPE: PRT
<213> ORGANISM: Simian immunodeficiency virus

<400> SEQUENCE: 571

Met Gln Ile Ile Arg Asp Ile Ile Asn Glu Glu Ala Ala Asp Trp
1               5                   10                  15

<210> SEQ ID NO 572
<211> LENGTH: 16
<212> TYPE: PRT
<213> ORGANISM: Simian immunodeficiency virus

<400> SEQUENCE: 572

Ile Asn Glu Glu Ala Ala Asp Trp Asp Leu Gln His Pro Gln Pro Ala
1               5                   10                  15

<210> SEQ ID NO 573
<211> LENGTH: 15
<212> TYPE: PRT
<213> ORGANISM: Simian immunodeficiency virus

<400> SEQUENCE: 573

Asp Leu Gln His Pro Gln Pro Ala Pro Gln Gln Gly Gln Leu Arg
1               5                   10                  15

<210> SEQ ID NO 574
<211> LENGTH: 15
<212> TYPE: PRT
<213> ORGANISM: Simian immunodeficiency virus

<400> SEQUENCE: 574

Ala Pro Gln Gln Gly Gln Leu Arg Glu Pro Ser Gly Ser Asp Ile
1               5                   10                  15

<210> SEQ ID NO 575
<211> LENGTH: 15
<212> TYPE: PRT
<213> ORGANISM: Simian immunodeficiency virus

<400> SEQUENCE: 575

Arg Glu Pro Ser Gly Ser Asp Ile Ala Gly Thr Thr Ser Ser Val
1               5                   10                  15
```

<210> SEQ ID NO 576
<211> LENGTH: 15
<212> TYPE: PRT
<213> ORGANISM: Simian immunodeficiency virus

<400> SEQUENCE: 576

Ile Ala Gly Thr Thr Ser Ser Val Asp Glu Gln Ile Gln Trp Met
1               5                   10                  15

<210> SEQ ID NO 577
<211> LENGTH: 15
<212> TYPE: PRT
<213> ORGANISM: Simian immunodeficiency virus

<400> SEQUENCE: 577

Val Asp Glu Gln Ile Gln Trp Met Tyr Arg Gln Gln Asn Pro Ile
1               5                   10                  15

<210> SEQ ID NO 578
<211> LENGTH: 15
<212> TYPE: PRT
<213> ORGANISM: Simian immunodeficiency virus

<400> SEQUENCE: 578

Met Tyr Arg Gln Gln Asn Pro Ile Pro Val Gly Asn Ile Tyr Arg
1               5                   10                  15

<210> SEQ ID NO 579
<211> LENGTH: 13
<212> TYPE: PRT
<213> ORGANISM: Simian immunodeficiency virus

<400> SEQUENCE: 579

Asn Pro Ile Pro Val Gly Asn Ile Tyr Arg Arg Trp Ile
1               5                   10

<210> SEQ ID NO 580
<211> LENGTH: 15
<212> TYPE: PRT
<213> ORGANISM: Simian immunodeficiency virus

<400> SEQUENCE: 580

Arg Arg Trp Ile Gln Leu Gly Leu Gln Lys Cys Val Arg Met Tyr
1               5                   10                  15

<210> SEQ ID NO 581
<211> LENGTH: 14
<212> TYPE: PRT
<213> ORGANISM: Simian immunodeficiency virus

<400> SEQUENCE: 581

Leu Gln Lys Cys Val Arg Met Tyr Asn Pro Thr Asn Ile Leu
1               5                   10

<210> SEQ ID NO 582
<211> LENGTH: 15
<212> TYPE: PRT
<213> ORGANISM: Simian immunodeficiency virus

<400> SEQUENCE: 582

Met Tyr Asn Pro Thr Asn Ile Leu Asp Val Lys Gln Gly Pro Lys
1               5                   10                  15

<210> SEQ ID NO 583

```
<210> SEQ ID NO 583
<211> LENGTH: 15
<212> TYPE: PRT
<213> ORGANISM: Simian immunodeficiency virus

<400> SEQUENCE: 583

Leu Asp Val Lys Gln Gly Pro Lys Glu Pro Phe Gln Ser Tyr Val
1               5                   10                  15

<210> SEQ ID NO 584
<211> LENGTH: 15
<212> TYPE: PRT
<213> ORGANISM: Simian immunodeficiency virus

<400> SEQUENCE: 584

Lys Glu Pro Phe Gln Ser Tyr Val Asp Arg Phe Tyr Lys Ser Leu
1               5                   10                  15

<210> SEQ ID NO 585
<211> LENGTH: 15
<212> TYPE: PRT
<213> ORGANISM: Simian immunodeficiency virus

<400> SEQUENCE: 585

Val Asp Arg Phe Tyr Lys Ser Leu Arg Ala Glu Gln Thr Asp Ala
1               5                   10                  15

<210> SEQ ID NO 586
<211> LENGTH: 14
<212> TYPE: PRT
<213> ORGANISM: Simian immunodeficiency virus

<400> SEQUENCE: 586

Leu Arg Ala Glu Gln Thr Asp Ala Ala Val Lys Asn Trp Met
1               5                   10

<210> SEQ ID NO 587
<211> LENGTH: 16
<212> TYPE: PRT
<213> ORGANISM: Simian immunodeficiency virus

<400> SEQUENCE: 587

Trp Met Thr Gln Thr Leu Leu Ile Gln Asn Ala Asn Pro Asp Cys Lys
1               5                   10                  15

<210> SEQ ID NO 588
<211> LENGTH: 13
<212> TYPE: PRT
<213> ORGANISM: Simian immunodeficiency virus

<400> SEQUENCE: 588

Ile Gln Asn Ala Asn Pro Asp Cys Lys Leu Val Leu Lys
1               5                   10

<210> SEQ ID NO 589
<211> LENGTH: 16
<212> TYPE: PRT
<213> ORGANISM: Simian immunodeficiency virus

<400> SEQUENCE: 589

Lys Gly Leu Gly Val Asn Pro Thr Leu Glu Glu Met Leu Thr Ala Arg
1               5                   10                  15

<210> SEQ ID NO 590
<211> LENGTH: 20
<212> TYPE: PRT
```

```
<213> ORGANISM: Simian immunodeficiency virus

<400> SEQUENCE: 590

Asn Pro Thr Leu Glu Glu Met Leu Thr Ala Cys Gln Gly Val Gly Gly
1               5                   10                  15

Pro Gly Gln Lys
            20

<210> SEQ ID NO 591
<211> LENGTH: 12
<212> TYPE: PRT
<213> ORGANISM: Simian immunodeficiency virus

<400> SEQUENCE: 591

Gly Val Gly Gly Pro Gly Gln Lys Ala Arg Leu Met
1               5                   10
```

I claim:

1. A method for inducing an immune response in a person or animal against an immunodeficiency virus, comprising administering one or more peptides, or a composition comprising said one or more peptides, to the person or animal, wherein said one or more peptides comprise one or more evolutionarily conserved epitopes, wherein said epitopes are conserved between two or more different immunodeficiency viruses, wherein at least one of said one or more peptides consists of the amino acid sequence of SEQ ID NO:290 and optionally one to five amino acids at the carboxyl terminus of said amino acid sequence.

2. The method according to claim 1, wherein said epitopes are conserved between HIV and FIV.

3. The method according to claim 1, wherein said epitopes are conserved between HIV, SIV, and FIV.

4. The method according to claim 1, wherein said epitope is a T-cell epitope.

5. The method according to claim 4, wherein said T cell epitope induces one or more T cell responses.

6. The method according to claim 5, wherein said one or more T cell responses comprises release of cytotoxins and/or cytokines.

7. The method according to claim 1, wherein said method further comprises administering a peptide, or a composition comprising said peptide, said peptide comprising the amino acid sequence of any of SEQ ID NOs:1-40, or any of SEQ ID NOs:45-289, or any of SEQ ID NOs:291-591.

8. The method according to claim 1, wherein said method further comprises administering a peptide, or a composition comprising said peptide, said peptide comprising the amino acid sequence of any of SEQ ID NOs:10, 21, 22, 23, 61, 62, 63, 64, 65, 78, 79, 163, 164, 165, 166, 167, 176, 177, 178, 179, 214, 215, 216, 217, 218, 288, 291, 301, 303, 304, 359, 361, 431, 432, 438, 442, 443, 453, 459, 460, 466, 479, 488, 492, or 493.

9. The method according to claim 1, wherein said method further comprises administering a peptide, or a composition comprising said peptide, said peptide comprising two or more amino acid sequences of any of SEQ ID NOs:10, 21, 22, 23, 61, 62, 63, 64, 65, 78, 79, 163, 164, 165, 166, 167, 176, 177, 178, 179, 214, 215, 216, 217, 218, 288, 291, 301, 303, 304, 359, 361, 431, 432, 438, 442, 443, 453, 459, 460, 466, 479, 488, 492, and/or 493.

10. The method according to claim 1, wherein said method further comprises administering a peptide, or a composition comprising said peptide, said peptide comprising the amino acid sequence of any of SEQ ID NOs:10, 21, 22, 23, 78, 79, 176, 177, 178, 179, 214, 215, 216, 217, 218, or 291.

11. The method according to claim 1, wherein said induced immune response is a CTL-associated immune response.

12. The method according to claim 1, wherein said induced immune response comprises a CD4+ and/or CD8+ T cell response.

13. The method according to claim 1, wherein the animal is a feline animal.

14. The method according to claim 1, wherein said induced immune response inhibits infection of the person or animal by said immunodeficiency virus.

15. The method according to claim 1, wherein said one or more peptides are provided in a multiple antigenic peptide (MAP) construct.

16. The method according to claim 15, wherein said MAP construct is provided with and/or administered with one or more adjuvants.

17. The method according to claim 1, wherein said at least one of said one or more peptides consists of the amino acid sequence of SEQ ID NO:290 and two amino acids at the carboxyl terminus of said amino acid sequence.

18. The method according to claim 17, wherein said two amino acids are alanine and lysine.

19. The method according to claim 1, wherein said one or more peptides, or said composition, are administered subcutaneously, intradermally, intraperitoneally, orally, or nasally, or by any combination thereof.

20. The method according to claim 1, wherein said composition comprises a pharmaceutically or biologically acceptable carrier, diluent and/or adjuvant.

* * * * *

UNITED STATES PATENT AND TRADEMARK OFFICE
CERTIFICATE OF CORRECTION

PATENT NO. : 10,905,757 B2
APPLICATION NO. : 15/881148
DATED : February 2, 2021
INVENTOR(S) : Janet K. Yamamoto Page 1 of 2

It is certified that error appears in the above-identified patent and that said Letters Patent is hereby corrected as shown below:

In the Specification

Column 11,
Line 44, "MEW lineage." should read --MHC lineage.--.

Column 12,
Line 21, "bind to MEW." should read --bind to MHC.--.

Column 18,
Line 17, "(Feigner et al., 1987)." should read --(Felgner *et al.*, 1987).--.

Column 25,
Line 11, "NBLAST and)(BLAST programs" should read --NBLAST and XBLAST programs--.
Lines 18-19, "programs (NBLAST and)(BLAST)" should read --programs (NBLAST and XBLAST)--.

Column 37,
Line 35, "Alexa F1.700" should read --Alexa Fl.700--.

Column 40,
Line 50, "86) AYWIDIGKWQVMEI (SEQ ID NO: 136)" should read --86) AYWTDTGKWQVMEI (SEQ ID NO: 136)--.

Column 57,
Line 40, "IFNα+/proliferation+" should read --IFNγ+/proliferation+--.
Line 49, "HU-specific IFNγ" should read --H11-specific IFNγ--.

Column 83,
Line 61, "with MAP1 b" should read --with MAP1b--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,905,757 B2

Column 84,
Line 24, "with MAP 1b" should read --with MAP1b--.

Column 93,
Line 44, "MEW class" should read --MHC class--.

Column 94,
Line 22, "Biochem J1997; 327:625-35." should read --*Biochem J* 1997; 327:625-35.--.

Column 95,
Line 36, "Levy Y," should read --Lévy Y,--.

Column 97,
Line 44, "B.A. Tones," should read --B.A. Torres,--.